(12) United States Patent
Caparrós-Wanderley et al.

(10) Patent No.: US 9,944,693 B2
(45) Date of Patent: Apr. 17, 2018

(54) HIV ANTIGENS AND ANTIBODIES AND COMPOSITIONS, USES AND METHODS THEREOF

(71) Applicant: PepTcell Limited, London (GB)

(72) Inventors: Wilson Caparrós-Wanderley, Aylesbury (GB); Gregory A. Stoloff, London (GB)

(73) Assignee: PepTcell Limited, London (GB)

( * ) Notice: Subject to any disclaimer, the term of this patent is extended or adjusted under 35 U.S.C. 154(b) by 142 days.

(21) Appl. No.: 14/564,075

(22) Filed: Dec. 8, 2014

(65) Prior Publication Data

US 2015/0158933 A1 Jun. 11, 2015

Related U.S. Application Data

(60) Provisional application No. 61/913,363, filed on Dec. 8, 2013, provisional application No. 62/038,824, filed on Aug. 18, 2014.

(51) Int. Cl.
| | |
|---|---|
| *A61K 45/06* | (2006.01) |
| *C07K 16/10* | (2006.01) |
| *G01N 33/569* | (2006.01) |
| *A61K 39/00* | (2006.01) |

(52) U.S. Cl.
CPC ...... *C07K 16/1045* (2013.01); *C07K 16/1072* (2013.01); *G01N 33/56988* (2013.01); *A61K 2039/505* (2013.01); *C07K 2317/565* (2013.01); *C07K 2317/73* (2013.01); *C07K 2317/734* (2013.01)

(58) Field of Classification Search
None
See application file for complete search history.

(56) References Cited

FOREIGN PATENT DOCUMENTS

| EP | 2581387 A1 | 4/2013 |
| WO | 2003089472 A2 | 10/2003 |
| WO | 2006007471 A1 | 1/2006 |
| WO | 2006088740 A2 | 8/2006 |

OTHER PUBLICATIONS

Pleguezuelos et al. (Virology Journal, Apr. 4, 2013, vol. 10, p. 1-13).*
Krichevsky, et al., "Antibody fragments selected by phage display against the nuclear localization signal of the HIV-1 Vpr protein inhibit nuclear import in permeabilized and intact cultured cells," Virology, (Jan. 2003), vol. 305, No. 1, pp. 77-92.
Sabbah, et al., "Development and Characterization of Ten Monoclonal Anti-Vpr Antibodies," Aids Research and Human Retroviruses, (Jul. 2006), vol. 22, No. 7, pp. 630-639 (Abstract only).

* cited by examiner

*Primary Examiner* — Agnieszka Boesen
(74) *Attorney, Agent, or Firm* — Entralta P.C.; Jeffrey M. McQuiston; Peter D. Weinstein

(57) ABSTRACT

The present specification discloses HIV antigens, immunogenic compositions and medicaments comprising such HIV antigens, methods and uses for such HIV antigens and immunogenic compositions and medicaments for making a α-HIV antibody, as well as α-HIV antibodies, therapeutic compositions an medicaments comprising such α-HIV antibodies, and methods and uses for such α-HIV antibodies and therapeutic compositions and medicaments for treating an HIV-based disease.

11 Claims, 12 Drawing Sheets

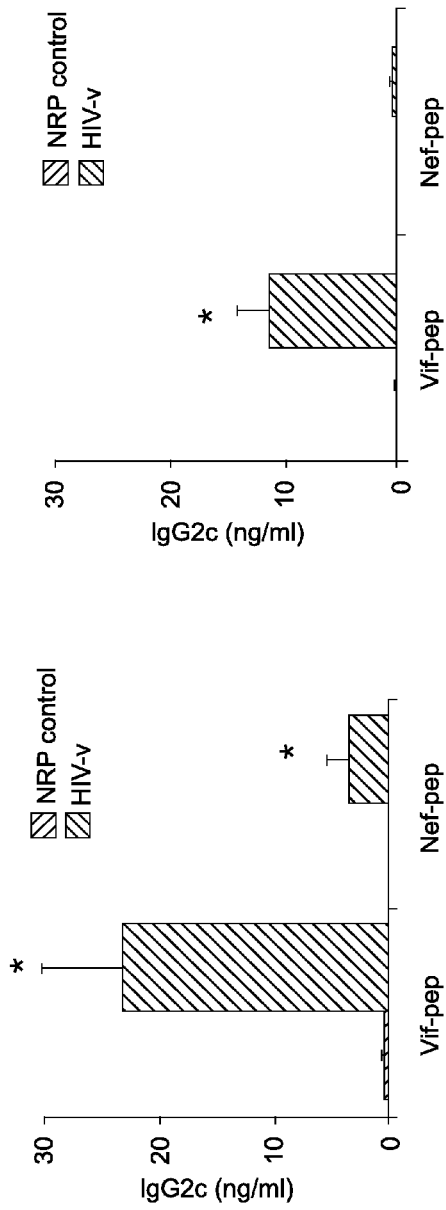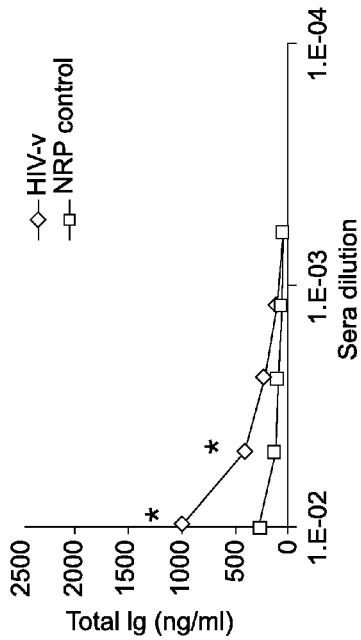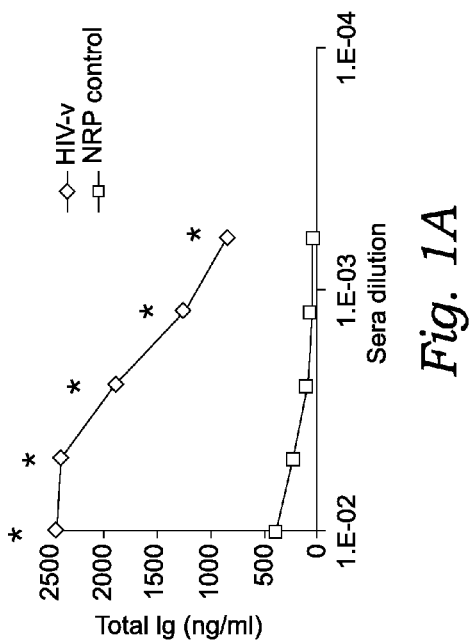
Fig. 1A  Fig. 1B  Fig. 1C  Fig. 1D

SEQUENCE LISTING

```
<160> NUMBER OF SEQ ID NOS: 45

<210> SEQ ID NO 1
<211> LENGTH: 30
<212> TYPE: PRT
<213> ORGANISM: Human Immunodeficiency Virus-1

<400> SEQUENCE: 1

Gly Asp Thr Trp Ala Gly Val Glu Ala Ile Ile Arg Ile Leu Gln Gln
1               5                   10                  15

Leu Leu Phe Ile His Phe Arg Ile Gly Cys Gln His Ser Arg
            20                  25                  30

<210> SEQ ID NO 2
<211> LENGTH: 40
<212> TYPE: PRT
<213> ORGANISM: Human Immunodeficiency Virus-1

<400> SEQUENCE: 2

Lys Val Gly Ser Leu Gln Tyr Leu Ala Leu Thr Ala Leu Ile Thr Pro
1               5                   10                  15

Lys Lys Ile Lys Pro Pro Leu Pro Ser Val Lys Lys Leu Thr Glu Asp
            20                  25                  30

Arg Trp Asn Lys Pro Gln Lys Thr
        35                  40

<210> SEQ ID NO 3
<211> LENGTH: 27
<212> TYPE: PRT
<213> ORGANISM: Human Immunodeficiency Virus-1

<400> SEQUENCE: 3

Glu Pro Val Pro Leu Gln Leu Pro Pro Leu Glu Arg Leu Thr Leu Asp
1               5                   10                  15

Cys Ser Glu Asp Cys Gly Thr Ser Gly Thr Gln
            20                  25

<210> SEQ ID NO 4
<211> LENGTH: 43
```

<212> TYPE: PRT
<213> ORGANISM: Human Immunodeficiency Virus-1

<400> SEQUENCE: 4

Tyr Lys Gly Ala Leu Asp Leu Ser His Phe Leu Lys Glu Lys Gly Gly
1               5                   10                  15

Leu Glu Gly Leu Ile Tyr Ser Gln Lys Arg Gln Asp Ile Leu Asp Leu
            20                  25                  30

Trp Val Tyr His Thr Gln Gly Tyr Phe Pro Asp
        35                  40

<210> SEQ ID NO 5
<211> LENGTH: 145
<212> TYPE: PRT
<213> ORGANISM: Mus musculus

<400> SEQUENCE: 5

Met Glu Cys Ser Trp Val Met Leu Leu Val Ser Thr Ala Thr Gly Val
1               5                   10                  15

His Ser Gln Val Gln Leu Gln Gln Pro Gly Ala Glu Leu Val Arg Pro
            20                  25                  30

Gly Thr Ser Val Lys Leu Ser Cys Lys Ala Ser Gly Tyr Thr Phe Thr
        35                  40                  45

Ser Tyr Trp Met His Trp Val Lys Gln Arg Pro Gly Gln Gly Leu Glu
    50                  55                  60

Trp Ile Gly Val Ile Asp Pro Ser Asp Ser Tyr Thr Asn Tyr Asn Gln
65                  70                  75                  80

Asn Phe Lys Gly Lys Ala Ser Leu Thr Val Asp Thr Ser Ser Ser Thr
                85                  90                  95

Ala Tyr Met Gln Leu Ser Ser Leu Thr Ser Glu Asp Ser Ala Val Tyr
            100                 105                 110

Tyr Cys Ala Arg Asp Asp Tyr Asp Tyr Trp Gly Gln Gly Thr Thr Leu
        115                 120                 125

Thr Val Ser Ser Ala Lys Thr Thr Ala Pro Ser Gly Tyr Pro Leu Ala
    130                 135                 140

Pro
145

<210> SEQ ID NO 6
<211> LENGTH: 144
<212> TYPE: PRT
<213> ORGANISM: Mus musculus

<400> SEQUENCE: 6

Met Gly Cys Ser Trp Val Ile Leu Leu Val Ser Thr Ala Thr Gly Val
1               5                   10                  15

His Ser Gln Val Gln Leu Gln Gln Pro Gly Ala Glu Leu Val Arg Pro
            20                  25                  30

Gly Thr Ser Val Lys Leu Ser Cys Lys Ala Ser Gly Tyr Thr Phe Thr
        35                  40                  45

Ser Tyr Trp Met His Trp Val Lys Gln Arg Pro Gly Gln Gly Leu Glu
    50                  55                  60

Trp Ile Gly Val Ile Asp Pro Ser Asp Ser Tyr Thr Asn Tyr Asn Gln
65                  70                  75                  80

Asn Phe Lys Gly Lys Ala Ser Leu Thr Val Asp Thr Ser Ser Gly Thr
                85                  90                  95

Ala Tyr Met Gln Leu Ser Ser Leu Thr Ser Glu Asp Ser Ala Val Tyr

```
                 100                 105                 110
Tyr Cys Ala Arg Asp Asp Tyr Asp Tyr Trp Gly Gln Gly Thr Thr Leu
            115                 120                 125

Thr Val Ser Ser Ala Lys Thr Thr Ala Pro Ser Val Phe Pro Leu Ala
            130                 135                 140

<210> SEQ ID NO 7
<211> LENGTH: 145
<212> TYPE: PRT
<213> ORGANISM: Mus musculus

<400> SEQUENCE: 7

Met Glu Trp Ser Cys Val Met Leu Leu Val Ser Thr Ala Thr Gly Val
1               5                   10                  15

His Ser Gln Val Gln Leu Gln Gln Pro Gly Ala Glu Leu Val Arg Pro
            20                  25                  30

Gly Thr Ser Val Lys Leu Ser Cys Lys Ala Ser Gly Tyr Thr Phe Thr
        35                  40                  45

Ser Tyr Trp Met His Trp Val Lys Gln Arg Pro Gly Gln Gly Leu Glu
    50                  55                  60

Trp Ile Gly Val Ile Asp Pro Ser Asp Ser Tyr Thr Asn Tyr Asn Gln
65                  70                  75                  80

Asn Phe Lys Gly Lys Ala Ser Leu Thr Val Asp Thr Ser Ser Ser Thr
                85                  90                  95

Ala Tyr Met Gln Leu Ser Ser Leu Thr Ser Glu Asp Ser Ala Val Tyr
            100                 105                 110

Tyr Cys Ala Arg Asp Asp Tyr Asp Tyr Trp Gly Gln Gly Thr Thr Leu
            115                 120                 125

Thr Val Ser Ser Ala Lys Thr Thr Ala Pro Ser Val Tyr Pro Leu Ala
            130                 135                 140

Pro
145

<210> SEQ ID NO 8
<211> LENGTH: 145
<212> TYPE: PRT
<213> ORGANISM: Mus musculus

<400> SEQUENCE: 8

Met Gly Trp Ser Cys Ile Met Leu Leu Val Ser Thr Ala Thr Gly Val
1               5                   10                  15

His Ser Gln Val Gln Leu Gln Gln Pro Gly Ala Glu Leu Val Arg Pro
            20                  25                  30

Gly Thr Ser Val Lys Leu Ser Cys Lys Ala Ser Gly Tyr Thr Phe Thr
        35                  40                  45

Ser Tyr Trp Met His Trp Val Lys Gln Arg Pro Gly Gln Gly Leu Glu
    50                  55                  60

Trp Ile Gly Val Ile Asp Pro Ser Asp Ser Tyr Thr Asn Tyr Asn Gln
65                  70                  75                  80

Asn Phe Lys Gly Lys Ala Ser Leu Thr Val Asp Thr Ser Ser Ser Thr
                85                  90                  95

Ala Tyr Met Gln Leu Ser Ser Leu Thr Ser Glu Asp Ser Ala Val Tyr
            100                 105                 110

Tyr Cys Ala Arg Asp Asp Tyr Asp Tyr Trp Gly Gln Gly Thr Thr Leu
            115                 120                 125

Thr Val Ser Ser Ala Lys Thr Thr Ala Pro Ser Val Tyr Pro Leu Ala
```

<210> SEQ ID NO 9
<211> LENGTH: 145
<212> TYPE: PRT
<213> ORGANISM: Mus musculus

<400> SEQUENCE: 9

Met Gly Trp Ser Cys Ile Met Phe Leu Val Ser Thr Ala Thr Gly Val
1               5                   10                  15

His Ser Gln Val Gln Leu Gln Gln Pro Gly Ala Glu Leu Val Arg Pro
            20                  25                  30

Gly Thr Ser Val Lys Leu Ser Cys Lys Ala Ser Gly Tyr Thr Phe Thr
        35                  40                  45

Ser Tyr Trp Met His Trp Val Lys Gln Arg Pro Gly Gln Gly Leu Glu
    50                  55                  60

Trp Ile Gly Val Ile Asp Pro Ser Asp Ser Tyr Thr Asn Tyr Asn Gln
65                  70                  75                  80

Asn Phe Lys Gly Lys Ala Ser Leu Thr Val Asp Thr Ser Ser Ser Thr
                85                  90                  95

Ala Tyr Met Gln Leu Ser Ser Leu Thr Ser Glu Asp Ser Ala Val Tyr
            100                 105                 110

Tyr Cys Ala Arg Asp Asp Tyr Asp Tyr Trp Gly Gln Gly Thr Thr Leu
        115                 120                 125

Thr Val Ser Ser Ala Lys Thr Thr Ala Pro Ser Val Tyr Pro Leu Ala
    130                 135                 140

Pro
145

<210> SEQ ID NO 10
<211> LENGTH: 145
<212> TYPE: PRT
<213> ORGANISM: Mus musculus

<400> SEQUENCE: 10

Met Gly Cys Ser Trp Val Met Leu Leu Val Ser Thr Ala Thr Gly Val
1               5                   10                  15

His Ser Gln Val Gln Leu Gln Gln Pro Gly Ala Glu Pro Val Arg Pro
            20                  25                  30

Gly Thr Ser Val Lys Leu Ser Cys Lys Ala Ser Gly Tyr Thr Phe Thr
        35                  40                  45

Ser Tyr Trp Met His Trp Val Lys Gln Arg Pro Gly Gln Gly Leu Glu
    50                  55                  60

Trp Ile Gly Val Ile Asp Pro Ser Asp Ser Tyr Thr Asn Tyr Asn Gln
65                  70                  75                  80

Asn Phe Lys Gly Lys Ala Ser Leu Thr Val Asp Thr Ser Ser Ser Thr
                85                  90                  95

Ala Tyr Met Gln Leu Ser Ser Leu Thr Ser Glu Asp Ser Ala Val Tyr
            100                 105                 110

Tyr Cys Ala Arg Asp Asp Tyr Asp Tyr Trp Gly Gln Gly Thr Thr Leu
        115                 120                 125

Thr Val Ser Ser Ala Lys Thr Thr Ala Pro Ser Val Tyr Pro Leu Ala
    130                 135                 140

Pro

<210> SEQ ID NO 11
<211> LENGTH: 144
<212> TYPE: PRT
<213> ORGANISM: Mus musculus

<400> SEQUENCE: 11

Met Gly Trp Ser Cys Val Met Leu Leu Val Ser Thr Ala Thr Gly Val
1               5                   10                  15

His Ser Gln Val Gln Leu Gln Gln Pro Gly Ala Glu Leu Val Arg Pro
                20                  25                  30

Gly Thr Ser Val Lys Leu Ser Cys Lys Ala Ser Gly Tyr Thr Phe Thr
            35                  40                  45

Ser Tyr Trp Met His Trp Val Lys Gln Arg Pro Gly Gln Gly Leu Glu
        50                  55                  60

Trp Ile Gly Val Ile Asp Pro Ser Asp Ser Tyr Thr Asn Tyr Asn Gln
65                  70                  75                  80

Asn Phe Lys Gly Lys Ala Ser Leu Thr Val Asp Thr Ser Ser Ser Thr
                85                  90                  95

Ala Tyr Met Gln Leu Ser Ser Leu Thr Pro Glu Asp Ser Ala Val Tyr
            100                 105                 110

Tyr Cys Ala Arg Asp Asp Tyr Asp Tyr Trp Gly Gln Gly Thr Thr Leu
        115                 120                 125

Thr Val Ser Ser Ala Lys Thr Thr Ala Pro Ser Val Phe Pro Leu Ala
    130                 135                 140

<210> SEQ ID NO 12
<211> LENGTH: 145
<212> TYPE: PRT
<213> ORGANISM: Mus musculus

<400> SEQUENCE: 12

Met Glu Trp Ser Trp Val Met Leu Leu Val Ser Thr Ala Thr Gly Val
1               5                   10                  15

His Ser Gln Val Gln Leu Gln Gln Pro Gly Ala Glu Leu Val Arg Pro
                20                  25                  30

Gly Thr Ser Val Lys Leu Ser Cys Lys Ala Ser Gly Tyr Thr Phe Thr
            35                  40                  45

Ser Tyr Trp Met His Trp Val Lys Gln Arg Pro Gly Gln Gly Leu Glu
        50                  55                  60

Trp Ile Gly Val Ile Asp Pro Ser Asp Ser Tyr Thr Asn Tyr Asn Gln
65                  70                  75                  80

Asn Phe Lys Gly Lys Ala Ser Leu Thr Val Asp Thr Ser Ser Ser Thr
                85                  90                  95

Ala Tyr Met Gln Leu Ser Ser Leu Thr Ser Glu Asp Ser Ala Val Tyr
            100                 105                 110

Tyr Cys Ala Arg Gly Asp Tyr Asp Tyr Trp Gly Gln Gly Thr Thr Leu
        115                 120                 125

Thr Val Ser Ser Ala Lys Thr Thr Ala Pro Ser Val Tyr Pro Leu Ala
    130                 135                 140

Pro
145

<210> SEQ ID NO 13
<211> LENGTH: 145
<212> TYPE: PRT

-continued

<213> ORGANISM: Mus musculus

<400> SEQUENCE: 13

Met Gly Trp Ser Cys Ile Ile Leu Leu Val Ser Thr Ala Thr Gly Val
1               5                   10                  15

His Ser Gln Val Gln Leu Gln Gln Pro Gly Ala Glu Leu Val Arg Pro
            20                  25                  30

Gly Thr Ser Val Lys Leu Ser Cys Lys Ala Ser Gly Tyr Thr Phe Thr
        35                  40                  45

Ser Tyr Trp Met His Trp Val Lys Gln Arg Pro Gly Gln Gly Leu Glu
    50                  55                  60

Trp Ile Gly Val Ile Asp Pro Ser Asp Ser Tyr Thr Asn Tyr Asn Gln
65                  70                  75                  80

Asn Phe Lys Gly Lys Ala Ser Leu Thr Val Asp Thr Ser Ser Ser Thr
                85                  90                  95

Ala Tyr Met Gln Leu Ser Ser Leu Thr Ser Glu Asp Ser Ala Val Tyr
            100                 105                 110

Tyr Cys Ala Arg Asp Asp Tyr Asp Tyr Trp Gly Gln Gly Thr Thr Leu
        115                 120                 125

Thr Val Ser Ser Ala Lys Thr Thr Ala Pro Ser Val Tyr Pro Leu Ala
    130                 135                 140

Pro
145

<210> SEQ ID NO 14
<211> LENGTH: 144
<212> TYPE: PRT
<213> ORGANISM: Mus musculus

<400> SEQUENCE: 14

Met Gly Cys Ser Trp Val Ile Leu Leu Val Ser Thr Ala Thr Gly Val
1               5                   10                  15

His Ser Gln Val Gln Leu Gln Gln Pro Gly Ala Glu Leu Val Arg Pro
            20                  25                  30

Gly Thr Ser Val Lys Leu Ser Cys Lys Ala Ser Gly Tyr Thr Phe Thr
        35                  40                  45

Ser Tyr Trp Met His Trp Val Lys Gln Arg Pro Gly Gln Gly Leu Glu
    50                  55                  60

Trp Ile Gly Val Ile Asp Pro Ser Asp Ser Tyr Thr Asn Tyr Asn Gln
65                  70                  75                  80

Asn Phe Lys Gly Lys Ala Ser Leu Thr Val Asp Thr Ser Ser Ser Thr
                85                  90                  95

Ala Tyr Met Gln Leu Ser Ser Leu Thr Ser Glu Asp Ser Ala Val Tyr
            100                 105                 110

Tyr Cys Ala Arg Asp Asp Tyr Asp Tyr Trp Gly Gln Gly Thr Thr Leu
        115                 120                 125

Thr Val Ser Ser Ala Lys Thr Thr Ala Pro Ser Val Phe Pro Leu Ala
    130                 135                 140

<210> SEQ ID NO 15
<211> LENGTH: 145
<212> TYPE: PRT
<213> ORGANISM: Mus musculus

<400> SEQUENCE: 15

Met Gly Trp Ser Trp Val Met Leu Leu Val Ser Thr Ala Thr Gly Val
1               5                   10                  15

```
His Ser Gln Val Gln Leu Gln Gln Pro Gly Ala Glu Leu Val Arg Pro
             20                  25                  30

Gly Thr Ser Val Lys Leu Ser Cys Lys Ala Ser Gly Tyr Thr Phe Thr
         35                  40                  45

Ser Tyr Trp Met His Trp Val Lys Gln Arg Pro Gly Gln Gly Leu Glu
 50                  55                  60

Trp Ile Gly Val Ile Asp Pro Ser Asp Ser Tyr Thr Asn Tyr Asn Gln
 65                  70                  75                  80

Asn Phe Lys Gly Lys Ala Ser Leu Thr Val Asp Thr Ser Ser Ser Thr
                 85                  90                  95

Ala Tyr Met Gln Leu Ser Ser Leu Thr Ser Glu Asp Ser Ala Val Tyr
             100                 105                 110

Tyr Cys Ala Arg Asp Asp Tyr Asp Tyr Trp Gly Arg Gly Thr Thr Leu
             115                 120                 125

Thr Val Ser Ser Ala Lys Thr Thr Ala Pro Ser Val Tyr Pro Leu Ala
         130                 135                 140

Pro
145

<210> SEQ ID NO 16
<211> LENGTH: 145
<212> TYPE: PRT
<213> ORGANISM: Mus musculus

<400> SEQUENCE: 16

Met Gly Trp Ser Cys Val Ile Leu Leu Val Ser Thr Ala Thr Gly Val
 1               5                  10                  15

His Ser Gln Val Gln Leu Gln Gln Pro Gly Ala Glu Leu Val Arg Pro
             20                  25                  30

Gly Thr Ser Val Lys Leu Ser Cys Lys Ala Ser Gly Tyr Thr Phe Thr
         35                  40                  45

Ser Tyr Trp Met Arg Trp Val Lys Gln Arg Pro Gly Gln Gly Leu Glu
 50                  55                  60

Trp Ile Gly Val Ile Asp Pro Ser Asp Ser Tyr Thr Asn Tyr Asn Gln
 65                  70                  75                  80

Asn Phe Lys Gly Lys Ala Ser Leu Thr Val Asp Thr Ser Ser Ser Thr
                 85                  90                  95

Ala Tyr Met Gln Leu Ser Ser Leu Thr Ser Glu Asp Ser Ala Val Tyr
             100                 105                 110

Tyr Cys Ala Arg Asp Asp Tyr Asp Tyr Trp Gly Gln Gly Thr Thr Leu
             115                 120                 125

Thr Val Ser Ser Ala Lys Thr Thr Ala Pro Ser Val Tyr Pro Leu Ala
         130                 135                 140

Pro
145

<210> SEQ ID NO 17
<211> LENGTH: 144
<212> TYPE: PRT
<213> ORGANISM: Mus musculus

<400> SEQUENCE: 17

Met Gly Trp Ser Cys Ile Met Leu Leu Val Ser Thr Ala Thr Gly Val
 1               5                  10                  15

His Ser Gln Val Gln Leu Gln Gln Pro Gly Ala Glu Pro Val Arg Pro
             20                  25                  30
```

Gly Thr Ser Val Lys Leu Ser Cys Lys Ala Ser Gly Tyr Thr Phe Thr
            35                  40                  45

Ser Tyr Trp Met His Trp Val Lys Gln Arg Pro Gly Gln Gly Leu Glu
50                  55                  60

Trp Ile Gly Val Ile Asp Pro Ser Asp Ser Tyr Thr Asn Tyr Asn Gln
65                  70                  75                  80

Asn Phe Lys Gly Lys Ala Ser Leu Thr Val Asp Thr Ser Ser Ser Thr
                85                  90                  95

Ala Tyr Met Gln Leu Ser Ser Leu Thr Ser Glu Asp Ser Ala Val Tyr
            100                 105                 110

Tyr Cys Ala Arg Asp Asp Tyr Asp Tyr Trp Gly Gln Gly Thr Thr Leu
            115                 120                 125

Thr Val Ser Ser Ala Lys Thr Thr Ala Pro Ser Val Phe Pro Leu Ala
            130                 135                 140

<210> SEQ ID NO 18
<211> LENGTH: 144
<212> TYPE: PRT
<213> ORGANISM: Mus musculus

<400> SEQUENCE: 18

Met Gly Trp Ser Cys Ile Met Leu Leu Val Ser Thr Ala Thr Gly Val
1               5                   10                  15

His Ser Gln Val Gln Leu Gln Gln Pro Gly Ala Glu Pro Val Arg Pro
                20                  25                  30

Gly Thr Ser Val Lys Leu Ser Cys Lys Ala Ser Gly Tyr Thr Phe Thr
            35                  40                  45

Ser Tyr Trp Met His Trp Val Lys Gln Arg Pro Gly Gln Gly Leu Glu
50                  55                  60

Trp Ile Gly Val Ile Asp Pro Ser Asp Ser Tyr Thr Asn Tyr Asn Gln
65                  70                  75                  80

Asn Phe Lys Gly Lys Ala Ser Leu Thr Val Asp Thr Ser Ser Ser Thr
                85                  90                  95

Ala Tyr Met Gln Leu Ser Ser Leu Thr Ser Glu Asp Ser Ala Val Tyr
            100                 105                 110

Tyr Cys Ala Arg Asp Asp Tyr Asp Tyr Trp Gly Gln Gly Thr Thr Leu
            115                 120                 125

Thr Val Ser Ser Ala Lys Thr Thr Ala Pro Ser Val Phe Pro Leu Ala
            130                 135                 140

<210> SEQ ID NO 19
<211> LENGTH: 144
<212> TYPE: PRT
<213> ORGANISM: Mus musculus

<400> SEQUENCE: 19

Met Lys Cys Ser Trp Val Met Phe Leu Val Ser Thr Ala Thr Gly Val
1               5                   10                  15

His Ser Gln Val Gln Leu Gln Gln Pro Gly Ala Glu Leu Val Arg Pro
                20                  25                  30

Gly Thr Ser Val Lys Leu Ser Cys Lys Ala Ser Gly Tyr Thr Phe Thr
            35                  40                  45

Ser Tyr Trp Met His Trp Val Lys Gln Arg Pro Gly Gln Gly Leu Glu
50                  55                  60

Trp Ile Gly Val Ile Asp Pro Ser Asp Ser Tyr Thr Asn Tyr Asn Gln
65                  70                  75                  80

```
Asn Phe Lys Gly Lys Ala Ser Leu Thr Val Asp Ser Ser Ser Thr
                85                  90                  95

Ala Tyr Met Gln Leu Ser Ser Leu Thr Ser Glu Asp Ser Ala Val Tyr
            100                 105                 110

Tyr Cys Ala Arg Asp Asp Tyr Asp Tyr Trp Gly Gln Gly Thr Thr Leu
            115                 120                 125

Thr Val Ser Ser Ala Lys Thr Thr Ala Pro Ser Val Phe Pro Leu Ala
130                 135                 140
```

<210> SEQ ID NO 20
<211> LENGTH: 114
<212> TYPE: PRT
<213> ORGANISM: Mus musculus

<400> SEQUENCE: 20

```
Gln Val Gln Leu Gln Gln Pro Gly Ala Glu Leu Val Arg Pro Gly Thr
1               5                   10                  15

Ser Val Lys Leu Ser Cys Lys Ala Ser Gly Tyr Thr Phe Thr Ser Tyr
                20                  25                  30

Trp Met His Trp Val Lys Gln Arg Pro Gly Gln Gly Leu Glu Trp Ile
            35                  40                  45

Gly Val Ile Asp Pro Ser Asp Ser Tyr Thr Asn Tyr Asn Gln Asn Phe
        50                  55                  60

Lys Gly Lys Ala Ser Leu Thr Val Asp Thr Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Asp Asp Tyr Asp Tyr Trp Gly Gln Gly Thr Thr Leu Thr Val
            100                 105                 110

Ser Ser
```

<210> SEQ ID NO 21
<211> LENGTH: 114
<212> TYPE: PRT
<213> ORGANISM: Mus musculus

<400> SEQUENCE: 21

```
Gln Val Gln Leu Gln Gln Pro Gly Ala Glu Leu Val Arg Pro Gly Thr
1               5                   10                  15

Ser Val Lys Leu Ser Cys Lys Ala Ser Gly Tyr Thr Phe Thr Ser Tyr
                20                  25                  30

Trp Met His Trp Val Lys Gln Arg Pro Gly Gln Gly Leu Glu Trp Ile
            35                  40                  45

Gly Val Ile Asp Pro Ser Asp Ser Tyr Thr Asn Tyr Asn Gln Asn Phe
        50                  55                  60

Lys Gly Lys Ala Ser Leu Thr Val Asp Thr Ser Ser Gly Thr Ala Tyr
65                  70                  75                  80

Met Gln Leu Ser Ser Leu Thr Ser Glu Asp Ser Ala Val Tyr Tyr Cys
                85                  90                  95

Ala Arg Asp Asp Tyr Asp Tyr Trp Gly Gln Gly Thr Thr Leu Thr Val
            100                 105                 110

Ser Ser
```

<210> SEQ ID NO 22
<211> LENGTH: 114
<212> TYPE: PRT

<213> ORGANISM: Mus musculus

<400> SEQUENCE: 22

Gln Val Gln Leu Gln Gln Pro Gly Ala Glu Pro Val Arg Pro Gly Thr
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Val Ile Asp Pro Ser Asp Ser Tyr Thr Asn Tyr Asn Gln Asn Phe
    50                  55                  60

Lys Gly Lys Ala Ser Leu Thr Val Asp Thr Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Asp Asp Tyr Asp Tyr Trp Gly Gln Gly Thr Thr Leu Thr Val
                100                 105                 110

Ser Ser

<210> SEQ ID NO 23
<211> LENGTH: 114
<212> TYPE: PRT
<213> ORGANISM: Mus musculus

<400> SEQUENCE: 23

Gln Val Gln Leu Gln Gln Pro Gly Ala Glu Leu Val Arg Pro Gly Thr
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Val Ile Asp Pro Ser Asp Ser Tyr Thr Asn Tyr Asn Gln Asn Phe
    50                  55                  60

Lys Gly Lys Ala Ser Leu Thr Val Asp Thr Ser Ser Ser Thr Ala Tyr
65                  70                  75                  80

Met Gln Leu Ser Ser Leu Thr Pro Glu Asp Ser Ala Val Tyr Tyr Cys
                85                  90                  95

Ala Arg Asp Asp Tyr Asp Tyr Trp Gly Gln Gly Thr Thr Leu Thr Val
                100                 105                 110

Ser Ser

<210> SEQ ID NO 24
<211> LENGTH: 114
<212> TYPE: PRT
<213> ORGANISM: Mus musculus

<400> SEQUENCE: 24

Gln Val Gln Leu Gln Gln Pro Gly Ala Glu Leu Val Arg Pro Gly Thr
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Val Ile Asp Pro Ser Asp Ser Tyr Thr Asn Tyr Asn Gln Asn Phe
    50                  55                  60

Lys Gly Lys Ala Ser Leu Thr Val Asp Thr Ser Ser Ser Thr Ala Tyr

```
                        65                  70                  75                  80

Met Gln Leu Ser Ser Leu Thr Ser Glu Asp Ser Ala Val Tyr Tyr Cys
                    85                  90                  95

Ala Arg Gly Asp Tyr Asp Tyr Trp Gly Gln Gly Thr Thr Leu Thr Val
                100                 105                 110

Ser Ser

<210> SEQ ID NO 25
<211> LENGTH: 114
<212> TYPE: PRT
<213> ORGANISM: Mus musculus

<400> SEQUENCE: 25

Gln Val Gln Leu Gln Gln Pro Gly Ala Glu Leu Val Arg Pro Gly Thr
1               5                   10                  15

Ser Val Lys Leu Ser Cys Lys Ala Ser Gly Tyr Thr Phe Thr Ser Tyr
                20                  25                  30

Trp Met His Trp Val Lys Gln Arg Pro Gly Gln Gly Leu Glu Trp Ile
            35                  40                  45

Gly Val Ile Asp Pro Ser Asp Ser Tyr Thr Asn Tyr Asn Gln Asn Phe
        50                  55                  60

Lys Gly Lys Ala Ser Leu Thr Val Asp Thr Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Asp Asp Tyr Asp Tyr Trp Gly Arg Gly Thr Thr Leu Thr Val
                100                 105                 110

Ser Ser

<210> SEQ ID NO 26
<211> LENGTH: 114
<212> TYPE: PRT
<213> ORGANISM: Mus musculus

<400> SEQUENCE: 26

Gln Val Gln Leu Gln Gln Pro Gly Ala Glu Leu Val Arg Pro Gly Thr
1               5                   10                  15

Ser Val Lys Leu Ser Cys Lys Ala Ser Gly Tyr Thr Phe Thr Ser Tyr
                20                  25                  30

Trp Met Arg Trp Val Lys Gln Arg Pro Gly Gln Gly Leu Glu Trp Ile
            35                  40                  45

Gly Val Ile Asp Pro Ser Asp Ser Tyr Thr Asn Tyr Asn Gln Asn Phe
        50                  55                  60

Lys Gly Lys Ala Ser Leu Thr Val Asp Thr Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Asp Asp Tyr Asp Tyr Trp Gly Gln Gly Thr Thr Leu Thr Val
                100                 105                 110

Ser Ser

<210> SEQ ID NO 27
<211> LENGTH: 114
<212> TYPE: PRT
<213> ORGANISM: Mus musculus

<400> SEQUENCE: 27
```

-continued

Gln Val Gln Leu Gln Gln Pro Gly Ala Glu Leu Val Arg Pro Gly Thr
1               5                   10                  15

Ser Val Lys Leu Ser Arg Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Val Ile Asp Pro Ser Asp Ser Tyr Thr Asn Tyr Asn Gln Asn Phe
    50                  55                  60

Lys Gly Lys Ala Ser Leu Thr Val Asp Thr Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Asp Asp Tyr Asp Tyr Trp Gly Gln Gly Thr Thr Leu Thr Val
            100                 105                 110

Ser Ser

<210> SEQ ID NO 28
<211> LENGTH: 8
<212> TYPE: PRT
<213> ORGANISM: Mus musculus

<400> SEQUENCE: 28

Gly Tyr Thr Phe Thr Ser Tyr Trp
1               5

<210> SEQ ID NO 29
<211> LENGTH: 8
<212> TYPE: PRT
<213> ORGANISM: Mus musculus

<400> SEQUENCE: 29

Ile Asp Pro Ser Asp Ser Tyr Thr
1               5

<210> SEQ ID NO 30
<211> LENGTH: 7
<212> TYPE: PRT
<213> ORGANISM: Mus musculus

<400> SEQUENCE: 30

Ala Arg Asp Asp Tyr Asp Tyr
1               5

<210> SEQ ID NO 31
<211> LENGTH: 163
<212> TYPE: PRT
<213> ORGANISM: Mus musculus

<400> SEQUENCE: 31

Met Val Leu Ile Leu Leu Leu Trp Val Ser Gly Ala Cys Ala Asp
1               5                   10                  15

Ile Val Met Thr Gln Ser Pro Ser Phe Leu Ala Met Ser Val Gly Gln
            20                  25                  30

Arg Val Thr Met Ser Cys Lys Ser Ser Gln Ser Leu Leu Lys Ser Ser
            35                  40                  45

Asn Gln Lys Asn Tyr Leu Ala Trp Tyr Gln Gln Lys Pro Gly Gln Ser
        50                  55                  60

Pro Lys Leu Leu Val Tyr Phe Ala Ser Thr Arg Glu Ser Gly Val Pro
65                  70                  75                  80

Asp Arg Phe Ile Gly Ser Gly Ser Gly Thr Asp Phe Thr Leu Thr Ile
            85                  90                  95

Asn Asn Val Gln Ala Glu Asp Leu Ala Asp Tyr Phe Cys Gln Gln His
            100                 105                 110

Tyr Ser Thr Pro Leu Thr Phe Gly Ala Gly Thr Lys Leu Glu Leu Lys
            115                 120                 125

Arg Ala Asp Ala Ala Pro Thr Val Ser Ile Phe Pro Pro Ser Ser Glu
            130                 135                 140

Gln Leu Thr Ser Gly Gly Ala Ser Val Val Cys Phe Leu Asn Asn Phe
145                 150                 155                 160

Tyr Pro Lys

<210> SEQ ID NO 32
<211> LENGTH: 172
<212> TYPE: PRT
<213> ORGANISM: Mus musculus

<400> SEQUENCE: 32

Met Gly Ile Lys Met Glu Ser Gln Ser Gln Val Leu Met Phe Leu Leu
1               5                   10                  15

Leu Trp Val Ser Gly Ala Cys Ala Asp Ile Val Met Thr Gln Ser Pro
            20                  25                  30

Ser Phe Leu Ala Met Ser Val Gly Gln Arg Val Thr Met Ser Cys Lys
            35                  40                  45

Ser Ser Gln Ser Leu Leu Lys Ser Ser Asn Gln Lys Asn Tyr Leu Ala
            50                  55                  60

Trp Tyr Gln Gln Lys Pro Gly Gln Ser Pro Lys Leu Leu Val Tyr Phe
65                  70                  75                  80

Ala Ser Thr Arg Glu Ser Gly Val Pro Asp Arg Phe Ile Gly Ser Gly
            85                  90                  95

Ser Gly Thr Asp Phe Thr Leu Thr Ile Asn Asn Val Gln Ala Glu Asp
            100                 105                 110

Leu Ala Asp Tyr Phe Cys Gln Gln His Tyr Ser Thr Pro Leu Thr Phe
            115                 120                 125

Gly Ala Gly Thr Lys Leu Glu Leu Lys Arg Ala Asp Ala Ala Pro Thr
            130                 135                 140

Val Ser Ile Phe Pro Pro Ser Glu Gln Leu Thr Ser Gly Gly Ala
145                 150                 155                 160

Ser Val Val Cys Phe Leu Asn Asn Phe Tyr Pro Lys
                165                 170

<210> SEQ ID NO 33
<211> LENGTH: 163
<212> TYPE: PRT
<213> ORGANISM: Mus musculus

<400> SEQUENCE: 33

Met Val Leu Met Ser Leu Leu Phe Trp Val Ser Gly Ala Cys Ala Asp
1               5                   10                  15

Ile Val Met Thr Gln Ser Pro Ser Phe Leu Ala Met Ser Val Gly Gln
            20                  25                  30

Arg Val Thr Met Ser Cys Lys Ser Ser Gln Ser Leu Leu Lys Ser Ser
            35                  40                  45

Asn Gln Lys Asn Tyr Leu Ala Trp Tyr Gln Gln Lys Pro Gly Gln Ser
            50                  55                  60

-continued

```
Pro Lys Leu Leu Val Tyr Phe Ala Ser Thr Arg Glu Ser Gly Val Pro
 65                  70                  75                  80

Asp Arg Phe Ile Gly Ser Gly Ser Gly Thr Asp Phe Thr Leu Thr Ile
                 85                  90                  95

Asn Asn Val Gln Ala Glu Asp Leu Ala Asp Tyr Phe Cys Gln Gln His
            100                 105                 110

Tyr Ser Thr Pro Leu Thr Phe Gly Ala Gly Thr Lys Leu Glu Leu Lys
        115                 120                 125

Arg Ala Asp Ala Ala Pro Thr Val Ser Ile Phe Pro Pro Ser Ser Glu
    130                 135                 140

Gln Leu Thr Ser Gly Gly Ala Ser Val Val Cys Phe Leu Asn Asn Phe
145                 150                 155                 160

Tyr Pro Lys

<210> SEQ ID NO 34
<211> LENGTH: 163
<212> TYPE: PRT
<213> ORGANISM: Mus musculus

<400> SEQUENCE: 34

Met Val Leu Met Leu Leu Leu Trp Val Ser Gly Ala Cys Ala Asp
 1               5                  10                  15

Ile Val Met Thr Gln Ser Pro Ser Phe Leu Ala Met Ser Val Gly Gln
                20                  25                  30

Arg Val Thr Met Ser Cys Lys Ser Ser Gln Ser Leu Leu Lys Ser Ser
            35                  40                  45

Asn Gln Lys Asn Tyr Leu Ala Trp Tyr Gln Gln Lys Pro Gly Gln Ser
 50                  55                  60

Pro Lys Leu Leu Val Tyr Phe Ala Ser Thr Arg Glu Ser Gly Val Pro
 65                  70                  75                  80

Asp Arg Phe Ile Gly Ser Gly Ser Gly Thr Asp Phe Thr Leu Thr Ile
                 85                  90                  95

Asn Asn Val Gln Ala Glu Asp Leu Ala Asp Tyr Phe Cys Gln Gln His
            100                 105                 110

Tyr Ser Thr Pro Leu Thr Phe Gly Ala Gly Thr Lys Leu Glu Leu Lys
        115                 120                 125

Arg Ala Asp Ala Ala Pro Thr Val Ser Ile Phe Pro Pro Ser Ser Glu
    130                 135                 140

Gln Leu Thr Ser Gly Gly Ala Ser Val Val Cys Phe Leu Asn Asn Phe
145                 150                 155                 160

Tyr Pro Arg

<210> SEQ ID NO 35
<211> LENGTH: 163
<212> TYPE: PRT
<213> ORGANISM: Mus musculus

<400> SEQUENCE: 35

Met Val Leu Met Leu Leu Leu Trp Val Ser Gly Ala Cys Ala Asp
 1               5                  10                  15

Ile Val Met Thr Gln Ser Pro Ser Phe Leu Ala Met Ser Val Gly Gln
                20                  25                  30

Arg Val Thr Met Ser Cys Lys Ser Ser Gln Ser Leu Leu Lys Ser Ser
            35                  40                  45

Asn Gln Lys Asn Tyr Leu Ala Trp Tyr Gln Gln Lys Pro Gly Gln Ser
 50                  55                  60
```

```
Pro Lys Leu Leu Val Tyr Phe Ala Ser Thr Arg Glu Ser Gly Val Pro
 65                  70                  75                  80

Asp Arg Phe Ile Gly Ser Gly Ser Gly Thr Asp Phe Thr Leu Thr Ile
                 85                  90                  95

Asn Asn Val Gln Thr Glu Asp Leu Ala Asp Tyr Phe Cys Gln Gln His
            100                 105                 110

Tyr Ser Thr Pro Leu Thr Phe Gly Ala Gly Thr Lys Leu Glu Leu Lys
        115                 120                 125

Arg Ala Asp Ala Ala Pro Thr Val Ser Ile Phe Pro Pro Ser Ser Glu
    130                 135                 140

Gln Leu Thr Ser Gly Gly Ala Ser Val Val Cys Phe Leu Asn Asn Phe
145                 150                 155                 160

Tyr Pro Lys

<210> SEQ ID NO 36
<211> LENGTH: 163
<212> TYPE: PRT
<213> ORGANISM: Mus musculus

<400> SEQUENCE: 36

Met Val Leu Ile Leu Leu Leu Trp Val Ser Gly Ala Cys Ala Asp
  1               5                  10                  15

Ile Val Met Thr Gln Ser Pro Ser Phe Leu Ala Met Ser Val Gly Gln
                 20                  25                  30

Arg Val Thr Met Ser Cys Lys Ser Ser Gln Ser Leu Leu Lys Ser Ser
             35                  40                  45

Asn Gln Lys Asn Tyr Leu Ala Trp Tyr Gln Gln Lys Pro Gly Gln Ser
 50                  55                  60

Pro Lys Leu Leu Val Tyr Phe Ala Ser Thr Arg Glu Ser Gly Val Pro
 65                  70                  75                  80

Asp Arg Phe Ile Gly Ser Gly Ser Gly Thr Asp Phe Thr Leu Thr Ile
                 85                  90                  95

Asn Asn Val Gln Ala Glu Asp Leu Ala Asp Tyr Phe Cys Gln Gln His
            100                 105                 110

Tyr Ser Thr Pro Leu Thr Phe Gly Ala Gly Thr Lys Leu Glu Leu Lys
        115                 120                 125

Arg Ala Asp Ala Ala Pro Thr Val Ser Ile Phe Pro Pro Ser Ser Glu
    130                 135                 140

Gln Leu Thr Ser Gly Gly Ala Ser Val Val Cys Phe Leu Asn Asn Phe
145                 150                 155                 160

Tyr Pro Arg

<210> SEQ ID NO 37
<211> LENGTH: 163
<212> TYPE: PRT
<213> ORGANISM: Mus musculus

<400> SEQUENCE: 37

Met Val Leu Met Leu Leu Leu Trp Val Ser Gly Ala Cys Ala Asp
  1               5                  10                  15

Ile Val Met Thr Gln Ser Pro Ser Phe Leu Ala Met Ser Val Gly Gln
                 20                  25                  30

Arg Val Thr Met Ser Cys Lys Ser Ser Gln Ser Leu Leu Lys Ser Ser
             35                  40                  45

Asn Gln Lys Asn Tyr Leu Ala Trp Tyr Gln Gln Lys Pro Gly Gln Ser
```

```
                50                  55                  60
Pro Lys Leu Leu Val Tyr Phe Ala Ser Thr Arg Glu Ser Gly Val Pro
 65                  70                  75                  80

Asp Arg Phe Ile Gly Ser Gly Ser Gly Thr Asp Phe Thr Leu Thr Ile
                 85                  90                  95

Asn Asn Val Gln Ala Glu Asp Leu Ala Asp Tyr Phe Cys Gln Gln His
                100                 105                 110

Tyr Ser Thr Pro Leu Thr Phe Gly Ala Gly Thr Lys Leu Glu Leu Lys
            115                 120                 125

Arg Ala Asp Ala Ala Pro Thr Val Ser Ile Phe Pro Pro Ser Ser Glu
        130                 135                 140

Gln Leu Thr Ser Gly Gly Val Ser Val Val Cys Phe Leu Asn Asn Phe
145                 150                 155                 160

Tyr Pro Arg

<210> SEQ ID NO 38
<211> LENGTH: 163
<212> TYPE: PRT
<213> ORGANISM: Mus musculus

<400> SEQUENCE: 38

Met Val Leu Met Leu Leu Leu Trp Val Ser Gly Ala Cys Ala Asp
  1               5                  10                  15

Ile Val Met Thr Gln Ser Pro Ser Phe Leu Ala Met Ser Val Gly Gln
                 20                  25                  30

Arg Val Thr Met Ser Cys Lys Ser Ser Gln Ser Leu Leu Lys Ser Ser
             35                  40                  45

Asn Gln Lys Asn Tyr Leu Ala Trp Tyr Gln Lys Pro Gly Gln Ser
 50                  55                  60

Pro Lys Leu Leu Val Tyr Phe Ala Ser Thr Arg Glu Ser Gly Val Pro
 65                  70                  75                  80

Asp Arg Phe Ile Gly Ser Gly Ser Gly Thr Asp Phe Thr Leu Thr Ile
                 85                  90                  95

Asn Asn Val Gln Ala Glu Asp Leu Ala Asp Tyr Phe Cys Gln Gln His
                100                 105                 110

Tyr Ser Thr Pro Leu Thr Phe Gly Ala Gly Thr Lys Leu Glu Leu Lys
            115                 120                 125

Arg Ala Asp Ala Ala Pro Thr Val Ser Ile Phe Pro Pro Ser Ser Glu
        130                 135                 140

Gln Leu Thr Ser Gly Gly Ala Ser Val Val Cys Phe Leu Asn Asn Phe
145                 150                 155                 160

Tyr Pro Lys

<210> SEQ ID NO 39
<211> LENGTH: 163
<212> TYPE: PRT
<213> ORGANISM: Mus musculus

<400> SEQUENCE: 39

Met Val Leu Met Leu Leu Leu Trp Val Ser Gly Ala Cys Ala Gly
  1               5                  10                  15

Ile Val Met Thr Gln Ser Pro Ser Phe Leu Ala Met Ser Val Gly Gln
                 20                  25                  30

Arg Val Thr Met Ser Cys Lys Ser Ser Gln Ser Leu Leu Lys Ser Ser
             35                  40                  45
```

```
Asn Gln Lys Asn Tyr Leu Ala Trp Tyr Gln Gln Lys Pro Gly Gln Ser
 50                  55                  60

Pro Lys Leu Leu Val Tyr Phe Ala Ser Thr Arg Glu Ser Gly Val Pro
 65                  70                  75                  80

Asp Arg Phe Ile Gly Ser Gly Ser Gly Thr Asp Phe Thr Leu Thr Ile
                 85                  90                  95

Asn Asn Val Gln Ala Glu Asp Leu Ala Asp Tyr Phe Cys Gln Gln His
            100                 105                 110

Tyr Ser Thr Pro Leu Thr Phe Gly Ala Gly Thr Lys Leu Glu Leu Lys
            115                 120                 125

Arg Ala Asp Ala Ala Pro Thr Val Ser Ile Phe Pro Pro Ser Ser Glu
130                 135                 140

Gln Leu Thr Ser Gly Gly Ala Ser Val Val Cys Phe Leu Asn Asn Phe
145                 150                 155                 160

Tyr Pro Arg

<210> SEQ ID NO 40
<211> LENGTH: 113
<212> TYPE: PRT
<213> ORGANISM: Mus musculus

<400> SEQUENCE: 40

Asp Ile Val Met Thr Gln Ser Pro Ser Phe Leu Ala Met Ser Val Gly
 1                   5                  10                  15

Gln Arg Val Thr Met Ser Cys Lys Ser Ser Gln Ser Leu Leu Lys Ser
                 20                  25                  30

Ser Asn Gln Lys Asn Tyr Leu Ala Trp Tyr Gln Gln Lys Pro Gly Gln
             35                  40                  45

Ser Pro Lys Leu Leu Val Tyr Phe Ala Ser Thr Arg Glu Ser Gly Val
         50                  55                  60

Pro Asp Arg Phe Ile Gly Ser Gly Ser Gly Thr Asp Phe Thr Leu Thr
 65                  70                  75                  80

Ile Asn Asn Val Gln Ala Glu Asp Leu Ala Asp Tyr Phe Cys Gln Gln
                 85                  90                  95

His Tyr Ser Thr Pro Leu Thr Phe Gly Ala Gly Thr Lys Leu Glu Leu
            100                 105                 110

Lys

<210> SEQ ID NO 41
<211> LENGTH: 113
<212> TYPE: PRT
<213> ORGANISM: Mus musculus

<400> SEQUENCE: 41

Asp Ile Val Met Thr Gln Ser Pro Ser Phe Leu Ala Met Ser Val Gly
 1                   5                  10                  15

Gln Arg Val Thr Met Ser Cys Lys Ser Ser Gln Ser Leu Leu Lys Ser
                 20                  25                  30

Ser Asn Gln Lys Asn Tyr Leu Ala Trp Tyr Gln Gln Lys Pro Gly Gln
             35                  40                  45

Ser Pro Lys Leu Leu Val Tyr Phe Ala Ser Thr Arg Glu Ser Gly Val
         50                  55                  60

Pro Asp Arg Phe Ile Gly Ser Gly Ser Gly Thr Asp Phe Thr Leu Thr
 65                  70                  75                  80

Ile Asn Asn Val Gln Thr Glu Asp Leu Ala Asp Tyr Phe Cys Gln Gln
                 85                  90                  95
```

```
His Tyr Ser Thr Pro Leu Thr Phe Gly Ala Gly Thr Lys Leu Glu Leu
            100                 105                 110
Lys

<210> SEQ ID NO 42
<211> LENGTH: 113
<212> TYPE: PRT
<213> ORGANISM: Mus musculus

<400> SEQUENCE: 42

Gly Ile Val Met Thr Gln Ser Pro Ser Phe Leu Ala Met Ser Val Gly
1               5                   10                  15

Gln Arg Val Thr Met Ser Cys Lys Ser Ser Gln Ser Leu Leu Lys Ser
            20                  25                  30

Ser Asn Gln Lys Asn Tyr Leu Ala Trp Tyr Gln Lys Pro Gly Gln
        35                  40                  45

Ser Pro Lys Leu Leu Val Tyr Phe Ala Ser Thr Arg Glu Ser Gly Val
    50                  55                  60

Pro Asp Arg Phe Ile Gly Ser Gly Ser Gly Thr Asp Phe Thr Leu Thr
65                  70                  75                  80

Ile Asn Asn Val Gln Ala Glu Asp Leu Ala Asp Tyr Phe Cys Gln Gln
                85                  90                  95

His Tyr Ser Thr Pro Leu Thr Phe Gly Ala Gly Thr Lys Leu Glu Leu
            100                 105                 110

Lys

<210> SEQ ID NO 43
<211> LENGTH: 12
<212> TYPE: PRT
<213> ORGANISM: Mus musculus

<400> SEQUENCE: 43

Gln Ser Leu Leu Lys Ser Ser Asn Gln Lys Asn Tyr
1               5                   10

<210> SEQ ID NO 44
<211> LENGTH: 3
<212> TYPE: PRT
<213> ORGANISM: Mus musculus

<400> SEQUENCE: 44

Phe Ala Ser
1

<210> SEQ ID NO 45
<211> LENGTH: 9
<212> TYPE: PRT
<213> ORGANISM: Mus musculus

<400> SEQUENCE: 45

Gln Gln His Tyr Ser Thr Pro Leu Thr
1               5
```

HIV ANTIGENS AND ANTIBODIES AND COMPOSITIONS, USES AND METHODS THEREOF

This application claims the benefit of priority and the filing date of U.S. Provisional Patent Application 61/913,363, filed on Dec. 8, 2013 and U.S. Provisional Patent Application 62/038,824, filed on Aug. 18, 2014, the contents of each of which are hereby incorporated by reference in its entirety.

Human immunodeficiency virus (HIV) is a member of the genus Lentivirus (slowly replicating retrovirus), part of the family Retroviridae. HIV causes acquired immunodeficiency syndrome (AIDS), a condition in humans in which progressive failure of the immune system allows life-threatening opportunistic infections and cancers to thrive. Infection with HIV occurs by the transfer of blood, semen, vaginal fluid, pre-ejaculate, or breast milk. Within these bodily fluids, HIV is present as both free virus particles and virus within infected immune cells.

HIV can infect a variety of immune cells vital in the human immune system such as, e.g., helper T cells (specifically $CD4^+$ T cells), macrophages, dendritic cells, and microglial cells. HIV entry to macrophages and $CD4^+$ T cells is mediated through interaction of the virion envelope glycoproteins (gp120) with the CD4 molecule on the target cells and also with chemokine co-receptors. HIV infection leads to low levels of $CD4^+$ T cells through a number of mechanisms including apoptosis of uninfected bystander cells, direct viral killing of infected cells, and killing of infected $CD4^+$ T cells by CD8 cytotoxic lymphocytes that recognize infected cells. When $CD4^+$ T cell numbers decline below a critical level, cell-mediated immunity is lost, and the body becomes progressively more susceptible to opportunistic infections.

For many years HIV infection was not a condition susceptible of treatment. When the disease was identified in 1981, existing anti-viral therapies were ineffective in controlling the damage that the virus would cause to a patient's immune system. The virus causes direct and indirect destruction of $CD4^+$ T cells, which are essential for a fully functioning immune system. As a patient's CD4+ T cell count diminishes, the disease becomes progressively worse. When the $CD4^+$ T cell count falls below a certain level, the patient is considered to have deteriorated to the point of having full-blown AIDS. Definitions of the point at which this occurs vary, but it is generally considered that it is arrived at in healthy HIV positive people with a $CD4^+$ T cell count of less than 200 per ml of blood. More recently, anti-viral therapies have improved, and the progression of the disease has been slowed considerably. Modern combinatorial therapies may (in some patients) delay the onset of full-blown AIDS indefinitely. However, these therapies are expensive, and place a burden on the patient requiring him or her to take a significant number tablets per day (many patients find it difficult to remember to take the required medicine) and in many cases leading to unpleasant side-effects (unsurprising when taking a cocktail containing many different pharmaceuticals, which has to be taken for life). Not only do current therapies suffer from these problems, but they are not curative, merely delaying onset of full-blown AIDS. Moreover, in recent years there has been increased number of reports indicating the appearance and spread of drug-resistant HIV drugs. Accordingly, there is a real and urgent need for a vaccine which could prevent and/or cure immunodeficiency viruses, such as HIV, and also prevent and/or cure AIDS.

Previously, attempts to develop HIV vaccines have been made by identifying an existing HIV strain and then producing a vaccine specific to that virus. Generally, vaccines have been based upon a B cell (antibody) response, the antibody being reactive with the surface antigens of the specific HIV strain against which it has been developed. Typically, the surface proteins comprising the antigens are variable from one HIV strain to the next, since mutation of the virus to produce a new virus tends to occur in the surface proteins. The consequence of this is that conventional HIV vaccines, if they were functional at all, would generally protect only against one specific virus strain, and not against a new strain that results from a mutation. Thus, a new vaccine would be required for protection against an emerging strain. The period of time between emergence of the new virus strain by mutation is very short. Within an infected individual new strains are arising all the time, as a result of the selective pressure imposed by that individual's immune system. As a result, the viral population found in an infected individual changes with time (over a period of weeks, months and years) without any requirement for re-infection due to the high mutation rate. Thus, the only likely way to target immunodeficiency virus infection in an individual, or to target potential new virus strains that might infect or develop in an individual, is to target a conserved region of the proteome. This approach is inherently problematic, since the dominant immune response to HIV is directed to sections that are themselves under a high rate of mutation, due to (a) immunological pressure and (b) low fidelity rates of the replicative machinery of the virus.

SUMMARY

Thus, aspects disclosed in the present specification provide an HIV antigens. An HIV antigen disclosed herein may trigger an immune response that produce an α-HIV1 antibody capable of binding an epitope present on a HIV virion, an epitope derived from an HIV virus, an epitope produced or altered by an HIV virus, and/or an epitope produced or altered by a cell infected by the HIV virus or expressing either the whole or part of the HIV virus genetic code.

Other aspects disclosed in the present specification provide immunogenic compositions comprising one or more HIV antigens disclosed herein. Compositions can further comprise an adjuvant.

Other aspects disclosed in the present specification provide methods of producing α-HIV1 antibodies using one or more HIV antigens disclosed herein and/or one or more immunogenic compositions disclosed herein. Aspects of this method may comprise the steps of (a) administering to an animal an immunogenic composition disclosed in the present specification; (b) collecting from the animal a sample containing an α-HIV antibody or an α-HIV antibody-producing cell; and (c) isolating the α-HIV antibody from the sample. The methods disclosed are useful for making either α-HIV monoclonal antibodies or α-HIV polyclonal antibodies.

Other aspects disclosed in the present specification provide α-HIV antibodies. α-HIV antibodies disclosed herein are capable of binding an epitope present on a HIV virion. Such α-HIV antibodies include both naturally-occurring and non-naturally-occurring antibodies, as well as, monoclonal α-HIV antibodies or polyclonal α-HIV antibodies.

Other aspect disclosed in the present specification provide methods of detecting a HIV infection. Aspects of this method may comprise the steps of (a) contacting a sample with an α-HIV antibody disclosed herein; and (b) detecting for the presence or absence of an antibody-antigen complex comprising the α-HIV antibody; wherein detection by the antibody-antigen complex is indicative of the presence of the HIV infection. The sample may undergo one or more purification steps before being contacted with an α-HIV antibody of step (a). In addition, the α-HIV antibody of step (c) may optionally be linked to a solid phase support. The method may detect a HIV virion, a component derived from an HIV virus, a component produced or altered by an HIV virus, and/or a component produced or altered by a cell infected by the HIV virus or expressing either the whole or part of the HIV virus genetic code.

Other aspects disclosed in the present specification provide methods of treating an individual infected with an HIV virus or having a HIV-based disease.

Other aspects disclosed in the present specification provide use of α-HIV antibody disclosed herein for the manufacture of a medicament.

Other aspects disclosed in the present specification provide use of an α-HIV antibody disclosed herein for treatment of an individual infected with an HIV virus.

BRIEF DESCRIPTION OF THE DRAWINGS

FIGS. 1A-D show results of HIV peptides antibody immunogenicity. FIG. 1A shows total Ig responses to the VIF peptide; FIG. 1B shows total Ig Responses to the NEF peptide; FIG. 1C shows IgG2c responses to the VIF and NEF peptides; and FIG. 1D shows IgG1 responses to the VIF and NEF peptides.

FIG. 3A shows FACs data from cells uninfected with HIV not treated with mouse serum; FIG. 3B shows FACs data from cells uninfected with HIV treated with post-vaccination mouse serum; FIG. 3C shows FACs data from HIV infected cells and treated with mouse serum; FIG. 3D shows FACs data from HIV infected cells and isotype controls; FIG. 3E shows FACs data from HIV infected cells treated with pre-vaccination mouse serum; and FIG. 3F shows FACs data from HIV infected cells treated with post-vaccination mouse serum.

FIG. 5A shows results from placebo animals; FIG. 5B shows results from HAD animals.

FIG. 6A shows HIV-v serum dilution against VPR peptide; FIG. 6B shows HIV-v serum dilution against VIF peptide; FIG. 6C shows HIV-v serum dilution against REV peptide; FIG. 6D shows HIV-v serum dilution against NEF peptide; FIG. 6E shows IgGc and IgG1 responses to the VIF peptide; and FIG. 6F shows IgGc and IgG1 responses to the VIF peptide.

DETAILED DESCRIPTION

Figure 2:
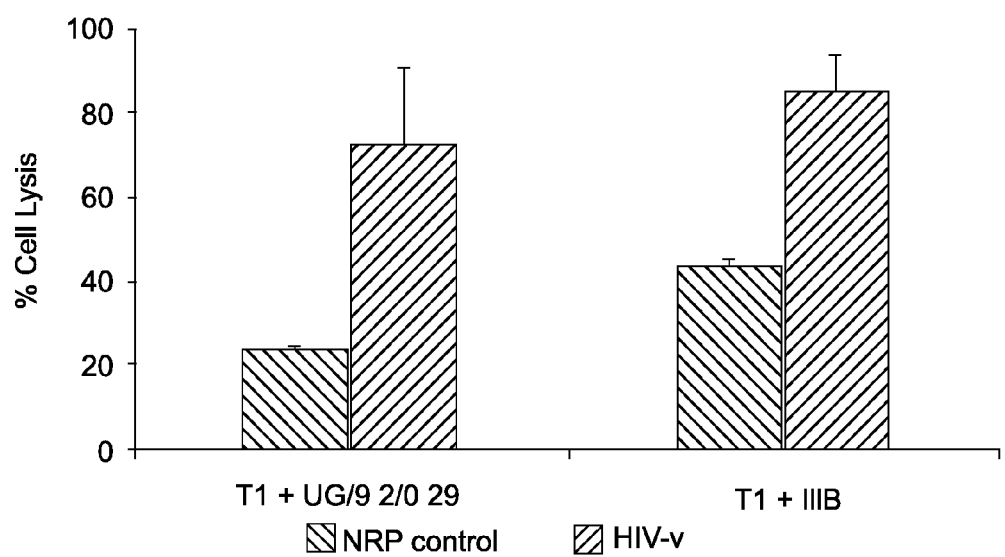
FIG. 2 shows polyclonal response to HIV-v.

Two types of HIV have been characterized: HIV-1 and HIV-2. HIV-1 is the virus that was initially discovered and termed both LAV and HTLV-III. It is more virulent, more infective, and is the cause of the majority of HIV infections globally. HIV-2 is much less pathogenic than HIV and because of its relatively poor capacity for transmission, HIV-2 is largely restricted to West Africa.

A HIV virion is roughly spherical viral particle having a diameter of about 120 nm. It is composed of two copies of positive single-stranded RNA enclosed by a conical capsid composed of 2,000 copies of the viral protein p24. The single-stranded RNA is tightly bound to nucleocapsid proteins, p7, and enzymes needed for the development of the virion such as reverse transcriptase, proteases, ribonuclease and integrase. A matrix composed of the viral protein p17 surrounds the capsid ensuring the integrity of the virion. The RNA genome consists of at least seven structural landmarks (LTR, TAR, RRE, PE, SLIP, CRS, and INS), and nine genes (gag, pol, and env, tat, rev, nef, vif, vpr, vpu, and sometimes a tenth tev, which is a fusion of tat env and rev), encoding 19 proteins. Three of these genes, gag, pol, and env, contain information needed to make the structural proteins for new virus particles. For example, env codes for a protein called gp160 that is broken down by a cellular protease to form gp120 and gp41. The six remaining genes, tat, rev, nef, vif, vpr, and vpu (or vpx in the case of HIV-2), are regulatory genes for proteins that control the ability of HIV to infect cells, produce new copies of virus (replicate), or cause disease.

Aspects of the present disclosure comprise, in part, a HIV antigen. An antigen is a molecule that elicits an immune response and includes, without limitation, peptides, polysaccharides and conjugates of lipids, such as, e.g., lipoproteins and glycolipids. An HIV antigen is any antigen, either directly derived and/or isolated from the HIV virus or expressed from the whole or a part of the HIV virus genetic code in any organism, that can elicit an immune response against a HIV virion, a component derived from an HIV virus, or a component produced or altered by an HIV virus or a cell infected by the HIV virus or expressing either the whole or part of the HIV virus genetic code. A component comprising an HIV virion includes, without limitation, the RNA genome of HIV, and any of the 19 proteins encoded by the RNA genome of HIV, and lipid membrane components of the HIV virion.

A HIV antigen must be large enough to be substantially unique in sequence, thus reducing the possibility of producing antibodies that are cross reactive against antigens other than a HIV antigen disclosed herein. Typically, a HIV antigen disclosed herein has a length of about 5 to about 100 amino acids.

In aspects of this embodiment, a HIV antigen disclosed herein may have a length of, e.g., about 5, about 6, about 7, about 8, about 9, about 10, about 11, about 12, about 13, about 14, about 15, about 16, about 17, about 18, about 19, about 20, about 25, about 30, about 35, about 40, about 45, about 50, about 55, about 60, about 65, about 70, or about 75 amino acids. In other aspects of this embodiment, a HIV antigen disclosed herein may have a length of, e.g., at least 5, at least 6, at least 7, at least 8, at least 9, at least 10, at least 11, at least 12, at least 13, at least 14, at least 15, at least 16, at least 17, at least 18, at least 19, at least 20, at least 25, at least 30, at least 35, at least 40, at least 45, at least 50, at least 55, at least 60, at least 65, at least 70, or at least 75 amino acids. In yet other aspects of this embodiment, a HIV antigen disclosed herein may have a length of, e.g., at most 5, at most 6, at most 7, at most 8, at most 9, at most 10, at most 11, at most 12, at most 13, at most 14, at most 15, at most 16, at most 17, at most 18, at most 19, at most 20, at most 25, at most 30, at most 35, at most 40, at most 45, at most 50, at most 55, at most 60, at most 65, at most 70, or at most 75 amino acids.

In still other aspects of this embodiment, a HIV antigen disclosed herein may have a length of, e.g., between about 7 to about 10 amino acids, about 7 to about 12 amino acids, about 7 to about 15 amino acids, about 7 to about 18 amino acids, about 7 to about 20 amino acids, about 7 to about 25 amino acids, about 7 to about 30 amino acids, about 7 to about 35 amino acids, about 7 to about 40 amino acids, about 7 to about 45 amino acids, about 7 to about 50 amino acids, about 7 to about 55 amino acids, about 7 to about 60 amino acids, about 7 to about 65 amino acids, about 7 to about 70 amino acids, about 7 to about 75 amino acids, about 10 to about 12 amino acids, about 10 to about 15 amino acids, about 10 to about 18 amino acids, about 10 to about 20 amino acids, about 10 to about 25 amino acids, about 10 to about 30 amino acids, about 10 to about 35 amino acids, about 10 to about 40 amino acids, about 10 to about 45 amino acids, about 10 to about 50 amino acids, about 10 to about 55 amino acids, about 10 to about 60 amino acids, about 10 to about 65 amino acids, about 10 to about 70 amino acids, about 10 to about 75 amino acids, about 12 to about 15 amino acids, about 12 to about 18 amino acids, about 12 to about 20 amino acids, about 12 to about 25 amino acids, about 12 to about 30 amino acids, about 12 to about 35 amino acids, about 12 to about 40 amino acids, about 12 to about 45 amino acids, about 12 to about 50 amino acids, about 12 to about 55 amino acids, about 12 to about 60 amino acids, about 12 to about 65 amino acids, about 12 to about 70 amino acids, about 12 to about 75 amino acids, about 15 to about 18 amino acids, about 15 to about 20 amino acids, about 15 to about 25 amino acids, about 15 to about 30 amino acids, about 15 to about 35 amino acids, about 15 to about 40 amino acids, about 15 to about 45 amino acids, about 15 to about 50 amino acids, about 15 to about 55 amino acids, about 15 to about 60 amino acids, about 15 to about 65 amino acids, about 15 to about 70 amino acids, about 15 to about 75 amino acids, about 18 to about 20 amino acids, about 18 to about 25 amino acids, about 18 to about 30 amino acids, about 18 to about 35 amino acids, about 18 to about 40 amino acids, about 18 to about 45 amino acids, about 18 to about 50 amino acids, about 18 to about 55 amino acids, about 18 to about 60 amino acids, about 18 to about 65 amino acids, about 18 to about 70 amino acids, about 18 to about 75 amino acids, about 20 to about 25 amino acids, about 20 to about 30 amino acids, about 20 to about 35 amino acids, about 20 to about 40 amino acids, about 20 to about 45 amino acids, about 20 to about 50 amino acids, about 20 to about 55 amino acids, about 20 to about 60 amino acids, about 20 to about 65 amino acids, about 20 to about 70 amino acids, about 20 to about 75 amino acids, about 25 to about 30 amino acids, about 25 to about 35 amino acids, about 25 to about 40 amino acids, about 25 to about 45 amino acids, about 25 to about 50 amino acids, about 25 to about 55 amino acids, about 25 to about 60 amino acids, about 25 to about 65 amino acids, about 25 to about 70 amino acids, about 25 to about 75 amino acids, about 30 to about 35 amino acids, about 30 to about 40 amino acids, about 30 to about 45 amino acids, about 30 to about 50 amino acids, about 30 to about 55 amino acids, about 30 to about 60 amino acids, about 30 to about 65 amino acids, about 30 to about 70 amino acids, about 30 to about 75 amino acids, about 35 to about 40 amino acids, about 35 to about 45 amino acids, about 35 to about 50 amino acids, about 35 to about 55 amino acids, about 35 to about 60 amino acids, about 35 to about 65 amino acids, about 35 to about 70 amino acids, about 35 to about 75 amino acids, about 40 to about 45 amino acids, about 40 to about 50 amino acids, about 40 to about 55 amino acids, about 40 to about 60 amino acids, about 40 to about 65 amino acids, about 40 to about 70 amino acids, about 40 to about 75 amino acids, about 45 to about 50 amino acids, about 45 to about 55 amino acids, about 45 to about 60 amino acids, about 45 to about 65 amino acids, about 45 to about 70 amino acids, about 45 to about 75 amino acids, about 50 to about 55 amino acids, about 50 to about 60 amino acids, about 50 to about 65 amino acids, about 50 to about 70 amino acids, or about 50 to about 75 amino acids.

In another embodiment, a HIV antigen disclosed herein comprises SEQ ID NO: 1, SEQ ID NO: 2, SEQ ID NO: 3, or SEQ ID NO: 4. In aspects of this embodiment, a HIV antigen disclosed herein has an amino acid identity of, e.g., at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, to SEQ ID NO: 1, SEQ ID NO: 2, SEQ ID NO: 3, or SEQ ID NO: 4. In yet other aspects of this embodiment, a HIV antigen disclosed herein has an amino acid identity in the range of, e.g., about 75% to about 100%, about 80% to about 100%, about 85% to about 100%, about 90% to about 100%, about 95% to about 100%, about 75% to about 99%, about 80% to about 99%, about 85% to about 99%, about 90% to about 99%, about 95% to about 99%, about 75% to about 97%, about 80% to about 97%, about 85% to about 97%, about 90% to about 97%, or about 95% to about 97%, to SEQ ID NO: 1, SEQ ID NO: 2, SEQ ID NO: 3, or SEQ ID NO: 4.

In other aspects of this embodiment, a HIV antigen disclosed herein comprises an amino acid sequence having a length of, e.g., at least 5 amino acids, at least 6 amino acids, at least 7 amino acids, at least 8 amino acids, at least 9 amino acids, at least 10 amino acids, at least 11 amino acids, at least 12 amino acids, at least 13 amino acids, at least 14 amino acids, at least 15 amino acids, at least 16 amino acids, at least 17 amino acids, at least 18 amino acids, at least 19 amino acids, at least 20 amino acids, at least 21 amino acids, at least 22 amino acids, at least 23 amino acids, at least 24 amino acids, or at least 25 amino acids, the amino acid sequence being taken from a contiguous amino acid subsequence of SEQ ID NO: 1, SEQ ID NO: 2, SEQ ID NO: 3, or SEQ ID NO: 4. In yet other aspects of this embodiment, a HIV antigen disclosed herein comprises an amino acid sequence having a length of, e.g., at most 5 amino acids, at most 6 amino acids, at most 7 amino acids, at most 8 amino acids, at most 9 amino acids, at most 10 amino acids, at most 11 amino acids, at most 12 amino acids, at most 13 amino acids, at most 14 amino acids, at most 15 amino acids, at most 16 amino acids, at most 17 amino acids, at most 18 amino acids, at most 19 amino acids, at most 20 amino acids, at most 21 amino acids, at most 22 amino acids, at most 23 amino acids, at most 24 amino acids, or at most 25 amino acids, the amino acid sequence being taken from a contiguous amino acid subsequence of SEQ ID NO: 1, SEQ ID NO: 2, SEQ ID NO: 3, or SEQ ID NO: 4.

In other aspects of this embodiment, a HIV antigen disclosed herein has, e.g., at least 1, 2, 3, 4, 5, 6, 7, 8, 9, 10, 11, 12, 13, 14, or 15 contiguous amino acid deletions, additions, and/or substitutions relative to SEQ ID NO: 1, SEQ ID NO: 2, SEQ ID NO: 3, OR SEQ ID NO: 4; or at most 1, 2, 3, 4, 5, 6, 7, 8, 9, 10, 11, 12, 13, 14, or 15 contiguous amino acid deletions, additions, and/or substitutions relative to SEQ ID NO: 1, SEQ ID NO: 2, SEQ ID NO: 3, OR SEQ ID NO: 4. In yet other aspects of this embodiment, a HIV antigen disclosed herein has, e.g., at least 1, 2, 3, 4, 5, 6, 7, 8, 9, 10, 11, 12, 13, 14, or 15 non-contiguous amino acid deletions, additions, and/or substitutions relative to SEQ ID NO: 1, SEQ ID NO: 2, SEQ ID NO: 3, OR SEQ ID NO: 4; or at most 1, 2, 3, 4, 5, 6, 7, 8, 9, 10, 11, 12, 13, 14, or 15 non-contiguous amino acid deletions, additions, and/or substitutions relative to SEQ ID NO: 1, SEQ ID NO: 2, SEQ ID NO: 3, OR SEQ ID NO: 4.

One or more carriers may be linked to a HIV antigen disclosed herein in order to enhance the immunogenicity of a HIV antigen that is immunogenic, non-immunogenic, or weakly immunogenic when not associated with the carrier. Non-limiting examples, include, e.g., a keyhole limpet hemacyanin (KLH), an ovalbumin (OVA), a thyroglobulin (THY), a bovine serum albumin (BSA), a soybean trypsin inhibitor (STI), or a multiple attachment peptide (MAP). A non-antigenic or weakly antigenic antigen can be made antigenic by coupling the antigen to a carrier. Various other carrier and methods for coupling an antigen to a carrier are described in, e.g., Harlow and Lane, supra, 1998a; Harlow and Lane, supra, 1998b; and David W. Waggoner, Jr. et al., *Immunogenicity-enhancing carriers and compositions thereof and methods of using the same*, U.S. Patent Publication No. 20040057958, each of which is incorporated by reference in its entirety. A HIV antigen disclosed herein may also be generated by expressing the antigen as a fusion protein. Methods for expressing polypeptide fusions are described in, e.g., Ausubel et al., Current Protocols in Molecular Biology (Supplement 47), John Wiley & Sons, New York (1999), each of which is incorporated by reference in its entirety.

Aspects of the present disclosure comprise, in part, an immunogenic composition. An immunogenic composition disclosed herein comprises one or more HIV antigens disclosed herein and optionally one or more adjuvants. An immunogenic composition comprising one or more HIV antigens disclosed herein, when administered to an individual, stimulates an immune response against the one or more HIV antigens, thereby producing α-HIV antibodies. An immune response is any response by the immune system of an individual to an immunogenic composition disclosed herein. Exemplary immune responses include, but are not limited to, cellular as well as local and systemic humoral immunity, such as, e.g., CTL responses, including antigen-specific induction of $CD8^+$ CTLs, helper T-cell responses, including T-cell proliferative responses and cytokine release, and B-cell responses including, e.g., an antibody producing response. In an aspect of this embodiment, an immunogenic composition is a vaccine.

In another aspect of this embodiment, an immunogenic composition is a medicament for the treatment of a HIV-based disease. In aspects of this embodiment, an HIV antigen disclosed herein is used to manufacture a medicament for the treatment of a HIV-based disease. In aspects of this embodiment, use of a HIV antigen disclosed herein is in an amount sufficient to treats a HIV-based disease by reducing one or more physiological conditions or symptom associated with a HIV infection or pathology. In other aspects of this embodiment, use of a HIV antigen disclosed herein is in an amount sufficient to immunize or vaccinate the individual against the HIV infection or pathology.

In one embodiment, an immunogenic composition disclosed herein comprises a single HIV antigen disclosed herein. In one embodiment, an immunogenic composition disclosed herein comprises a plurality of HIV antigens disclosed herein. In aspects of this embodiment, an immunogenic composition disclosed herein comprises, e.g., 1, 2, 3, 4, 5, 6, 7, 8, 9, 10, 11, 12, 13, 14, or 15 HIV antigens disclosed herein. In other aspects of this embodiment, an immunogenic composition disclosed herein comprises, e.g., at least 1, at least 2, at least 3, at least 4, at least 5, at least 6, at least 7, at least 8, at least 9, at least 10, at least 11, at least 12, at least 13, at least 14, or at least 15 HIV antigens disclosed herein. In yet other aspects of this embodiment, an immunogenic composition disclosed herein comprises, e.g., at most 1, at most 2, at most 3, at most 4, at most 5, at most 6, at most 7, at most 8, at most 9, at most 10, at most 11, at most 12, at most 13, at most 14, or at most 15 HIV antigens disclosed herein. In still other aspects of this embodiment, an immunogenic composition disclosed herein comprises, e.g., 1 to 2, 1 to 3, 1 to 4, 1 to 5, 1 to 6, 1 to 7, 1 to 8, 1 to 9, 1 to 10, 1 to 11, 1 to 12, 1 to 13, 1 to 14, 1 to 15, 2 to 3, 2 to 4, 2 to 5, 2 to 6, 2 to 7, 2 to 8, 2 to 9, 2 to 10, 2 to 11, 2 to 12, 2 to 13, 2 to 14, 2 to 15, 3 to 4, 3 to 5, 3 to 6, 3 to 7, 3 to 8, 3 to 9, 3 to 10, 3 to 11, 3 to 12, 3 to 13, 3 to 14, 3 to 15, 4 to 5, 4 to 6, 4 to 7, 4 to 8, 4 to 9, 4 to 10, 4 to 11, 4 to 12, 4 to 13, 4 to 14, 4 to 15, 5 to 6, 5 to 7, 5 to 8, 5 to 9, 5 to 10, 5 to 11, 5 to 12, 5 to 13, 5 to 14, 5 to 15, 6 to 7, 6 to 8, 6 to 9, 6 to 10, 6 to 11, 6 to 12, 6 to 13, 6 to 14, 6 to 15, 7 to 8, 7 to 9, 7 to 10, 7 to 11, 7 to 12, 7 to 13, 7 to 14, 7 to 15, 8 to 9, 8 to 10, 8 to 11, 8 to 12, 8 to 13, 8 to 14, 8 to 15, 9 to 10, 9 to 11, 9 to 12, 9 to 13, 9 to 14, 9 to 15, 10 to 11, 10 to 12, 10 to 13, 10 to 14, 10 to 15, 11 to 12, 11 to 13, 11 to 14, 11 to 15, 12 to 13, 12 to 14, 12 to 15, 13 to 14, 13 to 15, or 14-15 HIV antigens disclosed herein.

The amount of an HIV antigen disclosed herein included in an immunogenic composition is an amount sufficient to elicit an appropriate immune response in the individual. Typically, this amount is also one that does not cause significant adverse side effects. Such amount will vary depending on which specific HIV antigen or antigens are employed. An optimal amount for a particular immunogenic composition can be ascertained by standard studies involving observation of antibody titers and other responses in individuals. A primary immunogenic composition course may include 2 or 3 doses of an immunogenic composition, given at intervals optimal for providing an immunoprotective response.

Generally, an effective and safe amount of an HIV antigen disclosed herein included in an immunogenic composition varies from about 1 fg to 3,000 mg. In aspects of this embodiment, an amount of HIV antigen disclosed herein included in an immunogenic composition may be, e.g., about 1 fg, about 2 fg, about 3 fg, about 4 fg, about 5 fg, about 6 fg, about 7 fg, about 8 fg, about 9 fg, about 10 fg, about 15 fg, about 20 fg, about 25 fg, about 30 fg, about 35 fg, about 40 fg, about 45 fg, about 50 fg, about 55 fg, about 60 fg, about 65 fg, about 70 fg, about 75 fg, about 80 fg, about 85 fg, about 90 fg, about 95 fg, about 100 fg, about 110 fg, about 120 fg, about 130 fg, about 140 fg, about 150 fg, about 160 fg, about 170 fg, about 180 fg, about 190 fg, about 200 fg, about 210 fg, about 220 fg, about 230 fg, about 240 fg, about 250 fg, 260 fg, about 270 fg, about 280 fg, about 290 fg, about 300 fg, about 310 fg, about 320 fg, about 330 fg, about 340 fg, about 350 fg, 360 fg, about 370 fg, about 380 fg, about 390 fg, about 400 fg, about 410 fg, about 420 fg, about 430 fg, about 440 fg, about 450 fg, 460 fg, about 470 fg, about 480 fg, about 490 fg, about 500 fg, about 510 fg, about 520 fg, about 530 fg, about 540 fg, about 550 fg, 560 fg, about 570 fg, about 580 fg, about 590 fg, about 600 fg, about 610 fg, about 620 fg, about 630 fg, about 640 fg, about 650 fg, 660 fg, about 670 fg, about 680 fg, about 690 fg, about 700 fg, about 710 fg, about 720 fg, about 730 fg, about 740 fg, about 750 fg, 760 fg, about 770 fg, about 780 fg, about 790 fg, about 800 fg, about 810 fg, about 820 fg, about 830 fg, about 840 fg, about 850 fg, 860 fg, about 870 fg, about 880 fg, about 890 fg, about 900 fg, about 910 fg, about 920 fg, about 930 fg, about 940 fg, about 950 fg, 960 fg, about 970 fg, about 980 fg, about 990 fg, or about 1,000 fg.

In other aspects of this embodiment, an amount of HIV antigen disclosed herein included in an immunogenic composition may be, e.g., at least 1 fg, at least 2 fg, at least 3 fg, at least 4 fg, at least 5 fg, at least 6 fg, at least 7 fg, at least 8 fg, at least 9 fg, at least 10 fg, at least 15 fg, at least 20 fg, at least 25 fg, at least 30 fg, at least 35 fg, at least 40 fg, at least 45 fg, at least 50 fg, at least 55 fg, at least 60 fg, at least 65 fg, at least 70 fg, at least 75 fg, at least 80 fg, at least 85 fg, at least 90 fg, at least 95 fg, at least 100 fg, at least 110 fg, at least 120 fg, at least 130 fg, at least 140 fg, at least 150 fg, at least 160 fg, at least 170 fg, at least 180 fg, at least 190 fg, at least 200 fg, at least 210 fg, at least 220 fg, at least 230 fg, at least 240 fg, at least 250 fg, 260 fg, at least 270 fg, at least 280 fg, at least 290 fg, at least 300 fg, at least 310 fg, at least 320 fg, at least 330 fg, at least 340 fg, at least 350 fg, 360 fg, at least 370 fg, at least 380 fg, at least 390 fg, at least 400 fg, at least 410 fg, at least 420 fg, at least 430 fg, at least 440 fg, at least 450 fg, 460 fg, at least 470 fg, at least 480 fg, at least 490 fg, at least 500 fg, at least 510 fg, at least 520 fg, at least 530 fg, at least 540 fg, at least 550 fg, 560 fg, at least 570 fg, at least 580 fg, at least 590 fg, at least 600 fg, at least 610 fg, at least 620 fg, at least 630 fg, at least 640 fg, at least 650 fg, 660 fg, at least 670 fg, at least 680 fg, at least 690 fg, at least 700 fg, at least 710 fg, at least 720 fg, at least 730 fg, at least 740 fg, at least 750 fg, 760 fg, at least 770 fg, at least 780 fg, at least 790 fg, at least 800 fg, at least 810 fg, at least 820 fg, at least 830 fg, at least 840 fg, at least 850 fg, 860 fg, at least 870 fg, at least 880 fg, at least 890 fg, at least 900 fg, at least 910 fg, at least 920 fg, at least 930 fg, at least 940 fg, at least 950 fg, 960 fg, at least 970 fg, at least 980 fg, at least 990 fg, or at least 1,000 fg.

In yet other aspects of this embodiment, an amount of HIV antigen disclosed herein included in an immunogenic composition may be, e.g., at most 1 fg, at most 2 fg, at most 3 fg, at most 4 fg, at most 5 fg, at most 6 fg, at most 7 fg, at most 8 fg, at most 9 fg, at most 10 fg, at most 15 fg, at most 20 fg, at most 25 fg, at most 30 fg, at most 35 fg, at most 40 fg, at most 45 fg, at most 50 fg, at most 55 fg, at most 60 fg, at most 65 fg, at most 70 fg, at most 75 fg, at most 80 fg, at most 85 fg, at most 90 fg, at most 95 fg, at most 100 fg, at most 110 fg, at most 120 fg, at most 130 fg, at most 140 fg, at most 150 fg, at most 160 fg, at most 170 fg, at most 180 fg, at most 190 fg, at most 200 fg, at most 210 fg, at most 220 fg, at most 230 fg, at most 240 fg, at most 250 fg, 260 fg, at most 270 fg, at most 280 fg, at most 290 fg, at most 300 fg, at most 310 fg, at most 320 fg, at most 330 fg, at most 340 fg, at most 350 fg, 360 fg, at most 370 fg, at most 380 fg, at most 390 fg, at most 400 fg, at most 410 fg, at most 420 fg, at most 430 fg, at most 440 fg, at most 450 fg, 460 fg, at most 470 fg, at most 480 fg, at most 490 fg, at most 500 fg, at most 510 fg, at most 520 fg, at most 530 fg, at most 540 fg, at most 550 fg, 560 fg, at most 570 fg, at most 580 fg, at most 590 fg, at most 600 fg, at most 610 fg, at most 620 fg, at most 630 fg, at most 640 fg, at most 650 fg, 660 fg, at most 670 fg, at most 680 fg, at most 690 fg, at most 700 fg, at most 710 fg, at most 720 fg, at most 730 fg, at most 740 fg, at most 750 fg, 760 fg, at most 770 fg, at most 780 fg, at most 790 fg, at most 800 fg, at most 810 fg, at most 820 fg, at most 830 fg, at most 840 fg, at most 850 fg, 860 fg, at most 870 fg, at most 880 fg, at most 890 fg, at most 900 fg, at most 910 fg, at most 920 fg, at most 930 fg, at most 940 fg, at most 950 fg, 960 fg, at most 970 fg, at most 980 fg, at most 990 fg, or at most 1,000 fg.

In still other aspects of this embodiment, an amount of HIV antigen disclosed herein included in an immunogenic composition may be in the range of, e.g., about 1 fg to about 10 fg, about 1 fg to about 20 fg, about 1 fg to about 30 fg, about 1 fg to about 40 fg, about 1 fg to about 50 fg, about 1 fg to about 60 fg, about 1 fg to about 70 fg, about 1 fg to about 80 fg, about 1 fg to about 90 fg, about 1 fg to about 100 fg, about 1 fg to about 110 fg, about 1 fg to about 120 fg, about 1 fg to about 130 fg, about 1 fg to about 140 fg, about 1 fg to about 150 fg, about 5 fg to about 10 fg, about 5 fg to about 20 fg, about 5 fg to about 30 fg, about 5 fg to about 40 fg, about 5 fg to about 50 fg, about 5 fg to about 60 fg, about 5 fg to about 70 fg, about 5 fg to about 80 fg, about 5 fg to about 90 fg, about 5 fg to about 100 fg, about 5 fg to about 110 fg, about 5 fg to about 120 fg, about 5 fg to about 130 fg, about 5 fg to about 140 fg, about 5 fg to about 150 fg, about 10 fg to about 20 fg, about 10 fg to about 30 fg, about 10 fg to about 40 fg, about 10 fg to about 50 fg, about 10 fg to about 60 fg, about 10 fg to about 70 fg, about 10 fg to about 80 fg, about 10 fg to about 90 fg, about 10 fg to about 100 fg, about 10 fg to about 110 fg, about 10 fg to about 120 fg, about 10 fg to about 130 fg, about 10 fg to about 140 fg, about 10 fg to about 150 fg, about 10 fg to about 175 fg, about 10 fg to about 200 fg, about 10 fg to about 225 fg, about 10 fg to about 250 fg, about 25 fg to about 50 fg, about 25 fg to about 75 fg, about 25 fg to about 100 fg, about 25 fg to about 125 fg, about 25 fg to about 150 fg, about 25 fg to about 175 fg, about 25 fg to about 200 fg, about 25 fg to about 225 fg, about 25 fg to about 250 fg, about 50 fg to about 75 fg, about 50 fg to about 100 fg, about 50 fg to about 125 fg, about 50 fg to about 150 fg, about 50 fg to about 175 fg, about 50 fg to about 200 fg, about 50 fg to about 225 fg, about 50 fg to about 250 fg, about 75 fg to about 100 fg, about 75 fg to about 125 fg, about 75 fg to about 150 fg, about 75 fg to about 175 fg, about 75 fg to about 200 fg, about 75 fg to about 225 fg, or about 75 fg to about 250 fg.

In still other aspects of this embodiment, an amount of HIV antigen disclosed herein included in an immunogenic composition may be in the range of, e.g., about 100 fg to about 125 fg, about 100 fg to about 150 fg, about 100 fg to about 175 fg, about 100 fg to about 200 fg, about 100 fg to about 225 fg, about 100 fg to about 250 fg, about 100 fg to about 275 fg, about 100 fg to about 300 fg, about 100 fg to about 325 fg, about 100 fg to about 350 fg, about 100 fg to about 375 fg, about 100 fg to about 400 fg, about 100 fg to about 425 fg, about 100 fg to about 450 fg, about 100 fg to about 475 fg, about 100 fg to about 500 fg, about 100 fg to about 525 fg, about 100 fg to about 550 fg, about 100 fg to about 575 fg, about 100 fg to about 600 fg, about 125 fg to about 150 fg, about 125 fg to about 175 fg, about 125 fg to about 200 fg, about 125 fg to about 225 fg, about 125 fg to about 250 fg, about 125 fg to about 275 fg, about 125 fg to about 300 fg, about 125 fg to about 325 fg, about 125 fg to about 350 fg, about 125 fg to about 375 fg, about 125 fg to about 400 fg, about 125 fg to about 425 fg, about 125 fg to about 450 fg, about 125 fg to about 475 fg, about 125 fg to about 500 fg, about 125 fg to about 525 fg, about 125 fg to about 550 fg, about 125 fg to about 575 fg, about 125 fg to about 600 fg, about 150 fg to about 175 fg, about 150 fg to about 200 fg, about 150 fg to about 225 fg, about 150 fg to about 250 fg, about 150 fg to about 275 fg, about 150 fg to about 300 fg, about 150 fg to about 325 fg, about 150 fg to about 350 fg, about 150 fg to about 375 fg, about 150 fg to about 400 fg, about 150 fg to about 425 fg, about 150 fg to about 450 fg, about 150 fg to about 475 fg, about 150 fg to about 500 fg, about 150 fg to about 525 fg, about 150 fg to about 550 fg, about 150 fg to about 575 fg, about 150 fg to about 600 fg, about 200 fg to about 225 fg, about 200 fg to about 250 fg, about 200 fg to about 275 fg, about 200 fg to about 300 fg, about 200 fg to about 325 fg, about 200 fg to about 350 fg, about 200 fg to about 375 fg, about 200 fg to about 400 fg, about 200 fg to about 425 fg, about 200 fg to about 450 fg, about 200 fg to about 475 fg, about 200 fg to about 500 fg, about 200 fg to about 525 fg, about 200 fg to about 550 fg, about 200 fg to about 575 fg, about 200 fg to about 600 fg, about 200 fg to about 625 fg, about 200 fg to about 650 fg, about 200 fg to about 675 fg, about 200 fg to about 700 fg, about 200 fg to about 725 fg, about 200 fg to about 750 fg, about 200 fg to about 775 fg, about 200 fg to about 800 fg, about 200 fg to about 825 fg, about 200 fg to about 850 fg, about 200 fg to about 875 fg, about 200 fg to about 900 fg, about 200 fg to about 925 fg, about 200 fg to about 950 fg, about 200 fg to about 975 fg, about 200 fg to about 1,000 fg.

In still other aspects of this embodiment, an amount of HIV antigen disclosed herein included in an immunogenic composition may be in the range of, e.g., about 250 fg to about 275 fg, about 250 fg to about 300 fg, about 250 fg to about 325 fg, about 250 fg to about 350 fg, about 250 fg to about 375 fg, about 250 fg to about 400 fg, about 250 fg to about 425 fg, about 250 fg to about 450 fg, about 250 fg to about 475 fg, about 250 fg to about 500 fg, about 250 fg to about 525 fg, about 250 fg to about 550 fg, about 250 fg to about 575 fg, about 250 fg to about 600 fg, about 250 fg to about 625 fg, about 250 fg to about 650 fg, about 250 fg to about 675 fg, about 250 fg to about 700 fg, about 250 fg to about 725 fg, about 250 fg to about 750 fg, about 250 fg to about 775 fg, about 250 fg to about 800 fg, about 250 fg to about 825 fg, about 250 fg to about 850 fg, about 250 fg to about 875 fg, about 250 fg to about 900 fg, about 250 fg to about 925 fg, about 250 fg to about 950 fg, about 250 fg to about 975 fg, about 250 fg to about 1,000 fg, about 300 fg to about 325 fg, about 300 fg to about 350 fg, about 300 fg to about 375 fg, about 300 fg to about 400 fg, about 300 fg to about 425 fg, about 300 fg to about 450 fg, about 300 fg to about 475 fg, about 300 fg to about 500 fg, about 300 fg to about 525 fg, about 300 fg to about 550 fg, about 300 fg to about 575 fg, about 300 fg to about 600 fg, about 300 fg to about 625 fg, about 300 fg to about 650 fg, about 300 fg to about 675 fg, about 300 fg to about 700 fg, about 300 fg to about 725 fg, about 300 fg to about 750 fg, about 300 fg to about 775 fg, about 300 fg to about 800 fg, about 300 fg to about 825 fg, about 300 fg to about 850 fg, about 300 fg to about 875 fg, about 300 fg to about 900 fg, about 300 fg to about 925 fg, about 300 fg to about 950 fg, about 300 fg to about 975 fg, about 300 fg to about 1,000 fg, about 400 fg to about 425 fg, about 400 fg to about 450 fg, about 400 fg to about 475 fg, about 400 fg to about 500 fg, about 400 fg to about 525 fg, about 400 fg to about 550 fg, about 400 fg to about 575 fg, about 400 fg to about 600 fg, about 400 fg to about 625 fg, about 400 fg to about 650 fg, about 400 fg to about 675 fg, about 400 fg to about 700 fg, about 400 fg to about 725 fg, about 400 fg to about 750 fg, about 400 fg to about 775 fg, about 400 fg to about 800 fg, about 400 fg to about 825 fg, about 400 fg to about 850 fg, about 400 fg to about 875 fg, about 400 fg to about 900 fg, about 400 fg to about 925 fg, about 400 fg to about 950 fg, about 400 fg to about 975 fg, or about 400 fg to about 1,000 fg.

In still other aspects of this embodiment, an amount of HIV antigen disclosed herein included in an immunogenic composition may be in the range of, e.g., about 500 fg to about 525 fg, about 500 fg to about 550 fg, about 500 fg to about 575 fg, about 500 fg to about 600 fg, about 500 fg to about 625 fg, about 500 fg to about 650 fg, about 500 fg to about 675 fg, about 500 fg to about 700 fg, about 500 fg to about 725 fg, about 500 fg to about 750 fg, about 500 fg to about 775 fg, about 500 fg to about 800 fg, about 500 fg to about 825 fg, about 500 fg to about 850 fg, about 500 fg to about 875 fg, about 500 fg to about 900 fg, about 500 fg to about 925 fg, about 500 fg to about 950 fg, about 500 fg to about 975 fg, about 500 fg to about 1,000 fg, about 600 fg to about 625 fg, about 600 fg to about 650 fg, about 600 fg to about 675 fg, about 600 fg to about 700 fg, about 600 fg to about 725 fg, about 600 fg to about 750 fg, about 600 fg to about 775 fg, about 600 fg to about 800 fg, about 600 fg to about 825 fg, about 600 fg to about 850 fg, about 600 fg to about 875 fg, about 600 fg to about 900 fg, about 600 fg to about 925 fg, about 600 fg to about 950 fg, about 600 fg to about 975 fg, about 600 fg to about 1,000 fg, about 700 fg to about 725 fg, about 700 fg to about 750 fg, about 700 fg to about 775 fg, about 700 fg to about 800 fg, about 700 fg to about 825 fg, about 700 fg to about 850 fg, about 700 fg to about 875 fg, about 700 fg to about 900 fg, about 700 fg to about 925 fg, about 700 fg to about 950 fg, about 700 fg to about 975 fg, about 700 fg to about 1,000 fg, about 800 fg to about 825 fg, about 800 fg to about 850 fg, about 800 fg to about 875 fg, about 800 fg to about 900 fg, about 800 fg to about 925 fg, about 800 fg to about 950 fg, about 800 fg to about 975 fg, or about 800 fg to about 1,000 fg.

In aspects of this embodiment, an amount of HIV antigen disclosed herein included in an immunogenic composition may be, e.g., about 1 ng, about 2 ng, about 3 ng, about 4 ng, about 5 ng, about 6 ng, about 7 ng, about 8 ng, about 9 ng, about 10 ng, about 15 ng, about 20 ng, about 25 ng, about 30 ng, about 35 ng, about 40 ng, about 45 ng, about 50 ng, about 55 ng, about 60 ng, about 65 ng, about 70 ng, about 75 ng, about 80 ng, about 85 ng, about 90 ng, about 95 ng, about 100 ng, about 110 ng, about 120 ng, about 130 ng, about 140 ng, about 150 ng, about 160 ng, about 170 ng, about 180 ng, about 190 ng, about 200 ng, about 210 ng, about 220 ng, about 230 ng, about 240 ng, about 250 ng, 260 ng, about 270 ng, about 280 ng, about 290 ng, about 300 ng, about 310 ng, about 320 ng, about 330 ng, about 340 ng, about 350 ng, 360 ng, about 370 ng, about 380 ng, about 390 ng, about 400 ng, about 410 ng, about 420 ng, about 430 ng, about 440 ng, about 450 ng, 460 ng, about 470 ng, about 480 ng, about 490 ng, about 500 ng, about 510 ng, about 520 ng, about 530 ng, about 540 ng, about 550 ng, 560 ng, about 570 ng, about 580 ng, about 590 ng, about 600 ng, about 610 ng, about 620 ng, about 630 ng, about 640 ng, about 650 ng, 660 ng, about 670 ng, about 680 ng, about 690 ng, about 700 ng, about 710 ng, about 720 ng, about 730 ng, about 740 ng, about 750 ng, 760 ng, about 770 ng, about 780 ng, about 790 ng, about 800 ng, about 810 ng, about 820 ng, about 830 ng, about 840 ng, about 850 ng, 860 ng, about 870 ng, about 880 ng, about 890 ng, about 900 ng, about 910 ng, about 920 ng, about 930 ng, about 940 ng, about 950 ng, 960 ng, about 970 ng, about 980 ng, about 990 ng, or about 1,000 ng.

In other aspects of this embodiment, an amount of HIV antigen disclosed herein included in an immunogenic composition may be, e.g., at least 1 ng, at least 2 ng, at least 3 ng, at least 4 ng, at least 5 ng, at least 6 ng, at least 7 ng, at least 8 ng, at least 9 ng, at least 10 ng, at least 15 ng, at least 20 ng, at least 25 ng, at least 30 ng, at least 35 ng, at least 40 ng, at least 45 ng, at least 50 ng, at least 55 ng, at least 60 ng, at least 65 ng, at least 70 ng, at least 75 ng, at least 80 ng, at least 85 ng, at least 90 ng, at least 95 ng, at least 100 ng, at least 110 ng, at least 120 ng, at least 130 ng, at least 140 ng, at least 150 ng, at least 160 ng, at least 170 ng, at least 180 ng, at least 190 ng, at least 200 ng, at least 210 ng, at least 220 ng, at least 230 ng, at least 240 ng, at least 250 ng, 260 ng, at least 270 ng, at least 280 ng, at least 290 ng, at least 300 ng, at least 310 ng, at least 320 ng, at least 330 ng, at least 340 ng, at least 350 ng, 360 ng, at least 370 ng, at least 380 ng, at least 390 ng, at least 400 ng, at least 410 ng, at least 420 ng, at least 430 ng, at least 440 ng, at least 450 ng, 460 ng, at least 470 ng, at least 480 ng, at least 490 ng, at least 500 ng, at least 510 ng, at least 520 ng, at least 530 ng, at least 540 ng, at least 550 ng, 560 ng, at least 570 ng, at least 580 ng, at least 590 ng, at least 600 ng, at least 610 ng, at least 620 ng, at least 630 ng, at least 640 ng, at least 650 ng, 660 ng, at least 670 ng, at least 680 ng, at least 690 ng, at least 700 ng, at least 710 ng, at least 720 ng, at least 730 ng, at least 740 ng, at least 750 ng, 760 ng, at least 770 ng, at least 780 ng, at least 790 ng, at least 800 ng, at least 810 ng, at least 820 ng, at least 830 ng, at least 840 ng, at least 850 ng, 860 ng, at least 870 ng, at least 880 ng, at least 890 ng, at least 900 ng, at least 910 ng, at least 920 ng, at least 930 ng, at least 940 ng, at least 950 ng, 960 ng, at least 970 ng, at least 980 ng, at least 990 ng, or at least 1,000 ng.

In yet other aspects of this embodiment, an amount of HIV antigen disclosed herein included in an immunogenic composition may be, e.g., at most 1 ng, at most 2 ng, at most 3 ng, at most 4 ng, at most 5 ng, at most 6 ng, at most 7 ng, at most 8 ng, at most 9 ng, at most 10 ng, at most 15 ng, at most 20 ng, at most 25 ng, at most 30 ng, at most 35 ng, at most 40 ng, at most 45 ng, at most 50 ng, at most 55 ng, at most 60 ng, at most 65 ng, at most 70 ng, at most 75 ng, at most 80 ng, at most 85 ng, at most 90 ng, at most 95 ng, at most 100 ng, at most 110 ng, at most 120 ng, at most 130 ng, at most 140 ng, at most 150 ng, at most 160 ng, at most 170 ng, at most 180 ng, at most 190 ng, at most 200 ng, at most 210 ng, at most 220 ng, at most 230 ng, at most 240 ng, at most 250 ng, 260 ng, at most 270 ng, at most 280 ng, at most 290 ng, at most 300 ng, at most 310 ng, at most 320 ng, at most 330 ng, at most 340 ng, at most 350 ng, 360 ng, at most 370 ng, at most 380 ng, at most 390 ng, at most 400 ng, at most 410 ng, at most 420 ng, at most 430 ng, at most 440 ng, at most 450 ng, 460 ng, at most 470 ng, at most 480 ng, at most 490 ng, at most 500 ng, at most 510 ng, at most 520 ng, at most 530 ng, at most 540 ng, at most 550 ng, 560 ng, at most 570 ng, at most 580 ng, at most 590 ng, at most 600 ng, at most 610 ng, at most 620 ng, at most 630 ng, at most 640 ng, at most 650 ng, 660 ng, at most 670 ng, at most 680 ng, at most 690 ng, at most 700 ng, at most 710 ng, at most 720 ng, at most 730 ng, at most 740 ng, at most 750 ng, 760 ng, at most 770 ng, at most 780 ng, at most 790 ng, at most 800 ng, at most 810 ng, at most 820 ng, at most 830 ng, at most 840 ng, at most 850 ng, 860 ng, at most 870 ng, at most 880 ng, at most 890 ng, at most 900 ng, at most 910 ng, at most 920 ng, at most 930 ng, at most 940 ng, at most 950 ng, 960 ng, at most 970 ng, at most 980 ng, at most 990 ng, or at most 1,000 ng.

In still other aspects of this embodiment, an amount of HIV antigen disclosed herein included in an immunogenic composition may be in the range of, e.g., about 1 ng to about 10 ng, about 1 ng to about 20 ng, about 1 ng to about 30 ng, about 1 ng to about 40 ng, about 1 ng to about 50 ng, about 1 ng to about 60 ng, about 1 ng to about 70 ng, about 1 ng to about 80 ng, about 1 ng to about 90 ng, about 1 ng to about 100 ng, about 1 ng to about 110 ng, about 1 ng to about 120 ng, about 1 ng to about 130 ng, about 1 ng to about 140 ng, about 1 ng to about 150 ng, about 5 ng to about 10 ng, about 5 ng to about 20 ng, about 5 ng to about 30 ng, about 5 ng to about 40 ng, about 5 ng to about 50 ng, about 5 ng to about 60 ng, about 5 ng to about 70 ng, about 5 ng to about 80 ng, about 5 ng to about 90 ng, about 5 ng to about 100 ng, about 5 ng to about 110 ng, about 5 ng to about 120 ng, about 5 ng to about 130 ng, about 5 ng to about 140 ng, about 5 ng to about 150 ng, about 10 ng to about 20 ng, about 10 ng to about 30 ng, about 10 ng to about 40 ng, about 10 ng to about 50 ng, about 10 ng to about 60 ng, about 10 ng to about 70 ng, about 10 ng to about 80 ng, about 10 ng to about 90 ng, about 10 ng to about 100 ng, about 10 ng to about 110 ng, about 10 ng to about 120 ng, about 10 ng to about 130 ng, about 10 ng to about 140 ng, about 10 ng to about 150 ng, about 10 ng to about 175 ng, about 10 ng to about 200 ng, about 10 ng to about 225 ng, about 10 ng to about 250 ng, about 25 ng to about 50 ng, about 25 ng to about 75 ng, about 25 ng to about 100 ng, about 25 ng to about 125 ng, about 25 ng to about 150 ng, about 25 ng to about 175 ng, about 25 ng to about 200 ng, about 25 ng to about 225 ng, about 25 ng to about 250 ng, about 50 ng to about 75 ng, about 50 ng to about 100 ng, about 50 ng to about 125 ng, about 50 ng to about 150 ng, about 50 ng to about 175 ng, about 50 ng to about 200 ng, about 50 ng to about 225 ng, about 50 ng to about 250 ng, about 75 ng to about 100 ng, about 75 ng to about 125 ng, about 75 ng to about 150 ng, about 75 ng to about 175 ng, about 75 ng to about 200 ng, about 75 ng to about 225 ng, or about 75 ng to about 250 ng.

In still other aspects of this embodiment, an amount of HIV antigen disclosed herein included in an immunogenic composition may be in the range of, e.g., about 100 ng to about 125 ng, about 100 ng to about 150 ng, about 100 ng to about 175 ng, about 100 ng to about 200 ng, about 100 ng to about 225 ng, about 100 ng to about 250 ng, about 100 ng to about 275 ng, about 100 ng to about 300 ng, about 100 ng to about 325 ng, about 100 ng to about 350 ng, about 100 ng to about 375 ng, about 100 ng to about 400 ng, about 100 ng to about 425 ng, about 100 ng to about 450 ng, about 100 ng to about 475 ng, about 100 ng to about 500 ng, about 100 ng to about 525 ng, about 100 ng to about 550 ng, about 100 ng to about 575 ng, about 100 ng to about 600 ng, about 125 ng to about 150 ng, about 125 ng to about 175 ng, about 125 ng to about 200 ng, about 125 ng to about 225 ng, about 125 ng to about 250 ng, about 125 ng to about 275 ng, about 125 ng to about 300 ng, about 125 ng to about 325 ng, about 125 ng to about 350 ng, about 125 ng to about 375 ng, about 125 ng to about 400 ng, about 125 ng to about 425 ng, about 125 ng to about 450 ng, about 125 ng to about 475 ng, about 125 ng to about 500 ng, about 125 ng to about 525 ng, about 125 ng to about 550 ng, about 125 ng to about 575 ng, about 125 ng to about 600 ng, about 150 ng to about 175 ng, about 150 ng to about 200 ng, about 150 ng to about 225 ng, about 150 ng to about 250 ng, about 150 ng to about 275 ng, about 150 ng to about 300 ng, about 150 ng to about 325 ng, about 150 ng to about 350 ng, about 150 ng to about 375 ng, about 150 ng to about 400 ng, about 150 ng to about 425 ng, about 150 ng to about 450 ng, about 150 ng to about 475 ng, about 150 ng to about 500 ng, about 150 ng to about 525 ng, about 150 ng to about 550 ng, about 150 ng to about 575 ng, about 150 ng to about 600 ng, about 200 ng to about 225 ng, about 200 ng to about 250 ng, about 200 ng to about 275 ng, about 200 ng to about 300 ng, about 200 ng to about 325 ng, about 200 ng to about 350 ng, about 200 ng to about 375 ng, about 200 ng to about 400 ng, about 200 ng to about 425 ng, about 200 ng to about 450 ng, about 200 ng to about 475 ng, about 200 ng to about 500 ng, about 200 ng to about 525 ng, about 200 ng to about 550 ng, about 200 ng to about 575 ng, about 200 ng to about 600 ng, about 200 ng to about 625 ng, about 200 ng to about 650 ng, about 200 ng to about 675 ng, about 200 ng to about 700 ng, about 200 ng to about 725 ng, about 200 ng to about 750 ng, about 200 ng to about 775 ng, about 200 ng to about 800 ng, about 200 ng to about 825 ng, about 200 ng to about 850 ng, about 200 ng to about 875 ng, about 200 ng to about 900 ng, about 200 ng to about 925 ng, about 200 ng to about 950 ng, about 200 ng to about 975 ng, or about 200 ng to about 1,000 ng.

In still other aspects of this embodiment, an amount of HIV antigen disclosed herein included in an immunogenic composition may be in the range of, e.g., about 250 ng to about 275 ng, about 250 ng to about 300 ng, about 250 ng to about 325 ng, about 250 ng to about 350 ng, about 250 ng to about 375 ng, about 250 ng to about 400 ng, about 250 ng to about 425 ng, about 250 ng to about 450 ng, about 250 ng to about 475 ng, about 250 ng to about 500 ng, about 250 ng to about 525 ng, about 250 ng to about 550 ng, about 250 ng to about 575 ng, about 250 ng to about 600 ng, about 250 ng to about 625 ng, about 250 ng to about 650 ng, about 250 ng to about 675 ng, about 250 ng to about 700 ng, about 250 ng to about 725 ng, about 250 ng to about 750 ng, about 250 ng to about 775 ng, about 250 ng to about 800 ng, about 250 ng to about 825 ng, about 250 ng to about 850 ng, about 250 ng to about 875 ng, about 250 ng to about 900 ng, about 250 ng to about 925 ng, about 250 ng to about 950 ng, about 250 ng to about 975 ng, about 250 ng to about 1,000 ng, about 300 ng to about 325 ng, about 300 ng to about 350 ng, about 300 ng to about 375 ng, about 300 ng to about 400 ng, about 300 ng to about 425 ng, about 300 ng to about 450 ng, about 300 ng to about 475 ng, about 300 ng to about 500 ng, about 300 ng to about 525 ng, about 300 ng to about 550 ng, about 300 ng to about 575 ng, about 300 ng to about 600 ng, about 300 ng to about 625 ng, about 300 ng to about 650 ng, about 300 ng to about 675 ng, about 300 ng to about 700 ng, about 300 ng to about 725 ng, about 300 ng to about 750 ng, about 300 ng to about 775 ng, about 300 ng to about 800 ng, about 300 ng to about 825 ng, about 300 ng to about 850 ng, about 300 ng to about 875 ng, about 300 ng to about 900 ng, about 300 ng to about 925 ng, about 300 ng to about 950 ng, about 300 ng to about 975 ng, about 300 ng to about 1,000 ng, about 400 ng to about 425 ng, about 400 ng to about 450 ng, about 400 ng to about 475 ng, about 400 ng to about 500 ng, about 400 ng to about 525 ng, about 400 ng to about 550 ng, about 400 ng to about 575 ng, about 400 ng to about 600 ng, about 400 ng to about 625 ng, about 400 ng to about 650 ng, about 400 ng to about 675 ng, about 400 ng to about 700 ng, about 400 ng to about 725 ng, about 400 ng to about 750 ng, about 400 ng to about 775 ng, about 400 ng to about 800 ng, about 400 ng to about 825 ng, about 400 ng to about 850 ng, about 400 ng to about 875 ng, about 400 ng to about 900 ng, about 400 ng to about 925 ng, about 400 ng to about 950 ng, about 400 ng to about 975 ng, or about 400 ng to about 1,000 ng.

In still other aspects of this embodiment, an amount of HIV antigen disclosed herein included in an immunogenic composition may be in the range of, e.g., about 500 ng to about 525 ng, about 500 ng to about 550 ng, about 500 ng to about 575 ng, about 500 ng to about 600 ng, about 500 ng to about 625 ng, about 500 ng to about 650 ng, about 500 ng to about 675 ng, about 500 ng to about 700 ng, about 500 ng to about 725 ng, about 500 ng to about 750 ng, about 500 ng to about 775 ng, about 500 ng to about 800 ng, about 500 ng to about 825 ng, about 500 ng to about 850 ng, about 500 ng to about 875 ng, about 500 ng to about 900 ng, about 500 ng to about 925 ng, about 500 ng to about 950 ng, about 500 ng to about 975 ng, about 500 ng to about 1,000 ng, about 600 ng to about 625 ng, about 600 ng to about 650 ng, about 600 ng to about 675 ng, about 600 ng to about 700 ng, about 600 ng to about 725 ng, about 600 ng to about 750 ng, about 600 ng to about 775 ng, about 600 ng to about 800 ng, about 600 ng to about 825 ng, about 600 ng to about 850 ng, about 600 ng to about 875 ng, about 600 ng to about 900 ng, about 600 ng to about 925 ng, about 600 ng to about 950 ng, about 600 ng to about 975 ng, about 600 ng to about 1,000 ng, about 700 ng to about 725 ng, about 700 ng to about 750 ng, about 700 ng to about 775 ng, about 700 ng to about 800 ng, about 700 ng to about 825 ng, about 700 ng to about 850 ng, about 700 ng to about 875 ng, about 700 ng to about 900 ng, about 700 ng to about 925 ng, about 700 ng to about 950 ng, about 700 ng to about 975 ng, about 700 ng to about 1,000 ng, about 800 ng to about 825 ng, about 800 ng to about 850 ng, about 800 ng to about 875 ng, about 800 ng to about 900 ng, about 800 ng to about 925 ng, about 800 ng to about 950 ng, about 800 ng to about 975 ng, or about 800 ng to about 1,000 ng.

In aspects of this embodiment, an amount of HIV antigen disclosed herein included in an immunogenic composition may be, e.g., about 1 μg, about 2 μg, about 3 μg, about 4 μg, about 5 μg, about 6 μg, about 7 μg, about 8 μg, about 9 μg, about 10 μg, about 15 μg, about 20 μg, about 25 μg, about 30 μg, about 35 μg, about 40 μg, about 45 μg, about 50 μg, about 55 μg, about 60 μg, about 65 μg, about 70 μg, about 75 μg, about 80 μg, about 85 μg, about 90 μg, about 95 μg, about 100 μg, about 110 μg, about 120 μg, about 130 μg, about 140 μg, about 150 μg, about 160 μg, about 170 μg, about 180 μg, about 190 μg, about 200 μg, about 210 μg, about 220 μg, about 230 μg, about 240 μg, about 250 μg, 260 μg, about 270 μg, about 280 μg, about 290 μg, about 300 μg, about 310 μg, about 320 μg, about 330 μg, about 340 μg, about 350 μg, 360 μg, about 370 μg, about 380 μg, about 390 μg, about 400 μg, about 410 μg, about 420 μg, about 430 μg, about 440 μg, about 450 μg, 460 μg, about 470 μg, about 480 μg, about 490 μg, about 500 μg, about 510 μg, about 520 μg, about 530 μg, about 540 μg, about 550 μg, 560 μg, about 570 μg, about 580 μg, about 590 μg, about 600 μg, about 610 μg, about 620 μg, about 630 μg, about 640 μg, about 650 μg, 660 μg, about 670 μg, about 680 μg, about 690 μg, about 700 μg, about 710 μg, about 720 μg, about 730 μg, about 740 μg, about 750 μg, 760 μg, about 770 μg, about 780 μg, about 790 μg, about 800 μg, about 810 μg, about 820 μg, about 830 μg, about 840 μg, about 850 μg, 860 μg, about 870 μg, about 880 μg, about 890 μg, about 900 μg, about 910 μg, about 920 μg, about 930 μg, about 940 μg, about 950 μg, 960 μg, about 970 μg, about 980 μg, about 990 μg, or about 1,000 μg.

In other aspects of this embodiment, an amount of HIV antigen disclosed herein included in an immunogenic composition may be, e.g., at least 1 μg, at least 2 μg, at least 3 μg, at least 4 μg, at least 5 μg, at least 6 μg, at least 7 μg, at least 8 μg, at least 9 μg, at least 10 μg, at least 15 μg, at least 20 μg, at least 25 μg, at least 30 μg, at least 35 μg, at least 40 μg, at least 45 μg, at least 50 μg, at least 55 μg, at least 60 μg, at least 65 μg, at least 70 μg, at least 75 μg, at least 80 μg, at least 85 μg, at least 90 μg, at least 95 μg, at least 100 μg, at least 110 μg, at least 120 μg, at least 130 μg, at least 140 μg, at least 150 μg, at least 160 μg, at least 170 μg, at least 180 μg, at least 190 μg, at least 200 μg, at least 210 μg, at least 220 μg, at least 230 μg, at least 240 μg, at least 250 μg, 260 μg, at least 270 μg, at least 280 μg, at least 290 μg, at least 300 μg, at least 310 μg, at least 320 μg, at least 330 μg, at least 340 μg, at least 350 μg, 360 μg, at least 370 μg, at least 380 μg, at least 390 μg, at least 400 μg, at least 410 μg, at least 420 μg, at least 430 μg, at least 440 μg, at least 450 μg, 460 μg, at least 470 μg, at least 480 μg, at least 490 μg, at least 500 μg, at least 510 μg, at least 520 μg, at least 530 μg, at least 540 μg, at least 550 μg, 560 μg, at least 570 μg, at least 580 μg, at least 590 μg, at least 600 μg, at least 610 μg, at least 620 μg, at least 630 μg, at least 640 μg, at least 650 μg, 660 μg, at least 670 μg, at least 680 μg, at least 690 μg, at least 700 μg, at least 710 μg, at least 720 μg, at least 730 μg, at least 740 μg, at least 750 μg, 760 μg, at least 770 µg, at least 780 µg, at least 790 µg, at least 800 µg, at least 810 µg, at least 820 µg, at least 830 µg, at least 840 µg, at least 850 µg, 860 µg, at least 870 µg, at least 880 µg, at least 890 µg, at least 900 µg, at least 910 µg, at least 920 µg, at least 930 µg, at least 940 µg, at least 950 µg, 960 µg, at least 970 µg, at least 980 µg, at least 990 µg, or at least 1,000 µg.

In yet other aspects of this embodiment, an amount of HIV antigen disclosed herein included in an immunogenic composition may be, e.g., at most 1 µg, at most 2 µg, at most 3 µg, at most 4 µg, at most 5 µg, at most 6 µg, at most 7 µg, at most 8 µg, at most 9 µg, at most 10 µg, at most 15 µg, at most 20 µg, at most 25 µg, at most 30 µg, at most 35 µg, at most 40 µg, at most 45 µg, at most 50 µg, at most 55 µg, at most 60 µg, at most 65 µg, at most 70 µg, at most 75 µg, at most 80 µg, at most 85 µg, at most 90 µg, at most 95 µg, at most 100 µg, at most 110 µg, at most 120 µg, at most 130 µg, at most 140 µg, at most 150 µg, at most 160 µg, at most 170 µg, at most 180 µg, at most 190 µg, at most 200 µg, at most 210 µg, at most 220 µg, at most 230 µg, at most 240 µg, at most 250 µg, 260 µg, at most 270 µg, at most 280 µg, at most 290 µg, at most 300 µg, at most 310 µg, at most 320 µg, at most 330 µg, at most 340 µg, at most 350 µg, 360 µg, at most 370 µg, at most 380 µg, at most 390 µg, at most 400 µg, at most 410 µg, at most 420 µg, at most 430 µg, at most 440 µg, at most 450 µg, 460 µg, at most 470 µg, at most 480 µg, at most 490 µg, at most 500 µg, at most 510 µg, at most 520 µg, at most 530 µg, at most 540 µg, at most 550 µg, 560 µg, at most 570 µg, at most 580 µg, at most 590 µg, at most 600 µg, at most 610 µg, at most 620 µg, at most 630 µg, at most 640 µg, at most 650 µg, 660 µg, at most 670 µg, at most 680 µg, at most 690 µg, at most 700 µg, at most 710 µg, at most 720 µg, at most 730 µg, at most 740 µg, at most 750 µg, 760 µg, at most 770 µg, at most 780 µg, at most 790 µg, at most 800 µg, at most 810 µg, at most 820 µg, at most 830 µg, at most 840 µg, at most 850 µg, 860 µg, at most 870 µg, at most 880 µg, at most 890 µg, at most 900 µg, at most 910 µg, at most 920 µg, at most 930 µg, at most 940 µg, at most 950 µg, 960 µg, at most 970 µg, at most 980 µg, at most 990 µg, or at most 1,000 µg.

In still other aspects of this embodiment, an amount of HIV antigen disclosed herein included in an immunogenic composition may be in the range of, e.g., about 1 µg to about 10 µg, about 1 µg to about 20 µg, about 1 µg to about 30 µg, about 1 µg to about 40 µg, about 1 µg to about 50 µg, about 1 µg to about 60 µg, about 1 µg to about 70 µg, about 1 µg to about 80 µg, about 1 µg to about 90 µg, about 1 µg to about 100 µg, about 1 µg to about 110 µg, about 1 µg to about 120 µg, about 1 µg to about 130 µg, about 1 µg to about 140 µg, about 1 µg to about 150 µg, about 5 µg to about 10 µg, about 5 µg to about 20 µg, about 5 µg to about 30 µg, about 5 µg to about 40 µg, about 5 µg to about 50 µg, about 5 µg to about 60 µg, about 5 µg to about 70 µg, about 5 µg to about 80 µg, about 5 µg to about 90 µg, about 5 µg to about 100 µg, about 5 µg to about 110 µg, about 5 µg to about 120 µg, about 5 µg to about 130 µg, about 5 µg to about 140 µg, about 5 µg to about 150 µg, about 10 µg to about 20 µg, about 10 µg to about 30 µg, about 10 µg to about 40 µg, about 10 µg to about 50 µg, about 10 µg to about 60 µg, about 10 µg to about 70 µg, about 10 µg to about 80 µg, about 10 µg to about 90 µg, about 10 µg to about 100 µg, about 10 µg to about 110 µg, about 10 µg to about 120 µg, about 10 µg to about 130 µg, about 10 µg to about 140 µg, about 10 µg to about 150 µg, about 10 µg to about 175 µg, about 10 µg to about 200 µg, about 10 µg to about 225 µg, about 10 µg to about 250 µg, about 25 µg to about 50 µg, about 25 µg to about 75 µg, about 25 µg to about 100 µg, about 25 µg to about 125 µg, about 25 µg to about 150 µg, about 25 µg to about 175 µg, about 25 µg to about 200 µg, about 25 µg to about 225 µg, about 25 µg to about 250 µg, about 50 µg to about 75 µg, about 50 µg to about 100 µg, about 50 µg to about 125 µg, about 50 µg to about 150 µg, about 50 µg to about 175 µg, about 50 µg to about 200 µg, about 50 µg to about 225 µg, about 50 µg to about 250 µg, about 75 µg to about 100 µg, about 75 µg to about 125 µg, about 75 µg to about 150 µg, about 75 µg to about 175 µg, about 75 µg to about 200 µg, about 75 µg to about 225 µg, or about 75 µg to about 250 µg.

In still other aspects of this embodiment, an amount of HIV antigen disclosed herein included in an immunogenic composition may be in the range of, e.g., about 100 µg to about 125 µg, about 100 µg to about 150 µg, about 100 µg to about 175 µg, about 100 µg to about 200 µg, about 100 µg to about 225 µg, about 100 µg to about 250 µg, about 100 µg to about 275 µg, about 100 µg to about 300 µg, about 100 µg to about 325 µg, about 100 µg to about 350 µg, about 100 µg to about 375 µg, about 100 µg to about 400 µg, about 100 µg to about 425 µg, about 100 µg to about 450 µg, about 100 µg to about 475 µg, about 100 µg to about 500 µg, about 100 µg to about 525 µg, about 100 µg to about 550 µg, about 100 µg to about 575 µg, about 100 µg to about 600 µg, about 125 µg to about 150 µg, about 125 µg to about 175 µg, about 125 µg to about 200 µg, about 125 µg to about 225 µg, about 125 µg to about 250 µg, about 125 µg to about 275 µg, about 125 µg to about 300 µg, about 125 µg to about 325 µg, about 125 µg to about 350 µg, about 125 µg to about 375 µg, about 125 µg to about 400 µg, about 125 µg to about 425 µg, about 125 µg to about 450 µg, about 125 µg to about 475 µg, about 125 µg to about 500 µg, about 125 µg to about 525 µg, about 125 µg to about 550 µg, about 125 µg to about 575 µg, about 125 µg to about 600 µg, about 150 µg to about 175 µg, about 150 µg to about 200 µg, about 150 µg to about 225 µg, about 150 µg to about 250 µg, about 150 µg to about 275 µg, about 150 µg to about 300 µg, about 150 µg to about 325 µg, about 150 µg to about 350 µg, about 150 µg to about 375 µg, about 150 µg to about 400 µg, about 150 µg to about 425 µg, about 150 µg to about 450 µg, about 150 µg to about 475 µg, about 150 µg to about 500 µg, about 150 µg to about 525 µg, about 150 µg to about 550 µg, about 150 µg to about 575 µg, about 150 µg to about 600 µg, about 200 µg to about 225 µg, about 200 µg to about 250 µg, about 200 µg to about 275 µg, about 200 µg to about 300 µg, about 200 µg to about 325 µg, about 200 µg to about 350 µg, about 200 µg to about 375 µg, about 200 µg to about 400 µg, about 200 µg to about 425 µg, about 200 µg to about 450 µg, about 200 µg to about 475 µg, about 200 µg to about 500 µg, about 200 µg to about 525 µg, about 200 µg to about 550 µg, about 200 µg to about 575 µg, about 200 µg to about 600 µg, about 200 µg to about 625 µg, about 200 µg to about 650 µg, about 200 µg to about 675 µg, about 200 µg to about 700 µg, about 200 µg to about 725 µg, about 200 µg to about 750 µg, about 200 µg to about 775 µg, about 200 µg to about 800 µg, about 200 µg to about 825 µg, about 200 µg to about 850 µg, about 200 µg to about 875 µg, about 200 µg to about 900 µg, about 200 µg to about 925 µg, about 200 µg to about 950 µg, about 200 µg to about 975 µg, about 200 µg to about 1,000 µg.

In still other aspects of this embodiment, an amount of HIV antigen disclosed herein included in an immunogenic composition may be in the range of, e.g., about 250 µg to about 275 µg, about 250 µg to about 300 µg, about 250 µg to about 325 µg, about 250 µg to about 350 µg, about 250 µg to about 375 µg, about 250 µg to about 400 µg, about 250 µg to about 425 µg, about 250 µg to about 450 µg, about 250 µg to about 475 µg, about 250 µg to about 500 µg, about 250 µg to about 525 µg, about 250 µg to about 550 µg, about 250 µg to about 575 µg, about 250 µg to about 600 µg, about 250 µg to about 625 µg, about 250 µg to about 650 µg, about 250 µg to about 675 µg, about 250 µg to about 700 µg, about 250 µg to about 725 µg, about 250 µg to about 750 µg, about 250 µg to about 775 µg, about 250 µg to about 800 µg, about 250 µg to about 825 µg, about 250 µg to about 850 µg, about 250 µg to about 875 µg, about 250 µg to about 900 µg, about 250 µg to about 925 µg, about 250 µg to about 950 µg, about 250 µg to about 975 µg, about 250 µg to about 1,000 µg, about 300 µg to about 325 µg, about 300 µg to about 350 µg, about 300 µg to about 375 µg, about 300 µg to about 400 µg, about 300 µg to about 425 µg, about 300 µg to about 450 µg, about 300 µg to about 475 µg, about 300 µg to about 500 µg, about 300 µg to about 525 µg, about 300 µg to about 550 µg, about 300 µg to about 575 µg, about 300 µg to about 600 µg, about 300 µg to about 625 µg, about 300 µg to about 650 µg, about 300 µg to about 675 µg, about 300 µg to about 700 µg, about 300 µg to about 725 µg, about 300 µg to about 750 µg, about 300 µg to about 775 µg, about 300 µg to about 800 µg, about 300 µg to about 825 µg, about 300 µg to about 850 µg, about 300 µg to about 875 µg, about 300 µg to about 900 µg, about 300 µg to about 925 µg, about 300 µg to about 950 µg, about 300 µg to about 975 µg, about 300 µg to about 1,000 µg, about 400 µg to about 425 µg, about 400 µg to about 450 µg, about 400 µg to about 475 µg, about 400 µg to about 500 µg, about 400 µg to about 525 µg, about 400 µg to about 550 µg, about 400 µg to about 575 µg, about 400 µg to about 600 µg, about 400 µg to about 625 µg, about 400 µg to about 650 µg, about 400 µg to about 675 µg, about 400 µg to about 700 µg, about 400 µg to about 725 µg, about 400 µg to about 750 µg, about 400 µg to about 775 µg, about 400 µg to about 800 µg, about 400 µg to about 825 µg, about 400 µg to about 850 µg, about 400 µg to about 875 µg, about 400 µg to about 900 µg, about 400 µg to about 925 µg, about 400 µg to about 950 µg, about 400 µg to about 975 µg, about 400 µg to about 1,000 µg.

In still other aspects of this embodiment, an amount of HIV antigen disclosed herein included in an immunogenic composition may be in the range of, e.g., about 500 µg to about 525 µg, about 500 µg to about 550 µg, about 500 µg to about 575 µg, about 500 µg to about 600 µg, about 500 µg to about 625 µg, about 500 µg to about 650 µg, about 500 µg to about 675 µg, about 500 µg to about 700 µg, about 500 µg to about 725 µg, about 500 µg to about 750 µg, about 500 µg to about 775 µg, about 500 µg to about 800 µg, about 500 µg to about 825 µg, about 500 µg to about 850 µg, about 500 µg to about 875 µg, about 500 µg to about 900 µg, about 500 µg to about 925 µg, about 500 µg to about 950 µg, about 500 µg to about 975 µg, about 500 µg to about 1,000 µg, about 600 µg to about 625 µg, about 600 µg to about 650 µg, about 600 µg to about 675 µg, about 600 µg to about 700 µg, about 600 µg to about 725 µg, about 600 µg to about 750 µg, about 600 µg to about 775 µg, about 600 µg to about 800 µg, about 600 µg to about 825 µg, about 600 µg to about 850 µg, about 600 µg to about 875 µg, about 600 µg to about 900 µg, about 600 µg to about 925 µg, about 600 µg to about 950 µg, about 600 µg to about 975 µg, about 600 µg to about 1,000 µg, about 700 µg to about 725 µg, about 700 µg to about 750 µg, about 700 µg to about 775 µg, about 700 µg to about 800 µg, about 700 µg to about 825 µg, about 700 µg to about 850 µg, about 700 µg to about 875 µg, about 700 µg to about 900 µg, about 700 µg to about 925 µg, about 700 µg to about 950 µg, about 700 µg to about 975 µg, about 700 µg to about 1,000 µg, about 800 µg to about 825 µg, about 800 µg to about 850 µg, about 800 µg to about 875 µg, about 800 µg to about 900 µg, about 800 µg to about 925 µg, about 800 µg to about 950 µg, about 800 µg to about 975 µg, about 800 µg to about 1,000 µg.

In aspects of this embodiment, an amount of HIV antigen disclosed herein included in an immunogenic composition may be, e.g., about 1 mg, about 2 mg, about 3 mg, about 4 mg, about 5 mg, about 6 mg, about 7 mg, about 8 mg, about 9 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 110 mg, about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, 260 mg, about 270 mg, about 280 mg, about 290 mg, about 300 mg, about 310 mg, about 320 mg, about 330 mg, about 340 mg, about 350 mg, 360 mg, about 370 mg, about 380 mg, about 390 mg, about 400 mg, about 410 mg, about 420 mg, about 430 mg, about 440 mg, about 450 mg, 460 mg, about 470 mg, about 480 mg, about 490 mg, about 500 mg, about 510 mg, about 520 mg, about 530 mg, about 540 mg, about 550 mg, 560 mg, about 570 mg, about 580 mg, about 590 mg, about 600 mg, about 610 mg, about 620 mg, about 630 mg, about 640 mg, about 650 mg, 660 mg, about 670 mg, about 680 mg, about 690 mg, about 700 mg, about 710 mg, about 720 mg, about 730 mg, about 740 mg, about 750 mg, 760 mg, about 770 mg, about 780 mg, about 790 mg, about 800 mg, about 810 mg, about 820 mg, about 830 mg, about 840 mg, about 850 mg, 860 mg, about 870 mg, about 880 mg, about 890 mg, about 900 mg, about 910 mg, about 920 mg, about 930 mg, about 940 mg, about 950 mg, 960 mg, about 970 mg, about 980 mg, about 990 mg, about 1,000 mg, about 1,250 mg, about 1,500 mg, about 1,750 mg, about 2,000 mg, about 2,250 mg, about 2,500 mg, about 2,750 mg, or about 3,000 mg.

In other aspects of this embodiment, an amount of HIV antigen disclosed herein included in an immunogenic composition may be, e.g., at least 1 mg, at least 2 mg, at least 3 mg, at least 4 mg, at least 5 mg, at least 6 mg, at least 7 mg, at least 8 mg, at least 9 mg, at least 10 mg, at least 15 mg, at least 20 mg, at least 25 mg, at least 30 mg, at least 35 mg, at least 40 mg, at least 45 mg, at least 50 mg, at least 55 mg, at least 60 mg, at least 65 mg, at least 70 mg, at least 75 mg, at least 80 mg, at least 85 mg, at least 90 mg, at least 95 mg, at least 100 mg, at least 110 mg, at least 120 mg, at least 130 mg, at least 140 mg, at least 150 mg, at least 160 mg, at least 170 mg, at least 180 mg, at least 190 mg, at least 200 mg, at least 210 mg, at least 220 mg, at least 230 mg, at least 240 mg, at least 250 mg, 260 mg, at least 270 mg, at least 280 mg, at least 290 mg, at least 300 mg, at least 310 mg, at least 320 mg, at least 330 mg, at least 340 mg, at least 350 mg, 360 mg, at least 370 mg, at least 380 mg, at least 390 mg, at least 400 mg, at least 410 mg, at least 420 mg, at least 430 mg, at least 440 mg, at least 450 mg, 460 mg, at least 470 mg, at least 480 mg, at least 490 mg, at least 500 mg, at least 510 mg, at least 520 mg, at least 530 mg, at least 540 mg, at least 550 mg, 560 mg, at least 570 mg, at least 580 mg, at least 590 mg, at least 600 mg, at least 610 mg, at least 620 mg, at least 630 mg, at least 640 mg, at least 650 mg, 660 mg, at least 670 mg, at least 680 mg, at least 690 mg, at least 700 mg, at least 710 mg, at least 720 mg, at least 730 mg, at least 740 mg, at least 750 mg, 760 mg, at least 770 mg, at least 780 mg, at least 790 mg, at least 800 mg, at least 810 mg, at least 820 mg, at least 830 mg, at least 840 mg, at least 850 mg, 860 mg, at least 870 mg, at least 880 mg, at least 890 mg, at least 900 mg, at least 910 mg, at least 920 mg, at least 930 mg, at least 940 mg, at least 950 mg, 960 mg, at least 970 mg, at least 980 mg, at least 990 mg, at least 1,000 mg, at least 1,250 mg, at least 1,500 mg, at least 1,750 mg, at least 2,000 mg, at least 2,250 mg, at least 2,500 mg, at least 2,750 mg, or at least 3,000 mg.

In yet other aspects of this embodiment, an amount of HIV antigen disclosed herein included in an immunogenic composition may be, e.g., at most 1 mg, at most 2 mg, at most 3 mg, at most 4 mg, at most 5 mg, at most 6 mg, at most 7 mg, at most 8 mg, at most 9 mg, at most 10 mg, at most 15 mg, at most 20 mg, at most 25 mg, at most 30 mg, at most 35 mg, at most 40 mg, at most 45 mg, at most 50 mg, at most 55 mg, at most 60 mg, at most 65 mg, at most 70 mg, at most 75 mg, at most 80 mg, at most 85 mg, at most 90 mg, at most 95 mg, at most 100 mg, at most 110 mg, at most 120 mg, at most 130 mg, at most 140 mg, at most 150 mg, at most 160 mg, at most 170 mg, at most 180 mg, at most 190 mg, at most 200 mg, at most 210 mg, at most 220 mg, at most 230 mg, at most 240 mg, at most 250 mg, 260 mg, at most 270 mg, at most 280 mg, at most 290 mg, at most 300 mg, at most 310 mg, at most 320 mg, at most 330 mg, at most 340 mg, at most 350 mg, 360 mg, at most 370 mg, at most 380 mg, at most 390 mg, at most 400 mg, at most 410 mg, at most 420 mg, at most 430 mg, at most 440 mg, at most 450 mg, 460 mg, at most 470 mg, at most 480 mg, at most 490 mg, at most 500 mg, at most 510 mg, at most 520 mg, at most 530 mg, at most 540 mg, at most 550 mg, 560 mg, at most 570 mg, at most 580 mg, at most 590 mg, at most 600 mg, at most 610 mg, at most 620 mg, at most 630 mg, at most 640 mg, at most 650 mg, 660 mg, at most 670 mg, at most 680 mg, at most 690 mg, at most 700 mg, at most 710 mg, at most 720 mg, at most 730 mg, at most 740 mg, at most 750 mg, 760 mg, at most 770 mg, at most 780 mg, at most 790 mg, at most 800 mg, at most 810 mg, at most 820 mg, at most 830 mg, at most 840 mg, at most 850 mg, 860 mg, at most 870 mg, at most 880 mg, at most 890 mg, at most 900 mg, at most 910 mg, at most 920 mg, at most 930 mg, at most 940 mg, at most 950 mg, 960 mg, at most 970 mg, at most 980 mg, at most 990 mg, at most 1,000 mg, at most 1,250 mg, at most 1,500 mg, at most 1,750 mg, at most 2,000 mg, at most 2,250 mg, at most 2,500 mg, at most 2,750 mg, or at most 3,000 mg.

In still other aspects of this embodiment, an amount of HIV antigen disclosed herein included in an immunogenic composition may be in the range of, e.g., about 1 mg to about 10 mg, about 1 mg to about 20 mg, about 1 mg to about 30 mg, about 1 mg to about 40 mg, about 1 mg to about 50 mg, about 1 mg to about 60 mg, about 1 mg to about 70 mg, about 1 mg to about 80 mg, about 1 mg to about 90 mg, about 1 mg to about 100 mg, about 1 mg to about 110 mg, about 1 mg to about 120 mg, about 1 mg to about 130 mg, about 1 mg to about 140 mg, about 1 mg to about 150 mg, about 5 mg to about 10 mg, about 5 mg to about 20 mg, about 5 mg to about 30 mg, about 5 mg to about 40 mg, about 5 mg to about 50 mg, about 5 mg to about 60 mg, about 5 mg to about 70 mg, about 5 mg to about 80 mg, about 5 mg to about 90 mg, about 5 mg to about 100 mg, about 5 mg to about 110 mg, about 5 mg to about 120 mg, about 5 mg to about 130 mg, about 5 mg to about 140 mg, about 5 mg to about 150 mg, about 10 mg to about 20 mg, about 10 mg to about 30 mg, about 10 mg to about 40 mg, about 10 mg to about 50 mg, about 10 mg to about 60 mg, about 10 mg to about 70 mg, about 10 mg to about 80 mg, about 10 mg to about 90 mg, about 10 mg to about 100 mg, about 10 mg to about 110 mg, about 10 mg to about 120 mg, about 10 mg to about 130 mg, about 10 mg to about 140 mg, about 10 mg to about 150 mg, about 10 mg to about 175 mg, about 10 mg to about 200 mg, about 10 mg to about 225 mg, about 10 mg to about 250 mg, about 25 mg to about 50 mg, about 25 mg to about 75 mg, about 25 mg to about 100 mg, about 25 mg to about 125 mg, about 25 mg to about 150 mg, about 25 mg to about 175 mg, about 25 mg to about 200 mg, about 25 mg to about 225 mg, about 25 mg to about 250 mg, about 50 mg to about 75 mg, about 50 mg to about 100 mg, about 50 mg to about 125 mg, about 50 mg to about 150 mg, about 50 mg to about 175 mg, about 50 mg to about 200 mg, about 50 mg to about 225 mg, about 50 mg to about 250 mg, about 75 mg to about 100 mg, about 75 mg to about 125 mg, about 75 mg to about 150 mg, about 75 mg to about 175 mg, about 75 mg to about 200 mg, about 75 mg to about 225 mg, or about 75 mg to about 250 mg.

In still other aspects of this embodiment, an amount of HIV antigen disclosed herein included in an immunogenic composition may be in the range of, e.g., about 100 mg to about 125 mg, about 100 mg to about 150 mg, about 100 mg to about 175 mg, about 100 mg to about 200 mg, about 100 mg to about 225 mg, about 100 mg to about 250 mg, about 100 mg to about 275 mg, about 100 mg to about 300 mg, about 100 mg to about 325 mg, about 100 mg to about 350 mg, about 100 mg to about 375 mg, about 100 mg to about 400 mg, about 100 mg to about 425 mg, about 100 mg to about 450 mg, about 100 mg to about 475 mg, about 100 mg to about 500 mg, about 100 mg to about 525 mg, about 100 mg to about 550 mg, about 100 mg to about 575 mg, about 100 mg to about 600 mg, about 125 mg to about 150 mg, about 125 mg to about 175 mg, about 125 mg to about 200 mg, about 125 mg to about 225 mg, about 125 mg to about 250 mg, about 125 mg to about 275 mg, about 125 mg to about 300 mg, about 125 mg to about 325 mg, about 125 mg to about 350 mg, about 125 mg to about 375 mg, about 125 mg to about 400 mg, about 125 mg to about 425 mg, about 125 mg to about 450 mg, about 125 mg to about 475 mg, about 125 mg to about 500 mg, about 125 mg to about 525 mg, about 125 mg to about 550 mg, about 125 mg to about 575 mg, about 125 mg to about 600 mg, about 150 mg to about 175 mg, about 150 mg to about 200 mg, about 150 mg to about 225 mg, about 150 mg to about 250 mg, about 150 mg to about 275 mg, about 150 mg to about 300 mg, about 150 mg to about 325 mg, about 150 mg to about 350 mg, about 150 mg to about 375 mg, about 150 mg to about 400 mg, about 150 mg to about 425 mg, about 150 mg to about 450 mg, about 150 mg to about 475 mg, about 150 mg to about 500 mg, about 150 mg to about 525 mg, about 150 mg to about 550 mg, about 150 mg to about 575 mg, about 150 mg to about 600 mg, about 200 mg to about 225 mg, about 200 mg to about 250 mg, about 200 mg to about 275 mg, about 200 mg to about 300 mg, about 200 mg to about 325 mg, about 200 mg to about 350 mg, about 200 mg to about 375 mg, about 200 mg to about 400 mg, about 200 mg to about 425 mg, about 200 mg to about 450 mg, about 200 mg to about 475 mg, about 200 mg to about 500 mg, about 200 mg to about 525 mg, about 200 mg to about 550 mg, about 200 mg to about 575 mg, about 200 mg to about 600 mg, about 200 mg to about 625 mg, about 200 mg to about 650 mg, about 200 mg to about 675 mg, about 200 mg to about 700 mg, about 200 mg to about 725 mg, about 200 mg to about 750 mg, about 200 mg to about 775 mg, about 200 mg to about 800 mg, about 200 mg to about 825 mg, about 200 mg to about 850 mg, about 200 mg to about 875 mg, about 200 mg to about 900 mg, about 200 mg to about 925 mg, about 200 mg to about 950 mg, about 200 mg to about 975 mg, about 200 mg to about 1,000 mg, about 200 mg to about 1,250 mg, about 200 mg to about 1,500 mg, about 200 mg to about 1,750 mg, about 200 mg to about 2,000 mg, about 200 mg to about 2,250 mg, about 200 mg to about 2,500 mg, about 200 mg to about 2,750 mg, or about 200 mg to about 3,000 mg.

In still other aspects of this embodiment, an amount of HIV antigen disclosed herein included in an immunogenic composition may be in the range of, e.g., about 250 mg to about 275 mg, about 250 mg to about 300 mg, about 250 mg to about 325 mg, about 250 mg to about 350 mg, about 250 mg to about 375 mg, about 250 mg to about 400 mg, about 250 mg to about 425 mg, about 250 mg to about 450 mg, about 250 mg to about 475 mg, about 250 mg to about 500 mg, about 250 mg to about 525 mg, about 250 mg to about 550 mg, about 250 mg to about 575 mg, about 250 mg to about 600 mg, about 250 mg to about 625 mg, about 250 mg to about 650 mg, about 250 mg to about 675 mg, about 250 mg to about 700 mg, about 250 mg to about 725 mg, about 250 mg to about 750 mg, about 250 mg to about 775 mg, about 250 mg to about 800 mg, about 250 mg to about 825 mg, about 250 mg to about 850 mg, about 250 mg to about 875 mg, about 250 mg to about 900 mg, about 250 mg to about 925 mg, about 250 mg to about 950 mg, about 250 mg to about 975 mg, about 250 mg to about 1,000 mg, about 300 mg to about 325 mg, about 300 mg to about 350 mg, about 300 mg to about 375 mg, about 300 mg to about 400 mg, about 300 mg to about 425 mg, about 300 mg to about 450 mg, about 300 mg to about 475 mg, about 300 mg to about 500 mg, about 300 mg to about 525 mg, about 300 mg to about 550 mg, about 300 mg to about 575 mg, about 300 mg to about 600 mg, about 300 mg to about 625 mg, about 300 mg to about 650 mg, about 300 mg to about 675 mg, about 300 mg to about 700 mg, about 300 mg to about 725 mg, about 300 mg to about 750 mg, about 300 mg to about 775 mg, about 300 mg to about 800 mg, about 300 mg to about 825 mg, about 300 mg to about 850 mg, about 300 mg to about 875 mg, about 300 mg to about 900 mg, about 300 mg to about 925 mg, about 300 mg to about 950 mg, about 300 mg to about 975 mg, about 300 mg to about 1,000 mg, about 400 mg to about 425 mg, about 400 mg to about 450 mg, about 400 mg to about 475 mg, about 400 mg to about 500 mg, about 400 mg to about 525 mg, about 400 mg to about 550 mg, about 400 mg to about 575 mg, about 400 mg to about 600 mg, about 400 mg to about 625 mg, about 400 mg to about 650 mg, about 400 mg to about 675 mg, about 400 mg to about 700 mg, about 400 mg to about 725 mg, about 400 mg to about 750 mg, about 400 mg to about 775 mg, about 400 mg to about 800 mg, about 400 mg to about 825 mg, about 400 mg to about 850 mg, about 400 mg to about 875 mg, about 400 mg to about 900 mg, about 400 mg to about 925 mg, about 400 mg to about 950 mg, about 400 mg to about 975 mg, about 400 mg to about 1,000 mg, about 400 mg to about 1,250 mg, about 400 mg to about 1,500 mg, about 400 mg to about 1,750 mg, about 400 mg to about 2,000 mg, about 400 mg to about 2,250 mg, about 400 mg to about 2,500 mg, about 400 mg to about 2,750 mg, or about 400 mg to about 3,000 mg.

In still other aspects of this embodiment, an amount of HIV antigen disclosed herein included in an immunogenic composition may be in the range of, e.g., about 500 mg to about 525 mg, about 500 mg to about 550 mg, about 500 mg to about 575 mg, about 500 mg to about 600 mg, about 500 mg to about 625 mg, about 500 mg to about 650 mg, about 500 mg to about 675 mg, about 500 mg to about 700 mg, about 500 mg to about 725 mg, about 500 mg to about 750 mg, about 500 mg to about 775 mg, about 500 mg to about 800 mg, about 500 mg to about 825 mg, about 500 mg to about 850 mg, about 500 mg to about 875 mg, about 500 mg to about 900 mg, about 500 mg to about 925 mg, about 500 mg to about 950 mg, about 500 mg to about 975 mg, about 500 mg to about 1,000 mg, about 600 mg to about 625 mg, about 600 mg to about 650 mg, about 600 mg to about 675 mg, about 600 mg to about 700 mg, about 600 mg to about 725 mg, about 600 mg to about 750 mg, about 600 mg to about 775 mg, about 600 mg to about 800 mg, about 600 mg to about 825 mg, about 600 mg to about 850 mg, about 600 mg to about 875 mg, about 600 mg to about 900 mg, about 600 mg to about 925 mg, about 600 mg to about 950 mg, about 600 mg to about 975 mg, about 600 mg to about 1,000 mg, about 700 mg to about 725 mg, about 700 mg to about 750 mg, about 700 mg to about 775 mg, about 700 mg to about 800 mg, about 700 mg to about 825 mg, about 700 mg to about 850 mg, about 700 mg to about 875 mg, about 700 mg to about 900 mg, about 700 mg to about 925 mg, about 700 mg to about 950 mg, about 700 mg to about 975 mg, about 700 mg to about 1,000 mg, about 800 mg to about 825 mg, about 800 mg to about 850 mg, about 800 mg to about 875 mg, about 800 mg to about 900 mg, about 800 mg to about 925 mg, about 800 mg to about 950 mg, about 800 mg to about 975 mg, about 800 mg to about 1,000 mg, about 800 mg to about 1,250 mg, about 800 mg to about 1,500 mg, about 800 mg to about 1,750 mg, about 800 mg to about 2,000 mg, about 800 mg to about 2,250 mg, about 800 mg to about 2,500 mg, about 800 mg to about 2,750 mg, or about 800 mg to about 3,000 mg.

An immunogenic compositions disclosed herein may optionally and further comprise one or more adjuvants. An adjuvant is any substance or mixture of substances that increases or diversifies the immune response to a HIV antigen disclosed herein. An adjuvant may serve to reduce the number of immunizations or the amount of antigen required for protective immunization. Non-limiting adjuvants include, e.g., liposomes, oily phases, including, without limitation, the Freund type of adjuvants, such as, e.g., Freund's complete adjuvant (FCA); Freund's incomplete adjuvant (FIA); sapogenin glycosides, such as, e.g., saponins; carbopol; N-acetylmuramyl-L-alanyl-D-isoglutamine (commonly known as muramyl dipeptide or "MDP"); and lipopolysaccharide (LPS). Such adjuvants are generally used in the form of an emulsion with an aqueous phase, or, more commonly, with water-insoluble inorganic salts. These inorganic salts include aluminum hydroxide, zinc sulfate, colloidal iron hydroxide, calcium phosphate or calcium chloride.

Another example of an adjuvant are the aluminum-based adjuvants (or alum-based adjuvants). Aluminum-based adjuvants stimulates an immune response against co-administered antigens by precipitating antigens to form a "depot." Aluminum-based adjuvants primarily stimulate a $T_{H2}$ immune response. Commonly used alum-based adjuvants include aluminum hydroxide ($Al(OH)_3$), aluminum phosphate ($AlPO_4$), aluminum hydroxyphosphate, amorphous aluminum hydroxyphosphate sulfate (AAHS) and so-called "alum" $KAl(SO_4).12H_2O$.

Specific adjuvants and methods of making and using are described in, e.g., Gupta et al. Vaccine, 11: 993-306, 1993; Arnon, R. (Ed.) Synthetic Vaccines 1:83-92, CRC Press, Inc., Boca Raton, Fla., 1987; and David W. Waggoner, Jr. et al., Immunogenicity-Enhancing Carriers and Compositions Thereof and Methods of Using the Same, U.S. Patent Publication No. 20040057958 (Mar. 25, 2004). Additional adjuvants include any compound described in Chapter 7 (pp 141-227) of "Vaccine Design, The Subunit and Adjuvant Approach" (eds. Powell, M. F. and Newman, M. J.) Pharmaceutical Biotechnology, Volume 6, Plenum Press (New York). Examples from this compendium include Muramyl Dipeptide (MDP) and Montanide 720. Molecules such as Poly Inosine:Cytosine (Poly I:C) or plasmid DNA containing CpG motifs can also be administered as adjuvants in combination with antigens encapsulated in microparticles. In another example, the adjuvant is an agent that facilitates entry of the antigenic compound into the cytoplasm of a cell such as listeriolysin, streptolysin or a mixture thereof.

In one embodiment, an immunogenic composition disclosed herein does not comprises an adjuvant disclosed herein. In one embodiment, an immunogenic composition disclosed herein comprises a single adjuvant disclosed herein. In one embodiment, an immunogenic composition disclosed herein comprises a plurality of adjuvants disclosed herein. In aspects of this embodiment, an immunogenic composition disclosed herein comprises, e.g., 1, 2, 3, 4, or 5 adjuvants disclosed herein. In other aspects of this embodiment, an immunogenic composition disclosed herein comprises, e.g., at least 1, at least 2, at least 3, at least 4, or at least 5 adjuvants disclosed herein. In yet other aspects of this embodiment, an immunogenic composition disclosed herein comprises, e.g., at most 1, at most 2, at most 3, at most 4, or at most 5 adjuvants disclosed herein. In still other aspects of this embodiment, an immunogenic composition disclosed herein comprises, e.g., 1 to 2, 1 to 3, 1 to 4, 1 to 5, 2 to 3, 2 to 4, 2 to 5, 3 to 4, 3 to 5, or 4 to 5 adjuvants disclosed herein.

The amount of an adjuvant disclosed herein included in an immunogenic composition is an amount effective in increasing an appropriate immune response of the targeted HIV antigen in the individual. Typically, this amount is also one that does not cause significant adverse side effects. Such amount will vary depending on which adjuvant or adjuvants are employed. An optimal amount of an adjuvant for a particular immunogenic composition can be ascertained by standard studies involving observation of antibody titers and other responses in individuals.

Generally, an effective and safe dose of adjuvant disclosed herein varies from about 1 pg/mL to about 1,500 pg/mL concentration. In aspects of this embodiment, an amount of adjuvant disclosed herein included in an immunogenic composition may be, e.g., about 1 pg/mL, about 10 pg/mL, about 20 pg/mL, about 30 pg/mL, about 40 pg/mL, about 50 pg/mL, about 60 pg/mL, about 70 pg/mL, about 80 pg/mL, about 90 pg/mL, about 100 pg/mL, about 200 pg/mL, about 300 pg/mL, about 400 pg/mL, about 500 pg/mL, about 600 pg/mL, about 700 pg/mL, about 800 pg/mL, about 900 pg/mL, about 1 µg/mL, about 10 µg/mL, about 20 µg/mL, about 30 µg/mL, about 40 µg/mL, about 50 µg/mL, about 60 µg/mL, about 70 µg/mL, about 80 µg/mL, about 90 µg/mL, about 100 µg/mL, about 200 µg/mL, about 300 µg/mL, about 400 µg/mL, about 500 µg/mL, about 600 µg/mL, about 700 µg/mL, about 800 µg/mL, about 900 µg/mL, about 1,000 µg/mL, about 1,100 µg/mL, about 1,200 µg/mL, about 1,300 µg/mL, about 1,400 µg/mL, or about 1,500 µg/mL. In other aspects of this embodiment, an amount of adjuvant disclosed herein included in an immunogenic composition may be, e.g., at least 1 pg/mL, at least 10 pg/mL, at least 20 pg/mL, at least 30 pg/mL, at least 40 pg/mL, at least 50 pg/mL, at least 60 pg/mL, at least 70 pg/mL, at least 80 pg/mL, at least 90 pg/mL, at least 100 pg/mL, at least 200 pg/mL, at least 300 pg/mL, at least 400 pg/mL, at least 500 pg/mL, at least 600 pg/mL, at least 700 pg/mL, at least 800 pg/mL, at least 900 pg/mL, at least 1 µg/mL, at least 10 µg/mL, at least 20 µg/mL, at least 30 µg/mL, at least 40 µg/mL, at least 50 µg/mL, at least 60 µg/mL, at least 70 µg/mL, at least 80 µg/mL, at least 90 µg/mL, at least 100 µg/mL, at least 200 µg/mL, at least 300 µg/mL, at least 400 µg/mL, at least 500 µg/mL, at least 600 µg/mL, at least 700 µg/mL, at least 800 µg/mL, at least 900 µg/mL, at least 1,000 µg/mL, at least 1,100 µg/mL, at least 1,200 µg/mL, at least 1,300 µg/mL, at least 1,400 µg/mL, or at least 1,500 µg/mL. In yet other aspects of this embodiment, an amount of adjuvant disclosed herein included in an immunogenic composition may be, e.g., at most 1 pg/mL, at most 10 pg/mL, at most 20 pg/mL, at most 30 pg/mL, at most 40 pg/mL, at most 50 pg/mL, at most 60 pg/mL, at most 70 pg/mL, at most 80 pg/mL, at most 90 pg/mL, at most 100 pg/mL, at most 200 pg/mL, at most 300 pg/mL, at most 400 pg/mL, at most 500 pg/mL, at most 600 pg/mL, at most 700 pg/mL, at most 800 pg/mL, at most 900 pg/mL, at most 1 µg/mL, at most 10 µg/mL, at most 20 µg/mL, at most 30 µg/mL, at most 40 µg/mL, at most 50 µg/mL, at most 60 µg/mL, at most 70 µg/mL, at most 80 µg/mL, at most 90 µg/mL, at most 100 µg/mL, at most 200 µg/mL, at most 300 µg/mL, at most 400 µg/mL, at most 500 µg/mL, at most 600 µg/mL, at most 700 µg/mL, at most 800 µg/mL, at most 900 µg/mL, at most 1,000 µg/mL, at most 1,100 µg/mL, at most 1,200 µg/mL, at most 1,300 µg/mL, at most 1,400 µg/mL, or at most 1,500 µg/mL.

In still other aspects of this embodiment, an amount of adjuvant disclosed herein included in an immunogenic composition may be, e.g., about 1 pg/mL to about 10 pg/mL, about 1 pg/mL to about 20 pg/mL, about 1 pg/mL to about 30 pg/mL, about 1 pg/mL to about 40 pg/mL, about 1 pg/mL to about 50 pg/mL, about 1 pg/mL to about 60 pg/mL, about 1 pg/mL to about 70 pg/mL, about 1 pg/mL to about 80 pg/mL, about 1 pg/mL to about 90 pg/mL, about 1 pg/mL to about 100 pg/mL, about 10 pg/mL to about 100 pg/mL, about 10 pg/mL to about 200 pg/mL, about 10 pg/mL to about 300 pg/mL, about 10 pg/mL to about 400 pg/mL, about 10 pg/mL to about 500 pg/mL, about 10 pg/mL to about 600 pg/mL, about 10 pg/mL to about 700 pg/mL, about 10 pg/mL to about 800 pg/mL, about 10 pg/mL to about 900 pg/mL, about 10 pg/mL to about 1,000 pg/mL, about 50 pg/mL to about 100 pg/mL, about 50 pg/mL to about 200 pg/mL, about 50 pg/mL to about 300 pg/mL, about 50 pg/mL to about 400 pg/mL, about 50 pg/mL to about 500 pg/mL, about 50 pg/mL to about 600 pg/mL, about 50 pg/mL to about 700 pg/mL, about 50 pg/mL to about 800 pg/mL, about 50 pg/mL to about 900 pg/mL, about 50 pg/mL to about 1,000 pg/mL, about 100 pg/mL to about 200 pg/mL, about 100 pg/mL to about 300 pg/mL, about 100 pg/mL to about 400 pg/mL, about 100 pg/mL to about 500 pg/mL, about 100 pg/mL to about 600 pg/mL, about 100 pg/mL to about 700 pg/mL, about 100 pg/mL to about 800 pg/mL, about 100 pg/mL to about 900 pg/mL, about 100 pg/mL to about 1,000 pg/mL, about 500 pg/mL to about 1,000 pg/mL, about 1 µg/mL to about 10 µg/mL, about 1 µg/mL to about 20 µg/mL, about 1 µg/mL to about 30 µg/mL, about 1 µg/mL to about 40 µg/mL, about 1 µg/mL to about 50 µg/mL, about 1 µg/mL to about 60 µg/mL, about 1 µg/mL to about 70 µg/mL, about 1 µg/mL to about 80 µg/mL, about 1 µg/mL to about 90 µg/mL, about 1 µg/mL to about 100 µg/mL, about 10 µg/mL to about 20 µg/mL, about 10 µg/mL to about 30 µg/mL, about 10 µg/mL to about 40 µg/mL, about 10 µg/mL to about 50 µg/mL, about 10 µg/mL to about 60 µg/mL, about 10 µg/mL to about 70 µg/mL, about 10 µg/mL to about 80 µg/mL, about 10 µg/mL to about 90 µg/mL, about 10 µg/mL to about 100 µg/mL, or about 50 µg/mL to about 100 µg/mL.

In other aspects of this embodiment, an amount of adjuvant disclosed herein included in an immunogenic composition may be, e.g., about 100 µg/mL to about 200 µg/mL, about 100 µg/mL to about 300 µg/mL, about 100 µg/mL to about 400 µg/mL, about 100 µg/mL to about 500 µg/mL, about 100 µg/mL to about 600 µg/mL, about 100 µg/mL to about 700 µg/mL, about 100 µg/mL to about 800 µg/mL, about 100 µg/mL to about 900 µg/mL, about 100 µg/mL to about 1,000 µg/mL, about 100 µg/mL to about 1,200 µg/mL, about 100 µg/mL to about 1,300 µg/mL, about 100 µg/mL to about 1,400 µg/mL, about 100 µg/mL to about 1,500 µg/mL, about 200 µg/mL to about 300 µg/mL, about 200 µg/mL to about 400 µg/mL, about 200 µg/mL to about 500 µg/mL, about 200 µg/mL to about 600 µg/mL, about 200 µg/mL to about 700 µg/mL, about 200 µg/mL to about 800 µg/mL, about 200 µg/mL to about 900 µg/mL, about 200 µg/mL to about 1,000 µg/mL, about 200 µg/mL to about 1,200 µg/mL, about 200 µg/mL to about 1,300 µg/mL, about 200 µg/mL to about 1,400 µg/mL, about 200 µg/mL to about 1,500 µg/mL, about 300 µg/mL to about 400 µg/mL, about 300 µg/mL to about 500 µg/mL, about 300 µg/mL to about 600 µg/mL, about 300 µg/mL to about 700 µg/mL, about 300 µg/mL to about 800 µg/mL, about 300 µg/mL to about 900 µg/mL, about 300 µg/mL to about 1,000 µg/mL, about 300 µg/mL to about 1,200 µg/mL, about 300 µg/mL to about 1,300 µg/mL, about 300 µg/mL to about 1,400 µg/mL, about 300 µg/mL to about 1,500 µg/mL, about 400 µg/mL to about 500 µg/mL, about 400 µg/mL to about 600 µg/mL, about 400 µg/mL to about 700 µg/mL, about 400 µg/mL to about 800 µg/mL, about 400 µg/mL to about 900 µg/mL, about 400 µg/mL to about 1,000 µg/mL, about 400 µg/mL to about 1,200 µg/mL, about 400 µg/mL to about 1,300 µg/mL, about 400 µg/mL to about 1,400 µg/mL, about 400 µg/mL to about 1,500 µg/mL, about 500 µg/mL to about 600 µg/mL, about 500 µg/mL to about 700 µg/mL, about 500 µg/mL to about 800 µg/mL, about 500 µg/mL to about 900 µg/mL, about 500 µg/mL to about 1,000 µg/mL, about 500 µg/mL to about 1,200 µg/mL, about 500 µg/mL to about 1,300 µg/mL, about 500 µg/mL to about 1,400 µg/mL, about 500 µg/mL to about 1,500 µg/mL, about 600 µg/mL to about 700 µg/mL, about 600 µg/mL to about 800 µg/mL, about 600 µg/mL to about 900 µg/mL, about 600 µg/mL to about 1,000 µg/mL, about 600 µg/mL to about 1,200 µg/mL, about 600 µg/mL to about 1,300 µg/mL, about 600 µg/mL to about 1,400 µg/mL, about 600 µg/mL to about 1,500 µg/mL, about 700 µg/mL to about 800 µg/mL, about 700 µg/mL to about 900 µg/mL, about 700 µg/mL to about 1,000 µg/mL, about 700 µg/mL to about 1,200 µg/mL, about 700 µg/mL to about 1,300 µg/mL, about 700 µg/mL to about 1,400 µg/mL, about 700 µg/mL to about 1,500 µg/mL, about 800 µg/mL to about 900 µg/mL, about 800 µg/mL to about 1,000 µg/mL, about 800 µg/mL to about 1,200 µg/mL, about 800 µg/mL to about 1,300 µg/mL, about 800 µg/mL to about 1,400 µg/mL, about 800 µg/mL to about 1,500 µg/mL, about 900 µg/mL to about 1,000 µg/mL, about 900 µg/mL to about 1,200 µg/mL, about 900 µg/mL to about 1,300 µg/mL, about 900 µg/mL to about 1,400 µg/mL, about 900 µg/mL to about 1,500 µg/mL, about 1,000 µg/mL to about 1,200 µg/mL, about 1,000 µg/mL to about 1,300 µg/mL, about 1,000 µg/mL to about 1,400 µg/mL, about 1,000 µg/mL to about 1,500 µg/mL, about 1,100 µg/mL to about 1,200 µg/mL, about 1,100 µg/mL to about 1,300 µg/mL, about 1,100 µg/mL to about 1,400 µg/mL, about 1,100 µg/mL to about 1,500 µg/mL, about 1,200 µg/mL to about 1,300 µg/mL, about 1,200 µg/mL to about 1,400 µg/mL, about 1,200 µg/mL to about 1,500 µg/mL, about 1,300 µg/mL to about 1,500 µg/mL, or about 1,400 µg/mL to about 1,500 µg/mL.

An immunogenic composition disclosed herein may further comprise one or more pharmaceutically acceptable carriers. Pharmaceutically acceptable carriers useful in the immunogenic compositions disclosed herein include any compatible agent that is nontoxic to an individual at the dosages and concentrations employed, and has substantially no long term or permanent detrimental effect when administered and encompasses terms such as pharmacologically acceptable vehicle, stabilizer, solubilizer, diluent, additive, auxiliary or excipient. Such a carrier generally is mixed with an active compound, or permitted to dilute or enclose the active compound and can be a solid, semi-solid, or liquid agent. It is understood that the active ingredients can be soluble or can be delivered as a suspension in the desired carrier or diluent. A carrier disclosed herein may also act as an adjuvant. Any of a variety of pharmaceutically acceptable carriers can be used including, without limitation, aqueous media such as, e.g., water, saline, glycine, hyaluronic acid and the like; solid carriers such as, e.g., mannitol, lactose, starch, magnesium stearate, sodium saccharin, talcum, cellulose, glucose, sucrose, magnesium carbonate, and the like; solvents; dispersion media; coatings; antibacterial and antifungal agents; isotonic and absorption delaying agents; or any other inactive ingredient. Selection of a pharmacologically acceptable carrier can depend on the mode of administration. Except insofar as any pharmacologically acceptable carrier is incompatible with the active ingredient, its use in pharmaceutically acceptable compositions is contemplated. Non-limiting examples of specific uses of such pharmaceutical carriers can be found in PHARMACEUTICAL DOSAGE FORMS AND DRUG DELIVERY SYSTEMS (Howard C. Ansel et al., eds., Lippincott Williams & Wilkins Publishers, 7th ed. 1999); REMINGTON: THE SCIENCE AND PRACTICE OF PHARMACY (Alfonso R. Gennaro ed., Lippincott, Williams & Wilkins, 20th ed. 2000); GOODMAN & GILMAN'S THE PHARMACOLOGICAL BASIS OF THERAPEUTICS (Joel G. Hardman et al., eds., McGraw-Hill Professional, 10th ed. 2001); and HANDBOOK OF PHARMACEUTICAL EXCIPIENTS (Raymond C. Rowe et al., APhA Publications, 4th edition 2003).

An immunogenic composition disclosed herein may further comprise one or more pharmaceutically acceptable components (or pharmaceutical components), including, without limitation, buffers, preservatives, tonicity adjusters, salts, antioxidants, osmolality adjusting agents, physiological substances, pharmacological substances, bulking agents, emulsifying agents, wetting agents, sweetening or flavoring agents, and the like. Various buffers and means for adjusting pH can be used to prepare a pharmaceutical composition disclosed in the present specification, provided that the resulting preparation is pharmaceutically acceptable. Such buffers include, without limitation, acetate buffers, citrate buffers, phosphate buffers, neutral buffered saline, phosphate buffered saline and borate buffers. It is understood that acids or bases can be used to adjust the pH of a composition as needed. Pharmaceutically acceptable antioxidants include, without limitation, sodium metabisulfite, sodium thiosulfate, acetylcysteine, butylated hydroxyanisole and butylated hydroxytoluene. Useful preservatives include, without limitation, benzalkonium chloride, chlorobutanol, thimerosal, phenylmercuric acetate, phenylmercuric nitrate, a stabilized oxy chloro composition, such as, e.g., PURITE® and chelants, such as, e.g., DTPA or DTPA-bisamide, calcium DTPA, and CaNaDTPA-bisamide. Tonicity adjustors useful in a pharmaceutical composition include, without limitation, salts such as, e.g., sodium chloride, potassium chloride, mannitol or glycerin and other pharmaceutically acceptable tonicity adjustor. The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. It is understood that these and other substances known in the art of pharmacology can be included in a pharmaceutical composition.

Aspects of the present disclosure comprise, in part, a method for producing α-HIV antibodies. Generally, α-HIV antibodies disclosed herein are ones that can bind an epitope present on a HIV virion, an epitope derived from an HIV virus, an epitope produced or altered by an HIV virus, and/or an epitope produced or altered by a cell infected by the HIV virus or expressing either the whole or part of the HIV virus genetic code. In aspects of this embodiment, a method disclosed herein produces α-HIV antibodies that bind to an epitope present in SEQ ID NO: 1, SEQ ID NO: 2, SEQ ID NO: 3, OR SEQ ID NO: 4. Specific protocols for making and using antibodies as well as detecting, and measuring antibody binding specificity, binding affinity and binding avidity are known in the art. See, e.g., ANTIBODIES: A LABORATORY MANUAL (Edward Harlow & David Lane, eds., Cold Spring Harbor Laboratory Press, 2nd ed. 1998a); and USING ANTIBODIES: A LABORATORY MANUAL:PORTABLE PROTOCOL No. I (Edward Harlow & David Lane, Cold Spring Harbor Laboratory Press, 1998b); Molecular Cloning, A Laboratory Manual, 2001; and Current Protocols in Molecular Biology, 2004; David Anderson et al., Therapeutic Polypeptides, Nucleic Acids Encoding Same, and Methods of Use, U.S. Pat. No. 7,034,132 (Apr. 25, 2005); and Beatriz M. Carreno et al., Antibodies Against CTLA4, U.S. Pat. No. 7,034,121 (Apr. 25, 2006).

As a non-limiting example, α-HIV polyclonal antibodies disclosed herein can be produced by injecting an animal, such as, e.g., a rabbit, a goat, a mouse or another mammal, with one or more injections of a composition disclosed in the present specification. As another non-limiting example, α-HIV polyclonal antibodies disclosed herein can be produced by injecting an egg, such as, e.g., a chicken egg, with one or more injections of a composition disclosed in the present specification. The antibody titer in the immunized animal can be monitored over time by standard techniques, such as with an enzyme linked immunosorbent assay (ELISA) using immobilized antigen or a cell-based activity assay. If desired, polyclonal antibodies for an α-HIV antibody disclosed herein can be isolated from the mammal (e.g., from the blood) and further purified by known techniques, such as protein A affinity chromatography to obtain the IgG fraction, or by affinity purification against the peptide used for producing the antibodies.

As another non-limiting example, α-HIV monoclonal antibody disclosed herein can be produced using a hybridoma method. See e.g., Chapter 6 Monoclonal Antibodies, pp. 196-244, Harlow & Lane, supra, 1998a; and Chapter 7 Growing Hybridomas, pp. 245-282, Harlow & Lane, supra, 1998a; and Goding, pp. 59-103, Monoclonal Antibodies: Principles and Practice, Academic Press, (1986). In this method, a host animal, such as, e.g., a mouse, a hamster, or another appropriate host animal, is typically exposed to one or more injections of a HIV antigen disclosed herein to elicit lymphocytes that produce or are capable of producing α-HIV antibodies disclosed herein. The antibody titer in the immunized animal can be monitored over time by standard techniques, such as with an enzyme linked immunosorbent assay (ELISA) using immobilized antigen or a cell-based activity assay.

Alternatively, the lymphocytes can be immunized in vitro using a suitable cell culture line. At an appropriate time after immunization, e.g., when the antibody titers are highest, antibody-producing cells are isolated from the animal. Generally, either peripheral blood lymphocytes are used, if cells of human origin are desired, or spleen cells or lymph node cells are used, if non-human mammalian sources are desired. The isolated antibody-producing cells are fused with an immortal cell line using a suitable fusing agent, such as polyethylene glycol, to form a hybridoma cell. Immortalized cell lines are usually transformed mammalian cells, particularly myeloma cells of rodent, bovine and human origin. Typically, a murine myeloma cell line is fused with splenocytes harvested from an appropriately immunized mouse to produce the hybridoma. Preferred immortal cell lines are mouse myeloma cell lines that are sensitive to culture medium containing hypoxanthine, aminopterin and thymidine (HAT). Any of a number of myeloma cell lines can be used as a fusion partner according to standard techniques, e.g., the P3-NS1/1-Ag4-1, P3-x63-Ag8.653 or Sp2/O-Ag14 myeloma lines. Hybridoma cells resulting from the fusion are then selected using HAT medium, which kills unfused and unproductively fused myeloma cells (unfused splenocytes die after several days in culture because they are not transformed). The culture medium in which the hybridoma cells are grown can then be assayed for the presence of α-HIV monoclonal antibodies disclosed herein. For example, hybridoma supernatants can be screened using α-HIV positive media in an immunoprecipitation assay, in vitro binding assay, such as, e.g., a radioimmunoassay (RIA) or an enzyme-linked immunoabsorbent assay (ELISA), or in a cell-based activity assay. Such techniques and assays are known in the art. See e.g., Chapter 11 Immunoprecipitation, pp. 421-470, Harlow & Lane, supra, 1998a; Chapter 12 Immunoblotting, pp. 471-510, Harlow & Lane, supra, 1998a; Chapter 14 Immunoassays, pp. 553-612, Harlow & Lane, supra, 1998a. Additional studies can then be done to determine whether the antibody is also unreactive to a different epitope present in a protein. The binding affinity of an α-HIV monoclonal antibody can also be determined, e.g., by Scatchard analysis. See, e.g., Peter J. Munson and David Rodbard, Ligand: A Versatile Computerized Approach For Characterization of Ligand-Binding Systems, 107(1) Anal. Biochem. 220-239 (1980). After the desired hybridoma cells are identified, limiting dilution procedures are used to isolate clones originating from a single cell until a clonal cell line expressing the desired monoclonal antibody is obtained. Those antibodies that are sufficiently selective for the desired epitope and that bind with sufficiently high avidity are chosen for further characterization and study.

Another alternative for preparing an α-HIV monoclonal antibody disclosed herein is by screening a recombinant combinatorial immunoglobulin library, such as, e.g., an antibody phage display library, with a HIV antigen disclosed herein and isolate immunoglobulin library members that bind to the desired epitope. Kits for generating and screening phage display libraries are commercially available, such as, e.g., the Recombinant Phage Antibody System (Amersham GE Healthcare, Piscataway, N.J.); and the SurfZAP™ Phage Display Kit (Stratagene, La Jolla, Calif.). Additionally, examples of methods and reagents useful in generating and screening antibody display library can be found in, for example, Ladner et al. U.S. Pat. No. 5,223,409; Borrebaeck et al. U.S. Pat. No. 5,712,089; Griffiths et al. U.S. Pat. No. 5,885,793; Griffiths et al. U.S. Pat. No. 5,962,255; McCafferty et al. U.S. Pat. No. 5,969,108; Griffiths et al. U.S. Pat. No. 6,010,884; Jespers et al. U.S. Pat. No. 6,017,732; Borrebaeck et al. U.S. Pat. No. 6,027,930; Johnson et al. U.S. Pat. No. 6,140,471; McCafferty et al. U.S. Pat. No. 6,172,197, each of which is hereby incorporated by reference in its entirety.

Aspects of the present disclosure comprise, in part, isolating an α-HIV antibody disclosed herein from a sample. A sample refers to any biological matter that contains or potentially contains at least one α-HIV antibody disclosed herein, including, without limitation, blood, plasma, serum, lymph fluid, or α-HIV antibody-producing cell, such as, e.g., CD8 cells, CTL cells, helper T-cells and/or B-cells. The sample collected is based, in part, on the type of antibody to be isolated. For example, when isolating α-HIV polyclonal antibodies, an appropriate sample can be a blood sample, whereas when isolating α-HIV monoclonal antibodies, an appropriate sample can be an α-HIV antibody-producing cell such as a spleen cell or hybridoma. A variety of known methods can be used for collecting from an individual a sample containing the α-HIV antibody or α-HIV antibody-producing cell, see, e.g., Harlow & Lane, supra, 1998a; and Harlow & Lane, supra, 1998b. Methods of isolating such α-HIV antibodies, are well known to those skilled in the art. See, e.g., Harlow and Lane, supra, 1998a; and Harlow and Lane, supra, 1998b. For example, α-HIV polyclonal antibodies can be isolated from the sample by well known techniques, such as, e.g., affinity chromatography using protein A or protein G, which provide primarily the IgG fraction of immune serum. Subsequently, or alternatively, a specific HIV antigen disclosed herein can be immobilized on a column or magnetic beads to purify the α-HIV polyclonal antibodies by immunoaffinity chromatography. An α-HIV monoclonal antibody disclosed herein can be isolated from the culture medium or ascites fluid by conventional immunoglobulin purification procedures such as, e.g., protein A-Sepharose, hydroxylapatite chromatography, gel electrophoresis, dialysis, or affinity chromatography.

In an embodiment, a method of producing an α-HIV antibody disclosed herein comprises the steps (a) administering to an individual an immunogenic composition comprising a HIV antigen disclosed herein; (b) collecting from the individual a sample containing an α-HIV antibody or α-HIV antibody-producing cell; and (c) isolating the α-HIV antibody component from the sample. In an aspect of this embodiment, the α-HIV antibody disclosed herein is a polyclonal antibody. In another aspect of this embodiment, an α-HIV antibody disclosed herein is a monoclonal antibody. In a further aspect of this embodiment, an α-HIV monoclonal antibody disclosed herein is an IgG subtype.

Aspects of the present disclosure comprise, in part, an α-HIV antibody. An α-HIV antibody disclosed herein may selectively bind an epitope present on a HIV virion, an epitope derived from an HIV virus, an epitope produced or altered by an HIV virus, and/or an epitope produced or altered by a cell infected by the HIV virus or expressing either the whole or part of the HIV virus genetic code. An antibody refers to a molecule generated by an immune system that was made in response to a particular antigen that specifically binds to that antigen, and includes both naturally occurring antibodies and non-naturally occurring antibodies. An antibody can be a polyclonal antibody, a monoclonal antibody, a dimer, a multimer, a multispecific antibody, a humanized antibody, a chimeric antibody, bi-functional antibody, a cell-associated antibody like an Ig receptor, a linear antibody, a diabody, or a minibody, so long as the fragment exhibits the desired biological activity, and single chain derivatives of the same. An antibody can be a full-length immunoglobulin molecule comprising the VH and VL domains, as well as a light chain constant domain (CL) and heavy chain constant domains, CH1, CH2 and CH3, or an immunologically active fragment of a full-length immunoglobulin molecule, such as, e.g., a single domain antibody (sdAb), a single-chain variable fragment (scFv), a Fab fragment, a F(ab')2 fragment, a Fc fragment, a Fd fragment, a Fv fragment. An antibody can be derived from any vertebrate species (e.g., human, goat, horse, donkey, murine, rat, rabbit, or chicken), and can be of any type (e.g., IgG, IgE, IgM, IgD, and IgA), class (e.g., IgA, IgD, IgE, IgG, and IgM) or subclass (IgG1, IgG2, IgG3, IgG4, IgA1 and IgA2). For general disclosure on the structure of naturally occurring antibodies, non-naturally occurring antibodies, and antigenic compound-binding fragments thereof, see, e.g., Pluckthun in The Pharmacology of Monoclonal Antibodies, vol. 113, Rosenburg and Moore eds., Springer-Verlag, New York, pp. 269-315 (1994); Borrabeck, Antibody Engineering, 2d ed. (Oxford University Press 1995), each of which is hereby incorporated by reference in its entirety.

Naturally-occurring antibodies are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain (VH) followed by a number of constant domains. Each light chain has a variable domain at one end (VL) and a constant domain at its other end. The constant domain of the light chain is aligned with the first constant domain of the heavy chain, and the light-chain variable domain is aligned with the variable domain of the heavy chain. Particular amino acid residues are believed to form an interface between the light chain and heavy chain variable domains.

The complete antigen-recognition and antigen-binding site is contained within the variable domains of the antibody, i.e., the Fv fragment. This fragment includes a dimer of one heavy chain variable domain (VH) and one light chain variable domain (VL) in tight, non-covalent association. Each domain comprises four framework regions (FR), which largely adopting a β-sheet configuration, connected by three hypervariable regions, which form loops connecting, and in some cases form part of, the β-sheet structure. Each hypervariable region comprises an amino acid sequence corresponding to a complementarity determining region (CDRs). Collectively, it the three-dimensional configuration of the six CDR regions that define an antigen-binding site on the surface of the VH-VL dimmer that confers antigen-binding specificity. See e.g., Cyrus Chothia, et al., Conformations of Immunoglobulin Hypervariable Regions, Nature 342(6252): 877-883 (1989); Elvin A. Kabat, et al Sequences of Proteins of Immunological Interest, 5th Ed. Public Health Service, National Institutes of Health, Bethesda, Md. (1991), each of which is incorporated by reference in its entirety. The constant domains of the antibody are not involved directly in binding an antibody to an antigen, but exhibit various effector functions, such as participation of the antibody in antibody dependent cellular cytotoxicity.

A target antigen generally has one or more binding sites, also called epitopes, which are recognized by the CDR-formed antigen-binding site. An "epitope" is synonymous with "antigenic determinant" and refers to the site on a target antigen, such as, e.g., a peptide, polysaccharide or lipid-containing molecule, capable of specific binding to an immunoglobulin or T-cell receptor or otherwise interacting with a molecule. Each antibody that specifically binds to a different epitope has a different structure. Thus, one antigen may have more than one corresponding antibody.

Polyclonal antibodies refer to a heterogeneous population of antibody molecules that contain at least two species of antibody capable of binding to a particular antigen. By definition, a polyclonal antibody includes two different antibodies that bind to at least two different epitopes. Monoclonal antibodies refer to a substantially homogeneous population of antibody molecules that contain only one species of antibody capable of binding a particular antigen i.e., the individual antibodies comprising the population are identical except for possible naturally occurring mutations that may be present in minor amounts. By definition, a monoclonal antibody binds to a single epitope. Monoclonal antibodies are highly specific, being directed against a single antigenic site. Furthermore, in contrast to polyclonal antibodies, each monoclonal antibody is directed against a single determinant on the antigen. In addition to their specificity, the monoclonal antibodies are advantageous in that they may be synthesized uncontaminated by other antibodies. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present disclosure may be made by the hybridoma method first described by Kohler et al (1975) Nature 256:495, or may be made by recombinant DNA methods (see for example: U.S. Pat. No. 4,816,567; U.S. Pat. No. 5,807,715). The monoclonal antibodies may also be isolated from phage antibody libraries using the techniques described in Clackson et al (1991) Nature, 352: 624-628; Marks et al (1991) J. Mol. Biol., 222:581-597; for example.

Thus, in an embodiment, an α-HIV antibody comprises a heavy chain variable domain ($V_H$) and/or a light chain variable domain ($V_L$) that selectively binds to an epitope disclosed herein. In aspects of this embodiment, n α-HIV antibody comprises a heavy chain variable domain ($V_H$) and/or a light chain variable domain ($V_L$) that selectively binds to an epitope present in SEQ ID NO: 1, SEQ ID NO: 2, SEQ ID NO: 3, and/or SEQ ID NO: 4. In aspects of this embodiment, an α-HIV antibody specifically binds an epitope present in SEQ ID NO: 1, SEQ ID NO: 2, SEQ ID NO: 3, and/or SEQ ID NO: 4. In aspects of this embodiment, n α-HIV antibody comprises a heavy chain variable domain ($V_H$) and/or a light chain variable domain ($V_L$) that selectively binds to an epitope having an amino acid identity of, e.g., at least about 70%, at least about 75%, at least about 80%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99%, relative to SEQ ID NOs: 1-4. In other aspects of this embodiment, n α-HIV antibody comprises a heavy chain variable domain ($V_H$) and/or a light chain variable domain ($V_L$) that selectively binds to an epitope having an amino acid identity in the range of, e.g., about 75% to about 100%, about 80% to about 100%, about 85% to about 100%, about 90% to about 100%, about 95% to about 100%, about 75% to about 99%, about 80% to about 99%, about 85% to about 99%, about 90% to about 99%, about 95% to about 99%, about 75% to about 97%, about 80% to about 97%, about 85% to about 97%, about 90% to about 97%, or about 95% to about 97%, relative to SEQ ID NOs: 1-4. In yet other aspects of this embodiment, n α-HIV antibody comprises a heavy chain variable domain ($V_H$) and/or a light chain variable domain ($V_L$) that selectively binds to an epitope having, e.g., at least 1, at least 2, at least 3, or at least 4, contiguous and/or non-contiguous amino acid deletions, additions, and/or substitutions relative to SEQ ID NOs: 1-4; or at most 1, at most 2, at most 3, at most 4, contiguous and/or non-contiguous amino acid deletions, additions, and/or substitutions relative to SEQ ID NOs: 1-4. In still other aspects of this embodiment, n α-HIV antibody comprises a heavy chain variable domain ($V_H$) and/or a light chain variable domain ($V_L$) that selectively binds to an epitope having, e.g., about 1 to about 2, about 1 to about 3, about 1 to about 4, about 2 to about 3, about 2 to about 4, or about 3 to about 4 contiguous and/or non-contiguous amino acid deletions, additions, and/or substitutions relative to SEQ ID NOs: 1-4.

In other aspects of this embodiment, a heavy chain variable domain ($V_H$) comprises SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, or SEQ ID NO: 27. In yet other aspects of this embodiment, a heavy chain variable domain ($V_H$) disclosed herein comprises a sequence having an amino acid identity of, e.g., at least about 70%, at least about 75%, at least about 80%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99%, relative to any one of SEQ ID NOs: 5-27. In still other aspects of this embodiment, a heavy chain variable domain ($V_H$) disclosed herein comprises a sequence having an amino acid identity in the range of, e.g., about 75% to about 100%, about 80% to about 100%, about 85% to about 100%, about 90% to about 100%, about 95% to about 100%, about 75% to about 99%, about 80% to about 99%, about 85% to about 99%, about 90% to about 99%, about 95% to about 99%, about 75% to about 97%, about 80% to about 97%, about 85% to about 97%, about 90% to about 97%, or about 95% to about 97%, relative to any one of SEQ ID NOs: 5-27.

In other aspects of this embodiment, a heavy chain variable domain ($V_H$) disclosed herein comprises a sequence having, e.g., at least 1, at least 2, at least 3, at least 4, at least 5, at least 6, at least 7, at least 8, at least 9, at least 10, at least 11, at least 12, at least 13, at least 14, or at least 15 contiguous amino acid deletions, additions, and/or substitutions relative to any one of SEQ ID NOs: 5-27; or at most 1, at most 2, at most 3, at most 4, at most 5, at most 6, at most 7, at most 8, at most 9, at most 10, at most 11, at most 12, at most 13, at most 14, or at most 15 contiguous amino acid deletions, additions, and/or substitutions relative to any one of SEQ ID NOs: 5-27. In yet other aspects of this embodiment, a heavy chain variable domain ($V_H$) disclosed herein comprises a sequence having an, e.g., at least 1, at least 2, at least 3, at least 4, at least 5, at least 6, at least 7, at least 8, at least 9, at least 10, at least 11, at least 12, at least 13, at least 14, or at least 15 non-contiguous amino acid deletions, additions, and/or substitutions relative to any one of SEQ ID NOs: 5-27; or at most 1, at most 2, at most 3, at most 4, at most 5, at most 6, at most 7, at most 8, at most 9, at most 10, at most 11, at most 12, at most 13, at most 14, or at most 15 non-contiguous amino acid deletions, additions, and/or substitutions relative to any one of SEQ ID NOs: 5-27.

In another embodiment, an α-HIV antibody comprises a heavy chain variable domain ($V_H$) CDR1 region, a CDR2 region, a CDR3 region, or any combination thereof that selectively binds to an epitope disclosed herein. In aspects of this embodiment, an α-HIV antibody comprises a heavy chain variable domain ($V_H$) CDR1 region, a CDR2 region, a CDR3 region, or any combination thereof that selectively binds to an epitope present in SEQ ID NO: 1, SEQ ID NO: 2, SEQ ID NO: 3, and/or SEQ ID NO: 4. In aspects of this embodiment, an α-HIV antibody comprises a heavy chain variable domain ($V_H$) CDR1 region, a CDR2 region, a CDR3 region, or any combination thereof that selectively binds to an epitope present in sequence having an amino acid identity of, e.g., at least about 70%, at least about 75%, at least about 80%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99%, relative to SEQ ID NOs: 1-4. In other aspects of this embodiment, an α-HIV antibody comprises a heavy chain variable domain ($V_H$) CDR1 region, a CDR2 region, a CDR3 region, or any combination thereof that selectively binds to an epitope present in sequence having an amino acid identity in the range of, e.g., about 75% to about 100%, about 80% to about 100%, about 85% to about 100%, about 90% to about 100%, about 95% to about 100%, about 75% to about 99%, about 80% to about 99%, about 85% to about 99%, about 90% to about 99%, about 95% to about 99%, about 75% to about 97%, about 80% to about 97%, about 85% to about 97%, about 90% to about 97%, or about 95% to about 97%, relative to SEQ ID NOs: 1-4. In yet other aspects of this embodiment, an α-HIV antibody comprises a heavy chain variable domain ($V_H$) CDR1 region, a CDR2 region, a CDR3 region, or any combination thereof that selectively binds to an epitope present in sequence having, e.g., at least 1, at least 2, at least 3, or at least 4, contiguous and/or non-contiguous amino acid deletions, additions, and/or substitutions relative to SEQ ID NOs: 1-4; or at most 1, at most 2, at most 3, at most 4, contiguous and/or non-contiguous amino acid deletions, additions, and/or substitutions relative to SEQ ID NOs: 1-4. In still other aspects of this embodiment, an α-HIV antibody comprises a heavy chain variable domain ($V_H$) CDR1 region, a CDR2 region, a CDR3 region, or any combination thereof that selectively binds to an epitope present in sequence having, e.g., about 1 to about 2, about 1 to about 3, about 1 to about 4, about 2 to about 3, about 2 to about 4, or about 3 to about 4 contiguous and/or non-contiguous amino acid deletions, additions, and/or substitutions relative to SEQ ID NOs: 1-4.

In an aspect of this embodiment, a heavy chain variable domain ($V_H$) comprises a heavy chain variable domain ($V_H$) CDR1 region comprising SEQ ID NO: 28. In aspects of this embodiment, a heavy chain variable domain ($V_H$) CDR1 region disclosed herein has an amino acid identity of, e.g., at least about 70%, at least about 75%, at least about 80%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99%, relative to SEQ ID NO: 28. In other aspects of this embodiment, a heavy chain variable domain ($V_H$) CDR1 region disclosed herein has an amino acid identity in the range of, e.g., about 75% to about 100%, about 80% to about 100%, about 85% to about 100%, about 90% to about 100%, about 95% to about 100%, about 75% to about 99%, about 80% to about 99%, about 85% to about 99%, about 90% to about 99%, about 95% to about 99%, about 75% to about 97%, about 80% to about 97%, about 85% to about 97%, about 90% to about 97%, or about 95% to about 97%, relative to SEQ ID NO: 28. In yet other aspects of this embodiment, a heavy chain variable domain ($V_H$) CDR1 region disclosed herein has, e.g., at least 1, at least 2, at least 3, or at least 4, contiguous and/or non-contiguous amino acid deletions, additions, and/or substitutions relative to SEQ ID NO: 28; or at most 1, at most 2, at most 3, at most 4, contiguous and/or non-contiguous amino acid deletions, additions, and/or substitutions relative to SEQ ID NO: 28. In still other aspects of this embodiment, a heavy chain variable domain ($V_H$) CDR1 region disclosed herein has, e.g., about 1 to about 2, about 1 to about 3, about 1 to about 4, about 2 to about 3, about 2 to about 4, or about 3 to about 4 contiguous and/or non-contiguous amino acid deletions, additions, and/or substitutions relative to SEQ ID NO: 28.

In another aspect of this embodiment, a heavy chain variable domain ($V_H$) comprises a heavy chain variable domain ($V_H$) CDR2 region comprising SEQ ID NO: 29. In aspects of this embodiment, a heavy chain variable domain ($V_H$) CDR2 region disclosed herein has an amino acid identity of, e.g., at least about 70%, at least about 75%, at least about 80%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99%, relative to SEQ ID NO: 29. In other aspects of this embodiment, a heavy chain variable domain ($V_H$) CDR2 region disclosed herein has an amino acid identity in the range of, e.g., about 75% to about 100%, about 80% to about 100%, about 85% to about 100%, about 90% to about 100%, about 95% to about 100%, about 75% to about 99%, about 80% to about 99%, about 85% to about 99%, about 90% to about 99%, about 95% to about 99%, about 75% to about 97%, about 80% to about 97%, about 85% to about 97%, about 90% to about 97%, or about 95% to about 97%, relative to SEQ ID NO: 29. In yet other aspects of this embodiment, a heavy chain variable domain ($V_H$) CDR2 region disclosed herein has, e.g., at least 1, at least 2, at least 3, or at least 4, contiguous and/or non-contiguous amino acid deletions, additions, and/or substitutions relative to SEQ ID NO: 29; or at most 1, at most 2, at most 3, at most 4, contiguous and/or non-contiguous amino acid deletions, additions, and/or substitutions relative to SEQ ID NO: 29. In still other aspects of this embodiment, a heavy chain variable domain ($V_H$) CDR2 region disclosed herein has, e.g., about 1 to about 2, about 1 to about 3, about 1 to about 4, about 2 to about 3, about 2 to about 4, or about 3 to about 4 contiguous and/or non-contiguous amino acid deletions, additions, and/or substitutions relative to SEQ ID NO: 29.

In yet another aspect of this embodiment, a heavy chain variable domain ($V_H$) comprises a heavy chain variable domain ($V_H$) CDR3 region comprising SEQ ID NO: 30. In aspects of this embodiment, a heavy chain variable domain ($V_H$) CDR3 region disclosed herein has an amino acid identity of, e.g., at least about 70%, at least about 75%, at least about 80%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99%, relative to SEQ ID NO: 30. In other aspects of this embodiment, a heavy chain variable domain ($V_H$) CDR3 region disclosed herein has an amino acid identity in the range of, e.g., about 75% to about 100%, about 80% to about 100%, about 85% to about 100%, about 90% to about 100%, about 95% to about 100%, about 75% to about 99%, about 80% to about 99%, about 85% to about 99%, about 90% to about 99%, about 95% to about 99%, about 75% to about 97%, about 80% to about 97%, about 85% to about 97%, about 90% to about 97%, or about 95% to about 97%, relative to SEQ ID NO: 30. In yet other aspects of this embodiment, a heavy chain variable domain ($V_H$) CDR3 region disclosed herein has, e.g., at least 1, at least 2, at least 3, or at least 4, contiguous and/or non-contiguous amino acid deletions, additions, and/or substitutions relative to SEQ ID NO: 30; or at most 1, at most 2, at most 3, at most 4, contiguous and/or non-contiguous amino acid deletions, additions, and/or substitutions relative to SEQ ID NO: 30. In still other aspects of this embodiment, a heavy chain variable domain ($V_H$) CDR3 region disclosed herein has, e.g., about 1 to about 2, about 1 to about 3, about 1 to about 4, about 2 to about 3, about 2 to about 4, or about 3 to about 4 contiguous and/or non-contiguous amino acid deletions, additions, and/or substitutions relative to SEQ ID NO: 30.

In another embodiment, an α-HIV antibody comprises a light chain variable domain ($V_L$) CDR1 region, a CDR2 region, a CDR3 region, or any combination thereof that selectively binds an epitope disclosed herein. In aspects of this embodiment, an α-HIV antibody comprises a light chain variable domain ($V_L$) CDR1 region, a CDR2 region, a CDR3 region, or any combination thereof that selectively binds an epitope present in SEQ ID NO: 1, SEQ ID NO: 2, SEQ ID NO: 3, and/or SEQ ID NO: 4.

In other aspects of this embodiment, a light chain variable domain ($V_L$) comprises SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, or SEQ ID NO: 42. In yet other aspects of this embodiment, a light chain variable domain ($V_L$) disclosed herein comprises a sequence having an amino acid identity of, e.g., at least about 70%, at least about 75%, at least about 80%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99%, relative to any one of SEQ ID NOs: 31-42. In still other aspects of this embodiment, a light chain variable domain ($V_L$) disclosed herein comprises a sequence having an amino acid identity in the range of, e.g., about 75% to about 100%, about 80% to about 100%, about 85% to about 100%, about 90% to about 100%, about 95% to about 100%, about 75% to about 99%, about 80% to about 99%, about 85% to about 99%, about 90% to about 99%, about 95% to about 99%, about 75% to about 97%, about 80% to about 97%, about 85% to about 97%, about 90% to about 97%, or about 95% to about 97%, relative to any one of SEQ ID NOs: 31-42.

In other aspects of this embodiment, a light chain variable domain ($V_L$) disclosed herein comprises a sequence having, e.g., at least 1, at least 2, at least 3, at least 4, at least 5, at least 6, at least 7, at least 8, at least 9, at least 10, at least 11, at least 12, at least 13, at least 14, or at least 15 contiguous amino acid deletions, additions, and/or substitutions relative to any one of SEQ ID NOs: 31-42; or at most 1, at most 2, at most 3, at most 4, at most 5, at most 6, at most 7, at most 8, at most 9, at most 10, at most 11, at most 12, at most 13, at most 14, or at most 15 contiguous amino acid deletions, additions, and/or substitutions relative to any one of SEQ ID NOs: 31-42. In yet other aspects of this embodiment, a light chain variable domain ($V_L$) disclosed herein comprises a sequence having an, e.g., at least 1, at least 2, at least 3, at least 4, at least 5, at least 6, at least 7, at least 8, at least 9, at least 10, at least 11, at least 12, at least 13, at least 14, or at least 15 non-contiguous amino acid deletions, additions, and/or substitutions relative to any one of SEQ ID NOs: 31-42; or at most 1, at most 2, at most 3, at most 4, at most 5, at most 6, at most 7, at most 8, at most 9, at most 10, at most 11, at most 12, at most 13, at most 14, or at most 15 non-contiguous amino acid deletions, additions, and/or substitutions relative to any one of SEQ ID NOs: 31-42.

In another embodiment, an α-HIV antibody comprises a light chain variable domain ($V_L$) CDR1 region, a CDR2 region, a CDR3 region, or any combination thereof that selectively binds to an epitope disclosed herein. In aspects of this embodiment, an α-HIV antibody comprises a light chain variable domain ($V_L$) CDR1 region, a CDR2 region, a CDR3 region, or any combination thereof that selectively binds to an epitope present in SEQ ID NO: 1, SEQ ID NO: 2, SEQ ID NO: 3, and/or SEQ ID NO: 4. In aspects of this embodiment, an α-HIV antibody comprises a light chain variable domain ($V_L$) CDR1 region, a CDR2 region, a CDR3 region, or any combination thereof that selectively binds to an epitope present in sequence having an amino acid identity of, e.g., at least about 70%, at least about 75%, at least about 80%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99%, relative to SEQ ID NOs: 1-4. In other aspects of this embodiment, an α-HIV antibody comprises a light chain variable domain ($V_L$) CDR1 region, a CDR2 region, a CDR3 region, or any combination thereof that selectively binds to an epitope present in sequence having an amino acid identity in the range of, e.g., about 75% to about 100%, about 80% to about 100%, about 85% to about 100%, about 90% to about 100%, about 95% to about 100%, about 75% to about 99%, about 80% to about 99%, about 85% to about 99%, about 90% to about 99%, about 95% to about 99%, about 75% to about 97%, about 80% to about 97%, about 85% to about 97%, about 90% to about 97%, or about 95% to about 97%, relative to SEQ ID NOs: 1-4. In yet other aspects of this embodiment, an α-HIV antibody comprises a light chain variable domain ($V_L$) CDR1 region, a CDR2 region, a CDR3 region, or any combination thereof that selectively binds to an epitope present in sequence having, e.g., at least 1, at least 2, at least 3, or at least 4, contiguous and/or non-contiguous amino acid deletions, additions, and/or substitutions relative to SEQ ID NOs: 1-4; or at most 1, at most 2, at most 3, at most 4, contiguous and/or non-contiguous amino acid deletions, additions, and/or substitutions relative to SEQ ID NOs: 1-4. In still other aspects of this embodiment, an α-HIV antibody comprises a light chain variable domain ($V_L$) CDR1 region, a CDR2 region, a CDR3 region, or any combination thereof that selectively binds to an epitope present in sequence having, e.g., about 1 to about 2, about 1 to about 3, about 1 to about 4, about 2 to about 3, about 2 to about 4, or about 3 to about 4 contiguous and/or non-contiguous amino acid deletions, additions, and/or substitutions relative to SEQ ID NOs: 1-4.

In an aspect of this embodiment, a light chain variable domain ($V_L$) comprises a light chain variable domain ($V_L$) CDR1 region comprising SEQ ID NO: 43. In aspects of this embodiment, a light chain variable domain ($V_L$) CDR1 region disclosed herein has an amino acid identity of, e.g., at least about 70%, at least about 75%, at least about 80%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99%, relative to SEQ ID NO: 43. In other aspects of this embodiment, a light chain variable domain ($V_L$) CDR1 region disclosed herein has an amino acid identity in the range of, e.g., about 75% to about 100%, about 80% to about 100%, about 85% to about 100%, about 90% to about 100%, about 95% to about 100%, about 75% to about 99%, about 80% to about 99%, about 85% to about 99%, about 90% to about 99%, about 95% to about 99%, about 75% to about 97%, about 80% to about 97%, about 85% to about 97%, about 90% to about 97%, or about 95% to about 97%, relative to SEQ ID NO: 43. In yet other aspects of this embodiment, a light chain variable domain ($V_L$) CDR1 region disclosed herein has, e.g., at least 1, at least 2, at least 3, or at least 4, contiguous and/or non-contiguous amino acid deletions, additions, and/or substitutions relative to SEQ ID NO: 43; or at most 1, at most 2, at most 3, at most 4, contiguous and/or non-contiguous amino acid deletions, additions, and/or substitutions relative to SEQ ID NO: 43. In still other aspects of this embodiment, a light chain variable domain ($V_L$) CDR1 region disclosed herein has, e.g., about 1 to about 2, about 1 to about 3, about 1 to about 4, about 2 to about 3, about 2 to about 4, or about 3 to about 4 contiguous and/or non-contiguous amino acid deletions, additions, and/or substitutions relative to SEQ ID NO: 43.

In another aspect of this embodiment, a light chain variable domain ($V_L$) comprises a light chain variable domain ($V_L$) CDR2 region comprising SEQ ID NO: 44. In aspects of this embodiment, a light chain variable domain ($V_L$) CDR2 region disclosed herein has an amino acid identity of, e.g., at least about 70%, at least about 75%, at least about 80%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99%, relative to SEQ ID NO: 44. In other aspects of this embodiment, a light chain variable domain ($V_L$) CDR2 region disclosed herein has an amino acid identity in the range of, e.g., about 75% to about 100%, about 80% to about 100%, about 85% to about 100%, about 90% to about 100%, about 95% to about 100%, about 75% to about 99%, about 80% to about 99%, about 85% to about 99%, about 90% to about 99%, about 95% to about 99%, about 75% to about 97%, about 80% to about 97%, about 85% to about 97%, about 90% to about 97%, or about 95% to about 97%, relative to SEQ ID NO: 44. In yet other aspects of this embodiment, a light chain variable domain ($V_L$) CDR2 region disclosed herein has, e.g., at least 1, at least 2, at least 3, or at least 4, contiguous and/or non-contiguous amino acid deletions, additions, and/or substitutions relative to SEQ ID NO: 44; or at most 1, at most 2, at most 3, at most 4, contiguous and/or non-contiguous amino acid deletions, additions, and/or substitutions relative to SEQ ID NO: 44. In still other aspects of this embodiment, a light chain variable domain ($V_L$) CDR2 region disclosed herein has, e.g., about 1 to about 2, about 1 to about 3, about 1 to about 4, about 2 to about 3, about 2 to about 4, or about 3 to about 4 contiguous and/or non-contiguous amino acid deletions, additions, and/or substitutions relative to SEQ ID NO: 44.

In yet another aspect of this embodiment, a light chain variable domain ($V_L$) comprises a light chain variable domain ($V_L$) CDR3 region comprising SEQ ID NO: 45. In aspects of this embodiment, a light chain variable domain ($V_L$) CDR3 region disclosed herein has an amino acid identity of, e.g., at least about 70%, at least about 75%, at least about 80%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99%, relative to SEQ ID NO: 45. In other aspects of this embodiment, a light chain variable domain ($V_L$) CDR3 region disclosed herein has an amino acid identity in the range of, e.g., about 75% to about 100%, about 80% to about 100%, about 85% to about 100%, about 90% to about 100%, about 95% to about 100%, about 75% to about 99%, about 80% to about 99%, about 85% to about 99%, about 90% to about 99%, about 95% to about 99%, about 75% to about 97%, about 80% to about 97%, about 85% to about 97%, about 90% to about 97%, or about 95% to about 97%, relative to SEQ ID NO: 45. In yet other aspects of this embodiment, a light chain variable domain ($V_L$) CDR3 region disclosed herein has, e.g., at least 1, at least 2, at least 3, or at least 4, contiguous and/or non-contiguous amino acid deletions, additions, and/or substitutions relative to SEQ ID NO: 45; or at most 1, at most 2, at most 3, at most 4, contiguous and/or non-contiguous amino acid deletions, additions, and/or substitutions relative to SEQ ID NO: 45. In still other aspects of this embodiment, a light chain variable domain ($V_L$) CDR3 region disclosed herein has, e.g., about 1 to about 2, about 1 to about 3, about 1 to about 4, about 2 to about 3, about 2 to about 4, or about 3 to about 4 contiguous and/or non-contiguous amino acid deletions, additions, and/or substitutions relative to SEQ ID NO: 45.

Whether two sequences have high sequence identity (or homology) is routinely calculated using a percentage similarity or identity, terms that are well known in the art. Sequences for a HIV antigen may be compared to SEQ ID NOs: 1-4. Sequences for an α-HIV antibody may be compared to SEQ ID NOs: 5-45. The term "percent (%) amino acid sequence identity" with respect to any of SEQ ID NOs: 1-45 is defined as the percentage of amino acid residues in a candidate sequence that are identical with the amino acid residues in any of SEQ ID NOS: 1-45 amino acid sequence, after aligning the sequences and introducing gaps, if necessary, to achieve the maximum percent sequence identity, and not considering any conservative substitutions as part of the sequence identity. Any of a variety of sequence alignment methods can be used to determine percent identity, including, without limitation, global methods, local methods and hybrid methods, such as, e.g., segment approach methods. Protocols to determine percent identity are routine procedures within the scope of one skilled in the art and from the teaching herein.

Global methods align sequences from the beginning to the end of the molecule and determine the best alignment by adding up scores of individual residue pairs and by imposing gap penalties. Non-limiting methods include, e.g., CLUSTAL W, see, e.g., Julie D. Thompson et al., *CLUSTAL W: Improving the Sensitivity of Progressive Multiple Sequence Alignment Through Sequence Weighting, Position-Specific Gap Penalties and Weight Matrix Choice*, 22(22) Nucleic Acids Research 4673-4680 (1994); and iterative refinement, see, e.g., Osamu Gotoh, *Significant Improvement in Accuracy of Multiple Protein Sequence Alignments by Iterative Refinement as Assessed by Reference to Structural Alignments*, 264(4) J. Mol. Biol. 823-838 (1996).

Local methods align sequences by identifying one or more conserved motifs shared by all of the input sequences. Non-limiting methods include, e.g., Match-box, see, e.g., Eric Depiereux and Ernest Feytmans, *Match-Box: A Fundamentally New Algorithm for the Simultaneous Alignment of Several Protein Sequences*, 8(5) CABIOS 501-509 (1992); Gibbs sampling, see, e.g., C. E. Lawrence et al., *Detecting Subtle Sequence Signals: A Gibbs Sampling Strategy for Multiple Alignment*, 262(5131) Science 208-214 (1993); Align-M, see, e.g., Ivo Van Walle et al., *Align-M—A New Algorithm for Multiple Alignment of Highly Divergent Sequences*, 20(9) Bioinformatics, 1428-1435 (2004).

Hybrid methods combine functional aspects of both global and local alignment methods. Non-limiting methods include, e.g., segment-to-segment comparison, see, e.g., Burkhard Morgenstern et al., *Multiple DNA and Protein Sequence Alignment Based On Segment-To-Segment Comparison*, 93(22) Proc. Natl. Acad. Sci. U.S.A. 12098-12103 (1996); T-Coffee, see, e.g., Cédric Notredame et al., *T-Coffee: A Novel Algorithm for Multiple Sequence Alignment*, 302(1) J. Mol. Biol. 205-217 (2000); MUSCLE, see, e.g., Robert C. Edgar, *MUSCLE: Multiple Sequence Alignment With High Score Accuracy and High Throughput*, 32(5) Nucleic Acids Res. 1792-1797 (2004); and DIALIGN-T, see, e.g., Amarendran R Subramanian et al., *DIALIGN-T: An Improved Algorithm for Segment-Based Multiple Sequence Alignment*, 6(1) BMC Bioinformatics 66 (2005).

The present specification describes various polypeptide variants where one amino acid is substituted for another, such as, e.g., an HIV antigen, a heavy chain variable domain ($V_H$), a light chain variable domain ($V_L$), and a CDR 1, 2, and 3 region. A substitution can be assessed by a variety of factors, such as, e.g., the physic properties of the amino acid being substituted (Table 1) or how the original amino acid would tolerate a substitution (Table 2). The selections of which amino acid can be substituted for another amino acid in a polypeptide are known to a person of ordinary skill in the art.

TABLE 1

Amino Acid Properties

| Property | Amino Acids |
| --- | --- |
| Aliphatic | G, A, I, L, M, P, V |
| Aromatic | F, H, W, Y |
| C-beta branched | I, V, T |
| Hydrophobic | C, F, I, L, M, V, W |
| Small polar | D, N, P |
| Small non-polar | A, C, G, S, T |
| Large polar | E, H, K, Q, R, W, Y |
| Large non-polar | F, I, L, M, V |
| Charged | D, E, H, K, R |
| Uncharged | C, S, T |
| Negative | D, E |
| Positive | H, K, R |
| Acidic | D, E |
| Basic | K, R |
| Amide | N, Q |

TABLE 2

Amino Acid Substitutions

| Amino Acid | Favored Substitution | Neutral Substitutions | Disfavored substitution |
| --- | --- | --- | --- |
| A | G, S, T | C, E, I, K, M, L, P, Q, R, V | D, F, H, N, Y, W |
| C | F, S, Y, W | A, H, I, M, L, T, V | D, E, G, K, N, P, Q, R |
| D | E, N | G, H, K, P, Q, R, S, T | A, C, I, L, |
| E | D, K, Q | A, H, N, P, R, S, T | C, F, G, I, L, M, V, W, Y |
| F | M, L, W, Y | C, I, V | A, D, E, G, H, K, N, P, Q, R, S, T |
| G | A, S | D, K, N, P, Q, R | C, E, F, H, I, L, M, T, V, W, Y |
| H | N, Y | C, D, E, K, Q, R, S, T, W | A, F, G, I, L, M, P, V |
| I | V, L, M | A, C, T, F, Y | D, E, G, H, K, N, P, Q, R, S, W |
| K | Q, E, R | A, D, G, H, M, N, P, S, T | C, F, I, L, V, W, Y |
| L | F, I, M, V | A, C, W, Y | D, E, G, H, K, N, P, Q, R, S, T |
| M | F, I, L, V | A, C, R, Q, K, T, W, Y | D, E, G, H, N, P, S |
| N | D, H, S | E, G, K, Q, R, T | A, C, F, I, L, M, P, V, W, Y |
| P | — | A, D, E, G, K, Q, R, S, T | C, F, H, I, L, M, N, V, W, Y |
| Q | E, K, R | A, D, G, H, M, N, P, S, T | C, F, I, L, V, W, Y |
| R | K, Q | A, D, E, G, H, M, N, P, S, T | C, F, I, L, V, W, Y |
| S | A, N, T | C, D, E, G, H, K, P, Q, R, T | F, I, L, M, V, W, Y |
| T | S | A, C, D, E, H, I, K, M, N, P, Q, R, V | F, G, L, W, Y |
| V | I, L, M | A, C, F, T, Y | D, E, G, H, K, N, P, Q, R, S, W |
| W | F, Y | H, L, M | A, C, D, E, G, I, K, N, P, Q, R, S, T, V |
| Y | F, H, W | C, I, L, M, V | A, D, E, G, K, N, P, Q, R, S, T |

Matthew J. Betts and Robert, B. Russell, Amino Acid Properties and Consequences of Substitutions, pp. 289-316, In Bioinformatics for Geneticists, (eds Michael R. Barnes, Ian C. Gray, Wiley, 2003).

In aspects of this embodiment, a hydrophic amino acid at one particular position in an insulin-like protein disclosed herein can be substituted with another hydrophic amino acid. Examples of hydrophic amino acids include, e.g., C, F, I, L, M, V and W. In another aspect of this embodiment, an aliphatic amino acid at one particular position in an insulin-like protein disclosed herein can be substituted with another aliphatic amino acid. Examples of aliphatic amino acids include, e.g., A, I, L, P, and V. In yet another aspect of this embodiment, an aromatic amino acid at one particular position in an insulin-like protein disclosed herein can be substituted with another aromatic amino acid. Examples of aromatic amino acids include, e.g., F, H, W and Y. In still another aspect of this embodiment, a stacking amino acid at one particular position in an insulin-like protein disclosed herein can be substituted with another stacking amino acid. Examples of stacking amino acids include, e.g., F, H, W and Y. In a further aspect of this embodiment, a polar amino acid at one particular position in an insulin-like protein disclosed herein can be substituted with another polar amino acid.

Examples of polar amino acids include, e.g., D, E, K, N, Q, and R. In a further aspect of this embodiment, a less polar or indifferent amino acid at one particular position in an insulin-like protein disclosed herein can be substituted with another less polar or indifferent amino acid. Examples of less polar or indifferent amino acids include, e.g., A, H, G, P, S, T, and Y. In a yet further aspect of this embodiment, a positive charged amino acid at one particular position in an insulin-like protein disclosed herein can be substituted with another positive charged amino acid. Examples of positive charged amino acids include, e.g., K, R, and H. In a still further aspect of this embodiment, a negative charged amino acid at one particular position in an insulin-like protein disclosed herein can be substituted with another negative charged amino acid. Examples of negative charged amino acids include, e.g., D and E. In another aspect of this embodiment, a small amino acid at one particular position in an insulin-like protein disclosed herein can be substituted with another small amino acid. Examples of small amino acids include, e.g., A, D, G, N, P, S, and T. In yet another aspect of this embodiment, a C-beta branching amino acid at one particular position in an insulin-like protein disclosed herein can be substituted with another C-beta branching amino acid. Examples of C-beta branching amino acids include, e.g., I, T and V.

In yet another embodiment, an α-HIV antibody specifically binds an epitope disclosed herein. In aspects of this embodiment, an α-HIV antibody specifically binds an epitope present in SEQ ID NO: 1, SEQ ID NO: 2, SEQ ID NO: 3, and/or SEQ ID NO: 4. In aspects of this embodiment, an α-HIV antibody specifically binds an epitope having an amino acid identity of, e.g., at least about 70%, at least about 75%, at least about 80%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99%, relative to SEQ ID NOs: 1-4. In other aspects of this embodiment, an α-HIV antibody specifically binds an epitope having an amino acid identity in the range of, e.g., about 75% to about 100%, about 80% to about 100%, about 85% to about 100%, about 90% to about 100%, about 95% to about 100%, about 75% to about 99%, about 80% to about 99%, about 85% to about 99%, about 90% to about 99%, about 95% to about 99%, about 75% to about 97%, about 80% to about 97%, about 85% to about 97%, about 90% to about 97%, or about 95% to about 97%, relative to SEQ ID NOs: 1-4. In yet other aspects of this embodiment, an α-HIV antibody specifically binds an epitope having, e.g., at least 1, at least 2, at least 3, or at least 4, contiguous and/or non-contiguous amino acid deletions, additions, and/or substitutions relative to SEQ ID NOs: 1-4; or at most 1, at most 2, at most 3, at most 4, contiguous and/or non-contiguous amino acid deletions, additions, and/or substitutions relative to SEQ ID NOs: 1-4. In still other aspects of this embodiment, an α-HIV antibody specifically binds an epitope having, e.g., about 1 to about 2, about 1 to about 3, about 1 to about 4, about 2 to about 3, about 2 to about 4, or about 3 to about 4 contiguous and/or non-contiguous amino acid deletions, additions, and/or substitutions relative to SEQ ID NOs: 1-4.

As used herein, the term "selectively binds" or "selective binding", when made in reference to an antibody, refers to the discriminatory binding of the antibody to the indicated target epitope such that the antibody does not substantially cross react with non-target epitopes. The minimal size of a peptide epitope, as defined herein, is about five amino acids, and a peptide epitope typically comprises at least 5, at least 6, at least 7, at least 8, at least 9, at least 10, at least 11, at least 12, at least 13, at least 14, at least 15, or at least 20 amino acids. A peptide epitope may be discontinuous, i.e., it comprises amino acid residues that are not adjacent in the primary structure of the peptide but are brought together into an epitope by way of the secondary, tertiary, or quaternary structure of the peptide. Furthermore, it is also noted that an epitope might comprise a portion of a molecule other than an amino acid sequence, such as, e.g., a carbohydrate moiety, a lipid moiety like lipoproteins or glycolipids, or a chemically-modified amino acid moiety like a phosphorylated amino acid.

In aspects of this embodiment, an α-HIV antibody disclosed herein binds to an epitope comprising, e.g., at least 5, at least 6, at least 7, at least 8, at least 9, at least 10, at least 11, at least 12, at least 13, at least 14, at least 15, or at least 20 amino acids. In other aspects of this embodiment, an α-HIV antibody disclosed herein binds to an epitope comprising, e.g., at most 5, at most 6, at most 7, at most 8, at most 9, at most 10, at most 11, at most 12, at most 13, at most 14, at most 15, or at most 20 amino acids. In other aspects of this embodiment, an α-HIV antibody disclosed herein binds to an epitope comprising, e.g., about 5 to about 7, about 5 to about 8, about 7 to about 9, about 5 to about 10, about 5 to about 12, about 5 to about 15, about 5 to about 18, about 5 to about 20, about 6 to about 7, about 6 to about 8, about 6 to about 9, about 6 to about 10, about 6 to about 12, about 6 to about 15, about 6 to about 18, about 6 to about 20, about 7 to about 8, about 7 to about 9, about 7 to about 10, about 7 to about 12, about 7 to about 15, about 7 to about 18, about 7 to about 20, about 8 to about 9, about 8 to about 10, about 8 to about 12, about 8 to about 15, about 8 to about 18, about 8 to about 20, about 9 to about 10, about 9 to about 12, about 9 to about 15, about 9 to about 18, about 9 to about 20, about 10 to about 12, about 10 to about 15, about 10 to about 18, or about 10 to about 20.

In other aspects of this embodiment, an α-HIV antibody disclosed herein binds to an epitope comprising, e.g., at least 5, at least 6, at least 7, at least 8, at least 9, at least 10, at least 11, at least 12, at least 13, at least 14, at least 15, or at least 20 amino acids from SEQ ID NO: 1, SEQ ID NO: 2, SEQ ID NO: 3, and/or SEQ ID NO: 4. In other aspects of this embodiment, an α-HIV antibody disclosed herein binds to an epitope comprising, e.g., at most 5, at most 6, at most 7, at most 8, at most 9, at most 10, at most 11, at most 12, at most 13, at most 14, at most 15, or at most 20 amino acids from SEQ ID NO: 1, SEQ ID NO: 2, SEQ ID NO: 3, and/or SEQ ID NO: 4. In other aspects of this embodiment, an α-HIV antibody disclosed herein binds to an epitope comprising, e.g., about 5 to about 7, about 5 to about 8, about 7 to about 9, about 5 to about 10, about 5 to about 12, about 5 to about 15, about 5 to about 18, about 5 to about 20, about 6 to about 7, about 6 to about 8, about 6 to about 9, about 6 to about 10, about 6 to about 12, about 6 to about 15, about 6 to about 18, about 6 to about 20, about 7 to about 8, about 7 to about 9, about 7 to about 10, about 7 to about 12, about 7 to about 15, about 7 to about 18, about 7 to about 20, about 8 to about 9, about 8 to about 10, about 8 to about 12, about 8 to about 15, about 8 to about 18, about 8 to about 20, about 9 to about 10, about 9 to about 12, about 9 to about 15, about 9 to about 18, about 9 to about 20, about 10 to about 12, about 10 to about 15, about 10 to about 18, or about 10 to about 20 from SEQ ID NO: 1, SEQ ID NO: 2, SEQ ID NO: 3, and/or SEQ ID NO: 4.

Selective binding includes binding properties such as, e.g., binding affinity, binding specificity, and binding avidity.

Binding affinity refers to the length of time the antibody resides at its epitope binding site, and can be viewed as the strength with which an antibody binds its epitope. Binding affinity can be described an antibody's equilibrium dissociation constant (KD), which is defined as the ratio Kd/Ka at equilibrium. Where Ka is the antibody's association rate constant and kd is the antibody's dissociation rate constant. Binding affinity is determined by both the association and the dissociation and alone neither high association or low dissociation can ensure high affinity. The association rate constant (Ka), or on-rate constant (Kon), measures the number of binding events per unit time, or the propensity of the antibody and the antigen to associate reversibly into its antibody-antigen complex. The association rate constant is expressed in M-1 s-1, and is symbolized as follows: [Ab]×[Ag]×Kon. The larger the association rate constant, the more rapidly the antibody binds to its antigen, or the higher the binding affinity between antibody and antigen. The dissociation rate constant (Kd), or off-rate constant (Koff), measures the number of dissociation events per unit time propensity of an antibody-antigen complex to separate (dissociate) reversibly into its component molecules, namely the antibody and the antigen. The dissociation rate constant is expressed in s-1, and is symbolized as follows: [Ab+Ag]×Koff. The smaller the dissociation rate constant, the more tightly bound the antibody is to its antigen, or the higher the binding affinity between antibody and antigen. The equilibrium dissociation constant (KD) measures the rate at which new antibody-antigen complexes formed equals the rate at which antibody-antigen complexes dissociate at equilibrium. The equilibrium dissociation constant is expressed in M, and is defined as Koff/Kon=[Ab]×[Ag]/[Ab+Ag], where [Ab] is the molar concentration of the antibody, [Ag] is the molar concentration of the antigen, and [Ab+Ag] is the of molar concentration of the antibody-antigen complex, where all concentrations are of such components when the system is at equilibrium. The smaller the equilibrium dissociation constant, the more tightly bound the antibody is to its antigen, or the higher the binding affinity between antibody and antigen.

Thus, in an embodiment, the binding affinity of an α-HIV antibody disclosed herein may have an association rate constant of, e.g., less than $1\times10^5$ $M^{-1}$ $s^{-1}$, less than $1\times10^6$ $M^{-1}$ $s^{-1}$, less than $1\times10^7$ $M^{-1}$ $s^{-1}$, or less than $1\times10^8$ $M^{-1}$ $s^{-1}$. In another embodiment, the binding affinity of an α-HIV antibody disclosed herein may have an association rate constant of, e.g., more than $1\times10^5$ $M^{-1}$ $s^{-1}$, more than $1\times10^6$ $M^{-1}$ $s^{-1}$, more than $1\times10^7$ $M^{-1}$ $s^{-1}$, or more than $1\times10^8$ $M^{-1}$ $s^{-1}$. In other aspects, the binding affinity of an α-HIV antibody disclosed herein may have an association rate constant between $1\times10^5$ $M^{-1}$ $s^{-1}$ to $1\times10^8$ $M^{-1}$ $s^{-1}$, $1\times10^6$ $M^{-1}$ $s^{-1}$ to $1\times10^8$ $M^{-1}$ $s^{-1}$, $1\times10^5$ $M^{-1}$ $s^{-1}$ to $1\times10^7$ $M^{-1}$ $s^{-1}$, or $1\times10^6$ $M^{-1}$ $s^{-1}$ to $1\times10^7$ $M^{-1}$ $s^{-1}$.

In another embodiment, the binding affinity of an α-HIV antibody disclosed herein may have an association rate constant for an epitope other than an epitope present on a HIV virion, an epitope derived from an HIV virus, an epitope produced or altered by an HIV virus, and/or an epitope produced or altered by a cell infected by the HIV virus or expressing either the whole or part of the HIV virus genetic code of, e.g., less than $1\times10^0$ $M^{-1}$ $s^{-1}$, less than $1\times10^1$ less than $1\times10^2$ $M^{-1}$ $s^{-1}$, less than $1\times10^3$ $M^{-1}$ $s^{-1}$, or less than $1\times10^4$ $M^{-1}$ $s^{-1}$. In another embodiment, the binding affinity of an α-HIV antibody disclosed herein may have an association rate constant for an epitope other than an epitope present on a HIV virion, an epitope derived from an HIV virus, an epitope produced or altered by an HIV virus, and/or an epitope produced or altered by a cell infected by the HIV virus or expressing either the whole or part of the HIV virus genetic code of, e.g., at most $1\times10^0$ $M^{-1}$ $s^{-1}$, at most $1\times10^1$ $M^{-1}$ $s^{-1}$, at most $1\times10^2$ $M^{-1}$ $s^{-1}$, at most $1\times10^3$ $M^{-1}$ $s^{-1}$, or at most $1\times10^4$ $M^{-1}$ $s^{-1}$.

In another embodiment, the binding affinity of an α-HIV antibody disclosed herein may have a disassociation rate constant of less than $1\times10^{-3}$ $s^{-1}$, less than $1\times10^{-4}$ $s^{-1}$, or less than $1\times10^{-5}$ $s^{-1}$. In other aspects of this embodiment, the binding affinity of an α-HIV antibody disclosed herein may have a disassociation rate constant of, e.g., less than $1.0\times10^{-4}$ $s^{-1}$, less than $2.0\times10^{-4}$ $s^{-1}$, less than $3.0\times10^{-4}$ $s^{-1}$, less than $4.0\times10^{-4}$ $s^{-1}$, less than $5.0\times10^{-4}$ $s^{-1}$, less than $6.0\times10^{-4}$ $s^{-1}$, less than $7.0\times10^{-4}$ $s^{-1}$, less than $8.0\times10^{-4}$ $s^{-1}$, or less than $9.0\times10^{-4}$ $s^{-1}$. In another embodiment, the binding affinity of an α-HIV antibody disclosed herein may have a disassociation rate constant of, e.g., more than $1\times10^{-3}$ $s^{-1}$, more than $1\times10^{-4}$ $s^{-1}$, or more than $1\times10^{-5}$ $s^{-1}$. In other aspects of this embodiment, the binding affinity of an α-HIV antibody disclosed herein may have a disassociation rate constant of, e.g., more than $1.0\times10^{-4}$ $s^{-1}$, more than $2.0\times10^{-4}$ $s^{-1}$, more than $3.0\times10^{-4}$ $s^{-1}$, more than $4.0\times10^{-4}$ $s^{-1}$, more than $5.0\times10^{-4}$ $s^{-1}$, more than $6.0\times10^{-4}$ $s^{-1}$, more than $7.0\times10^{-4}$ $s^{-1}$, more than $8.0\times10^{-4}$ $s^{-1}$, or more than $9.0\times10^{-4}$ $s^{-1}$. In other aspects, the binding affinity of an α-HIV antibody disclosed herein may have a disassociation rate constant between $1\times10^{-3}$ $s^{-1}$ to $1\times10^{-5}$ $s^{-1}$, $1\times10^{-3}$ $s^{-1}$ to $1\times10^{-4}$ $s^{-1}$, or $1\times10^{-4}$ $s^{-1}$ to $1\times10^{-5}$ $s^{-1}$.

In another embodiment, the binding affinity of an α-HIV antibody disclosed herein may have an equilibrium disassociation constant of less than 0.500 nM. In aspects of this embodiment, the binding affinity of an α-HIV antibody disclosed may have an equilibrium disassociation constant of, e.g., less than 0.500 nM, less than 0.450 nM, less than 0.400 nM, less than 0.350 nM, less than 0.300 nM, less than 0.250 nM, less than 0.200 nM, less than 0.150 nM, less than 0.100 nM, or less than 0.050 nM. In another embodiment, the binding affinity of an α-HIV antibody disclosed herein may have an equilibrium disassociation constant of more than 0.500 nM. In aspects of this embodiment, the binding affinity of an α-HIV antibody disclosed herein may have an equilibrium disassociation constant of, e.g., more than 0.500 nM, more than 0.450 nM, more than 0.400 nM, more than 0.350 nM, more than 0.300 nM, more than 0.250 nM, more than 0.200 nM, more than 0.150 nM, more than 0.100 nM, or more than 0.050 nM.

Binding specificity is the ability of an antibody to discriminate between a molecule containing its epitope and a molecule that does not contain that epitope. One way to measure binding specificity is to compare the Kon association rate of the antibody for a molecule containing its epitope relative to the Kon association rate of the antibody for a molecule that does not contain that epitope. For example, comparing the association rate constant (Ka) of an α-HIV antibody that selectively binds to an epitope disclosed herein relative to an epitope not present on a HIV virion, not derived from an HIV virus, not produced or altered by an HIV virus, and/or not produced or altered by a cell infected by the HIV virus or expressing either the whole or part of the HIV virus genetic code. In aspects of this embodiment, an α-HIV antibody disclosed herein may have an association rate constant (Ka) for an epitope not present on a HIV virion, not derived from an HIV virus, not produced or altered by an HIV virus, and/or not produced or altered by a cell infected by the HIV virus or expressing either the whole or part of the HIV virus genetic code of, e.g., less than $1\times10^0$ $M^{-1}$ $s^{-1}$, less than $1\times10^1$ $M^{-1}$ $s^{-1}$ less than $1\times10^2$ $M^{-1}$ $s^{-1}$ less than $1\times10^3$ M$^{-1}$ s$^{-1}$, or less than $1\times10^4$ M$^{-1}$ s$^{-1}$. In other aspects of this embodiment, an α-HIV antibody disclosed herein may have an association rate constant (Ka) for an epitope not present on a HIV virion, not derived from an HIV virus, not produced or altered by an HIV virus, and/or not produced or altered by a cell infected by the HIV virus or expressing either the whole or part of the HIV virus genetic code of, e.g., at most $1\times10^0$ M$^{-1}$ s$^{-1}$, at most $1\times10^1$ M$^{-1}$ s$^{-1}$, at most $1\times10^2$ M$^{-1}$ s$^{-1}$, at most $1\times10^3$ M$^{-1}$ s$^{-1}$, or at most $1\times10^4$ M$^{-1}$ s$^{-1}$.

In other aspects of this embodiment, an α-HIV antibody disclosed herein may have an association rate constant (Ka) for its epitope relative to an epitope not present on a HIV virion, not derived from an HIV virus, not produced or altered by an HIV virus, and/or not produced or altered by a cell infected by the HIV virus or expressing either the whole or part of the HIV virus genetic code of, e.g., at least 2-fold more, at least 3-fold more, at least 4-fold more, at least 5-fold more, at least 6-fold more, at least 7-fold more, at least 8-fold more, or at least 9-fold more. In yet other aspects of this embodiment, an α-HIV antibody disclosed herein may have an association rate constant (Ka) for its epitope relative to an epitope not present on a HIV virion, not derived from an HIV virus, not produced or altered by an HIV virus, and/or not produced or altered by a cell infected by the HIV virus or expressing either the whole or part of the HIV virus genetic code of, e.g., at least 10-fold more, at least 100-fold more, at least 1,000-fold more or at least 10,000-fold more.

In other aspects of this embodiment, an α-HIV antibody disclosed herein may have an association rate constant (Ka) for its epitope relative to an epitope not present on a HIV virion, not derived from an HIV virus, not produced or altered by an HIV virus, and/or not produced or altered by a cell infected by the HIV virus or expressing either the whole or part of the HIV virus genetic code of, e.g., at most 1-fold more, at most 2-fold more, at most 3-fold more, at most 4-fold more, at most 5-fold more, at most 6-fold more, at most 7-fold more, at most 8-fold more, or at most 9-fold more. In yet other aspects of this embodiment, α-HIV antibody disclosed herein may have an association rate constant (Ka) for its epitope relative to an epitope not present on a HIV virion, not derived from an HIV virus, not produced or altered by an HIV virus, and/or not produced or altered by a cell infected by the HIV virus or expressing either the whole or part of the HIV virus genetic code of, e.g., at most 10-fold more, at most 100-fold more, at most 1,000-fold more or at most 10,000-fold more.

The binding specificity of an α-HIV antibody disclosed herein may also be characterized as a ratio that such an α-HIV antibody can discriminate its epitope relative to an epitope not present on a HIV virion, not derived from an HIV virus, not produced or altered by an HIV virus, and/or not produced or altered by a cell infected by the HIV virus or expressing either the whole or part of the HIV virus genetic code. In aspects of this embodiment, an α-HIV antibody disclosed herein may have a binding specificity ratio for its epitope relative to an epitope not present on a HIV virion, not derived from an HIV virus, not produced or altered by an HIV virus, and/or not produced or altered by a cell infected by the HIV virus or expressing either the whole or part of the HIV virus genetic code of, e.g., at least 2:1, at least 3:1, at least 4:1, at least 5:1, at least 64:1, at least 7:1, at least 8:1, at least 9:1, at least 10:1, at least 15:1, at least 20:1, at least 25:1, at least 30:1, at least 35:1, or at least 40:1.

Binding avidity, also known as functional affinity, refers to the sum total of the functional binding strength between a multivalent antibody and its antigen. Antibody molecules can have more than one binding site (e.g., 2 for IgG, 10 for IgM), and many antigens contain more than one antigenic site. While binding avidity of an antibody depends on the binding affinities of the individual antibody binding sites, binding avidity is greater than the binding affinity as all the antibody-antigen interactions must be broken simultaneously for the antibody to dissociate completely. It is envisioned that an α-HIV antibody disclosed herein may selectively bind to any and all epitopes for that antibody.

Aspects of the present specification disclose, in part, a therapeutic composition. A therapeutic composition disclosed herein may comprise one or more α-HIV antibodies disclosed herein and optionally may further comprise one or more pharmaceutical acceptable carriers. As used herein "pharmaceutically acceptable" refers to any molecular entity or composition that does not produce an adverse, allergic or other untoward or unwanted reaction when administered to an individual. As used herein, the term "therapeutic composition" is synonymous with "pharmaceutically acceptable therapeutic composition" and refers to a therapeutically effective concentration of an active ingredient, such as, e.g., an α-HIV antibody disclosed herein. A therapeutic composition comprising an α-HIV antibody disclosed herein is useful for medical and veterinary applications. A therapeutic composition may be administered to an individual alone, or in combination with other supplementary active ingredients, agents, drugs or hormones. The therapeutic compositions may be manufactured using any of a variety of processes, including, without limitation, conventional mixing, dissolving, granulating, dragee-making, levigating, emulsifying, encapsulating, entrapping, and lyophilizing. The therapeutic composition can take any of a variety of forms including, without limitation, a sterile solution, suspension, emulsion, lyophilizate, tablet, pill, pellet, capsule, powder, syrup, elixir or any other dosage form suitable for administration.

The amount of an α-HIV antibody disclosed herein included in a therapeutic composition is an amount sufficient to elicit an appropriate therapeutic response in the individual. Typically, this amount is also one that does not cause significant adverse side effects. Such amount will vary depending on which specific α-HIV antibody or antibodies are employed. An optimal amount for a particular therapeutic composition can be ascertained by standard studies involving observation of antibody titers and other responses in individuals.

Generally, an effective and safe amount of an α-HIV antibody disclosed herein included in an therapeutic composition varies from about 1 ng to 1,000 mg. In aspects of this embodiment, an amount of an α-HIV antibody disclosed herein included in a therapeutic composition may be, e.g., about 1 ng, about 2 ng, about 3 ng, about 4 ng, about 5 ng, about 6 ng, about 7 ng, about 8 ng, about 9 ng, about 10 ng, about 15 ng, about 20 ng, about 25 ng, about 30 ng, about 35 ng, about 40 ng, about 45 ng, about 50 ng, about 55 ng, about 60 ng, about 65 ng, about 70 ng, about 75 ng, about 80 ng, about 85 ng, about 90 ng, about 95 ng, about 100 ng, about 110 ng, about 120 ng, about 130 ng, about 140 ng, about 150 ng, about 160 ng, about 170 ng, about 180 ng, about 190 ng, about 200 ng, about 210 ng, about 220 ng, about 230 ng, about 240 ng, about 250 ng, 260 ng, about 270 ng, about 280 ng, about 290 ng, about 300 ng, about 310 ng, about 320 ng, about 330 ng, about 340 ng, about 350 ng, 360 ng, about 370 ng, about 380 ng, about 390 ng, about 400 ng, about 410 ng, about 420 ng, about 430 ng, about 440 ng, about 450 ng, 460 ng, about 470 ng, about 480 ng, about 490 ng, about 500 ng, about 510 ng, about 520 ng, about 530 ng, about 540 ng, about 550 ng, 560 ng, about 570 ng, about 580 ng, about 590 ng, about 600 ng, about 610 ng, about 620 ng, about 630 ng, about 640 ng, about 650 ng, 660 ng, about 670 ng, about 680 ng, about 690 ng, about 700 ng, about 710 ng, about 720 ng, about 730 ng, about 740 ng, about 750 ng, 760 ng, about 770 ng, about 780 ng, about 790 ng, about 800 ng, about 810 ng, about 820 ng, about 830 ng, about 840 ng, about 850 ng, 860 ng, about 870 ng, about 880 ng, about 890 ng, about 900 ng, about 910 ng, about 920 ng, about 930 ng, about 940 ng, about 950 ng, 960 ng, about 970 ng, about 980 ng, about 990 ng, or about 1,000 ng.

In other aspects of this embodiment, an amount of α-HIV antibody disclosed herein included in a therapeutic composition may be, e.g., at least 1 ng, at least 2 ng, at least 3 ng, at least 4 ng, at least 5 ng, at least 6 ng, at least 7 ng, at least 8 ng, at least 9 ng, at least 10 ng, at least 15 ng, at least 20 ng, at least 25 ng, at least 30 ng, at least 35 ng, at least 40 ng, at least 45 ng, at least 50 ng, at least 55 ng, at least 60 ng, at least 65 ng, at least 70 ng, at least 75 ng, at least 80 ng, at least 85 ng, at least 90 ng, at least 95 ng, at least 100 ng, at least 110 ng, at least 120 ng, at least 130 ng, at least 140 ng, at least 150 ng, at least 160 ng, at least 170 ng, at least 180 ng, at least 190 ng, at least 200 ng, at least 210 ng, at least 220 ng, at least 230 ng, at least 240 ng, at least 250 ng, 260 ng, at least 270 ng, at least 280 ng, at least 290 ng, at least 300 ng, at least 310 ng, at least 320 ng, at least 330 ng, at least 340 ng, at least 350 ng, 360 ng, at least 370 ng, at least 380 ng, at least 390 ng, at least 400 ng, at least 410 ng, at least 420 ng, at least 430 ng, at least 440 ng, at least 450 ng, 460 ng, at least 470 ng, at least 480 ng, at least 490 ng, at least 500 ng, at least 510 ng, at least 520 ng, at least 530 ng, at least 540 ng, at least 550 ng, 560 ng, at least 570 ng, at least 580 ng, at least 590 ng, at least 600 ng, at least 610 ng, at least 620 ng, at least 630 ng, at least 640 ng, at least 650 ng, 660 ng, at least 670 ng, at least 680 ng, at least 690 ng, at least 700 ng, at least 710 ng, at least 720 ng, at least 730 ng, at least 740 ng, at least 750 ng, 760 ng, at least 770 ng, at least 780 ng, at least 790 ng, at least 800 ng, at least 810 ng, at least 820 ng, at least 830 ng, at least 840 ng, at least 850 ng, 860 ng, at least 870 ng, at least 880 ng, at least 890 ng, at least 900 ng, at least 910 ng, at least 920 ng, at least 930 ng, at least 940 ng, at least 950 ng, 960 ng, at least 970 ng, at least 980 ng, at least 990 ng, or at least 1,000 ng.

In yet other aspects of this embodiment, an amount of α-HIV antibody disclosed herein included in a therapeutic composition may be, e.g., at most 1 ng, at most 2 ng, at most 3 ng, at most 4 ng, at most 5 ng, at most 6 ng, at most 7 ng, at most 8 ng, at most 9 ng, at most 10 ng, at most 15 ng, at most 20 ng, at most 25 ng, at most 30 ng, at most 35 ng, at most 40 ng, at most 45 ng, at most 50 ng, at most 55 ng, at most 60 ng, at most 65 ng, at most 70 ng, at most 75 ng, at most 80 ng, at most 85 ng, at most 90 ng, at most 95 ng, at most 100 ng, at most 110 ng, at most 120 ng, at most 130 ng, at most 140 ng, at most 150 ng, at most 160 ng, at most 170 ng, at most 180 ng, at most 190 ng, at most 200 ng, at most 210 ng, at most 220 ng, at most 230 ng, at most 240 ng, at most 250 ng, 260 ng, at most 270 ng, at most 280 ng, at most 290 ng, at most 300 ng, at most 310 ng, at most 320 ng, at most 330 ng, at most 340 ng, at most 350 ng, 360 ng, at most 370 ng, at most 380 ng, at most 390 ng, at most 400 ng, at most 410 ng, at most 420 ng, at most 430 ng, at most 440 ng, at most 450 ng, 460 ng, at most 470 ng, at most 480 ng, at most 490 ng, at most 500 ng, at most 510 ng, at most 520 ng, at most 530 ng, at most 540 ng, at most 550 ng, 560 ng, at most 570 ng, at most 580 ng, at most 590 ng, at most 600 ng, at most 610 ng, at most 620 ng, at most 630 ng, at most 640 ng, at most 650 ng, 660 ng, at most 670 ng, at most 680 ng, at most 690 ng, at most 700 ng, at most 710 ng, at most 720 ng, at most 730 ng, at most 740 ng, at most 750 ng, 760 ng, at most 770 ng, at most 780 ng, at most 790 ng, at most 800 ng, at most 810 ng, at most 820 ng, at most 830 ng, at most 840 ng, at most 850 ng, 860 ng, at most 870 ng, at most 880 ng, at most 890 ng, at most 900 ng, at most 910 ng, at most 920 ng, at most 930 ng, at most 940 ng, at most 950 ng, 960 ng, at most 970 ng, at most 980 ng, at most 990 ng, or at most 1,000 ng.

In still other aspects of this embodiment, an amount of α-HIV antibody disclosed herein included in a therapeutic composition may be in the range of, e.g., about 1 ng to about 10 ng, about 1 ng to about 20 ng, about 1 ng to about 30 ng, about 1 ng to about 40 ng, about 1 ng to about 50 ng, about 1 ng to about 60 ng, about 1 ng to about 70 ng, about 1 ng to about 80 ng, about 1 ng to about 90 ng, about 1 ng to about 100 ng, about 1 ng to about 110 ng, about 1 ng to about 120 ng, about 1 ng to about 130 ng, about 1 ng to about 140 ng, about 1 ng to about 150 ng, about 5 ng to about 10 ng, about 5 ng to about 20 ng, about 5 ng to about 30 ng, about 5 ng to about 40 ng, about 5 ng to about 50 ng, about 5 ng to about 60 ng, about 5 ng to about 70 ng, about 5 ng to about 80 ng, about 5 ng to about 90 ng, about 5 ng to about 100 ng, about 5 ng to about 110 ng, about 5 ng to about 120 ng, about 5 ng to about 130 ng, about 5 ng to about 140 ng, about 5 ng to about 150 ng, about 10 ng to about 20 ng, about 10 ng to about 30 ng, about 10 ng to about 40 ng, about 10 ng to about 50 ng, about 10 ng to about 60 ng, about 10 ng to about 70 ng, about 10 ng to about 80 ng, about 10 ng to about 90 ng, about 10 ng to about 100 ng, about 10 ng to about 110 ng, about 10 ng to about 120 ng, about 10 ng to about 130 ng, about 10 ng to about 140 ng, about 10 ng to about 150 ng, about 10 ng to about 175 ng, about 10 ng to about 200 ng, about 10 ng to about 225 ng, about 10 ng to about 250 ng, about 25 ng to about 50 ng, about 25 ng to about 75 ng, about 25 ng to about 100 ng, about 25 ng to about 125 ng, about 25 ng to about 150 ng, about 25 ng to about 175 ng, about 25 ng to about 200 ng, about 25 ng to about 225 ng, about 25 ng to about 250 ng, about 50 ng to about 75 ng, about 50 ng to about 100 ng, about 50 ng to about 125 ng, about 50 ng to about 150 ng, about 50 ng to about 175 ng, about 50 ng to about 200 ng, about 50 ng to about 225 ng, about 50 ng to about 250 ng, about 75 ng to about 100 ng, about 75 ng to about 125 ng, about 75 ng to about 150 ng, about 75 ng to about 175 ng, about 75 ng to about 200 ng, about 75 ng to about 225 ng, or about 75 ng to about 250 ng.

In still other aspects of this embodiment, an amount of α-HIV antibody disclosed herein included in a therapeutic composition may be in the range of, e.g., about 100 ng to about 125 ng, about 100 ng to about 150 ng, about 100 ng to about 175 ng, about 100 ng to about 200 ng, about 100 ng to about 225 ng, about 100 ng to about 250 ng, about 100 ng to about 275 ng, about 100 ng to about 300 ng, about 100 ng to about 325 ng, about 100 ng to about 350 ng, about 100 ng to about 375 ng, about 100 ng to about 400 ng, about 100 ng to about 425 ng, about 100 ng to about 450 ng, about 100 ng to about 475 ng, about 100 ng to about 500 ng, about 100 ng to about 525 ng, about 100 ng to about 550 ng, about 100 ng to about 575 ng, about 100 ng to about 600 ng, about 125 ng to about 150 ng, about 125 ng to about 175 ng, about 125 ng to about 200 ng, about 125 ng to about 225 ng, about 125 ng to about 250 ng, about 125 ng to about 275 ng, about 125 ng to about 300 ng, about 125 ng to about 325 ng, about 125 ng to about 350 ng, about 125 ng to about 375 ng, about 125 ng to about 400 ng, about 125 ng to about 425 ng, about 125 ng to about 450 ng, about 125 ng to about 475 ng, about 125 ng to about 500 ng, about 125 ng to about 525 ng, about 125 ng to about 550 ng, about 125 ng to about 575 ng, about 125 ng to about 600 ng, about 150 ng to about 175 ng, about 150 ng to about 200 ng, about 150 ng to about 225 ng, about 150 ng to about 250 ng, about 150 ng to about 275 ng, about 150 ng to about 300 ng, about 150 ng to about 325 ng, about 150 ng to about 350 ng, about 150 ng to about 375 ng, about 150 ng to about 400 ng, about 150 ng to about 425 ng, about 150 ng to about 450 ng, about 150 ng to about 475 ng, about 150 ng to about 500 ng, about 150 ng to about 525 ng, about 150 ng to about 550 ng, about 150 ng to about 575 ng, about 150 ng to about 600 ng, about 200 ng to about 225 ng, about 200 ng to about 250 ng, about 200 ng to about 275 ng, about 200 ng to about 300 ng, about 200 ng to about 325 ng, about 200 ng to about 350 ng, about 200 ng to about 375 ng, about 200 ng to about 400 ng, about 200 ng to about 425 ng, about 200 ng to about 450 ng, about 200 ng to about 475 ng, about 200 ng to about 500 ng, about 200 ng to about 525 ng, about 200 ng to about 550 ng, about 200 ng to about 575 ng, about 200 ng to about 600 ng, about 200 ng to about 625 ng, about 200 ng to about 650 ng, about 200 ng to about 675 ng, about 200 ng to about 700 ng, about 200 ng to about 725 ng, about 200 ng to about 750 ng, about 200 ng to about 775 ng, about 200 ng to about 800 ng, about 200 ng to about 825 ng, about 200 ng to about 850 ng, about 200 ng to about 875 ng, about 200 ng to about 900 ng, about 200 ng to about 925 ng, about 200 ng to about 950 ng, about 200 ng to about 975 ng, or about 200 ng to about 1,000 ng.

In still other aspects of this embodiment, an amount of α-HIV antibody disclosed herein included in a therapeutic composition may be in the range of, e.g., about 250 ng to about 275 ng, about 250 ng to about 300 ng, about 250 ng to about 325 ng, about 250 ng to about 350 ng, about 250 ng to about 375 ng, about 250 ng to about 400 ng, about 250 ng to about 425 ng, about 250 ng to about 450 ng, about 250 ng to about 475 ng, about 250 ng to about 500 ng, about 250 ng to about 525 ng, about 250 ng to about 550 ng, about 250 ng to about 575 ng, about 250 ng to about 600 ng, about 250 ng to about 625 ng, about 250 ng to about 650 ng, about 250 ng to about 675 ng, about 250 ng to about 700 ng, about 250 ng to about 725 ng, about 250 ng to about 750 ng, about 250 ng to about 775 ng, about 250 ng to about 800 ng, about 250 ng to about 825 ng, about 250 ng to about 850 ng, about 250 ng to about 875 ng, about 250 ng to about 900 ng, about 250 ng to about 925 ng, about 250 ng to about 950 ng, about 250 ng to about 975 ng, about 250 ng to about 1,000 ng, about 300 ng to about 325 ng, about 300 ng to about 350 ng, about 300 ng to about 375 ng, about 300 ng to about 400 ng, about 300 ng to about 425 ng, about 300 ng to about 450 ng, about 300 ng to about 475 ng, about 300 ng to about 500 ng, about 300 ng to about 525 ng, about 300 ng to about 550 ng, about 300 ng to about 575 ng, about 300 ng to about 600 ng, about 300 ng to about 625 ng, about 300 ng to about 650 ng, about 300 ng to about 675 ng, about 300 ng to about 700 ng, about 300 ng to about 725 ng, about 300 ng to about 750 ng, about 300 ng to about 775 ng, about 300 ng to about 800 ng, about 300 ng to about 825 ng, about 300 ng to about 850 ng, about 300 ng to about 875 ng, about 300 ng to about 900 ng, about 300 ng to about 925 ng, about 300 ng to about 950 ng, about 300 ng to about 975 ng, about 300 ng to about 1,000 ng, about 400 ng to about 425 ng, about 400 ng to about 450 ng, about 400 ng to about 475 ng, about 400 ng to about 500 ng, about 400 ng to about 525 ng, about 400 ng to about 550 ng, about 400 ng to about 575 ng, about 400 ng to about 600 ng, about 400 ng to about 625 ng, about 400 ng to about 650 ng, about 400 ng to about 675 ng, about 400 ng to about 700 ng, about 400 ng to about 725 ng, about 400 ng to about 750 ng, about 400 ng to about 775 ng, about 400 ng to about 800 ng, about 400 ng to about 825 ng, about 400 ng to about 850 ng, about 400 ng to about 875 ng, about 400 ng to about 900 ng, about 400 ng to about 925 ng, about 400 ng to about 950 ng, about 400 ng to about 975 ng, or about 400 ng to about 1,000 ng.

In still other aspects of this embodiment, an amount of α-HIV antibody disclosed herein included in a therapeutic composition may be in the range of, e.g., about 500 ng to about 525 ng, about 500 ng to about 550 ng, about 500 ng to about 575 ng, about 500 ng to about 600 ng, about 500 ng to about 625 ng, about 500 ng to about 650 ng, about 500 ng to about 675 ng, about 500 ng to about 700 ng, about 500 ng to about 725 ng, about 500 ng to about 750 ng, about 500 ng to about 775 ng, about 500 ng to about 800 ng, about 500 ng to about 825 ng, about 500 ng to about 850 ng, about 500 ng to about 875 ng, about 500 ng to about 900 ng, about 500 ng to about 925 ng, about 500 ng to about 950 ng, about 500 ng to about 975 ng, about 500 ng to about 1,000 ng, about 600 ng to about 625 ng, about 600 ng to about 650 ng, about 600 ng to about 675 ng, about 600 ng to about 700 ng, about 600 ng to about 725 ng, about 600 ng to about 750 ng, about 600 ng to about 775 ng, about 600 ng to about 800 ng, about 600 ng to about 825 ng, about 600 ng to about 850 ng, about 600 ng to about 875 ng, about 600 ng to about 900 ng, about 600 ng to about 925 ng, about 600 ng to about 950 ng, about 600 ng to about 975 ng, about 600 ng to about 1,000 ng, about 700 ng to about 725 ng, about 700 ng to about 750 ng, about 700 ng to about 775 ng, about 700 ng to about 800 ng, about 700 ng to about 825 ng, about 700 ng to about 850 ng, about 700 ng to about 875 ng, about 700 ng to about 900 ng, about 700 ng to about 925 ng, about 700 ng to about 950 ng, about 700 ng to about 975 ng, about 700 ng to about 1,000 ng, about 800 ng to about 825 ng, about 800 ng to about 850 ng, about 800 ng to about 875 ng, about 800 ng to about 900 ng, about 800 ng to about 925 ng, about 800 ng to about 950 ng, about 800 ng to about 975 ng, or about 800 ng to about 1,000 ng.

In aspects of this embodiment, an amount of an α-HIV antibody disclosed herein included in a therapeutic composition may be, e.g., about 1 μg, about 2 μg, about 3 μg, about 4 μg, about 5 μg, about 6 μg, about 7 μg, about 8 μg, about 9 μg, about 10 μg, about 15 μg, about 20 μg, about 25 μg, about 30 μg, about 35 μg, about 40 μg, about 45 μg, about 50 μg, about 55 μg, about 60 μg, about 65 μg, about 70 μg, about 75 μg, about 80 μg, about 85 μg, about 90 μg, about 95 μg, about 100 μg, about 110 μg, about 120 μg, about 130 μg, about 140 μg, about 150 μg, about 160 μg, about 170 μg, about 180 μg, about 190 μg, about 200 μg, about 210 μg, about 220 μg, about 230 μg, about 240 μg, about 250 μg, 260 μg, about 270 μg, about 280 μg, about 290 μg, about 300 μg, about 310 μg, about 320 μg, about 330 μg, about 340 μg, about 350 μg, 360 μg, about 370 μg, about 380 μg, about 390 μg, about 400 μg, about 410 μg, about 420 μg, about 430 μg, about 440 μg, about 450 μg, 460 μg, about 470 μg, about 480 μg, about 490 μg, about 500 μg, about 510 μg, about 520 μg, about 530 μg, about 540 μg, about 550 μg, 560 μg, about 570 μg, about 580 μg, about 590 μg, about 600 μg, about 610 μg, about 620 μg, about 630 μg, about 640 μg, about 650 μg, 660 μg, about 670 μg, about 680 μg, about 690 μg, about 700 μg, about 710 μg, about 720 μg, about 730 μg, about 740 μg, about 750 μg, 760 μg, about 770 μg, about 780 μg, about 790 μg, about 800 μg, about 810 μg, about 820 μg, about 830 μg, about 840 μg, about 850 μg, 860 μg, about 870 μg, about 880 μg, about 890 μg, about 900 μg, about 910 μg, about 920 μg, about 930 µg, about 940 µg, about 950 µg, 960 µg, about 970 µg, about 980 µg, about 990 µg, or about 1,000 µg.

In other aspects of this embodiment, an amount of α-HIV antibody disclosed herein included in a therapeutic composition may be, e.g., at least 1 µg, at least 2 µg, at least 3 µg, at least 4 µg, at least 5 µg, at least 6 µg, at least 7 µg, at least 8 µg, at least 9 µg, at least 10 µg, at least 15 µg, at least 20 µg, at least 25 µg, at least 30 µg, at least 35 µg, at least 40 µg, at least 45 µg, at least 50 µg, at least 55 µg, at least 60 µg, at least 65 µg, at least 70 µg, at least 75 µg, at least 80 µg, at least 85 µg, at least 90 µg, at least 95 µg, at least 100 µg, at least 110 µg, at least 120 µg, at least 130 µg, at least 140 µg, at least 150 µg, at least 160 µg, at least 170 µg, at least 180 µg, at least 190 µg, at least 200 µg, at least 210 µg, at least 220 µg, at least 230 µg, at least 240 µg, at least 250 µg, 260 µg, at least 270 µg, at least 280 µg, at least 290 µg, at least 300 µg, at least 310 µg, at least 320 µg, at least 330 µg, at least 340 µg, at least 350 µg, 360 µg, at least 370 µg, at least 380 µg, at least 390 µg, at least 400 µg, at least 410 µg, at least 420 µg, at least 430 µg, at least 440 µg, at least 450 µg, 460 µg, at least 470 µg, at least 480 µg, at least 490 µg, at least 500 µg, at least 510 µg, at least 520 µg, at least 530 µg, at least 540 µg, at least 550 µg, 560 µg, at least 570 µg, at least 580 µg, at least 590 µg, at least 600 µg, at least 610 µg, at least 620 µg, at least 630 µg, at least 640 µg, at least 650 µg, 660 µg, at least 670 µg, at least 680 µg, at least 690 µg, at least 700 µg, at least 710 µg, at least 720 µg, at least 730 µg, at least 740 µg, at least 750 µg, 760 µg, at least 770 µg, at least 780 µg, at least 790 µg, at least 800 µg, at least 810 µg, at least 820 µg, at least 830 µg, at least 840 µg, at least 850 µg, 860 µg, at least 870 µg, at least 880 µg, at least 890 µg, at least 900 µg, at least 910 µg, at least 920 µg, at least 930 µg, at least 940 µg, at least 950 µg, 960 µg, at least 970 µg, at least 980 µg, at least 990 µg, or at least 1,000 µg.

In yet other aspects of this embodiment, an amount of α-HIV antibody disclosed herein included in a therapeutic composition may be, e.g., at most 1 µg, at most 2 µg, at most 3 µg, at most 4 µg, at most 5 µg, at most 6 µg, at most 7 µg, at most 8 µg, at most 9 µg, at most 10 µg, at most 15 µg, at most 20 µg, at most 25 µg, at most 30 µg, at most 35 µg, at most 40 µg, at most 45 µg, at most 50 µg, at most 55 µg, at most 60 µg, at most 65 µg, at most 70 µg, at most 75 µg, at most 80 µg, at most 85 µg, at most 90 µg, at most 95 µg, at most 100 µg, at most 110 µg, at most 120 µg, at most 130 µg, at most 140 µg, at most 150 µg, at most 160 µg, at most 170 µg, at most 180 µg, at most 190 µg, at most 200 µg, at most 210 µg, at most 220 µg, at most 230 µg, at most 240 µg, at most 250 µg, 260 µg, at most 270 µg, at most 280 µg, at most 290 µg, at most 300 µg, at most 310 µg, at most 320 µg, at most 330 µg, at most 340 µg, at most 350 µg, 360 µg, at most 370 µg, at most 380 µg, at most 390 µg, at most 400 µg, at most 410 µg, at most 420 µg, at most 430 µg, at most 440 µg, at most 450 µg, 460 µg, at most 470 µg, at most 480 µg, at most 490 µg, at most 500 µg, at most 510 µg, at most 520 µg, at most 530 µg, at most 540 µg, at most 550 µg, 560 µg, at most 570 µg, at most 580 µg, at most 590 µg, at most 600 µg, at most 610 µg, at most 620 µg, at most 630 µg, at most 640 µg, at most 650 µg, 660 µg, at most 670 µg, at most 680 µg, at most 690 µg, at most 700 µg, at most 710 µg, at most 720 µg, at most 730 µg, at most 740 µg, at most 750 µg, 760 µg, at most 770 µg, at most 780 µg, at most 790 µg, at most 800 µg, at most 810 µg, at most 820 µg, at most 830 µg, at most 840 µg, at most 850 µg, 860 µg, at most 870 µg, at most 880 µg, at most 890 µg, at most 900 µg, at most 910 µg, at most 920 µg, at most 930 µg, at most 940 µg, at most 950 µg, 960 µg, at most 970 µg, at most 980 µg, at most 990 µg, or at most 1,000 µg.

In still other aspects of this embodiment, an amount of α-HIV antibody disclosed herein included in a therapeutic composition may be in the range of, e.g., about 1 µg to about 10 µg, about 1 µg to about 20 µg, about 1 µg to about 30 µg, about 1 µg to about 40 µg, about 1 µg to about 50 µg, about 1 µg to about 60 µg, about 1 µg to about 70 µg, about 1 µg to about 80 µg, about 1 µg to about 90 µg, about 1 µg to about 100 µg, about 1 µg to about 110 µg, about 1 µg to about 120 µg, about 1 µg to about 130 µg, about 1 µg to about 140 µg, about 1 µg to about 150 µg, about 5 µg to about 10 µg, about 5 µg to about 20 µg, about 5 µg to about 30 µg, about 5 µg to about 40 µg, about 5 µg to about 50 µg, about 5 µg to about 60 µg, about 5 µg to about 70 µg, about 5 µg to about 80 µg, about 5 µg to about 90 µg, about 5 µg to about 100 µg, about 5 µg to about 110 µg, about 5 µg to about 120 µg, about 5 µg to about 130 µg, about 5 µg to about 140 µg, about 5 µg to about 150 µg, about 10 µg to about 20 µg, about 10 µg to about 30 µg, about 10 µg to about 40 µg, about 10 µg to about 50 µg, about 10 µg to about 60 µg, about 10 µg to about 70 µg, about 10 µg to about 80 µg, about 10 µg to about 90 µg, about 10 µg to about 100 µg, about 10 µg to about 110 µg, about 10 µg to about 120 µg, about 10 µg to about 130 µg, about 10 µg to about 140 µg, about 10 µg to about 150 µg, about 10 µg to about 175 µg, about 10 µg to about 200 µg, about 10 µg to about 225 µg, about 10 µg to about 250 µg, about 25 µg to about 50 µg, about 25 µg to about 75 µg, about 25 µg to about 100 µg, about 25 µg to about 125 µg, about 25 µg to about 150 µg, about 25 µg to about 175 µg, about 25 µg to about 200 µg, about 25 µg to about 225 µg, about 25 µg to about 250 µg, about 50 µg to about 75 µg, about 50 µg to about 100 µg, about 50 µg to about 125 µg, about 50 µg to about 150 µg, about 50 µg to about 175 µg, about 50 µg to about 200 µg, about 50 µg to about 225 µg, about 50 µg to about 250 µg, about 75 µg to about 100 µg, about 75 µg to about 125 µg, about 75 µg to about 150 µg, about 75 µg to about 175 µg, about 75 µg to about 200 µg, about 75 µg to about 225 µg, or about 75 µg to about 250 µg.

In still other aspects of this embodiment, an amount of α-HIV antibody disclosed herein included in a therapeutic composition may be in the range of, e.g., about 100 µg to about 125 µg, about 100 µg to about 150 µg, about 100 µg to about 175 µg, about 100 µg to about 200 µg, about 100 µg to about 225 µg, about 100 µg to about 250 µg, about 100 µg to about 275 µg, about 100 µg to about 300 µg, about 100 µg to about 325 µg, about 100 µg to about 350 µg, about 100 µg to about 375 µg, about 100 µg to about 400 µg, about 100 µg to about 425 µg, about 100 µg to about 450 µg, about 100 µg to about 475 µg, about 100 µg to about 500 µg, about 100 µg to about 525 µg, about 100 µg to about 550 µg, about 100 µg to about 575 µg, about 100 µg to about 600 µg, about 125 µg to about 150 µg, about 125 µg to about 175 µg, about 125 µg to about 200 µg, about 125 µg to about 225 µg, about 125 µg to about 250 µg, about 125 µg to about 275 µg, about 125 µg to about 300 µg, about 125 µg to about 325 µg, about 125 µg to about 350 µg, about 125 µg to about 375 µg, about 125 µg to about 400 µg, about 125 µg to about 425 µg, about 125 µg to about 450 µg, about 125 µg to about 475 µg, about 125 µg to about 500 µg, about 125 µg to about 525 µg, about 125 µg to about 550 µg, about 125 µg to about 575 µg, about 125 µg to about 600 µg, about 150 µg to about 175 µg, about 150 µg to about 200 µg, about 150 µg to about 225 µg, about 150 µg to about 250 µg, about 150 µg to about 275 µg, about 150 µg to about 300 µg, about 150 µg to about 325 µg, about 150 µg to about 350 µg, about 150 µg to about 375 µg, about 150 µg to about 400 µg, about 150 µg to about 425 µg, about 150 µg to about 450 µg, about 150 µg to about 475 µg, about 150 µg to about 500 µg, about 150 µg to about 525 µg, about 150 µg to about 550 µg, about 150 µg to about 575 µg, about 150 µg to about 600 µg, about 200 µg to about 225 µg, about 200 µg to about 250 µg, about 200 µg to about 275 µg, about 200 µg to about 300 µg, about 200 µg to about 325 µg, about 200 µg to about 350 µg, about 200 µg to about 375 µg, about 200 µg to about 400 µg, about 200 µg to about 425 µg, about 200 µg to about 450 µg, about 200 µg to about 475 µg, about 200 µg to about 500 µg, about 200 µg to about 525 µg, about 200 µg to about 550 µg, about 200 µg to about 575 µg, about 200 µg to about 600 µg, about 200 µg to about 625 µg, about 200 µg to about 650 µg, about 200 µg to about 675 µg, about 200 µg to about 700 µg, about 200 µg to about 725 µg, about 200 µg to about 750 µg, about 200 µg to about 775 µg, about 200 µg to about 800 µg, about 200 µg to about 825 µg, about 200 µg to about 850 µg, about 200 µg to about 875 µg, about 200 µg to about 900 µg, about 200 µg to about 925 µg, about 200 µg to about 950 µg, about 200 µg to about 975 µg, or about 200 µg to about 1,000 µg.

In still other aspects of this embodiment, an amount of α-HIV antibody disclosed herein included in a therapeutic composition may be in the range of, e.g., about 250 µg to about 275 µg, about 250 µg to about 300 µg, about 250 µg to about 325 µg, about 250 µg to about 350 µg, about 250 µg to about 375 µg, about 250 µg to about 400 µg, about 250 µg to about 425 µg, about 250 µg to about 450 µg, about 250 µg to about 475 µg, about 250 µg to about 500 µg, about 250 µg to about 525 µg, about 250 µg to about 550 µg, about 250 µg to about 575 µg, about 250 µg to about 600 µg, about 250 µg to about 625 µg, about 250 µg to about 650 µg, about 250 µg to about 675 µg, about 250 µg to about 700 µg, about 250 µg to about 725 µg, about 250 µg to about 750 µg, about 250 µg to about 775 µg, about 250 µg to about 800 µg, about 250 µg to about 825 µg, about 250 µg to about 850 µg, about 250 µg to about 875 µg, about 250 µg to about 900 µg, about 250 µg to about 925 µg, about 250 µg to about 950 µg, about 250 µg to about 975 µg, about 250 µg to about 1,000 µg, about 300 µg to about 325 µg, about 300 µg to about 350 µg, about 300 µg to about 375 µg, about 300 µg to about 400 µg, about 300 µg to about 425 µg, about 300 µg to about 450 µg, about 300 µg to about 475 µg, about 300 µg to about 500 µg, about 300 µg to about 525 µg, about 300 µg to about 550 µg, about 300 µg to about 575 µg, about 300 µg to about 600 µg, about 300 µg to about 625 µg, about 300 µg to about 650 µg, about 300 µg to about 675 µg, about 300 µg to about 700 µg, about 300 µg to about 725 µg, about 300 µg to about 750 µg, about 300 µg to about 775 µg, about 300 µg to about 800 µg, about 300 µg to about 825 µg, about 300 µg to about 850 µg, about 300 µg to about 875 µg, about 300 µg to about 900 µg, about 300 µg to about 925 µg, about 300 µg to about 950 µg, about 300 µg to about 975 µg, about 300 µg to about 1,000 µg, about 400 µg to about 425 µg, about 400 µg to about 450 µg, about 400 µg to about 475 µg, about 400 µg to about 500 µg, about 400 µg to about 525 µg, about 400 µg to about 550 µg, about 400 µg to about 575 µg, about 400 µg to about 600 µg, about 400 µg to about 625 µg, about 400 µg to about 650 µg, about 400 µg to about 675 µg, about 400 µg to about 700 µg, about 400 µg to about 725 µg, about 400 µg to about 750 µg, about 400 µg to about 775 µg, about 400 µg to about 800 µg, about 400 µg to about 825 µg, about 400 µg to about 850 µg, about 400 µg to about 875 µg, about 400 µg to about 900 µg, about 400 µg to about 925 µg, about 400 µg to about 950 µg, about 400 µg to about 975 µg, or about 400 µg to about 1,000 µg.

In still other aspects of this embodiment, an amount of α-HIV antibody disclosed herein included in a therapeutic composition may be in the range of, e.g., about 500 µg to about 525 µg, about 500 µg to about 550 µg, about 500 µg to about 575 µg, about 500 µg to about 600 µg, about 500 µg to about 625 µg, about 500 µg to about 650 µg, about 500 µg to about 675 µg, about 500 µg to about 700 µg, about 500 µg to about 725 µg, about 500 µg to about 750 µg, about 500 µg to about 775 µg, about 500 µg to about 800 µg, about 500 µg to about 825 µg, about 500 µg to about 850 µg, about 500 µg to about 875 µg, about 500 µg to about 900 µg, about 500 µg to about 925 µg, about 500 µg to about 950 µg, about 500 µg to about 975 µg, about 500 µg to about 1,000 µg, about 600 µg to about 625 µg, about 600 µg to about 650 µg, about 600 µg to about 675 µg, about 600 µg to about 700 µg, about 600 µg to about 725 µg, about 600 µg to about 750 µg, about 600 µg to about 775 µg, about 600 µg to about 800 µg, about 600 µg to about 825 µg, about 600 µg to about 850 µg, about 600 µg to about 875 µg, about 600 µg to about 900 µg, about 600 µg to about 925 µg, about 600 µg to about 950 µg, about 600 µg to about 975 µg, about 600 µg to about 1,000 µg, about 700 µg to about 725 µg, about 700 µg to about 750 µg, about 700 µg to about 775 µg, about 700 µg to about 800 µg, about 700 µg to about 825 µg, about 700 µg to about 850 µg, about 700 µg to about 875 µg, about 700 µg to about 900 µg, about 700 µg to about 925 µg, about 700 µg to about 950 µg, about 700 µg to about 975 µg, about 700 µg to about 1,000 µg, about 800 µg to about 825 µg, about 800 µg to about 850 µg, about 800 µg to about 875 µg, about 800 µg to about 900 µg, about 800 µg to about 925 µg, about 800 µg to about 950 µg, about 800 µg to about 975 µg, or about 800 µg to about 1,000 µg.

In aspects of this embodiment, an amount of α-HIV antibody disclosed herein included in a therapeutic composition may be, e.g., about 1 mg, about 2 mg, about 3 mg, about 4 mg, about 5 mg, about 6 mg, about 7 mg, about 8 mg, about 9 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 110 mg, about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, 260 mg, about 270 mg, about 280 mg, about 290 mg, about 300 mg, about 310 mg, about 320 mg, about 330 mg, about 340 mg, about 350 mg, 360 mg, about 370 mg, 380 mg, about 390 mg, about 400 mg, about 410 mg, about 420 mg, about 430 mg, about 440 mg, about 450 mg, 460 mg, about 470 mg, about 480 mg, about 490 mg, about 500 mg, about 510 mg, about 520 mg, about 530 mg, about 540 mg, about 550 mg, 560 mg, about 570 mg, about 580 mg, about 590 mg, about 600 mg, about 610 mg, about 620 mg, about 630 mg, about 640 mg, about 650 mg, 660 mg, about 670 mg, about 680 mg, about 690 mg, about 700 mg, about 710 mg, about 720 mg, about 730 mg, about 740 mg, about 750 mg, 760 mg, about 770 mg, about 780 mg, about 790 mg, about 800 mg, about 810 mg, about 820 mg, about 830 mg, about 840 mg, about 850 mg, 860 mg, about 870 mg, about 880 mg, about 890 mg, about 900 mg, about 910 mg, about 920 mg, about 930 mg, about 940 mg, about 950 mg, 960 mg, about 970 mg, about 980 mg, about 990 mg, or about 1,000 mg.

In other aspects of this embodiment, an amount of α-HIV antibody disclosed herein included in a therapeutic composition may be, e.g., at least 1 mg, at least 2 mg, at least 3 mg, at least 4 mg, at least 5 mg, at least 6 mg, at least 7 mg, at least 8 mg, at least 9 mg, at least 10 mg, at least 15 mg, at least 20 mg, at least 25 mg, at least 30 mg, at least 35 mg, at least 40 mg, at least 45 mg, at least 50 mg, at least 55 mg, at least 60 mg, at least 65 mg, at least 70 mg, at least 75 mg, at least 80 mg, at least 85 mg, at least 90 mg, at least 95 mg, at least 100 mg, at least 110 mg, at least 120 mg, at least 130 mg, at least 140 mg, at least 150 mg, at least 160 mg, at least 170 mg, at least 180 mg, at least 190 mg, at least 200 mg, at least 210 mg, at least 220 mg, at least 230 mg, at least 240 mg, at least 250 mg, 260 mg, at least 270 mg, at least 280 mg, at least 290 mg, at least 300 mg, at least 310 mg, at least 320 mg, at least 330 mg, at least 340 mg, at least 350 mg, 360 mg, at least 370 mg, at least 380 mg, at least 390 mg, at least 400 mg, at least 410 mg, at least 420 mg, at least 430 mg, at least 440 mg, at least 450 mg, 460 mg, at least 470 mg, at least 480 mg, at least 490 mg, at least 500 mg, at least 510 mg, at least 520 mg, at least 530 mg, at least 540 mg, at least 550 mg, 560 mg, at least 570 mg, at least 580 mg, at least 590 mg, at least 600 mg, at least 610 mg, at least 620 mg, at least 630 mg, at least 640 mg, at least 650 mg, 660 mg, at least 670 mg, at least 680 mg, at least 690 mg, at least 700 mg, at least 710 mg, at least 720 mg, at least 730 mg, at least 740 mg, at least 750 mg, 760 mg, at least 770 mg, at least 780 mg, at least 790 mg, at least 800 mg, at least 810 mg, at least 820 mg, at least 830 mg, at least 840 mg, at least 850 mg, 860 mg, at least 870 mg, at least 880 mg, at least 890 mg, at least 900 mg, at least 910 mg, at least 920 mg, at least 930 mg, at least 940 mg, at least 950 mg, 960 mg, at least 970 mg, at least 980 mg, at least 990 mg, or at least 1,000 mg.

In yet other aspects of this embodiment, an amount of α-HIV antibody disclosed herein included in a therapeutic composition may be, e.g., at most 1 mg, at most 2 mg, at most 3 mg, at most 4 mg, at most 5 mg, at most 6 mg, at most 7 mg, at most 8 mg, at most 9 mg, at most 10 mg, at most 15 mg, at most 20 mg, at most 25 mg, at most 30 mg, at most 35 mg, at most 40 mg, at most 45 mg, at most 50 mg, at most 55 mg, at most 60 mg, at most 65 mg, at most 70 mg, at most 75 mg, at most 80 mg, at most 85 mg, at most 90 mg, at most 95 mg, at most 100 mg, at most 110 mg, at most 120 mg, at most 130 mg, at most 140 mg, at most 150 mg, at most 160 mg, at most 170 mg, at most 180 mg, at most 190 mg, at most 200 mg, at most 210 mg, at most 220 mg, at most 230 mg, at most 240 mg, at most 250 mg, 260 mg, at most 270 mg, at most 280 mg, at most 290 mg, at most 300 mg, at most 310 mg, at most 320 mg, at most 330 mg, at most 340 mg, at most 350 mg, 360 mg, at most 370 mg, at most 380 mg, at most 390 mg, at most 400 mg, at most 410 mg, at most 420 mg, at most 430 mg, at most 440 mg, at most 450 mg, 460 mg, at most 470 mg, at most 480 mg, at most 490 mg, at most 500 mg, at most 510 mg, at most 520 mg, at most 530 mg, at most 540 mg, at most 550 mg, 560 mg, at most 570 mg, at most 580 mg, at most 590 mg, at most 600 mg, at most 610 mg, at most 620 mg, at most 630 mg, at most 640 mg, at most 650 mg, 660 mg, at most 670 mg, at most 680 mg, at most 690 mg, at most 700 mg, at most 710 mg, at most 720 mg, at most 730 mg, at most 740 mg, at most 750 mg, 760 mg, at most 770 mg, at most 780 mg, at most 790 mg, at most 800 mg, at most 810 mg, at most 820 mg, at most 830 mg, at most 840 mg, at most 850 mg, 860 mg, at most 870 mg, at most 880 mg, at most 890 mg, at most 900 mg, at most 910 mg, at most 920 mg, at most 930 mg, at most 940 mg, at most 950 mg, 960 mg, at most 970 mg, at most 980 mg, at most 990 mg, or at most 1,000 mg.

In still other aspects of this embodiment, an amount of α-HIV antibody disclosed herein included in a therapeutic composition may be in the range of, e.g., about 1 mg to about 10 mg, about 1 mg to about 20 mg, about 1 mg to about 30 mg, about 1 mg to about 40 mg, about 1 mg to about 50 mg, about 1 mg to about 60 mg, about 1 mg to about 70 mg, about 1 mg to about 80 mg, about 1 mg to about 90 mg, about 1 mg to about 100 mg, about 1 mg to about 110 mg, about 1 mg to about 120 mg, about 1 mg to about 130 mg, about 1 mg to about 140 mg, about 1 mg to about 150 mg, about 5 mg to about 10 mg, about 5 mg to about 20 mg, about 5 mg to about 30 mg, about 5 mg to about 40 mg, about 5 mg to about 50 mg, about 5 mg to about 60 mg, about 5 mg to about 70 mg, about 5 mg to about 80 mg, about 5 mg to about 90 mg, about 5 mg to about 100 mg, about 5 mg to about 110 mg, about 5 mg to about 120 mg, about 5 mg to about 130 mg, about 5 mg to about 140 mg, about 5 mg to about 150 mg, about 10 mg to about 20 mg, about 10 mg to about 30 mg, about 10 mg to about 40 mg, about 10 mg to about 50 mg, about 10 mg to about 60 mg, about 10 mg to about 70 mg, about 10 mg to about 80 mg, about 10 mg to about 90 mg, about 10 mg to about 100 mg, about 10 mg to about 110 mg, about 10 mg to about 120 mg, about 10 mg to about 130 mg, about 10 mg to about 140 mg, about 10 mg to about 150 mg, about 10 mg to about 175 mg, about 10 mg to about 200 mg, about 10 mg to about 225 mg, about 10 mg to about 250 mg, about 25 mg to about 50 mg, about 25 mg to about 75 mg, about 25 mg to about 100 mg, about 25 mg to about 125 mg, about 25 mg to about 150 mg, about 25 mg to about 175 mg, about 25 mg to about 200 mg, about 25 mg to about 225 mg, about 25 mg to about 250 mg, about 50 mg to about 75 mg, about 50 mg to about 100 mg, about 50 mg to about 125 mg, about 50 mg to about 150 mg, about 50 mg to about 175 mg, about 50 mg to about 200 mg, about 50 mg to about 225 mg, about 50 mg to about 250 mg, about 75 mg to about 100 mg, about 75 mg to about 125 mg, about 75 mg to about 150 mg, about 75 mg to about 175 mg, about 75 mg to about 200 mg, about 75 mg to about 225 mg, or about 75 mg to about 250 mg.

In still other aspects of this embodiment, an amount of α-HIV antibody disclosed herein included in a therapeutic composition may be in the range of, e.g., about 100 mg to about 125 mg, about 100 mg to about 150 mg, about 100 mg to about 175 mg, about 100 mg to about 200 mg, about 100 mg to about 225 mg, about 100 mg to about 250 mg, about 100 mg to about 275 mg, about 100 mg to about 300 mg, about 100 mg to about 325 mg, about 100 mg to about 350 mg, about 100 mg to about 375 mg, about 100 mg to about 400 mg, about 100 mg to about 425 mg, about 100 mg to about 450 mg, about 100 mg to about 475 mg, about 100 mg to about 500 mg, about 100 mg to about 525 mg, about 100 mg to about 550 mg, about 100 mg to about 575 mg, about 100 mg to about 600 mg, about 125 mg to about 150 mg, about 125 mg to about 175 mg, about 125 mg to about 200 mg, about 125 mg to about 225 mg, about 125 mg to about 250 mg, about 125 mg to about 275 mg, about 125 mg to about 300 mg, about 125 mg to about 325 mg, about 125 mg to about 350 mg, about 125 mg to about 375 mg, about 125 mg to about 400 mg, about 125 mg to about 425 mg, about 125 mg to about 450 mg, about 125 mg to about 475 mg, about 125 mg to about 500 mg, about 125 mg to about 525 mg, about 125 mg to about 550 mg, about 125 mg to about 575 mg, about 125 mg to about 600 mg, about 150 mg to about 175 mg, about 150 mg to about 200 mg, about 150 mg to about 225 mg, about 150 mg to about 250 mg, about 150 mg to about 275 mg, about 150 mg to about 300 mg, about 150 mg to about 325 mg, about 150 mg to about 350 mg, about 150 mg to about 375 mg, about 150 mg to about 400 mg, about 150 mg to about 425 mg, about 150 mg to about 450 mg, about 150 mg to about 475 mg, about 150 mg to about 500 mg, about 150 mg to about 525 mg, about 150 mg to about 550 mg, about 150 mg to about 575 mg, about 150 mg to about 600 mg, about 200 mg to about 225 mg, about 200 mg to about 250 mg, about 200 mg to about 275 mg, about 200 mg to about 300 mg, about 200 mg to about 325 mg, about 200 mg to about 350 mg, about 200 mg to about 375 mg, about 200 mg to about 400 mg, about 200 mg to about 425 mg, about 200 mg to about 450 mg, about 200 mg to about 475 mg, about 200 mg to about 500 mg, about 200 mg to about 525 mg, about 200 mg to about 550 mg, about 200 mg to about 575 mg, about 200 mg to about 600 mg, about 200 mg to about 625 mg, about 200 mg to about 650 mg, about 200 mg to about 675 mg, about 200 mg to about 700 mg, about 200 mg to about 725 mg, about 200 mg to about 750 mg, about 200 mg to about 775 mg, about 200 mg to about 800 mg, about 200 mg to about 825 mg, about 200 mg to about 850 mg, about 200 mg to about 875 mg, about 200 mg to about 900 mg, about 200 mg to about 925 mg, about 200 mg to about 950 mg, about 200 mg to about 975 mg, or about 200 mg to about 1,000 mg.

In still other aspects of this embodiment, an amount of α-HIV antibody disclosed herein included in a therapeutic composition may be in the range of, e.g., about 250 mg to about 275 mg, about 250 mg to about 300 mg, about 250 mg to about 325 mg, about 250 mg to about 350 mg, about 250 mg to about 375 mg, about 250 mg to about 400 mg, about 250 mg to about 425 mg, about 250 mg to about 450 mg, about 250 mg to about 475 mg, about 250 mg to about 500 mg, about 250 mg to about 525 mg, about 250 mg to about 550 mg, about 250 mg to about 575 mg, about 250 mg to about 600 mg, about 250 mg to about 625 mg, about 250 mg to about 650 mg, about 250 mg to about 675 mg, about 250 mg to about 700 mg, about 250 mg to about 725 mg, about 250 mg to about 750 mg, about 250 mg to about 775 mg, about 250 mg to about 800 mg, about 250 mg to about 825 mg, about 250 mg to about 850 mg, about 250 mg to about 875 mg, about 250 mg to about 900 mg, about 250 mg to about 925 mg, about 250 mg to about 950 mg, about 250 mg to about 975 mg, about 250 mg to about 1,000 mg, about 300 mg to about 325 mg, about 300 mg to about 350 mg, about 300 mg to about 375 mg, about 300 mg to about 400 mg, about 300 mg to about 425 mg, about 300 mg to about 450 mg, about 300 mg to about 475 mg, about 300 mg to about 500 mg, about 300 mg to about 525 mg, about 300 mg to about 550 mg, about 300 mg to about 575 mg, about 300 mg to about 600 mg, about 300 mg to about 625 mg, about 300 mg to about 650 mg, about 300 mg to about 675 mg, about 300 mg to about 700 mg, about 300 mg to about 725 mg, about 300 mg to about 750 mg, about 300 mg to about 775 mg, about 300 mg to about 800 mg, about 300 mg to about 825 mg, about 300 mg to about 850 mg, about 300 mg to about 875 mg, about 300 mg to about 900 mg, about 300 mg to about 925 mg, about 300 mg to about 950 mg, about 300 mg to about 975 mg, about 300 mg to about 1,000 mg, about 400 mg to about 425 mg, about 400 mg to about 450 mg, about 400 mg to about 475 mg, about 400 mg to about 500 mg, about 400 mg to about 525 mg, about 400 mg to about 550 mg, about 400 mg to about 575 mg, about 400 mg to about 600 mg, about 400 mg to about 625 mg, about 400 mg to about 650 mg, about 400 mg to about 675 mg, about 400 mg to about 700 mg, about 400 mg to about 725 mg, about 400 mg to about 750 mg, about 400 mg to about 775 mg, about 400 mg to about 800 mg, about 400 mg to about 825 mg, about 400 mg to about 850 mg, about 400 mg to about 875 mg, about 400 mg to about 900 mg, about 400 mg to about 925 mg, about 400 mg to about 950 mg, about 400 mg to about 975 mg, or about 400 mg to about 1,000 mg.

In still other aspects of this embodiment, an amount of α-HIV antibody disclosed herein included in a therapeutic composition may be in the range of, e.g., about 500 mg to about 525 mg, about 500 mg to about 550 mg, about 500 mg to about 575 mg, about 500 mg to about 600 mg, about 500 mg to about 625 mg, about 500 mg to about 650 mg, about 500 mg to about 675 mg, about 500 mg to about 700 mg, about 500 mg to about 725 mg, about 500 mg to about 750 mg, about 500 mg to about 775 mg, about 500 mg to about 800 mg, about 500 mg to about 825 mg, about 500 mg to about 850 mg, about 500 mg to about 875 mg, about 500 mg to about 900 mg, about 500 mg to about 925 mg, about 500 mg to about 950 mg, about 500 mg to about 975 mg, about 500 mg to about 1,000 mg, about 600 mg to about 625 mg, about 600 mg to about 650 mg, about 600 mg to about 675 mg, about 600 mg to about 700 mg, about 600 mg to about 725 mg, about 600 mg to about 750 mg, about 600 mg to about 775 mg, about 600 mg to about 800 mg, about 600 mg to about 825 mg, about 600 mg to about 850 mg, about 600 mg to about 875 mg, about 600 mg to about 900 mg, about 600 mg to about 925 mg, about 600 mg to about 950 mg, about 600 mg to about 975 mg, about 600 mg to about 1,000 mg, about 700 mg to about 725 mg, about 700 mg to about 750 mg, about 700 mg to about 775 mg, about 700 mg to about 800 mg, about 700 mg to about 825 mg, about 700 mg to about 850 mg, about 700 mg to about 875 mg, about 700 mg to about 900 mg, about 700 mg to about 925 mg, about 700 mg to about 950 mg, about 700 mg to about 975 mg, about 700 mg to about 1,000 mg, about 800 mg to about 825 mg, about 800 mg to about 850 mg, about 800 mg to about 875 mg, about 800 mg to about 900 mg, about 800 mg to about 925 mg, about 800 mg to about 950 mg, about 800 mg to about 975 mg, or about 800 mg to about 1,000 mg.

A therapeutic composition disclosed herein can optionally include one or more pharmaceutically acceptable carriers that facilitate processing of an active ingredient into therapeutic compositions. As used herein, the term "pharmacologically acceptable carriers" is synonymous with "pharmacological carriers" and means any compound that has substantially no long term or permanent detrimental effect when administered and encompasses terms such as "pharmacologically acceptable vehicle, stabilizer, diluent, additive, auxiliary or excipient." Such a carrier generally is mixed with an active compound, or permitted to dilute or enclose the active compound and can be a solid, semi-solid, or liquid agent. It is understood that the active ingredients can be soluble or can be delivered as a suspension in the desired carriers. Any of a variety of pharmaceutically acceptable carrier can be used including, without limitation, aqueous media such as, e.g., water, saline, glycine, hyaluronic acid and the like; solid carriers such as, e.g., mannitol, lactose, starch, magnesium stearate, sodium saccharin, talcum, cellulose, glucose, sucrose, magnesium carbonate, and the like; solvents; dispersion media; coatings; antibacterial and antifungal agents; isotonic and absorption delaying agents; or any other inactive ingredient. Selection of a pharmacologically acceptable carrier can depend on the mode of administration. Except insofar as any pharmacologically acceptable carrier is incompatible with the active ingredient, its use in pharmaceutically acceptable compositions is contemplated. Non-limiting examples of specific uses of such pharmaceutical carriers can be found in PHARMACEUTICAL DOSAGE FORMS AND DRUG DELIVERY SYSTEMS (Howard C. Ansel et al., eds., Lippincott Williams & Wilkins Publishers, 7$^{th}$ ed. 1999); REMINGTON: THE SCIENCE AND PRACTICE OF PHARMACY (Alfonso R. Gennaro ed., Lippincott, Williams & Wilkins, 20th ed. 2000); GOODMAN & GILMAN'S THE PHARMACOLOGICAL BASIS OF THERAPEUTICS (Joel G. Hardman et al., eds., McGraw-Hill Professional, 10$^{th}$ ed. 2001); and HANDBOOK OF PHARMACEUTICAL EXCIPIENTS (Raymond C. Rowe et al., APhA Publications, 4$^{th}$ edition 2003). These protocols are routine procedures and any modifications are well within the scope of one skilled in the art and from the teaching herein.

It is further envisioned that a therapeutic composition disclosed herein can optionally include, without limitation, other pharmaceutically acceptable components (or pharmaceutical components), including, without limitation, buffers, preservatives, tonicity adjusters, salts, antioxidants, osmolality adjusting agents, physiological substances, pharmacological substances, bulking agents, emulsifying agents, wetting agents, sweetening or flavoring agents, and the like. Various buffers and means for adjusting pH can be used to prepare a therapeutic composition disclosed herein, provided that the resulting preparation is pharmaceutically acceptable. Such buffers include, without limitation, acetate buffers, citrate buffers, phosphate buffers, neutral buffered saline, phosphate buffered saline and borate buffers. It is understood that acids or bases can be used to adjust the pH of a composition as needed. Pharmaceutically acceptable antioxidants include, without limitation, sodium metabisulfite, sodium thiosulfate, acetylcysteine, butylated hydroxyanisole and butylated hydroxytoluene. Useful preservatives include, without limitation, benzalkonium chloride, chlorobutanol, thimerosal, phenylmercuric acetate, phenylmercuric nitrate, a stabilized oxy chloro composition and chelants, such as, e.g., DTPA or DTPA-bisamide, calcium DTPA, and CaNaDTPA-bisamide. Tonicity adjustors useful in a pharmaceutical composition include, without limitation, salts such as, e.g., sodium chloride, potassium chloride, mannitol or glycerin and other pharmaceutically acceptable tonicity adjustor. An active ingredient, such as, e.g., an α-HIV antibody disclosed herein, may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. It is understood that these and other substances known in the art of pharmacology can be included in a therapeutic composition.

Aspects of the present specification disclose, in part, a method of treating a HIV-based disease. Such methods include therapeutic (following HIV infection) and prophylactic (prior to HIV exposure, infection or pathology). For example, therapeutic and prophylactic methods of treating an individual for a HIV infection include treatment of an individual having or at risk of having a HIV infection or pathology, treating an individual with a HIV infection, and methods of protecting an individual from a HIV infection, to decrease or reduce the probability of a HIV infection in an individual, to decrease or reduce susceptibility of an individual to a HIV infection, or to inhibit or prevent a HIV infection in an individual, and to decrease, reduce, inhibit or suppress transmission of a HIV from an infected individual to an uninfected individual. Such methods include administering an immunogenic composition disclosed herein to therapeutically or prophylactically treat (vaccinate or immunize) an individual having or at risk of having a HIV infection or pathology. Accordingly, methods can treat the HIV infection or pathology, or provide the individual with protection from infection (e.g., prophylactic protection).

In one embodiment, a method of treating a HIV-based disease comprises administering to an individual in need thereof an α-HIV antibody or therapeutic composition disclosed herein in an amount sufficient to reduce one or more physiological conditions or symptom associated with a HIV infection or pathology, thereby treating the HIV-based disease. In aspects of this embodiment, a therapeutic composition comprises one or more α-HIV antibodies disclosed herein.

In one embodiment, an α-HIV antibody or therapeutic composition disclosed herein is used to treat a HIV-based disease. Use of an α-HIV antibody or therapeutic composition disclosed herein treats a HIV-based disease by reducing one or more physiological conditions or symptom associated with a HIV infection or pathology. In aspects of this embodiment, administration of an α-HIV or therapeutic composition disclosed herein is in an amount sufficient to reduce one or more physiological conditions or symptom associated with a HIV infection or pathology, thereby treating the HIV-based disease. In other aspects of this embodiment, administration of an α-HIV or therapeutic composition disclosed herein is in an amount sufficient to increase, induce, enhance, augment, promote or stimulate HIV clearance or removal; or decrease, reduce, inhibit, suppress, prevent, control, or limit transmission of HIV to another individual.

In one embodiment, a method of treating a HIV-based disease comprises administering to an individual in need thereof a HIV antigen or immunogenic composition disclosed herein in an amount sufficient to immunize or vaccinate the individual against the HIV infection or pathology, thereby treating the HIV-based disease. In aspects of this embodiment, an immunogenic composition comprises one or more HIV antigens disclosed herein. In other aspects of this embodiment, administration of an immunogenic composition disclosed herein is in an amount sufficient to increase, induce, enhance, augment, promote or stimulate an immune response against a HIV. In yet other aspects of this embodiment, administration of an immunogenic composition disclosed herein is in an amount sufficient to increase, induce, enhance, augment, promote or stimulate HIV clearance or removal; or decrease, reduce, inhibit, suppress, prevent, control, or limit transmission of HIV to another individual.

In one embodiment, a method of treating a HIV-based disease comprises administering to an individual in need thereof a HIV antigen or immunogenic composition disclosed herein in an amount sufficient to protect the individual against a HIV infection or pathology, thereby treating the HIV-based disease. In aspects of this embodiment, an immunogenic composition comprises one or more HIV antigens disclosed herein. In other aspects of this embodiment, administration of an immunogenic composition disclosed herein is in an amount sufficient to immunize or vaccinate the individual against the HIV infection or pathology, or reduce, decrease, limit, control or inhibit susceptibility to a HIV infection or pathology.

In one embodiment, a HIV antigen or immunogenic composition disclosed herein is used to treat a HIV-based disease. In an aspect of this embodiment, use of a HIV antigen or immunogenic composition disclosed herein is in an amount sufficient to immunize or vaccinate the individual against the HIV infection or pathology.

A HIV-based disease refers to any condition, disease or disorder where a pathophysiology effect is due to the presence of HIV. An HIV includes and HIV-1 and a HIV-2.

Aspects of the present invention provide, in part, an individual. An individual comprises any mammal including a human, and a human can be a patient.

A method disclosed herein comprises a treatment for a HIV-based disease. A treatment comprises any therapeutic or beneficial effect, including any objective or individually measurable or detectable improvement or benefit provided to a particular individual. A therapeutic or beneficial effect can but need not be complete ablation of all or any particular adverse condition, symptom, disorder, illness, disease or complication caused by or associated with a HIV infection, proliferation, replication, or pathology. Thus, a satisfactory clinical endpoint is achieved when there is an incremental improvement or a partial reduction in an adverse condition, symptom, disorder, illness, disease or complication caused by or associated with a HIV infection, proliferation, replication, or pathology, or an inhibition, decrease, reduction, suppression, prevention, limit or control of worsening or progression of one or more conditions, adverse symptoms, disorders, illnesses, diseases or complications caused by or associated with a HIV infection, proliferation, replication, or pathology over a short or long duration.

In aspects of this embodiment, a method of treatment or use disclosed herein may reduce, decrease, inhibited, limit, delay or prevent a HIV infection, proliferation, replication, or pathology. In other aspects of this embodiment, a method of treatment or use disclosed herein may reduce, decrease, suppress, limit, control or inhibit HIV virion numbers or titer; reduce, decrease, suppress, limit, control or inhibit HIV virion proliferation or replication; reduce, decrease, suppress, limit, control or inhibit the amount of a HIV protein synthesized; reduce, decrease, suppress, limit, control or inhibit the amount of a HIV virion nucleic acid replicated; and/or increase or stabilize the number of circulating CD4+ T cells. In yet other aspects of this embodiment, a method of treatment or use disclosed herein may decrease, reduce, inhibit, suppresses, prevent, control or limit one or more adverse conditions, symptoms, disorders, illnesses, diseases or complications caused by or associated with a HIV infection, proliferation or replication, or pathology. In still other aspects of this embodiment, a method of treatment or use disclosed herein may improve, accelerate, facilitate, enhance, augment, or hasten recovery of an individual from a HIV infection or pathology, or one or more adverse symptoms, disorders, illnesses, diseases or complications caused by or associated with HIV infection, proliferation or replication, or pathology.

In other aspects of this embodiment, a method of treatment or use disclosed herein may stabilize a HIV infection, pathology, or an adverse condition, symptom, disorder, illness, disease or complication caused by or associated with a HIV infection, proliferation, replication, or pathology. In yet other aspects of this embodiment, a method of treatment or use disclosed herein may decrease, reduce, inhibit, suppress, limit or control transmission of a HIV virus from an infected individual to an uninfected individual. In still other aspects of this embodiment, a method of treatment or use disclosed herein may reduce or eliminate the need, dosage frequency or amount of a concurrent or subsequent treatment such as another drug or other agent used for treating an individual having or at risk of having a HIV infection or pathology. For example, reducing an amount of an adjunct therapy, for example, a reduction or decrease of a treatment for a HIV infection or pathology, or a vaccination or immunization protocol is considered a beneficial effect. In addition, reducing or decreasing an amount of a HIV antigen used for vaccination or immunization of an individual to provide protection to the individual is considered a beneficial effect.

One or more physiological conditions or symptom associated with a HIV infection or pathology will respond to a method of treatment disclosed herein. The symptoms of HIV infection or pathology vary, depending on the phase of infection: primary or acute HIV infection, clinical latent infection, early symptomatic HIV infection, and AIDS. The majority of people infected by HIV develop a flu-like illness within a month or two after the virus enters the body. This illness, known as primary or acute HIV infection, may last for a few weeks. Although the symptoms of primary HIV infection may be mild enough to go unnoticed, the amount of virus in the blood stream (viral load) is particularly high at this time. As a result, HIV infection spreads more efficiently during primary infection than during the next stage of infection. Possible symptoms include fever, muscle soreness, rash, headache, sore throat, mouth or genital ulcers, swollen lymph glands, mainly on the neck, joint pain, night sweats, and diarrhea. In some individuals, persistent swelling of lymph nodes occurs during clinical latent HIV. Otherwise, there are no specific signs and symptoms. HIV remains in the body, however, as free virus and in infected white blood cells. Clinical latent infection typically lasts eight to 10 years. A few individuals stay in this stage even longer, but others progress to more-severe disease much sooner. As the virus continues to multiply and destroy immune cells, an individual may develop mild infections or chronic symptoms such as fever, fatigue, swollen lymph nodes, often one of the first signs of HIV infection, diarrhea, weight loss, cough, and shortness of breath. The disease typically progresses to AIDS in about 10 years. By the time AIDS develops, the immune system has been severely damaged, making the individual susceptible to opportunistic infections, diseases that wouldn't trouble an individual with a healthy immune system. The signs and symptoms of some of these infections may include soaking night sweats, shaking chills, fever higher, cough, shortness of breath, chronic diarrhea, persistent white spots or lesions on tongue or in mouth, headaches, persistent, unexplained fatigue, blurred and distorted vision, weight loss, skin rashes, or skin bumps.

Aspects of the present invention provide, in part, administering a composition comprising a TVEMP. As used herein, the term "administering" refers to any delivery mechanism that provides an immunogenic composition or therapeutic composition disclosed herein to an individual that potentially results in a clinically, therapeutically, or experimentally beneficial result. The actual delivery mechanism used to administer a composition disclosed herein to an individual can be determined by a person of ordinary skill in the art by taking into account factors, including, without limitation, the type of HIV-based disease, the location of the HIV-based disease, the cause of the HIV-based disease, the severity of the HIV-based disease, the degree of relief desired for HIV-based disease, the duration of relief desired for HIV-based disease, the particular HIV antigen, α-HIV antibody, immunogenic composition, and/or therapeutic composition used, the rate of excretion of the particular HIV antigen, α-HIV antibody, immunogenic composition, and/or therapeutic composition used, the pharmacodynamics of the particular HIV antigen, α-HIV antibody, immunogenic composition, and/or therapeutic composition used, the nature of the other compounds to be included in the immunogenic or therapeutic composition, the particular route of administration, the particular characteristics, history and risk factors of the individual, such as, e.g., age, weight, general health and the like, or any combination thereof.

A composition disclosed herein can be administered to an individual using a cellular uptake approach. Administration of a composition disclosed herein using a cellular uptake approach comprise a variety of enteral or parenteral approaches including, without limitation, oral administration in any acceptable form, such as, e.g., tablet, liquid, capsule, powder, or the like; topical administration in any acceptable form, such as, e.g., drops, spray, creams, gels or ointments; intravascular administration in any acceptable form, such as, e.g., intravenous injection, intravenous infusion, intra-arterial injection, intra-arterial infusion and catheter instillation into the vasculature; peri- and intra-tissue administration in any acceptable form, such as, e.g., intraperitoneal injection, intramuscular injection, subcutaneous injection, subcutaneous infusion, intraocular injection, retinal injection, or sub-retinal injection or epidural injection; intravesicular administration in any acceptable form, such as, e.g., catheter instillation; and by placement device, such as, e.g., an implant, a patch, a pellet, a catheter, an osmotic pump, a suppository, a bioerodible delivery system, a non-bioerodible delivery system or another implanted extended or slow release system. An exemplary list of biodegradable polymers and methods of use are described in, e.g., *Handbook of Biodegradable Polymers* (Abraham J. Domb et al., eds., Overseas Publishers Association, 1997).

A HIV antigen, α-HIV antibody, immunogenic composition, and/or therapeutic composition disclosed herein is administered in an amount sufficient to treat an HIV-based disease. In aspects of this embodiment, the amount of HIV antigen, α-HIV antibody, immunogenic composition, and/or therapeutic composition administered is an amount sufficient to reduce one or more physiological conditions or symptom associated with a HIV infection or pathology, an amount sufficient to immunize or vaccinate the individual against the HIV infection or pathology, or an amount sufficient to protect the individual against a HIV infection or pathology. As used herein, the term "amount sufficient" includes "effective amount", "effective dose", "therapeutically effective amount" or "therapeutically effective dose" and refers to the minimum amount of a HIV antigen, α-HIV antibody, immunogenic composition, and/or therapeutic composition necessary to achieve the desired therapeutic effect and includes an amount sufficient to reduce or inhibit one or more physiological conditions or symptom associated with a HIV infection or pathology.

In aspects of this embodiment, an effective amount of a HIV antigen, α-HIV antibody, immunogenic composition, and/or therapeutic composition disclosed herein reduces or inhibits one or more physiological conditions or symptom associated with a HIV infection or pathology by, e.g., at least 10%, at least 20%, at least 30%, at least 40%, at least 50%, at least 60%, at least 70%, at least 80%, at least 90% or at least 100%. In other aspects of this embodiment, an effective amount of a HIV antigen, α-HIV antibody, immunogenic composition, and/or therapeutic composition disclosed herein reduces or inhibits one or more physiological conditions or symptom associated with a HIV infection or pathology by, e.g., at most 10%, at most 20%, at most 30%, at most 40%, at most 50%, at most 60%, at most 70%, at most 80%, at most 90% or at most 100%. In yet other aspects of this embodiment, an effective amount of a HIV antigen, α-HIV antibody, immunogenic composition, and/or therapeutic composition disclosed herein reduces or inhibits one or more physiological conditions or symptom associated with a HIV infection or pathology by, e.g., about 10% to about 100%, about 10% to about 90%, about 10% to about 80%, about 10% to about 70%, about 10% to about 60%, about 10% to about 50%, about 10% to about 40%, about 20% to about 100%, about 20% to about 90%, about 20% to about 80%, about 20% to about 70%, about 20% to about 60%, about 20% to about 50%, about 20% to about 40%, about 30% to about 100%, about 30% to about 90%, about 30% to about 80%, about 30% to about 70%, about 30% to about 60%, or about 30% to about 50%. In still other aspects of this embodiment, an effective amount of a HIV antigen, α-HIV antibody, immunogenic composition, and/or therapeutic composition disclosed herein reduces or inhibits one or more physiological conditions or symptom associated with a HIV infection or pathology for, e.g., at least one week, at least one month, at least two months, at least three months, at least four months, at least five months, at least six months, at least seven months, at least eight months, at least nine months, at least ten months, at least eleven months, or at least twelve months.

The actual effective amount of a HIV antigen, α-HIV antibody, immunogenic composition, and/or therapeutic composition disclosed herein to be administered to an individual can be determined by a person of ordinary skill in the art by taking into account factors, including, without limitation, the type of HIV-based disease, the location of the HIV-based disease, the cause of the HIV-based disease, the severity of the HIV-based disease, the degree of relief desired for HIV-based disease, the duration of relief desired for HIV-based disease, the particular HIV antigen, α-HIV antibody, immunogenic composition, and/or therapeutic composition used, the rate of excretion of the particular HIV antigen, α-HIV antibody, immunogenic composition, and/or therapeutic composition used, the pharmacodynamics of the particular HIV antigen, α-HIV antibody, immunogenic composition, and/or therapeutic composition used, the nature of the other compounds to be included in the immunogenic or therapeutic composition, the particular route of administration used, the particular characteristics, history and risk factors of the individual, such as, e.g., age, weight, general health and the like, or any combination thereof. Additionally, where repeated administration of a HIV antigen, α-HIV antibody, immunogenic composition, and/or therapeutic composition disclosed herein is used, the actual therapeutically effective amount will further depend upon factors, including, without limitation, the frequency of administration, the half-life of a HIV antigen, α-HIV antibody, immunogenic composition, and/or therapeutic composition disclosed herein, or any combination thereof. It is known by a person of ordinary skill in the art that an effective amount of a HIV antigen, α-HIV antibody, immunogenic composition, and/or therapeutic composition disclosed herein can be extrapolated from in vitro assays and in vivo administration studies using animal models prior to administration to humans. Wide variations in the necessary effective amount are to be expected in view of the differing efficiencies of the various routes of administration. For instance, oral administration generally would be expected to require higher dosage levels than administration by intravenous or intravitreal injection. Variations in these dosage levels can be adjusted using standard empirical routines of optimization, which are well-known to a person of ordinary skill in the art. The precise therapeutically effective dosage levels and patterns are preferably determined by the attending physician in consideration of the above-identified factors.

In other aspects of this embodiment, an effective amount of a HIV antigen, α-HIV antibody, immunogenic composition, and/or therapeutic composition disclosed herein generally is in the range of about 0.001 mg/kg/day to about 100 mg/kg/day. In aspects of this embodiment, an effective amount of a HIV antigen, α-HIV antibody, immunogenic composition, and/or therapeutic composition disclosed herein may be, e.g., at least 0.001 mg/kg/day, at least 0.01 mg/kg/day, at least 0.1 mg/kg/day, at least 1.0 mg/kg/day, at least 5.0 mg/kg/day, at least 10 mg/kg/day, at least 15 mg/kg/day, at least 20 mg/kg/day, at least 25 mg/kg/day, at least 30 mg/kg/day, at least 35 mg/kg/day, at least 40 mg/kg/day, at least 45 mg/kg/day, or at least 50 mg/kg/day.

In other aspects of this embodiment, an effective amount of a HIV antigen, α-HIV antibody, immunogenic composition, and/or therapeutic composition disclosed herein may be in the range of, e.g., about 0.001 mg/kg/day to about 10 mg/kg/day, about 0.001 mg/kg/day to about 15 mg/kg/day, about 0.001 mg/kg/day to about 20 mg/kg/day, about 0.001 mg/kg/day to about 25 mg/kg/day, about 0.001 mg/kg/day to about 30 mg/kg/day, about 0.001 mg/kg/day to about 35 mg/kg/day, about 0.001 mg/kg/day to about 40 mg/kg/day, about 0.001 mg/kg/day to about 45 mg/kg/day, about 0.001 mg/kg/day to about 50 mg/kg/day, about 0.001 mg/kg/day to about 75 mg/kg/day, or about 0.001 mg/kg/day to about 100 mg/kg/day. In yet other aspects of this embodiment, an effective amount of a HIV antigen, α-HIV antibody, immunogenic composition, and/or therapeutic composition disclosed herein may be in the range of, e.g., about 0.01 mg/kg/day to about 10 mg/kg/day, about 0.01 mg/kg/day to about 15 mg/kg/day, about 0.01 mg/kg/day to about 20 mg/kg/day, about 0.01 mg/kg/day to about 25 mg/kg/day, about 0.01 mg/kg/day to about 30 mg/kg/day, about 0.01 mg/kg/day to about 35 mg/kg/day, about 0.01 mg/kg/day to about 40 mg/kg/day, about 0.01 mg/kg/day to about 45 mg/kg/day, about 0.01 mg/kg/day to about 50 mg/kg/day, about 0.01 mg/kg/day to about 75 mg/kg/day, or about 0.01 mg/kg/day to about 100 mg/kg/day. In still other aspects of this embodiment, an effective amount of a HIV antigen, α-HIV antibody, immunogenic composition, and/or therapeutic composition disclosed herein may be in the range of, e.g., about 0.1 mg/kg/day to about 10 mg/kg/day, about 0.1 mg/kg/day to about 15 mg/kg/day, about 0.1 mg/kg/day to about 20 mg/kg/day, about 0.1 mg/kg/day to about 25 mg/kg/day, about 0.1 mg/kg/day to about 30 mg/kg/day, about 0.1 mg/kg/day to about 35 mg/kg/day, about 0.1 mg/kg/day to about 40 mg/kg/day, about 0.1 mg/kg/day to about 45 mg/kg/day, about 0.1 mg/kg/day to about 50 mg/kg/day, about 0.1 mg/kg/day to about 75 mg/kg/day, or about 0.1 mg/kg/day to about 100 mg/kg/day.

In other aspects of this embodiment, an effective amount of a HIV antigen, α-HIV antibody, immunogenic composition, and/or therapeutic composition disclosed herein may be in the range of, e.g., about 1 mg/kg/day to about 10 mg/kg/day, about 1 mg/kg/day to about 15 mg/kg/day, about 1 mg/kg/day to about 20 mg/kg/day, about 1 mg/kg/day to about 25 mg/kg/day, about 1 mg/kg/day to about 30 mg/kg/day, about 1 mg/kg/day to about 35 mg/kg/day, about 1 mg/kg/day to about 40 mg/kg/day, about 1 mg/kg/day to about 45 mg/kg/day, about 1 mg/kg/day to about 50 mg/kg/day, about 1 mg/kg/day to about 75 mg/kg/day, or about 1 mg/kg/day to about 100 mg/kg/day. In yet other aspects of this embodiment, an effective amount of a therapeutic compound disclosed herein may be in the range of, e.g., about 5 mg/kg/day to about 10 mg/kg/day, about 5 mg/kg/day to about 15 mg/kg/day, about 5 mg/kg/day to about 20 mg/kg/day, about 5 mg/kg/day to about 25 mg/kg/day, about 5 mg/kg/day to about 30 mg/kg/day, about 5 mg/kg/day to about 35 mg/kg/day, about 5 mg/kg/day to about 40 mg/kg/day, about 5 mg/kg/day to about 45 mg/kg/day, about 5 mg/kg/day to about 50 mg/kg/day, about 5 mg/kg/day to about 75 mg/kg/day, or about 5 mg/kg/day to about 100 mg/kg/day.

In other aspects of this embodiment, an effective amount of a HIV antigen, α-HIV antibody, immunogenic composition, and/or therapeutic composition disclosed herein generally is in the range of about 0.001 mg/day to about 100 mg/day. In aspects of this embodiment, an effective amount of a HIV antigen, α-HIV antibody, immunogenic composition, and/or therapeutic composition disclosed herein may be, e.g., at least 0.001 mg/day, at least 0.01 mg/day, at least 0.1 mg/day, at least 1.0 mg/day, at least 5.0 mg/day, at least 10 mg/day, at least 15 mg/day, at least 20 mg/day, at least 25 mg/day, at least 30 mg/day, at least 35 mg/day, at least 40 mg/day, at least 45 mg/day, or at least 50 mg/day.

In other aspects of this embodiment, an effective amount of a HIV antigen, α-HIV antibody, immunogenic composition, and/or therapeutic composition disclosed herein may be in the range of, e.g., about 0.001 mg/day to about 10 mg/day, about 0.001 mg/day to about 15 mg/day, about 0.001 mg/day to about 20 mg/day, about 0.001 mg/day to about 25 mg/day, about 0.001 mg/day to about 30 mg/day, about 0.001 mg/day to about 35 mg/day, about 0.001 mg/day to about 40 mg/day, about 0.001 mg/day to about 45 mg/day, about 0.001 mg/day to about 50 mg/day, about 0.001 mg/day to about 75 mg/day, or about 0.001 mg/day to about 100 mg/day. In yet other aspects of this embodiment, an effective amount of a HIV antigen, α-HIV antibody, immunogenic composition, and/or therapeutic composition disclosed herein may be in the range of, e.g., about 0.01 mg/day to about 10 mg/day, about 0.01 mg/day to about 15 mg/day, about 0.01 mg/day to about 20 mg/day, about 0.01 mg/day to about 25 mg/day, about 0.01 mg/day to about 30 mg/day, about 0.01 mg/day to about 35 mg/day, about 0.01 mg/day to about 40 mg/day, about 0.01 mg/day to about 45 mg/day, about 0.01 mg/day to about 50 mg/day, about 0.01 mg/day to about 75 mg/day, or about 0.01 mg/day to about 100 mg/day. In still other aspects of this embodiment, an effective amount of a HIV antigen, α-HIV antibody, immunogenic composition, and/or therapeutic composition disclosed herein may be in the range of, e.g., about 0.1 mg/day to about 10 mg/day, about 0.1 mg/day to about 15 mg/day, about 0.1 mg/day to about 20 mg/day, about 0.1 mg/day to about 25 mg/day, about 0.1 mg/day to about 30 mg/day, about 0.1 mg/day to about 35 mg/day, about 0.1 mg/day to about 40 mg/day, about 0.1 mg/day to about 45 mg/day, about 0.1 mg/day to about 50 mg/day, about 0.1 mg/day to about 75 mg/day, or about 0.1 mg/day to about 100 mg/day.

In other aspects of this embodiment, an effective amount of a HIV antigen, α-HIV antibody, immunogenic composition, and/or therapeutic composition disclosed herein may be in the range of, e.g., about 1 mg/day to about 10 mg/day, about 1 mg/day to about 15 mg/day, about 1 mg/day to about 20 mg/day, about 1 mg/day to about 25 mg/day, about 1 mg/day to about 30 mg/day, about 1 mg/day to about 35 mg/day, about 1 mg/day to about 40 mg/day, about 1 mg/day to about 45 mg/day, about 1 mg/day to about 50 mg/day, about 1 mg/day to about 75 mg/day, or about 1 mg/day to about 100 mg/day. In yet other aspects of this embodiment, an effective amount of a therapeutic compound disclosed herein may be in the range of, e.g., about 5 mg/day to about 10 mg/day, about 5 mg/day to about 15 mg/day, about 5 mg/day to about 20 mg/day, about 5 mg/day to about 25 mg/day, about 5 mg/day to about 30 mg/day, about 5 mg/day to about 35 mg/day, about 5 mg/day to about 40 mg/day, about 5 mg/day to about 45 mg/day, about 5 mg/day to about 50 mg/day, about 5 mg/day to about 75 mg/day, or about 5 mg/day to about 100 mg/day.

Dosing can be single dosage or cumulative (serial dosing), and can be readily determined by one skilled in the art. For instance, treatment of a HIV-based disease may comprise a one-time administration of an effective amount of a HIV antigen, α-HIV antibody, immunogenic composition, and/or therapeutic composition disclosed herein. As a non-limiting example, an effective amount of a HIV antigen, α-HIV antibody, immunogenic composition, and/or therapeutic composition disclosed herein can be administered once to an individual, e.g., as a single injection or deposition. Alternatively, treatment of a HIV-based disease may comprise multiple administrations of an effective amount of a HIV antigen, α-HIV antibody, immunogenic composition, and/or therapeutic composition disclosed herein carried out over a range of time periods, such as, e.g., daily, once every few days, weekly, monthly or yearly. As a non-limiting example, a HIV antigen, α-HIV antibody, immunogenic composition, and/or therapeutic composition disclosed herein can be administered one, two, three, four, five or six times yearly to an individual. The timing of administration can vary from individual to individual, depending upon such factors as the severity of an individual's symptoms. For example, an effective amount of a HIV antigen, α-HIV antibody, immunogenic composition, and/or therapeutic composition disclosed herein can be administered to an individual once every three months for an indefinite period of time, or until the individual no longer requires therapy. A person of ordinary skill in the art will recognize that the condition of the individual can be monitored throughout the course of treatment and that the effective amount of a HIV antigen, α-HIV antibody, immunogenic composition, and/or therapeutic composition disclosed herein that is administered can be adjusted accordingly.

A composition comprising a HIV antigen, α-HIV antibody, immunogenic composition, and/or therapeutic composition disclosed herein can also be administered to an individual in combination with other therapeutic compounds to increase the overall therapeutic effect of the treatment. The use of multiple compounds to treat an indication can increase the beneficial effects while reducing the presence of side effects.

Aspects of the present specification disclose, in part, an immuno-based method for detecting an HIV infection. The methods disclosed herein may detect a HIV virion, a component derived from an HIV virus, a component produced or altered by an HIV virus, and/or a component produced or altered by a cell infected by the HIV virus or expressing either the whole or part of the HIV virus genetic code. An immuno-based method of detecting disclosed herein utilizes a HIV antigen disclosed herein and/or an α-HIV antibody disclosed herein. The immuno-based methods disclosed herein can be evaluated by several parameters including, e.g., accuracy, precision, limit of detection (LOD), limits of quantitation (LOQ), range, specificity, selectivity, linearity, ruggedness, and system suitability. The accuracy of a method is the measure of exactness of an analytical method, or the closeness of agreement between the measured value and the value that is accepted as a conventional true value or an accepted reference value. The precision of a method is the degree of agreement among individual test results, when the procedure is applied repeatedly to multiple samplings of a homogeneous sample. As such, precision evaluates 1) within assay variability; 2) within-day variability (repeatability); and 3) between-day variability (intermediate precision); and 4) between-lab variability (reproducibility). Coefficient of variation (CV %) is a quantitative measure of precision expressed relative to the observed or theoretical mean value. In aspects of this embodiment, an immuno-based method include, without limitation, Western blot analysis, ELISA, and immunoprecipitation.

The disclosures of US 2010/0055119 and US 2013/0039937 are each incorporated by reference in its entirety.

Aspects of the present specification can also be described as follows:

1. A HIV antigen, wherein the HIV antigen is SEQ ID NO: 1, SEQ ID NO: 2, SEQ ID NO: 3, or SEQ ID NO: 4, or a peptide having 75% amino acid identity SEQ ID NO: 1, SEQ ID NO: 2, SEQ ID NO: 3, or SEQ ID NO: 4, or a peptide of at least 7 contiguous amino acids from SEQ ID NO: 1, SEQ ID NO: 2, SEQ ID NO: 3, or SEQ ID NO: 4.

2. The HIV antigen according to embodiment 1, wherein the peptide having 75% amino acid identity SEQ ID NO: 1, SEQ ID NO: 2, SEQ ID NO: 3, or SEQ ID NO: 4 comprises at least 1 contiguous amino acid deletion, addition, and/or substitution relative to SEQ ID NO: 1, SEQ ID NO: 2, SEQ ID NO: 3, or SEQ ID NO: 4

3. The HIV antigen according to embodiment 1, wherein the peptide having 75% amino acid identity SEQ ID NO: 1, SEQ ID NO: 2, SEQ ID NO: 3, or SEQ ID NO: 4 comprises at least 1 non-contiguous amino acid deletion, addition, and/or substitution relative to SEQ ID NO: 1, SEQ ID NO: 2, SEQ ID NO: 3, or SEQ ID NO: 4

4. The HIV antigen according to embodiment 1, wherein the peptide having 75% amino acid identity SEQ ID NO: 1, SEQ ID NO: 2, SEQ ID NO: 3, or SEQ ID NO: 4 comprises at most 11 contiguous amino acid deletion, addition, and/or substitution relative to SEQ ID NO: 1, SEQ ID NO: 2, SEQ ID NO: 3, or SEQ ID NO: 4

5. The HIV antigen according to embodiment 1, wherein the peptide having 75% amino acid identity SEQ ID NO: 1, SEQ ID NO: 2, SEQ ID NO: 3, or SEQ ID NO: 4 comprises at most 11 non-contiguous amino acid deletion, addition, and/or substitution relative to SEQ ID NO: 1, SEQ ID NO: 2, SEQ ID NO: 3, or SEQ ID NO: 4

6. An immunogenic composition comprising one or more HIV antigens as defined in any one of embodiments 1-5.

7. The immunogenic composition according to embodiment 6, wherein the one or more HIV antigens are each present in an amount of between about 1 mg to about 1,000 mg.

8. The immunogenic composition according to embodiment 6 or embodiment 7, wherein the immunogenic composition further comprises one or more adjuvants or no adjuvants at all.

9. The immunogenic composition according to any one of embodiments 6-8, wherein the one or more adjuvants are each present in an amount of between about 1 pg/mL to about 1,500 μg/mL.

10. A method of making an α-HIV antibody, the method comprising the steps of a) administering to an individual an immunogenic composition as defined in any one of embodiments 6-9; and b) collecting from the individual a sample containing an α-HIV antibody or α-HIV antibody-producing cell.

11. The method according to embodiment 10, wherein the method further includes isolating the α-HIV antibody component from the sample.

12. The method according to embodiment 10 or embodiment 11, wherein the α-HIV antibody is a monoclonal antibody or a polyclonal antibody.

13. An isolated α-HIV antibody, wherein the isolated α-HIV antibody selectively binds an epitope present on a HIV virion, an epitope derived from an HIV virus, an epitope produced or altered by an HIV virus, and/or an epitope produced or altered by a cell infected by the HIV virus or expressing either the whole or part of the HIV virus genetic code.

14. The isolated α-HIV antibody according to embodiment 13, wherein the isolated α-HIV antibody is obtained from a vertebrate.
15. The isolated α-HIV antibody according to embodiment 13 or embodiment 14, wherein the isolated α-HIV antibody is an IgG class, an IgE class, an IgM class, an IgD class, or an IgA class.
16. The isolated α-HIV antibody according to embodiment 15, wherein the IgG class comprises an IgG1 subclass, an IgG2 subclass, an IgG3 subclass, or an IgG4 subclass.
17. The isolated α-HIV antibody according to embodiment 15, wherein the IgA class comprises an IgA1 subclass or an IgA2 subclass.
18. The isolated α-HIV antibody according to any one of embodiments 13-17, wherein the isolated α-HIV antibody is a polyclonal antibody, a monoclonal antibody, a dimer, a multimer, a multispecific antibody, a humanized antibody, a chimeric antibody, a bi-functional antibody, a cell-associated antibody like an Ig receptor, a linear antibody, a diabody, or a minibody, a single chain derivative, or an immunologically active fragment.
19. The isolated α-HIV antibody according to embodiment 18, wherein the single chain derivative is a single domain antibody (sdAb) or a single-chain variable fragment (scFv).
20. The isolated α-HIV antibody according to embodiment 18, wherein the immunologically active fragment is a Fab fragment, a F(ab')2 fragment, a Fc fragment, a Fd fragment, or a Fv fragment.
21. The isolated α-HIV antibody according to any one of embodiments 13-20, wherein the isolated α-HIV antibody comprises a heavy chain variable domain ($V_H$) and/or a light chain variable domain ($V_L$).
21. The isolated α-HIV antibody according to any one of embodiments 13-21, wherein the isolated α-HIV antibody comprises a heavy chain variable domain ($V_H$) CDR1 region, a CDR2 region, a CDR3 region, or any combination thereof.
23. The isolated α-HIV antibody according to any one of embodiments 13-22, wherein the isolated α-HIV antibody comprises a light chain variable domain ($V_L$) CDR1 region, a CDR2 region, a CDR3 region, or any combination thereof.
24. The isolated α-HIV antibody according to any one of embodiments 13-23, wherein the eptiope is SEQ ID NO: 1, SEQ ID NO: 2, SEQ ID NO: 3, and/or SEQ ID NO: 4, or sequence having an amino acid identity of at least about 70%, at least about 75%, at least about 80%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% relative to SEQ ID NOs: 1-4, or sequence having an amino acid identity in the range of about 75% to about 100%, about 80% to about 100%, about 85% to about 100%, about 90% to about 100%, about 95% to about 100%, about 75% to about 99%, about 80% to about 99%, about 85% to about 99%, about 90% to about 99%, about 95% to about 99%, about 75% to about 97%, about 80% to about 97%, about 85% to about 97%, about 90% to about 97%, or about 95% to about 97%, relative to SEQ ID NOs: 1-4, or sequence having at least 1, at least 2, at least 3, or at least 4, contiguous and/or non-contiguous amino acid deletions, additions, and/or substitutions relative to SEQ ID NOs: 1-4, or a sequence having at most 1, at most 2, at most 3, at most 4, contiguous and/or non-contiguous amino acid deletions, additions, and/or substitutions relative to SEQ ID NOs: 1-4, or sequence having about 1 to about 2, about 1 to about 3, about 1 to about 4, about 2 to about 3, about 2 to about 4, or about 3 to about 4 contiguous and/or non-contiguous amino acid deletions, additions, and/or substitutions relative to SEQ ID NOs: 1-4.
25. The isolated α-HIV antibody according to any one of embodiments 13-24, wherein the isolated α-HIV antibody has a variable heavy chain ($V_H$) region comprises SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, or SEQ ID NO: 27, or a sequence having an amino acid identity of at least about 70%, at least about 75%, at least about 80%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99%, relative to any one of SEQ ID NOs: 5-27, or a sequence having an amino acid identity in the range of about 75% to about 100%, about 80% to about 100%, about 85% to about 100%, about 90% to about 100%, about 95% to about 100%, about 75% to about 99%, about 80% to about 99%, about 85% to about 99%, about 90% to about 99%, about 95% to about 99%, about 75% to about 97%, about 80% to about 97%, about 85% to about 97%, about 90% to about 97%, or about 95% to about 97%, relative to any one of SEQ ID NOs: 5-27, or a sequence having at least 1, at least 2, at least 3, at least 4, at least 5, at least 6, at least 7, at least 8, at least 9, at least 10, at least 11, at least 12, at least 13, at least 14, or at least 15 contiguous amino acid deletions, additions, and/or substitutions relative to any one of SEQ ID NOs: 5-27, or a sequence having at most 1, at most 2, at most 3, at most 4, at most 5, at most 6, at most 7, at most 8, at most 9, at most 10, at most 11, at most 12, at most 13, at most 14, or at most 15 contiguous amino acid deletions, additions, and/or substitutions relative to any one of SEQ ID NOs: 5-27, or a sequence having at least 1, at least 2, at least 3, at least 4, at least 5, at least 6, at least 7, at least 8, at least 9, at least 10, at least 11, at least 12, at least 13, at least 14, or at least 15 non-contiguous amino acid deletions, additions, and/or substitutions relative to any one of SEQ ID NOs: 5-27, or a sequence having at most 1, at most 2, at most 3, at most 4, at most 5, at most 6, at most 7, at most 8, at most 9, at most 10, at most 11, at most 12, at most 13, at most 14, or at most 15 non-contiguous amino acid deletions, additions, and/or substitutions relative to any one of SEQ ID NOs: 5-27.
26. The isolated α-HIV antibody according to any one of embodiments 13-25, wherein the isolated α-HIV antibody has a variable light chain ($V_L$) region comprising SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, or SEQ ID NO: 42, or a sequence having an amino acid identity of at least about 70%, at least about 75%, at least about 80%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99%, relative to any one of SEQ ID NOs: 31-42, or a sequence having an amino acid identity in the range of about 75% to about 100%, about 80% to about 100%, about 85% to about 100%, about 90% to about 100%, about 95% to about 100%, about 75% to about 99%, about 80% to about 99%, about 85% to about 99%, about 90% to about 99%, about 95% to about 99%, about 75% to about 97%, about 80% to about 97%, about 85% to about 97%, about 90% to about 97%, or about 95% to about 97%, relative to any one of SEQ ID NOs: 31-42, or a sequence having at least 1, at least 2, at least 3, at least 4, at least 5, at least 6, at least 7, at least 8, at least 9, at least 10, at least 11, at least 12, at least 13, at least 14, or at least 15 contiguous amino acid deletions, additions, and/or substitutions relative to any one of SEQ ID NOs: 31-42, or a sequence having at most 1, at most 2, at most 3, at most 4, at most 5, at most 6, at most 7, at most 8, at most 9, at most 10, at most 11, at most 12, at most 13, at most 14, or at most 15 contiguous amino acid deletions, additions, and/or substitutions relative to any one of SEQ ID NOs: 31-42, or a sequence having at least 1, at least 2, at least 3, at least 4, at least 5, at least 6, at least 7, at least 8, at least 9, at least 10, at least 11, at least 12, at least 13, at least 14, or at least 15 non-contiguous amino acid deletions, additions, and/or substitutions relative to any one of SEQ ID NOs: 31-42, or a sequence having at most 1, at most 2, at most 3, at most 4, at most 5, at most 6, at most 7, at most 8, at most 9, at most 10, at most 11, at most 12, at most 13, at most 14, or at most 15 non-contiguous amino acid deletions, additions, and/or substitutions relative to any one of SEQ ID NOs: 31-42.

27. The isolated α-HIV antibody according to any one of embodiments 13-26, wherein the isolated α-HIV antibody comprises at least a $V_H$ CDR1 having an amino acid sequence of SEQ ID NO: 27, or a sequence having an amino acid identity of at least about 70%, at least about 75%, at least about 80%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99%, relative to SEQ ID NO: 27, or a sequence having an amino acid identity in the range of about 75% to about 100%, about 80% to about 100%, about 85% to about 100%, about 90% to about 100%, about 95% to about 100%, about 75% to about 99%, about 80% to about 99%, about 85% to about 99%, about 90% to about 99%, about 95% to about 99%, about 75% to about 97%, about 80% to about 97%, about 85% to about 97%, about 90% to about 97%, or about 95% to about 97%, relative to SEQ ID NO: 27, or a sequence having at least 1, at least 2, at least 3, or at least 4, contiguous and/or non-contiguous amino acid deletions, additions, and/or substitutions relative to SEQ ID NO: 27, or a sequence having at most 1, at most 2, at most 3, at most 4, contiguous and/or non-contiguous amino acid deletions, additions, and/or substitutions relative to SEQ ID NO: 27, a sequence having about 1 to about 2, about 1 to about 3, about 1 to about 4, about 2 to about 3, about 2 to about 4, or about 3 to about 4 contiguous and/or non-contiguous amino acid deletions, additions, and/or substitutions relative to SEQ ID NO: 27.

28. The isolated α-HIV antibody according to any one of embodiments 13-27, wherein the isolated α-HIV antibody comprises at least a $V_H$ CDR2 having an amino acid sequence of SEQ ID NO: 28, or a sequence having an amino acid identity of at least about 70%, at least about 75%, at least about 80%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99%, relative to SEQ ID NO: 28, or a sequence having an amino acid identity in the range of about 75% to about 100%, about 80% to about 100%, about 85% to about 100%, about 90% to about 100%, about 95% to about 100%, about 75% to about 99%, about 80% to about 99%, about 85% to about 99%, about 90% to about 99%, about 95% to about 99%, about 75% to about 97%, about 80% to about 97%, about 85% to about 97%, about 90% to about 97%, or about 95% to about 97%, relative to SEQ ID NO: 28, or a sequence having at least 1, at least 2, at least 3, or at least 4, contiguous and/or non-contiguous amino acid deletions, additions, and/or substitutions relative to SEQ ID NO: 28, or a sequence having at most 1, at most 2, at most 3, at most 4, contiguous and/or non-contiguous amino acid deletions, additions, and/or substitutions relative to SEQ ID NO: 28, a sequence having about 1 to about 2, about 1 to about 3, about 1 to about 4, about 2 to about 3, about 2 to about 4, or about 3 to about 4 contiguous and/or non-contiguous amino acid deletions, additions, and/or substitutions relative to SEQ ID NO: 28.

29. The isolated α-HIV antibody according to any one of embodiments 13-28, wherein the isolated α-HIV antibody comprises at least a $V_H$ CDR3 having an amino acid sequence of SEQ ID NO: 29, or a sequence having an amino acid identity of at least about 70%, at least about 75%, at least about 80%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99%, relative to SEQ ID NO: 29, or a sequence having an amino acid identity in the range of about 75% to about 100%, about 80% to about 100%, about 85% to about 100%, about 90% to about 100%, about 95% to about 100%, about 75% to about 99%, about 80% to about 99%, about 85% to about 99%, about 90% to about 99%, about 95% to about 99%, about 75% to about 97%, about 80% to about 97%, about 85% to about 97%, about 90% to about 97%, or about 95% to about 97%, relative to SEQ ID NO: 29, or a sequence having at least 1, at least 2, at least 3, or at least 4, contiguous and/or non-contiguous amino acid deletions, additions, and/or substitutions relative to SEQ ID NO: 29, or a sequence having at most 1, at most 2, at most 3, at most 4, contiguous and/or non-contiguous amino acid deletions, additions, and/or substitutions relative to SEQ ID NO: 29, a sequence having about 1 to about 2, about 1 to about 3, about 1 to about 4, about 2 to about 3, about 2 to about 4, or about 3 to about 4 contiguous and/or non-contiguous amino acid deletions, additions, and/or substitutions relative to SEQ ID NO: 29.

30. The isolated α-HIV antibody according to any one of embodiments 13-29, wherein the isolated α-HIV antibody comprises at least a $V_L$ CDR1 having an amino acid sequence of SEQ ID NO: 43, or a sequence having an amino acid identity of at least about 70%, at least about 75%, at least about 80%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99%, relative to SEQ ID NO: 43, or a sequence having an amino acid identity in the range of about 75% to about 100%, about 80% to about 100%, about 85% to about 100%, about 90% to about 100%, about 95% to about 100%, about 75% to about 99%, about 80% to about 99%, about 85% to about 99%, about 90% to about 99%, about 95% to about 99%, about 75% to about 97%, about 80% to about 97%, about 85% to about 97%, about 90% to about 97%, or about 95% to about 97%, relative to SEQ ID NO: 43, or a sequence having at least 1, at least 2, at least 3, or at least 4, contiguous and/or non-contiguous amino acid deletions, additions, and/or substitutions relative to SEQ ID NO: 43, or a sequence having at most 1, at most 2, at most 3, at most 4, contiguous and/or non-contiguous amino acid deletions, additions, and/or substitutions relative to SEQ ID NO: 43, a sequence having about 1 to about 2, about 1 to about 3, about 1 to about 4, about 2 to about 3, about 2 to about 4, or about 3 to about 4 contiguous and/or non-contiguous amino acid deletions, additions, and/or substitutions relative to SEQ ID NO: 43.

31. The isolated α-HIV antibody according to any one of embodiments 13-30, wherein the isolated α-HIV antibody comprises at least a $V_L$ CDR1 having an amino acid sequence of SEQ ID NO: 44, or a sequence having an amino acid identity of at least about 70%, at least about 75%, at least about 80%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99%, relative to SEQ ID NO: 44, or a sequence having an amino acid identity in the range of about 75% to about 100%, about 80% to about 100%, about 85% to about 100%, about 90% to about 100%, about 95% to about 100%, about 75% to about 99%, about 80% to about 99%, about 85% to about 99%, about 90% to about 99%, about 95% to about 99%, about 75% to about 97%, about 80% to about 97%, about 85% to about 97%, about 90% to about 97%, or about 95% to about 97%, relative to SEQ ID NO: 44, or a sequence having at least 1, at least 2, at least 3, or at least 4, contiguous and/or non-contiguous amino acid deletions, additions, and/or substitutions relative to SEQ ID NO: 44, or a sequence having at most 1, at most 2, at most 3, at most 4, contiguous and/or non-contiguous amino acid deletions, additions, and/or substitutions relative to SEQ ID NO: 44, a sequence having about 1 to about 2, about 1 to about 3, about 1 to about 4, about 2 to about 3, about 2 to about 4, or about 3 to about 4 contiguous and/or non-contiguous amino acid deletions, additions, and/or substitutions relative to SEQ ID NO: 44.

32. The isolated α-HIV antibody according to any one of embodiments 13-31, wherein the isolated α-HIV antibody comprises at least a $V_L$ CDR1 having an amino acid sequence of SEQ ID NO: 45, or a sequence having an amino acid identity of at least about 70%, at least about 75%, at least about 80%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99%, relative to SEQ ID NO: 45, or a sequence having an amino acid identity in the range of about 75% to about 100%, about 80% to about 100%, about 85% to about 100%, about 90% to about 100%, about 95% to about 100%, about 75% to about 99%, about 80% to about 99%, about 85% to about 99%, about 90% to about 99%, about 95% to about 99%, about 75% to about 97%, about 80% to about 97%, about 85% to about 97%, about 90% to about 97%, or about 95% to about 97%, relative to SEQ ID NO: 45, or a sequence having at least 1, at least 2, at least 3, or at least 4, contiguous and/or non-contiguous amino acid deletions, additions, and/or substitutions relative to SEQ ID NO: 45, or a sequence having at most 1, at most 2, at most 3, at most 4, contiguous and/or non-contiguous amino acid deletions, additions, and/or substitutions relative to SEQ ID NO: 45, a sequence having about 1 to about 2, about 1 to about 3, about 1 to about 4, about 2 to about 3, about 2 to about 4, or about 3 to about 4 contiguous and/or non-contiguous amino acid deletions, additions, and/or substitutions relative to SEQ ID NO: 45.

33. The isolated α-HIV antibody according to any one of embodiments 13-32, wherein the isolated α-HIV antibody has an association rate constant of less than $1\times10^5$ $M^{-1}$ $s^{-1}$ for an epitope.

34. The isolated α-HIV antibody according to any one of embodiments 13-33, wherein the isolated α-HIV antibody has an association rate constant of between $1\times10^5$ $M^{-1}$ $s^{-1}$ to $1\times10^3$ $s^{-1}$ for an epitope.

35. The isolated α-HIV antibody according to any one of embodiments 13-34, wherein the isolated α-HIV antibody has an disassociation rate constant of less than $1\times10^{-3}$ $s^{-1}$ for an epitope.

36. The isolated α-HIV antibody according to any one of embodiments 13-35, wherein the isolated α-HIV antibody has an disassociation rate constant of between $1\times10^{-3}$ $s^{-1}$ to $1\times10^{-5}$ $s^{-1}$ for an epitope.

37. The isolated α-HIV antibody according to any one of embodiments 13-36, wherein the isolated α-HIV antibody has an equilibrium disassociation rate constant of less than 0.500 nM for an epitope.

38. The isolated α-HIV antibody according to any one of embodiments 13-37, wherein the isolated α-HIV antibody has an equilibrium disassociation rate constant of between 0.050 nM to 0.500 nM for an epitope.

39. A therapeutic composition comprising one or more α-HIV antibodies as defined in any one of embodiments 13-38.

40. The therapeutic composition according to embodiment 39, wherein the one or more α-HIV antibodies are each present in an amount of between about 1 μg to about 3,000 mg.

41. The therapeutic composition according to embodiment 39 or embodiment 40, wherein the therapeutic composition further comprises one or more pharmaceutical acceptable carriers.

42. A method of treating a HIV-based disease, the method comprising the step of administering to an individual in need thereof an α-HIV antibody as defined in any one of embodiments 13-38 or therapeutic composition as defined in any one of embodiments 39-41 in an amount sufficient to reduce one or more physiological conditions or symptom associated with a HIV infection or pathology, thereby treating the HIV-based disease.

43. The method according to embodiment 42, wherein the administration of the α-HIV antibody or the therapeutic composition is in an amount sufficient to increase, induce, enhance, augment, promote or stimulate HIV clearance or removal, or decrease, reduce, inhibit, suppress, prevent, control, or limit transmission of HIV to another individual.

44. The method according to embodiment 42 or embodiment 43, wherein the administration of the α-HIV antibody or the therapeutic composition is in an amount sufficient to reduce, decrease, suppress, limit, control or inhibit HIV virion numbers or titer; reduce, decrease, suppress, limit, control or inhibit HIV virion proliferation or replication; reduce, decrease, suppress, limit, control or inhibit the amount of a HIV protein synthesized; reduce, decrease, suppress, limit, control or inhibit the amount of a HIV virion nucleic acid replicated, and/or increase or stabilize the number of circulating CD4+ T cells.

45. The method according to any one of embodiments 42-44, wherein the administration of the α-HIV antibody or the therapeutic composition reduces one or more physiological conditions or symptom associated with a HIV infection or pathology by at least 10%.

46. The method according to any one of embodiments 42-45, wherein the administration of the α-HIV antibody or the therapeutic composition reduces one or more physiological conditions or symptom associated with a HIV infection or pathology by at least one week.

47. The method according to any one of embodiments 42-46, wherein the one or more physiological conditions or symptom comprise fever, chills, fatigue, muscle soreness, skin rash, skin bumps, headache, sore throat, mouth or genital ulcers, white spots or lesions on tongue or in mouth, swollen lymph glands, mainly on the neck, joint pain, night sweats, diarrhea, weight loss, blurred and distorted vision, cough, and/or shortness of breath.

48. Use of an α-HIV antibody as defined in any one of embodiments 13-38 or therapeutic composition as defined in any one of embodiments 39-41 to treat a HIV-based disease.

49. A method of treating a HIV-based disease, the method comprising the step of administering to an individual in need thereof a HIV antigen as defined in any one of embodiments 1-5 or an immunogenic composition as defined in any one of embodiments 6-9 in an amount sufficient to immunize or vaccinate the individual against the HIV infection or pathology, thereby treating the HIV-based disease.

50. A method of treating a HIV-based disease comprises administering to an individual in need thereof a HIV antigen as defined in any one of embodiments 1-5 or an immunogenic composition as defined in any one of embodiments 6-9 in an amount sufficient to protect the individual against a HIV infection or pathology, thereby treating the HIV-based disease.

51. The method according to embodiment 50, wherein the administration of the HIV antigen or the immunogenic composition is in an amount sufficient to increase, induce, enhance, augment, promote or stimulate an immune response against a HIV.

52. The method according to embodiment 50 or embodiment 51, wherein the administration of the HIV antigen or the immunogenic composition is in an amount sufficient to immunize or vaccinate the individual against the HIV infection or pathology.

53. The method according to any one of embodiments 43-45, wherein the administration of the HIV antigen or the immunogenic composition is in an amount sufficient to reduce, decrease, limit, control or inhibit susceptibility to a HIV infection or pathology.

54. The method according to any one of embodiments 50-53, wherein the administration of the HIV antigen or the immunogenic composition is in an amount sufficient to increase, induce, enhance, augment, promote or stimulate HIV clearance or removal, or decrease, reduce, inhibit, suppress, prevent, control, or limit transmission of HIV to another individual.

55. Use of a HIV antigen as defined in any one of embodiments 1-5 for the manufacture of a medicament.

56. Use of an immunogenic composition as defined in any one of embodiments 6-9 for the manufacture of a medicament.

57. Use of an α-HIV antibody as defined in any one of embodiments 13-38 for the manufacture of a medicament.

58. Use of a therapeutic composition as defined in any one of embodiments 39-41 for the manufacture of a medicament.

59. A method of detecting a HIV infection, the method comprising the steps of: a) contacting a sample with an α-HIV antibody as defined in any one of embodiments 13-38; and b) detecting for the presence or absence of an antibody-antigen complex comprising the α-HIV antibody; wherein detection by the antibody-antigen complex is indicative of the presence of a HIV infection.

60. The method according to embodiment 59, wherein the sample undergoes one or more purification steps before being contacted with an α-HIV antibody of step (a).

61. The method according to embodiment 59 or embodiment 60, wherein the α-HIV antibody of step (c) is linked to a solid phase support 62. The method according to any one of embodiments 59-61, wherein an antigen of the antibody-antigen complex is a HIV virion, a component derived from an HIV virus, a component produced or altered by an HIV virus, and/or a component produced or altered by a cell infected by the HIV virus or expressing either the whole or part of the HIV virus genetic code.

63. The method according to any one of embodiments 59-62, wherein the detecting step (c) is performed using a Western blot analysis, an ELISA, or an immunoprecipitation.

EXAMPLES

The following non-limiting examples are provided for illustrative purposes only in order to facilitate a more complete understanding of the disclosed subject matter. These examples should not be construed to limit any of the embodiments described in the present specification, including those pertaining to HIV antigens, α-HIV antibodies, immunogenic compositions, therapeutic compositions, or methods and uses for treating a HIV-based disease.

Example 1

HIV Peptides Antibody Immunogenicity

A total of 12 C57BL/6 mice (1:1 M:F, n=6 per group) were immunized subcutaneously at the base of the tail on Days 1 by injecting 200 µL of HIV-v or NRP-v. HIV-v is an immune admixture comprising 10 nmol each of four multi-epitope synthetic peptides and PBS emulsified 1:1 with the adjuvant Montanide ISA-51 (Seppic, France). Each peptide was manufactured by Fmoc chemistry (Bachem AG, Switzerland) in accordance with Good Manufacturing Practice (GMP). The four peptide were: a 30 amino acid peptide corresponding to residues 51 to 80 of a VPR protein from HIV (SEQ ID NO: 1); a 40 amino acid peptide corresponding to residues 142 to 181 of a VIF protein from HIV (SEQ ID NO: 2); a 27 amino acid peptide corresponding to residues 69 to 95 of a REV protein from HIV (SEQ ID NO:

3); and a 43 amino acid peptide corresponding to residues 51 to 80 of a NEF protein from HIV (SEQ ID NO: 4). These sequences were identified in silico through multiple sequence (ClustalW) and immunogenicity analysis of all HIV-1 and HIV-2 protein sequences available at the National Centre for Biotechnology Information (NCBI) database. Each polypeptide represents a short region of high sequence conservation (≥70%) containing >5 human T-cell epitopes. NRP-v is an immune admixture comprising an equimolar mix of multi-epitope non-HIV derived polypeptides. Pre-immunisation sera was collected as a control. All animals received 200 μL of the immune mixture as booster immunizations on Day 15 (200 μL dose). Sera was collected on Day 21.

Antibody titres were assessed by ELISA. ELISA 96-well plates were coated overnight at +4° C. with 2 μM of single HIV-v peptides [VPR peptide (SEQ ID NO: 1); VIF peptide (SEQ ID NO: 2); REV peptide (SEQ ID NO: 3); and NEF peptide (SEQ ID NO: 4)] in PBS (Sigma). Plates were washed with PBS+0.05% Tween 20 (Sigma) (PBS-T) and blocked for 1 hour with 1% BSA Fraction V (Sigma) in PBS. After washing with PBS-T, test sera samples were added. Following 2 hours incubation, plates were washed with PBS-T and either HRP-conjugated goat anti-mouse-Ig (Sigma), HRP-goat anti-mouse IgG1 (AbD Serotec) or HRP-rat anti-mouse IgG2a/c (BD Biosciences) was added. After 1 hour incubation, plates were washed with PBS-T and TMB substrate (Sigma) was added. The reaction was stopped with 0.5 M $H_2SO_4$ and absorbance was read at 450 nm. Antibody concentrations were quantified against purified total Ig (Sigma), IgG2c (BD Biosciences) and IgG1 (AbD Serotec) standards. Sera samples from each individual were tested separately in triplicates at various dilutions (1:100, 1:200, 1:400, 1:800 and 1:1600). Statistically significant increases in the immune responses to antigens between the HIV-v and NRP-vaccinated animals were established by non-parametric Mann-Whitney analysis. A positive response, indicated by an asterisk (*) was defined as an increment of at least 100% over the background (control) response with a statistical significance of p<0.05.

The results indicate that immunization with HIV-v elicited significant total IgG responses against both VIF (FIG. 1 B) and NEF (FIG. 1 D), but not against VPR (FIG. 1 A) or REV (FIG. 1 C). In addition, significant levels of both IgG2c and IgG1 were produced against VIF (FIGS. 1E & 1F), whilst the NEF peptide only elicited a significant IgG2c response (FIGS. 1E & 1F).

Example 2

HIV VIF Polyclonal Sera Antibody Activation of Complement

A total of 12 C57BL/6 mice (1:1 M:F, n=6 per group) were immunized subcutaneously at the base of the tail on Days 1 by injecting 200 μL of VIF-v. VIF-v is an immune mixture comprising 40 nmol of the multi-eptitope synthetic peptide VIF (SEQ ID NO: 2) and PBS emulsified 1:1 with the adjuvant Montanide ISA-51 (Seppic, France). Pre-immunisation sera was collected as a control. All animals received 200 μL of the immune mixture as booster immunizations on Day 15, Day 29 and Day 43 (200 μL dose). Sera was collected on Day 121.

T1 cells, naturally-infected with HIV-1 strain IIIB or field isolate UG/92/029 (Clade A) (Southern Research Institute), were seeded at 6×10³ cells/well in flat bottom 96-well plates together with heat-inactivated test sera diluted 1/100 in PBS and baby rabbit complement (AbD Serotec) in IMDM (Sigma) supplemented with 50 IU/50 μg/mL of penicillin/streptomycin (Sigma) and 10% FCS. After incubation for 2 hours, cell lysis (Experimental Release) was measured using the LDH-based CYTOTOX 96® Non-Radioactive Cytotoxicity Assay according to manufacturer's instructions (Promega). The dynamic range of the assay was determined using as minimum LDH release (MIN) non-infected T1 cells incubated with baby rabbit complement in PBS without sera and as maximum LDH release (MAX) cells lysed with Triton X-100. The percentage of Specific Immune Lysis (% SIL) was calculated using the following formula: % SIL=100×(Experimental Release−MIN Release)/(MAX Release−MIN Release).

FIG. 2 shows that sera from HIV-v immunised animals induced a significantly higher level of lysis of HIV infected T1 cells than sera from NRP-v immunised animals (72.8%±17.8 vs 23.9%±1.1 for UG/92/029 infected cells, and 85.7%±8.2 vs 44.8%±1.0 for IIIB infected cells). This data clearly proves that immunization elicited HIV-v specific antibodies (including both NEF-peptide-specific and VIF-peptide-specific antibodies) and that these antibodies, when present in the media surrounding the cells, can specifically access and recognize naturally presented HIV derived epitopes produced only in infected cells. Recognition of these epitopes by the antibodies triggers a complement response that delivers a cytolitic shock to the infected cell and kills it.

The different levels of cell lysis induced by the NRP-v sera against cells infected with the two test strains of HIV-1 do not detract from the clear anti-viral effector function of the HIV-v specific sera, but they do reflect two important features of the assay. Firstly, the baseline lysis (0%) for both the IIIB and the UG/92/029 infected T1 cells is defined by non-infected T1 cells in the presence of complement. Viral antigens on the surface of infected cells are known to spontaneously activate the alternative complement pathway, which is antibody independent, see, e.g., Rødgaard, et al., Complement receptor type I (CR1, CD35) expression on peripheral T lymphocytes both CD4− and CD8− positive cells express CR1, Complement Inflamm. 8: 303-309 (1991). As a result, the observed increase over baseline in the lysis caused by NRP-v is probably due to a nonspecific release of LDH enzyme during the assay. Secondly, in preparation for this assay, T1 cells were infected with the different viral strains and only used as targets when intracellular HIV p24 expression was maximal. For strain IIIB that corresponded to 2 days post-infection (42% cellular viability) whilst for strain UG/92/029 it was 10 days post-infection (61.2% cellular viability). As the assay measures release on the medium of a strict intracellular enzyme (LDH), which is also known to leak through damaged membranes, the higher non-specific response (i.e. against NRP-v) observed against the IIIb infected T1 cells (44.8%) is consistent and entirely correlates with its reduced cell viability (42%) at the point of maximum HIV p24 expression.

Example 3

HIV Flow Cytometry Analysis

A total of 12 C57BL/6 mice (1:1 M:F, n=6 per group) were immunized subcutaneously at the base of the tail on Days 1 by injecting 200 μL of VIF-v. VIF-v is an immune mixture comprising 40 nmol of the multi-eptitope synthetic peptide VIF (SEQ ID NO: 2) and PBS emulsified 1:1 with the adjuvant Montanide ISA-51 (Seppic, France). Pre-immunisation sera was collected as a control. All animals received 200 μL of the immune mixture as booster immunizations on Day 15, Day 29 and Day 43 (200 μL dose). Sera was collected on Day 121.

Figure 3A:
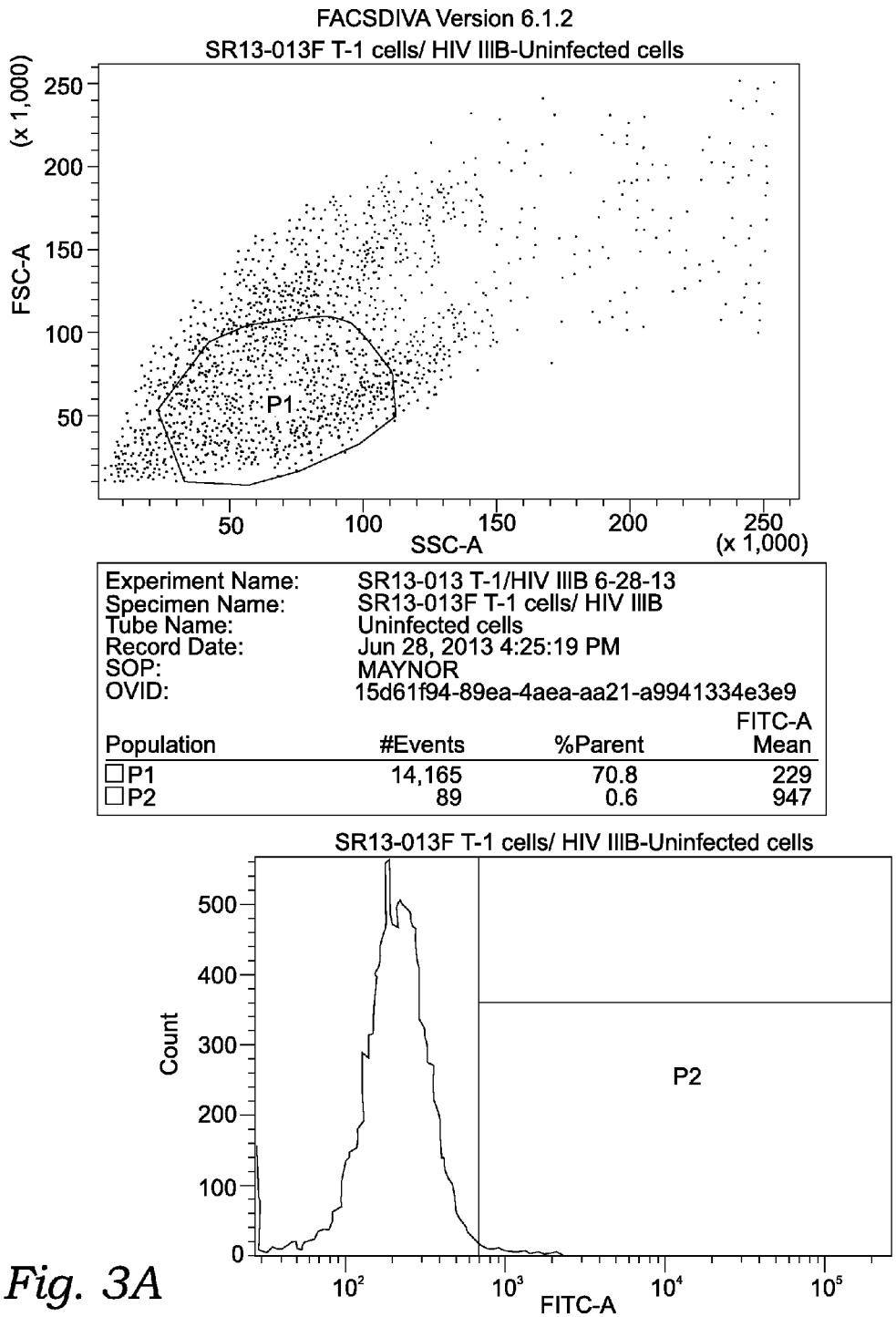
FIGS. 3A-F show results from flow cytometry analysis.
Figure 3B:
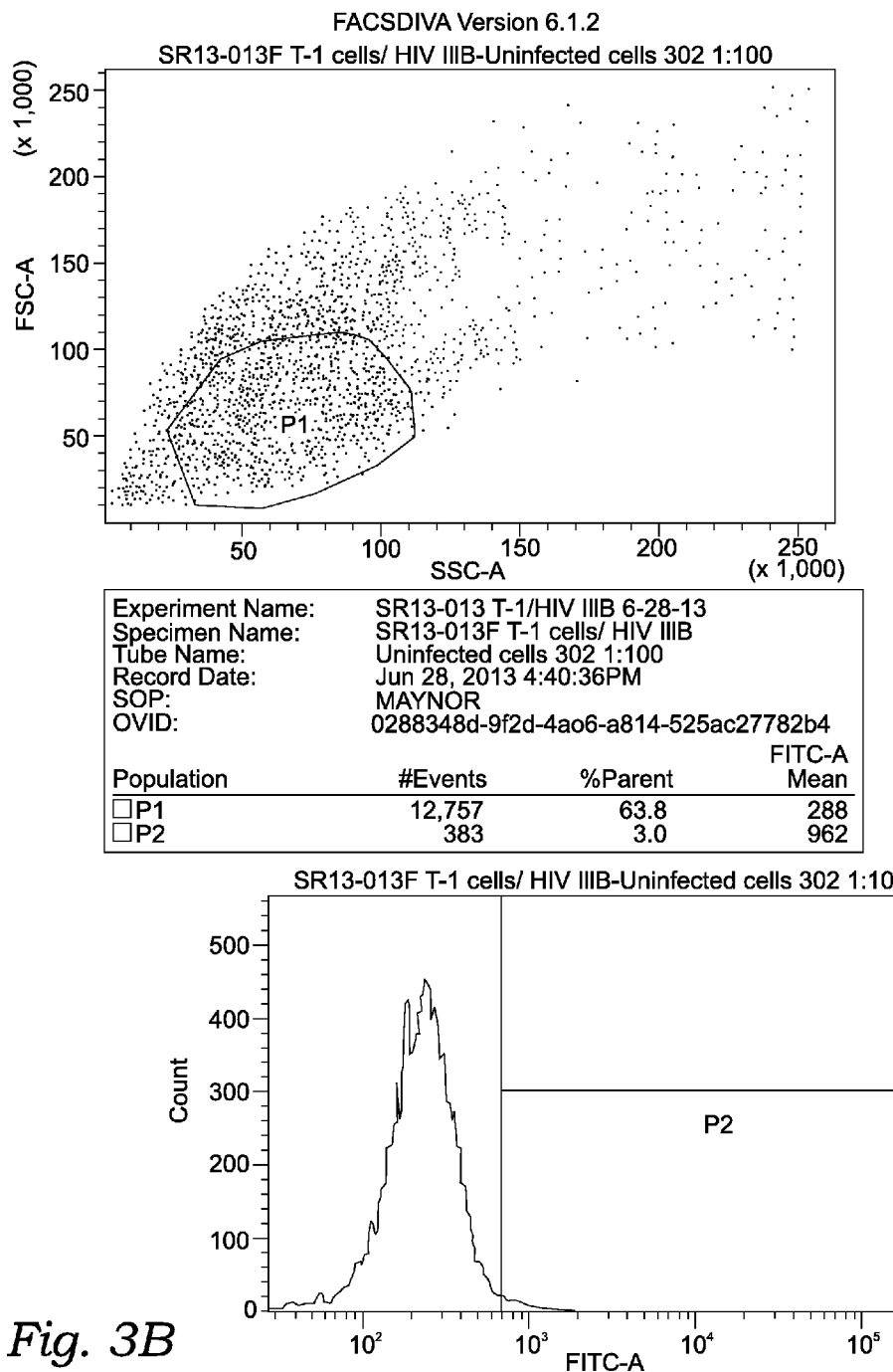
Figure 3C:
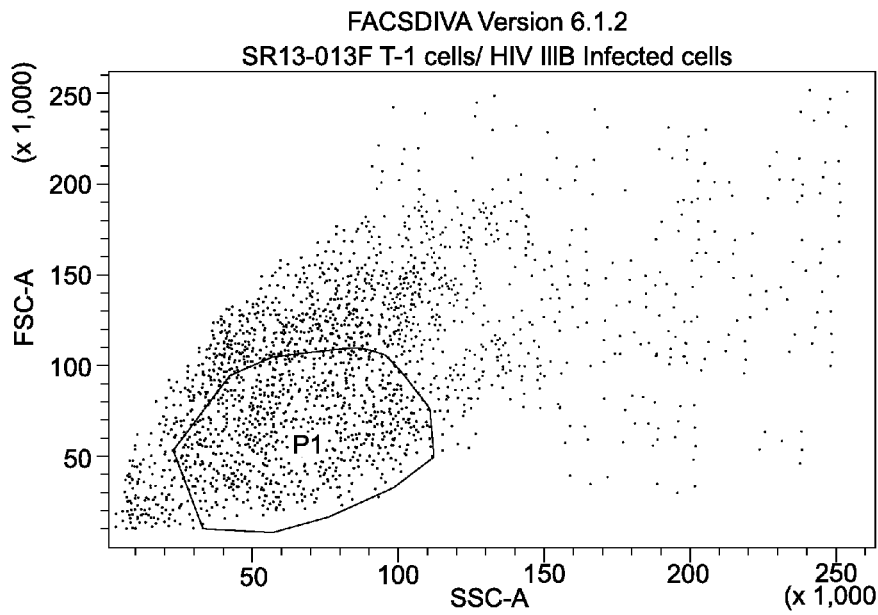
Figure 3C:
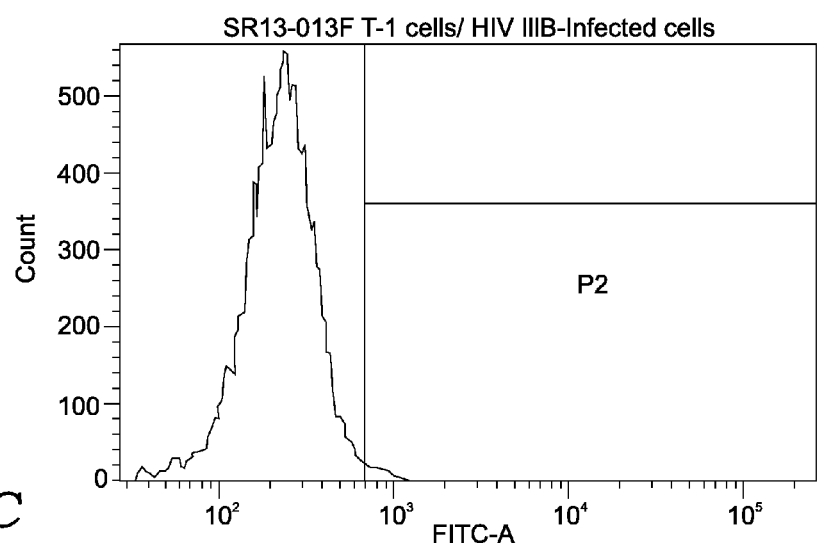
Figure 3D:
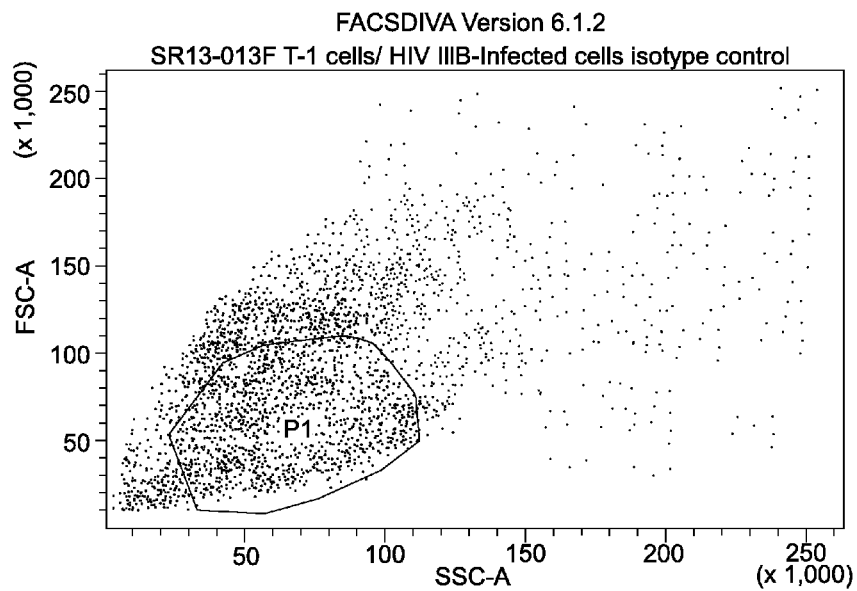
Figure 3D:
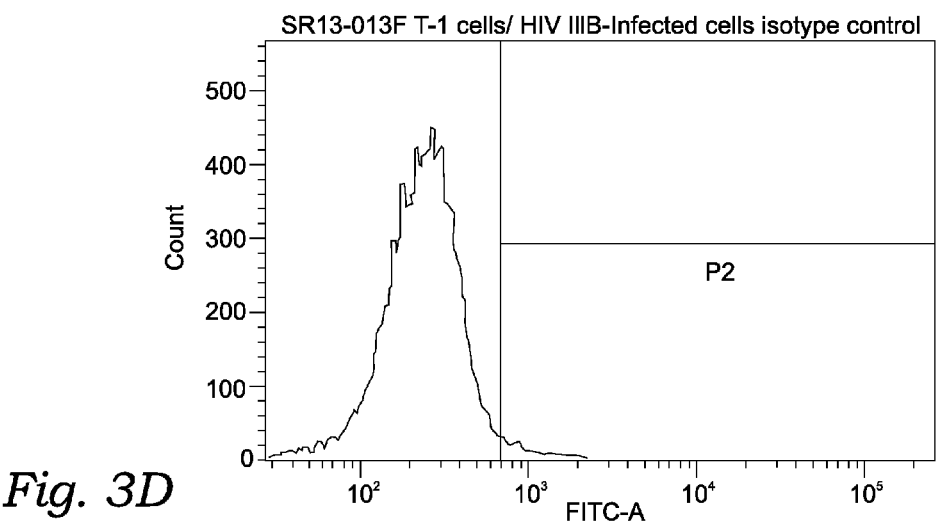
Figure 3E:
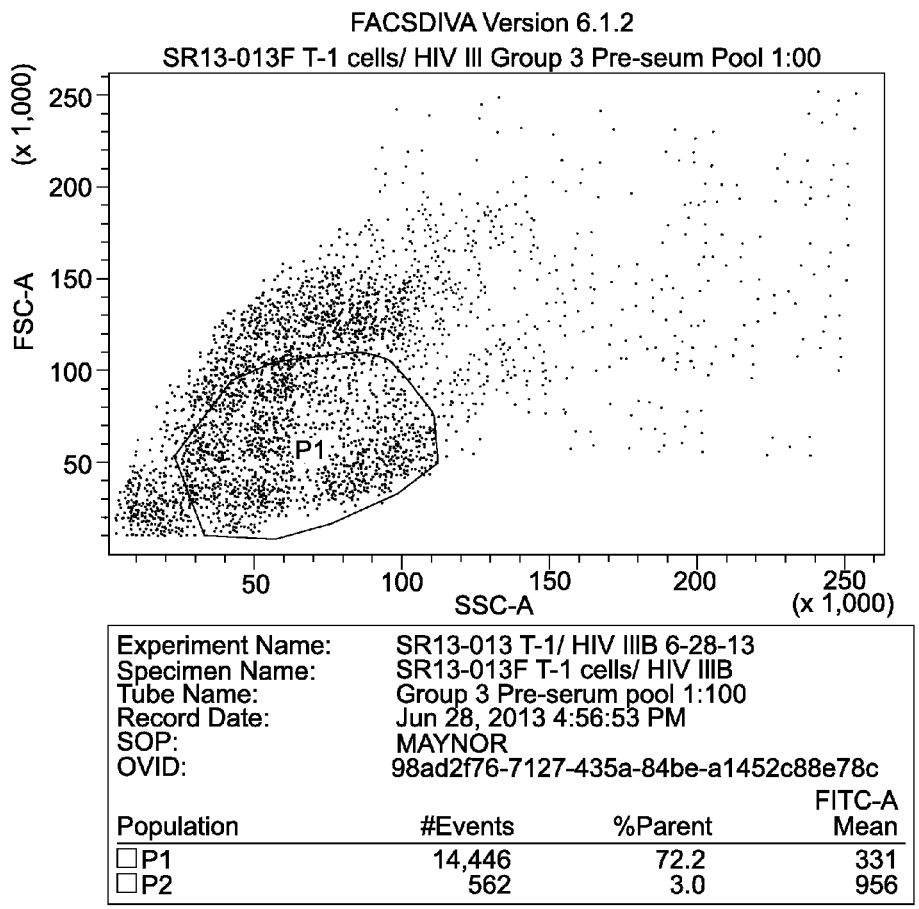
Figure 3E:
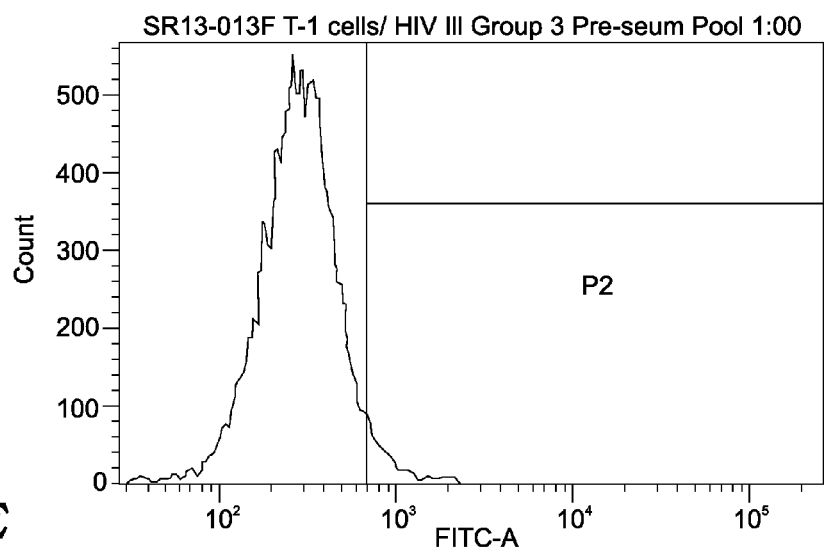
Figure 3F:
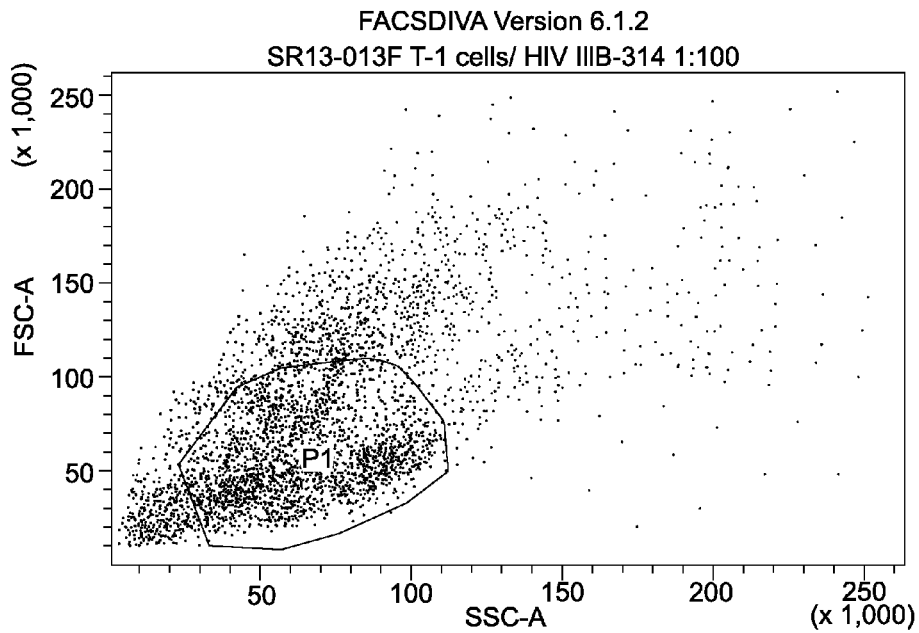
Figure 3F:
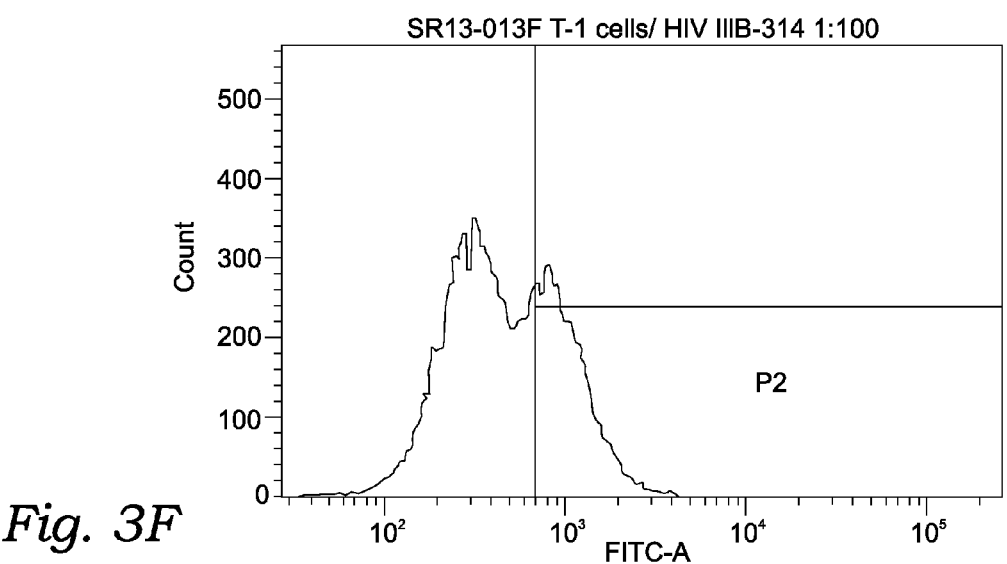
Figure 4:
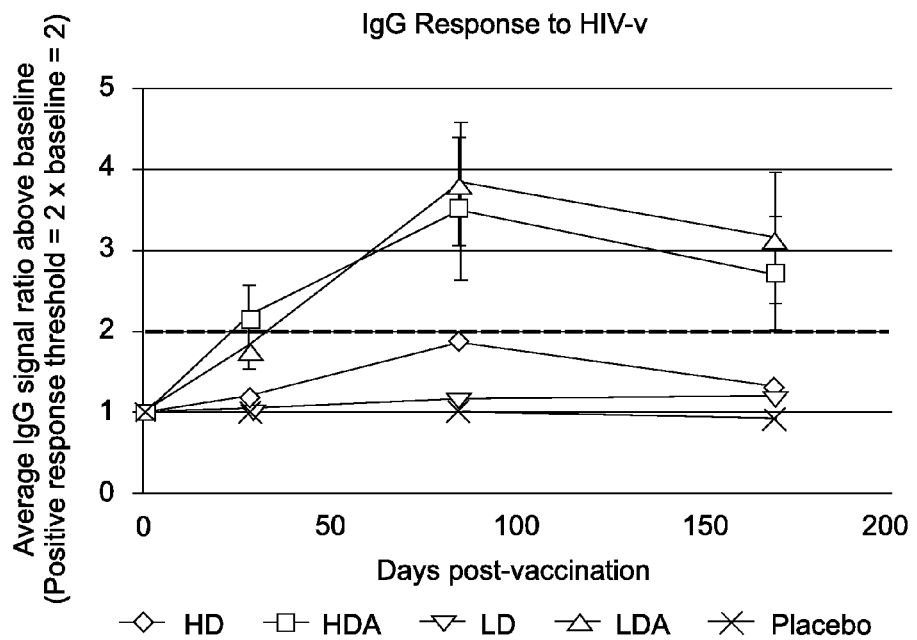
FIG. 4 shows IgG response to HIV-v.
Figure 5A:
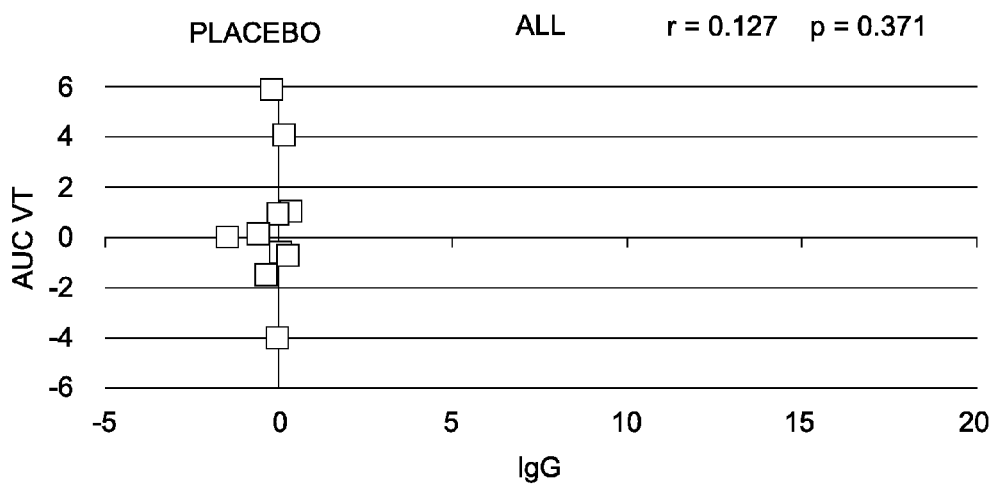
FIGS. 5A-B show results of HIV antibody generation.
Figure 5B:
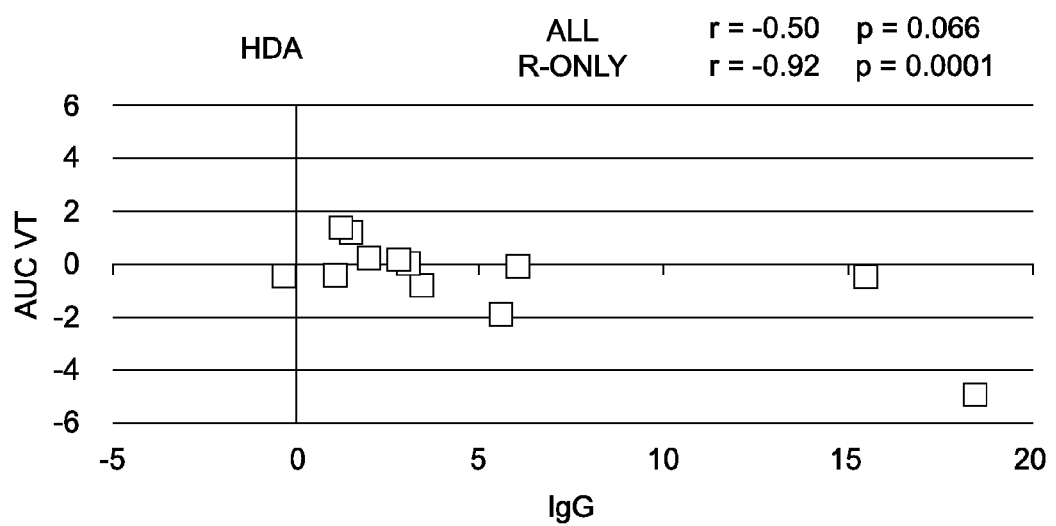
Figure 6C:
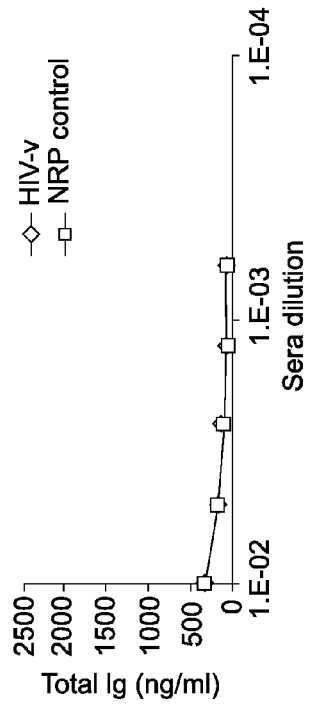
FIGS. 6A-F show Total Ig and IgG isotype responses to the HIV-v polypeptide components.
Figure 6D:
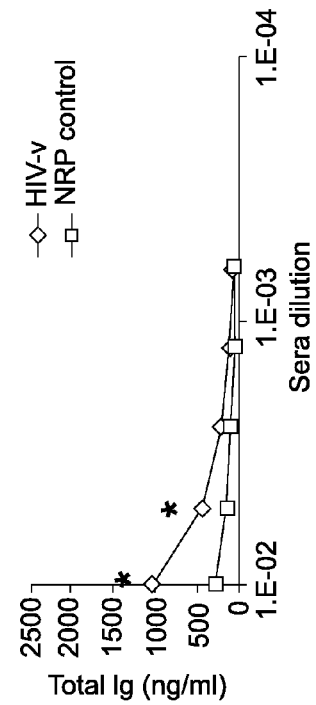
Figure 6A:
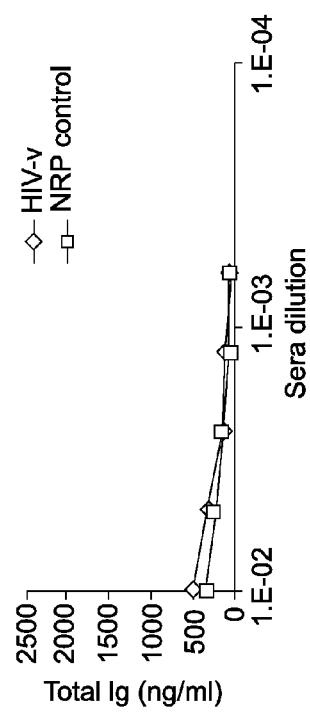
Figure 6B:
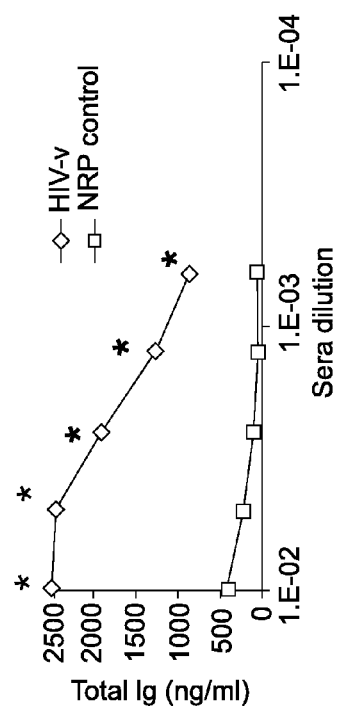
Figure 6E:
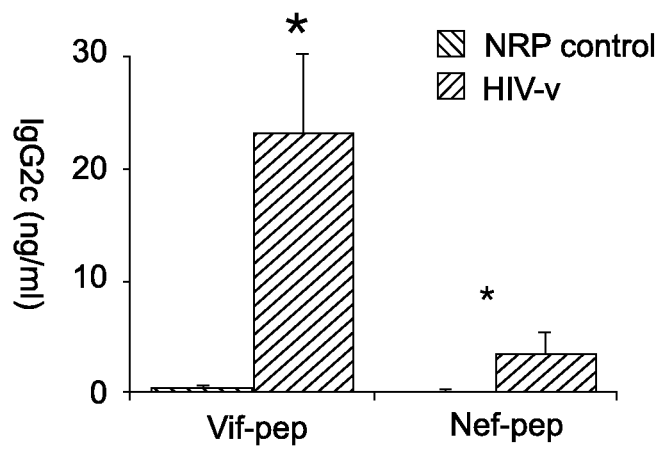
Figure 6F:
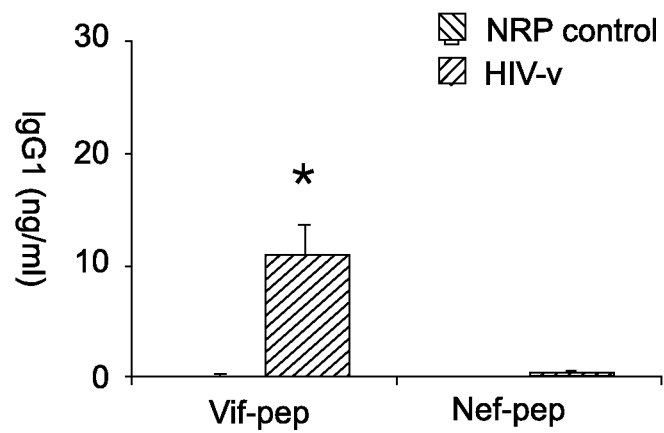

The ability of HIV VIF peptide antibody to bind VIF protein on the cell surface antigen of HIV infected T1 cells was tested by two-step surface staining and flow cytometry (FACS). Single cell suspensions of infected HIV-1 strain IIIB infected T1 human cells were prepared, 1×10⁶ cells added into 5 mL polystyrene tubes and the preparation washed twice with FACS buffer (FB). FcR blocker was added to the FACS tube and incubated 15 minutes at 4° C. Each tube was washed with FB 100 μL of pre- or post-vaccination serum, diluted in FB (1:100, 1:400 and 1:1600), added. The tubes were incubated on ice for 30 minutes and washed twice with FB. After adding 100 μL of optimally diluted anti-mouse IgG-PE (or FITC) secondary antibody, tubes were incubated on ice for 30 minutes, washed twice with FB and analyzed with BD FACSCantoII. Results show that α-VIF antibodies detected a protein from HIV infected cells (Table 3, 32.1% positive; FIG. 3F) but not in uninfected control samples (Table 3, 0.6% to 3.8% positive; FIGS. 3A-4E), indicating that α-VIF antibodies detect the natural VIF protein on the surface of HIV infected cells.

TABLE 3

Flow Cytometry Results

| Animal ID | Dilution | % positive | MFI |
|---|---|---|---|
| Uninfected cells no serum | none | 0.6 | 947 |
| Uninfected cells Post-vaccination serum | 1:100 | 3.0 | 962 |
| Infected cells no serum | none | 1.1 | 900 |
| Infected Isotype control | 1:100 | 1.9 | 971 |
| Infected cells pre-vaccination serum | 1:100 | 3.8 | 956 |
| Infected cells post-vaccination serum | 1:100 | 32.1 | 1141 |

Example 4

HIV VIF Monoclonal Antibody Activation of Complement

Splenocytes of animals immunized with VIF-v (see Example 2) were harvested and fused with immortalized progenitors. Fused hybridomas were cloned by limiting dilution assay in 96 well plates by stimulation with HIV VIF-v peptide. Hybridoma clones that proliferated were harvested, and their growth media supernatants tested for complement activation against HIV infected T1 cells (see below). Clones that were positive in the complement assay were again cloned by limiting dilution assay and tested for complement activity against HIV infected T1 cells. This process of cloning and selection was repeated a total of four to five times.

T1 cells, naturally-infected with HIV-1 strain IIIB or field isolate UG/92/029 (Clade A) (Southern Research Institute), were seeded at 6×10³ cells/well in flat bottom 96-well plates together with Hybridoma clone supernatant either neat or diluted 1/10 or 1/100 in PBS and baby rabbit complement (AbD Serotec) in IMDM (Sigma) supplemented with 50 IU/50 μg/mL of penicillin/streptomycin (Sigma) and 10% FCS. After incubation for 2 hours, cell lysis (Experimental Release) was measured using the LDH-based CYTOTOX 96® Non-Radioactive Cytotoxicity Assay according to manufacturer's instructions (Promega).

Results are shown in Table 4. The data clearly shows that, at all dilutions tested, media from all clones of HIV-VIF-peptide specific Monoclonal antibody (i.e. 52C3.F12.G1.D9, 52C3.F12.G1.E9, 52C3.H5.F10.D5, 52C3.H5.F10.E8, 52C3.H3.H2.B9.D5 and 52C3.H3.H2.B9.G10) induced releases of intracellular LDH (i.e. cell lysis) between 18- and 52-fold higher than that induced by media not containing the MAb (No-Hybridoma media). The observation that the magnitude of the effect is dose dependent reflects the specific nature of the antibody response. Also, differences in the magnitude of the response amongst the different clones reflect the different affinities of the different antibodies for their target (i.e. epitopes of VIF naturally produced and presented in cells infected by HIV) and or for the complement molecules. None of these differences, however, detract from the efficacy of the clones in achieving their intend aim: to allow the complement mediated killing of human cells infected with HIV virus.

TABLE 4

HIV VIF Monoclonal Antibody Complement Assay

| Sample ID | LDH Release - OD 450 nm (TEST - BKG) | | |
|---|---|---|---|
| | Neat | 1:10 | 1:100 |
| No-Hybridoma media | 0.048 | 0.003 | 0.001 |
| 52C3.F12.G1.D9 (12/2/13) | 1.014 | 0.111 | 0.018 |
| 52C3.F12.G1.E9 (12/2/13) IgG | 1.254 | 0.148 | 0.018 |
| 52C3.H5.F10.D5 (12/2/13) IgG | 2.515 | 0.293 | 0.039 |
| 52C3.H5.F10.E8 (12/2/13) IgG | 2.543 | 0.288 | 0.037 |
| 52C3.H3.H2.B9.D5 (12/2/13) IgG | 2.024 | 0.238 | 0.025 |
| 52C3.H3.H2.B9.G10 (12/2/13) IgG | 1.764 | 0.196 | 0.032 |

Example 5

Sequencing of Monoclonal Antibodies

To determine the amino acid sequences for the variable heavy ($V_H$) and variable light ($V_L$) chains of an α-HIV monoclonal antibody disclosed herein, polynucleotide molecules encoding these regions from hybridomas 52C3F12G1E9, 52C3H3H2B9G10, and 52C3H5F10E8 were sequenced. mRNA was extracted and purified from each hybridoma using standard protocols and reversed transcribed into cDNA using oligo(dT) primers. Specific murine constant domain primers were used to amplify the cDNA by PCR after cDNA production to determine the isotype of the antibody. Degenerate $V_H$ and $V_L$ primers were used to amplify the variable domains from the cDNA. $V_H$ and $V_L$ PCR products were gel purified to remove small fragments, cloned into a TA vector (Invitrogen, Carlsbad, Calif.), transformed into TOP10 cells and screened by PCR for positive transformants. Five independent clones for each chain were sequenced on an ABI3130xl Genetic Analyzer and alignments of $V_H$ and $V_L$ chains and consensus sequences were determined.

The $V_H$ chain consensus amino acid sequence for an α-HIV monoclonal antibody disclosed herein was SEQ ID NO: 8 for hybridomas 52C3F12G1E9 and 52C3H3H2B9G10 and SEQ ID NO: 14 for hybridoma 52C3H5F10E8. Amino acid variant to SEQ ID NO: 8 include SEQ ID NO: 5, SEQ ID NO: 6, SEQ ID NO: 7, SEQ ID NO: 9, SEQ ID NO: 10, SEQ ID NO: 11, SEQ ID NO: 12, and SEQ ID NO: 13. Amino acid variant to SEQ ID NO: 14 include SEQ ID NO: 15, SEQ ID NO: 16, SEQ ID NO:

17, SEQ ID NO: 18, and SEQ ID NO: 19. The $V_H$ variable domain consensus amino acid sequence for an α-HIV monoclonal antibody disclosed herein comprises SEQ ID NO: 20 and an amino acid variants to this $V_H$ variable domain consensus amino acid sequence comprises SEQ ID NO: 21, SEQ ID NO: 22, SEQ ID NO: 23, SEQ ID NO: 24, SEQ ID NO: 25, SEQ ID NO: 26, and SEQ ID NO: 27.

The $V_L$ chain consensus amino acid sequence for an α-HIV monoclonal antibody disclosed herein was SEQ ID NO: 31 for hybridoma 52C3F12G1E9, SEQ ID NO: 34 for hybridoma 52C3H3H2B9G10, and SEQ ID NO: 38 for hybridoma 52C3H5F10E8. Amino acid variant to SEQ ID NO: 31 include SEQ ID NO: 32 and SEQ ID NO: 33. Amino acid variant to SEQ ID NO: 34 include SEQ ID NO: 35 and SEQ ID NO: 36. Amino acid variant to SEQ ID NO: 38 include SEQ ID NO: 37 and SEQ ID NO: 39. The $V_L$ variable domain consensus amino acid sequence for an α-HIV monoclonal antibody disclosed herein comprises SEQ ID NO: 40 and an amino acid variants to this $V_L$ variable domain consensus amino acid sequence comprises SEQ ID NO: 41 and SEQ ID NO: 42.

The amino acid sequences comprising the $V_H$ and $V_L$ CDR domains of an α-HIV monoclonal antibody disclosed herein are given in Table 5.

TABLE 5

CDR Sequences of $V_H$ and $V_L$ Domains from α-HIV Monoclonal Antibodies

| CDR | Sequence | Identified In | SEQ ID NO: |
|---|---|---|---|
| $V_H$ CDR 1 | GYTFTSYW | 52C3F12G1E9<br>52C3H3H2B9G10<br>52C3H5F10E8 | 28 |
| $V_H$ CDR 2 | IDPSDSYT | 52C3F12G1E9<br>52C3H3H2B9G10<br>52C3H5F10E8 | 29 |
| $V_H$ CDR 3 | ARDDYDY | 52C3F12G1E9<br>52C3H3H2B9G10<br>52C3H5F10E8 | 30 |
| $V_L$ CDR 1 | QSLLKSSNQKNY | 52C3F12G1E9<br>52C3H3H2B9G10<br>52C3H5F10E8 | 43 |
| $V_L$ CDR 2 | FAS | 52C3F12G1E9<br>52C3H3H2B9G10<br>52C3H5F10E8 | 44 |
| $V_L$ CDR 3 | QQHYSTPLT | 52C3F12G1E9<br>52C3H3H2B9G10<br>52C3H5F10E8 | 45 |

Example 6

Clinical Study

HIV-v was assessed in a randomized, double blind multi-center study (North Manchester General Hospital, Royal London Hospital, Brighton and Sussex University Hospitals, Royal Hallamshire Sheffield Teaching Hospitals, Chelsea and Westminster Hospital and Guys and St. Thomas' Hospital). Volunteers were cART naïve HIV-positive males aged 18-50 years with viral loads of 5,000-500,000 copies/mL, CD4+ T-cell counts >350/mL and no signs of any AIDS defining illness or Hepatitis B/C co-infection.

Subject volunteers were randomized sequentially using PRISYM (BIOTEC Ltd, UK) into one of five treatment groups (1:1 ratio). Volunteers received a single 1.0 mL subcutaneous immunization or placebo on Day 0 as follows: Treatment Group 1, Low Dose (LD), 250 mg HIV-v in saline; Treatment Group 2, Low Dose Adjuvant (LDA), 250 mg HIV-v in saline emulsified with adjuvant Montanide ISA-51 (Seppic, France); Treatment Group 3, High Dose (HD), 500 mg HIV-v in saline; Treatment Group 4, High Dose Adjuvant (HAD), 500 mg HIV-v in saline emulsified with adjuvant Montanide ISA-51 (Seppic, France); and Treatment Group 5, Placebo, either saline alone or ISA-51 emulsified saline. Volunteers were monitored for 168 days post-vaccination. Local and systemic reactogenicity were assessed until Day 30, and hematological, biochemical and urine analysis were performed on Days 0, 14 and 28. Adverse event interviews were conducted on days 7, 14, 21 and 28. Immunogenicity and efficacy were assessed on Days 0, 14, 28, 56, 84, 112, 140 and 168. Inter-group differences were analyzed by Kruskal-Wallis and Wilcoxon tests.

HIV-v specific IgG responses were determined in 1/200 serum dilution by validated direct ELISA. Variations from pre-vaccination were calculated as changes in IgG response ratio [i.e. (Mean $OD_{450}$ Day X)/(Baseline OD450 Day 0)]. Baseline is defined as the Mean OD450 or its STDEV, whichever is greater, pre-vaccination (Day 0). Volunteers with IgG response ratios ≥2 pot-vaccination were considered seropositive. Greater than 75% of volunteers immunized with adjuvanted HIV-v (either Low Dose or High Dose) induced an antibody response. Subjects with HIV-v pre-dosing responses ≥2-fold their negative control responses were considered to have pre-existing HIV-v antibody immunity (FIG. 4). Subjects with post-dose HIV-v responses ≥2-fold their pre-dose responses were considered HIV-v responders, but only if this post-dose response was also ≥2-fold the negative control response.

HIV Viral Load was determined by PCR (COBAS AmpliPrep/COBAS TaqMan HIV-1 Test, version 2.0). Variations from pre-vaccination were calculated as changes in viral count ratio [i.e. (HIV Viral Load day X)/(HIV Viral Load day 0)]. No statistical correlation exists between HIV-v antibody responses and reductions in viral load in Placebo patients (FIG. 5A). In patients that received HIGH dose adjuvanted HIV-v, the statistical correlation between HIV-v antibody responses and reductions in viral load has a p value of 0.066 if both responders and non-responders (i.e. those with and without antibody responses to HIV-v are included) (FIG. 5B). However, if only those with HIV-v antibody responses are included, then the statistical correlation between HIV-v antibody responses and reductions in viral load has a p value of 0.0001 (FIG. 5B).

Total Ig and IgG isotype responses to the HIV-v polypeptide components was also determined. Responses were measured by ELISA in sera from HIV-v or NRP-v immunised HLA-A*0201 transgenic mice. Total Ig responses to the VPR (A), VIF (B), REF (C) and NEF (D) peptides are represented as average ng/mL (±SEM) versus sera dilution. IgG2c (E) and IgG1 (F) responses to VIF and NEF peptides were quantified in a 1:200 serum dilution. A positive response, indicated by an asterisk (*) was defined as an increment of at least 100% over the background response with a statistical significance of $p<0.05$. $CD4^+$ T cell counts were determined by flow cytometry (CYTO-STAT/tetraCHROME kit). Variations from pre-vaccination were calculated as changes in the cell count ratio [i.e. (CD4+ T cell count day X)/(CD4+ T cell count day 0)].

Results are shown in FIG. 6. IFN-γ responses of PBMCs were determined by validated IFN-γ ELISA (BD, Human IFN-γ kit 555142) following 24 hour in vitro stimulation with HIV-v. Response levels were calculated as the % IFN-γ response [i.e. 100*(HIV-v response−response to media alone)/(response to ConA−response to media alone]. Volunteers with % IFN-γ responses both >50% their Day 0 response and >15% the ConA response were considered positive for cellular immunity.

Example 7

Complement Mediated Killing of Latent HIV Infected Human Cells

In order to assess the ability of monoclonal α-VIF antibodies to lyse blood cells infected with HIV, peripheral blood mononuclear cells (PBMCs) from HIV infected patients will be obtained by leukapheresis and ficoll-hypaque centrifugation. CD4+ T cells will be isolated using a cell separation system (StemCell Technologies). Subsequently, resting CD4+ T cells will be isolated by depleting CD25+, HLA-DR+, and CD69+ CD4+ T cells using PE-conjugated antibodies (BD Biosciences) and anti-PE microbeads (Miltenyi Biotec). Cells will be cultured in RPMI 1640-based medium in plates coated anti-CD3 and soluble anti-CD28 antibody. To determine the frequency of resting CD4+ T cells carrying HIV DNA, real-time polymerase chain reaction (PCR) will be performed on genomic DNA isolated from resting CD4+ T cells (Qiagen). Cultured cells will be seeded at 6×103 cells/well in flat bottom 96-well plates together with heat inactivated test sera (diluted 1/100 in PBS) and baby rabbit complement (AbD Serotec). After 2 hours incubation, cell lysis (Experimental Release) will be measured using the LDH based CYTO TOX 96® Non-Radioactive Cytotoxicity Assay according to manufacturer's instructions (Promega). The dynamic range of the assay will be determined using as minimum LDH release (MIN) cells incubated with baby rabbit complement in PBS without sera and as maximum LDH release (MAX) cells lysed with Triton X-100. Incubation of latently infected CD4+ T cells from HIV+ patients with monoclonal α-VIF antibodies will most likely result in a significant and specific increase in cell death compared to that observed in the same cells incubated with either complement alone or an irrelevant monoclonal antibody.

In closing, it is to be understood that although aspects of the present specification are highlighted by referring to specific embodiments, one skilled in the art will readily appreciate that these disclosed embodiments are only illustrative of the principles of the subject matter disclosed herein. Therefore, it should be understood that the disclosed subject matter is in no way limited to a particular methodology, protocol, and/or reagent, etc., described herein. As such, various modifications or changes to or alternative configurations of the disclosed subject matter can be made in accordance with the teachings herein without departing from the spirit of the present specification. Lastly, the terminology used herein is for the purpose of describing particular embodiments only, and is not intended to limit the scope of the present invention, which is defined solely by the claims. Accordingly, the present invention is not limited to that precisely as shown and described.

Certain embodiments of the present invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the present invention to be practiced otherwise than specifically described herein. Accordingly, this invention includes all modifications and equivalents of the subject matter recited in the claims appended hereto as permitted by applicable law. Moreover, any combination of the above-described embodiments in all possible variations thereof is encompassed by the invention unless otherwise indicated herein or otherwise clearly contradicted by context.

Groupings of alternative embodiments, elements, or steps of the present invention are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. For instance, as mass spectrometry instruments can vary slightly in determining the mass of a given analyte, the term "about" in the context of the mass of an ion or the mass/charge ratio of an ion refers to +/−0.50 atomic mass unit.

At the very least, and not as an attempt to limit the application of the doctrine of equivalents to the scope of the claims, each numerical indication should at least be construed in light of the number of reported significant digits and by applying ordinary rounding techniques.

Use of the terms "may" or "can" in reference to an embodiment or aspect of an embodiment also carries with it the alternative meaning of "may not" or "cannot." As such, if the present specification discloses that an embodiment or an aspect of an embodiment may be or can be included as part of the inventive subject matter, then the negative limitation or exclusionary proviso is also explicitly meant, meaning that an embodiment or an aspect of an embodiment may not be or cannot be included as part of the inventive subject matter. In a similar manner, use of the term "optionally" in reference to an embodiment or aspect of an embodiment means that such embodiment or aspect of the embodiment may be included as part of the inventive subject matter or may not be included as part of the inventive subject matter. Whether such a negative limitation or exclusionary proviso applies will be based on whether the negative limitation or exclusionary proviso is recited in the claimed subject matter.

Notwithstanding that the numerical ranges and values setting forth the broad scope of the invention are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein.

The terms "a," "an," "the" and similar referents used in the context of describing the present invention (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the present invention and does not pose a limitation on the scope of the invention otherwise claimed. No language in the present specification should be construed as indicating any non-claimed element essential to the practice of the invention.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the present invention so claimed are inherently or expressly described and enabled herein.

All patents, patent publications, and other publications referenced and identified in the present specification are individually and expressly incorporated herein by reference in their entirety for the purpose of describing and disclosing, for example, the compositions and methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The invention claimed is:

1. An isolated α-HIV monoclonal antibody, the isolated α-HIV monoclonal antibody comprising a heavy chain variable domain ($V_H$) and a light chain variable domain ($V_L$)
wherein the heavy chain variable domain comprises a $V_H$ CDR1 region, a $V_H$ CDR2 region, and a $V_H$ CDR3 region; wherein the $V_H$ CDR1 has an amino acid sequence of SEQ ID NO: 28, the $V_H$ CDR2 has an amino acid sequence of SEQ ID NO: 29, and the $V_H$ CDR3 has an amino acid sequence of SEQ ID NO: 30, wherein the light chain variable domain comprises a $V_L$ CDR1 region, a $V_L$ CDR2 region, and a $V_L$ CDR3 region, wherein the $V_L$ CDR1 has an amino acid sequence of SEQ ID NO: 43,
the $V_L$ CDR2 has an amino acid sequence of SEQ ID NO: 44 and
the $V_L$ CDR3 has an amino acid sequence of SEQ ID NO: 45;

wherein the isolated α-HIV monoclonal antibody selectively binds an epitope present on a HIV virion, an epitope derived from an HIV virus, an epitope produced or altered by an HIV virus, and/or an epitope produced or altered by a cell infected by the HIV virus or expressing either the whole or part of the HIV virus genetic code.

2. The isolated α-HIV monoclonal antibody according to claim 1, wherein the epitope is SEQ ID NO: 1, SEQ ID NO: 2, SEQ ID NO: 3, and/or SEQ ID NO: 4.

3. The isolated α-HIV monoclonal antibody according to claim 1, wherein the heavy chain variable domain ($V_H$) comprises SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 25, SEQ ID NO: 26, or SEQ ID NO: 27.

4. The isolated α-HIV monoclonal antibody according to claim 1, wherein the light chain variable domain ($V_L$) comprises SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, or SEQ ID NO: 42.

5. A therapeutic composition comprising one or more α-HIV antibodies as defined in claim 1 and one or more pharmaceutical acceptable carriers.

6. A method of detecting a HIV infection, the method comprising the steps of: a) contacting a sample with an α-HIV monoclonal antibody as defined in claim 1; and b) detecting for the presence or absence of an antibody-antigen complex comprising the α-HIV monoclonal antibody; wherein detection by the antibody-antigen complex is indicative of the presence of a HIV infection.

7. The isolated α-HIV monoclonal antibody according to claim 1, wherein the isolated α-HIV monoclonal antibody has an association rate constant of less than $1 \times 10^5$ $M^{-1}$ $s^{-1}$ for an epitope.

8. The isolated α-HIV antibody according to claim 1, wherein the isolated α-HIV monoclonal antibody has a disassociation rate constant of less than $1 \times 10^{-3}$ $s^{-1}$ for an epitope.

9. The isolated α-HIV antibody according to claim 1, wherein the isolated α-HIV monoclonal antibody has an equilibrium disassociation rate constant of less than 0.500 nM for an epitope.

10. The isolated α-HIV antibody according to claim 1, wherein the isolated α-HIV antibody is a dimer, a multimer, a multispecific antibody, a humanized antibody, a chimeric antibody, bi-functional antibody, a cell-associated antibody, a linear antibody, a diabody, or a minibody.

11. The therapeutic composition according to claim 5, wherein the one or more α-HIV monoclonal antibodies are each present in an amount of between about 1 μg to about 3,000 mg.

* * * * *